US012779050B2

(12) United States Patent
Arai et al.

(10) Patent No.: US 12,779,050 B2
(45) Date of Patent: Nov. 3, 2026

(54) IONIZABLE LIPIDS FOR NUCLEIC ACID DELIVERY

(71) Applicant: EISAI R&D MANAGEMENT CO., LTD., Tokyo (JP)

(72) Inventors: Kenzo Arai, Ibaraki (JP); Masashi Seki, Ibaraki (JP); Yosuke Kaburagi, Ibaraki (JP); Taro Asaba, Ibaraki (JP); Takayuki Miyazaki, Ibaraki (JP); Yasuaki Kamada, Ibaraki (JP)

(73) Assignee: Eisai R&D Management Co., Ltd., Tokyo (JP)

( * ) Notice: Subject to any disclaimer, the term of this patent is extended or adjusted under 35 U.S.C. 154(b) by 0 days.

(21) Appl. No.: 19/432,393

(22) Filed: Dec. 24, 2025

(65) Prior Publication Data

US 2026/0183424 A1 Jul. 2, 2026

(30) Foreign Application Priority Data

Dec. 26, 2024 (JP) ................................ 2024-231204

(51) Int. Cl.

*A61K 48/00* (2006.01)
*C07C 229/12* (2006.01)
*C07D 211/62* (2006.01)
*C07D 223/06* (2006.01)

(52) U.S. Cl.

CPC ........ *A61K 48/0033* (2013.01); *C07C 229/12* (2013.01); *C07D 211/62* (2013.01); *C07D 223/06* (2013.01)

(58) Field of Classification Search

CPC .............. A61K 48/0033; C07C 229/12; C07D 211/62; C07D 223/06

See application file for complete search history.

(56) References Cited

U.S. PATENT DOCUMENTS

| | | | |
|---|---|---|---|
| 8,158,601 | B2 | 4/2012 | Chen et al. |
| 9,873,669 | B2 | 1/2018 | Suzuki et al. |
| 10,081,598 | B2 | 9/2018 | Suzuki et al. |
| 10,131,633 | B2 | 11/2018 | Suzuki et al. |
| 10,501,416 | B2 | 12/2019 | Suzuki et al. |
| 10,947,193 | B2 | 3/2021 | Suzuki et al. |
| 2010/0324120 | A1 | 12/2010 | Chen et al. |
| 2011/0256175 | A1 | 10/2011 | Hope et al. |
| 2012/0027803 | A1 | 2/2012 | Manoharan et al. |
| 2012/0183602 | A1 | 7/2012 | Chen et al. |
| 2013/0108685 | A1 | 5/2013 | Kuboyama et al. |
| 2013/0178541 | A1 | 7/2013 | Stanton et al. |
| 2013/0195920 | A1 | 8/2013 | Maier et al. |
| 2015/0030670 | A1 | 1/2015 | Platscher et al. |
| 2015/0133519 | A1 | 5/2015 | Colletti et al. |
| 2015/0166465 | A1 | 6/2015 | Chen et al. |
| 2015/0174261 | A1 | 6/2015 | Kuboyama et al. |
| 2015/0273068 | A1 | 10/2015 | Maier et al. |
| 2015/0306039 | A1 | 10/2015 | Akinc et al. |
| 2015/0343062 | A1 | 12/2015 | Kuboyama et al. |
| 2015/0361434 | A1 | 12/2015 | Stanton et al. |
| 2016/0009637 | A1 | 1/2016 | Manoharan et al. |
| 2016/0095924 | A1 | 4/2016 | Hope et al. |
| 2016/0257951 | A1 | 9/2016 | Koizumi et al. |
| 2016/0304487 | A1 | 10/2016 | Kuboyama et al. |
| 2016/0317458 | A1 | 11/2016 | Brito et al. |
| 2016/0326116 | A1 | 11/2016 | Suzuki et al. |
| 2016/0367638 | A1 | 12/2016 | Byers et al. |
| 2017/0135962 | A1 | 5/2017 | Colletti |
| 2017/0143631 | A1 | 5/2017 | Chen et al. |
| 2017/0224619 | A1 | 8/2017 | Hosoe et al. |
| 2017/0233734 | A1 | 8/2017 | Akinc et al. |
| 2017/0334852 | A1 | 11/2017 | Suzuki et al. |
| 2018/0000939 | A1 | 1/2018 | Stanton et al. |
| 2018/0051285 | A1 | 2/2018 | Koizumi et al. |
| 2018/0065920 | A1 | 3/2018 | Manoharan et al. |
| 2018/0105493 | A1 | 4/2018 | Suzuki et al. |
| 2018/0193279 | A1 | 7/2018 | Colletti et al. |
| 2019/0218180 | A1 | 7/2019 | Suzuki et al. |
| 2019/0374646 | A1 | 12/2019 | Maier et al. |
| 2020/0080086 | A1 | 3/2020 | Koizumi et al. |
| 2020/0222540 | A1 | 7/2020 | Stanton et al. |
| 2020/0308111 | A1 | 10/2020 | Suzuki et al. |
| 2021/0128474 | A1 | 5/2021 | Strodiot et al. |
| 2022/0105187 | A1 | 4/2022 | Maier et al. |
| 2022/0111053 | A1 | 4/2022 | Maier et al. |
| 2022/0125927 | A1 | 4/2022 | Maier et al. |
| 2022/0175928 | A1 | 6/2022 | Maier et al. |
| 2022/0175929 | A1 | 6/2022 | Maier et al. |
| 2022/0175930 | A1 | 6/2022 | Maier et al. |

(Continued)

FOREIGN PATENT DOCUMENTS

| | | | |
|---|---|---|---|
| CN | 101163796 | A | 4/2008 |
| CN | 102245590 | A | 11/2011 |

(Continued)

OTHER PUBLICATIONS

English translation of CN114874106A. Translated from Google Patents on Jul. 21, 2026. 48 pages. (Year: 2026).*
Notice of Allowance in Canadian Patent Application No. 3,084,657, dated Mar. 20, 2026, 1 page.
Certificate of Correction in U.S. Appl. No. 15/533,576, dated Dec. 31, 2019, 7 pages.
Corrected Notice of Allowability in U.S. Appl. No. 16/897,752, dated Dec. 9, 2020, 7 pages.
Corrected Notice of Allowability in U.S. Appl. No. 16/897,752, dated Nov. 24, 2020, 3 pages.
Extended European Search Report in European Patent Application No. 15735252.7, dated Jun. 8, 2017, 5 pages.
Extended European Search Report in European Patent Application No. 15873148.9, dated May 4, 2018, 7 pages.
Extended European Search Report in European Patent Application No. 17815482.9, dated Jan. 22, 2020, 5 pages.

(Continued)

*Primary Examiner* — Doan T Phan
(74) *Attorney, Agent, or Firm* — Fish & Richardson P.C.

(57) ABSTRACT

The present disclosure provides an ionizable lipid that can be used for nucleic acid delivery into cytoplasm. An ionizable lipid of the present disclosure is, for example, a compound represented by formula (I) or a pharmaceutically acceptable salt thereof.

8 Claims, No Drawings

Specification includes a Sequence Listing.

(56) References Cited

U.S. PATENT DOCUMENTS

| | | | | |
|---|---|---|---|---|
| 2022/0249670 | A1 | 8/2022 | Maier et al. | |
| 2022/0347302 | A1 | 11/2022 | Maier et al. | |
| 2023/0000989 | A1 | 1/2023 | Stanton et al. | |
| 2023/0256098 | A1 | 8/2023 | Maier et al. | |
| 2023/0348361 | A1* | 11/2023 | Zhang .................. | A61K 9/5123 |
| 2024/0245778 | A1 | 7/2024 | Maier et al. | |
| 2024/0269289 | A1 | 8/2024 | Maier et al. | |
| 2024/0285767 | A1 | 8/2024 | Maier et al. | |
| 2024/0285768 | A1 | 8/2024 | Maier et al. | |
| 2024/0335385 | A1 | 10/2024 | Sago et al. | |
| 2024/0398956 | A1 | 12/2024 | Maier et al. | |
| 2026/0035338 | A1 | 2/2026 | Li et al. | |

FOREIGN PATENT DOCUMENTS

| | | | | |
|---|---|---|---|---|
| CN | 102625696 | A | 8/2012 | |
| CN | 102884041 | A | 1/2013 | |
| CN | 103096875 | A | 5/2013 | |
| CN | 103167866 | A | 6/2013 | |
| CN | 105916839 | A | 8/2016 | |
| CN | 107207413 | A | 9/2017 | |
| CN | 114874106 | A * | 8/2022 | .............. A61P 35/00 |
| CN | 114874106 | B | 4/2023 | |
| EP | 3093283 | B1 | 12/2018 | |
| EP | 3239132 | B1 | 3/2019 | |
| EP | 3733647 | A1 | 11/2020 | |
| EP | 3476832 | B1 | 4/2023 | |
| JP | 2012-530059 | A | 11/2012 | |
| JP | 2013-533224 | A | 8/2013 | |
| JP | 2015-500835 | A | 1/2015 | |
| JP | 2020-521781 | A | 7/2020 | |
| RU | 2014141547 | A | 5/2016 | |
| TW | 201532614 | A | 9/2015 | |
| TW | 201534578 | A | 9/2015 | |
| TW | 201619137 | A | 6/2016 | |
| TW | 201630883 | A | 9/2016 | |
| TW | 201726599 | A | 8/2017 | |
| TW | 201726600 | A | 8/2017 | |
| WO | WO 2010/042877 | A1 | 4/2010 | |
| WO | WO 2010/144740 | A1 | 12/2010 | |
| WO | WO 2011/153493 | A2 | 12/2011 | |
| WO | WO 2012/040184 | A2 | 3/2012 | |
| WO | WO 2012/061259 | A2 | 5/2012 | |
| WO | WO 2013/059496 | A1 | 4/2013 | |
| WO | WO 2013/086354 | A1 | 6/2013 | |
| WO | WO 2013/135360 | A1 | 9/2013 | |
| WO | WO 2013/158579 | A1 | 10/2013 | |
| WO | WO 2014/089239 | A1 | 6/2014 | |
| WO | WO 2015/095346 | A1 | 6/2015 | |
| WO | WO 2015/095351 | A1 | 6/2015 | |
| WO | WO 2015/105131 | A1 | 7/2015 | |
| WO | WO 2016/104580 | A1 | 6/2016 | |
| WO | WO 2017/222016 | A1 | 12/2017 | |
| WO | WO 2018/220553 | A1 | 12/2018 | |
| WO | WO 2019/131580 | A1 | 7/2019 | |
| WO | WO 2023/121975 | A1 | 6/2023 | |
| WO | WO 2024/078614 | A1 | 4/2024 | |

OTHER PUBLICATIONS

Extended European Search Report in European Patent Application No. 18895319.4, dated Jul. 23, 2021, 4 pages.

Gindy et al., "Stabilization of Ostwald Ripening in Low Molecular Weight Amino Lipid Nanoparticles for Systemic Delivery of siRNA Therapeutics," Mol. Pharmaceutics, 2014, 3, 11(11):4143-53.

International Preliminary Report on Patentability in International Application No. PCT/JP2015/050295, dated Jul. 12, 2016, 9 pages (with English Translation).

International Preliminary Report on Patentability in International Application No. PCT/JP2017/023052, dated Feb. 21, 2019, 15 pages (with English Translation).

International Search Report in International Application No. PCT/JP2015/050295, dated Feb. 17, 2015, 2 pages.

International Search Report in International Application No. PCT/JP2015/085969, dated Mar. 15, 2016, 6 pages (with English translation).

International Search Report in International Application No. PCT/JP2017/023051, dated Sep. 5, 2017, 1 page.

International Search Report in International Application No. PCT/JP2018/047440, dated Feb. 19, 2019, 2 pages.

Jayaraman et al., "Maximizing the Potency of siRNA Lipid Nanoparticles for Hepatic Gene Silencing In Vivo," Angew. Chem. Int. Ed., 2012, 51:8529-8533.

Notice of Allowance in Australian Patent Application No. 2017282459, dated Apr. 13, 2021, 133 pages.

Notice of Allowance in Canadian Patent Application No. 2,935,914, dated Oct. 14, 2021, 1 page.

Notice of Allowance in Canadian Patent Application No. 2,969,664, dated Jan. 17, 2022, 1 page.

Notice of Allowance in Canadian Patent Application No. 3,020,271, dated Jun. 13, 2024, 1 page.

Notice of Allowance in Chinese Patent Application No. 201580003735.2, dated Jul. 10, 2018, 4 pages (with English translation).

Notice of Allowance in Chinese Patent Application No. 201580068712.X, dated Mar. 12, 2019, 4 pages (with English translation).

Notice of Allowance in Chinese Patent Application No. 201780035314.7, dated Mar. 9, 2022, 4 pages (with English translation).

Notice of Allowance in European Patent Application No. 15735252.7, dated Jul. 12, 2018, 70 pages.

Notice of Allowance in European Patent Application No. 15873148.9, dated Oct. 19, 2018, 99 pages.

Notice of Allowance in European Patent Application No. 17815482.9, dated Nov. 16, 2022, 136 pages.

Notice of Allowance in European Patent Application No. 18895319.4 dated Feb. 11, 2022, 104 pages.

Notice of Allowance in Israeli Patent Application No. 262574, dated Jul. 27, 2021, 131 pages (with English translation).

Notice of Allowance in Japanese Patent Application No. 2015-556822, dated Aug. 7, 2018, 5 pages (with English translation).

Notice of Allowance in Japanese Patent Application No. 2016-566429, dated Sep. 3, 2019, 5 pages (with English translation).

Notice of Allowance in Japanese Patent Application No. 2018-524158, dated Apr. 13, 2021, 5 pages (with English translation).

Notice of Allowance in Japanese Patent Application No. 2019-561687, dated Oct. 4, 2022, 5 pages (with English translation).

Notice of Allowance in Korean Patent Application No. 10-2018-7034307, dated Dec. 17, 2021, 4 pages (with English translation).

Notice of Allowance in Mexican Patent Application No. MXa2018015236, dated Jul. 1, 2021, 4 pages (with English translation).

Notice of Allowance in Russian Patent Application No. 2018143237, dated Nov. 27, 2020, 24 pages (with English translation).

Notice of Allowance in Singaporean Patent Application No. 11201808928Y, dated Sep. 12, 2022, 4 pages.

Notice of Allowance in Taiwanese Patent Application No. 104100437, dated Nov. 27, 2018, 8 pages (with English translation).

Notice of Allowance in Taiwanese Patent Application No. 104143612, dated May 6, 2020, 6 pages (with English translation).

Notice of Allowance in Taiwanese Patent Application No. 106120878, dated Jul. 22, 2021, 4 pages (with English translation).

Notice of Allowance in Taiwanese Patent Application No. 107146930, dated Feb. 17, 2023, 8 pages (with English translation).

Notice of Allowance in U.S. Appl. No. 15/109,512, dated Sep. 18, 2017, 9 pages.

Notice of Allowance in U.S. Appl. No. 15/533,576, dated Jul. 20, 2018, 7 pages.

Notice of Allowance in U.S. Appl. No. 15/841,652, dated Oct. 1, 2018, 10 pages.

Notice of Allowance in U.S. Appl. No. 16/307,202, dated Aug. 1, 2019, 6 pages.

Notice of Allowance in U.S. Appl. No. 16/307,202, dated May 30, 2019, 11 pages.

Notice of Allowance in U.S. Appl. No. 16/307,202, dated Sep. 19, 2019, 9 pages.

Notice of Allowance in U.S. Appl. No. 16/897,752, dated Oct. 30, 2020, 18 pages.

(56) References Cited

OTHER PUBLICATIONS

Office Action in Australian Patent Application No. 2017282459, dated Sep. 22, 2020, 4 pages.
Office Action in Brazilian Patent Application No. 112018075123-5, dated May 14, 2024, 9 pages (with English translation).
Office Action in Brazilian Patent Application No. 112018075123-5, dated May 11, 2021, 8 pages (with English translation).
Office Action in Canadian Patent Application No. 2,935,914, dated Mar. 12, 2021, 4 pages.
Office Action in Canadian Patent Application No. 2,969,664, dated May 27, 2021, 4 pages.
Office Action in Canadian Patent Application No. 3,020,271, dated Jun. 6, 2023, 7 pages.
Office Action in Canadian Patent Application No. 3,084,657, dated Nov. 19, 2024, 4 pages.
Office Action in Chinese Patent Application No. 201580003735.2, dated Dec. 21, 2017, 7 pages (with English translation).
Office Action in Chinese Patent Application No. 201580003735.2, dated May 27, 2017, 10 pages (with English Translation).
Office Action in Chinese Patent Application No. 201580068712.X, dated Sep. 6, 2018, 13 pages (with English Translation).
Office Action in Chinese Patent Application No. 201780035314.7, dated Jun. 28, 2021, 10 pages (with English translation).
Office Action in Chinese Patent Application No. 201880077566.0, dated Aug. 31, 2023, 12 pages (with English translation).
Office Action in Chinese Patent Application No. 201880077566.0, dated Mar. 24, 2023, 12 pages (with English translation).
Office Action in Chinese Patent Application No. 201880077566.0, dated Oct. 28, 2022, 15 pages (with English translation).
Office Action in European Patent Application No. 15735252.7, dated Jul. 12, 2018, 70 pages.
Office Action in European Patent Application No. 17815482.9, dated Jun. 30, 2021, 4 pages.
Office Action in Indian Patent Application No. 201847045536, dated Sep. 30, 2020, 6 pages.
Office Action in Israeli Patent Application No. 262574, dated Jun. 24, 2020, 6 pages (with English translation).
Office Action in Japanese Patent Application No. 2016-566429, dated Apr. 23, 2019, 6 pages (with English Translation).
Office Action in Russian Patent Application No. 2018143237, dated Jul. 24, 2020, 9 pages (with English translation).
Office Action in Singaporean Patent Application No. 11201808928Y, dated Oct. 10, 2018, 2 pages.
Office Action in Taiwanese Patent Application No. 104100437, dated Aug. 31, 2018, 6 pages (with English Translation).
Office Action in Taiwanese Patent Application No. 104143612, dated Oct. 2, 2019, 7 pages (with English Translation).
Office Action in Taiwanese Patent Application No. 106120878, dated Apr. 15, 2021, 9 pages (with English translation).
Office Action in Taiwanese Patent Application No. 107146930, dated Aug. 15, 2022, 7 pages (with English translation).
Office Action in U.S. Appl. No. 15/109,512, dated May 19, 2017, 8 pages.
Office Action in U.S. Appl. No. 15/841,652, dated May 18, 2018, 8 pages.
Oral Hearing in Indian Patent Application No. 201847045536, dated Jun. 4, 2021, 2 pages.
Request in Certificate of Correction in U.S. Appl. No. 15/533,576, dated Nov. 22, 2019, 16 pages.
Response to Examiner's Telephone Call in Canadian Patent Application No. 3,020,271, dated May 21, 2024, 22 pages.
Response to Extended European Search Report in European Patent Application No. 15735252.7, dated Dec. 15, 2017, 130 pages.
Response to Extended European Search Report in European Patent Application No. 15873148.9, dated Aug. 17, 2018, 93 pages.
Response to Extended European Search Report in European Patent Application No. 17815482.9, dated May 19, 2020, 3 pages.
Response to Extended European Search Report in European Patent Application No. 18895319.4, dated Sep. 8, 2021, 1 page.
Response to Office Action (Formal Requirements) in Singaporean Patent Application No. 11201808928Y, dated Nov. 15, 2018, 5 pages.
Response to Office Action in Australian Patent Application No. 2017282459, dated Mar. 25, 2021, 10 pages.
Response to Office Action in Brazilian Patent Application No. 112018075123-5, dated Jul. 9, 2024, 28 pages (with English translation).
Response to Office Action in Brazilian Patent Application No. BR112018075123-5, dated Aug. 5, 2021, 10 pages (with English translation).
Response to Office Action in Canadian Patent Application No. 2,935,914 dated Jun. 3, 2021, 6 pages.
Response to Office Action in Canadian Patent Application No. 2,969,664, Sep. 2, 2021, 14 pages.
Response to Office Action in Canadian Patent Application No. 3,020,271, dated Oct. 3, 2023, 29 pages.
Response to Office Action in Canadian Patent Application No. 3,084,657 dated Feb. 21, 2025, 28 pages.
Response to Office Action in Chinese Patent Application No. 201580003735.2 dated Feb. 28, 2018, 18 pages (with English translation).
Response to Office Action in Chinese Patent Application No. 201580003735.2, dated Sep. 25, 2017, 5 pages (with English translation).
Response to Office Action in Chinese Patent Application No. 201580068712.X dated Nov. 14, 2018, 28 pages (with English translation).
Response to Office Action in Chinese Patent Application No. 201780035314.7 dated Dec. 23, 2021, 30 pages (with English translation).
Response to Office Action in Chinese Patent Application No. 201880077566.0 dated Dec. 12, 2023, 26 pages (with English translation).
Response to Office Action in Chinese Patent Application No. 201880077566.0 dated Jan. 13, 2023, 10 pages (with English translation).
Response to Office Action in Chinese Patent Application No. 201880077566.0, dated Aug. 7, 2023, 30 pages (with English translation).
Response to Office Action in European Patent Application No. 17815482.9, dated Sep. 14, 2021, 229 pages.
Response to Office Action in Indian Patent Application No. 201847045536, dated Mar. 25, 2021, 89 pages.
Response to Office Action in Israeli Patent Application No. 262574, dated Oct. 8, 2020, 4 pages (with English translation).
Response to Office Action in Japanese Patent Application No. 2016-566429, dated Aug. 9, 2019, 12 pages (with English translation).
Response to Office Action in Russian Patent Application No. 2018143237, dated Oct. 20, 2020, 23 pages (with English translation).
Response to Office Action in Taiwanese Patent Application No. 104100437, dated Nov. 16, 2018, 30 pages (with English translation).
Response to Office Action in Taiwanese Patent Application No. 104143612, dated Dec. 26, 2019, 29 pages (with English translation).
Response to Office Action in Taiwanese Patent Application No. 106120878, dated Jul. 16, 2021, 22 pages (with English translation).
Response to Office Action in Taiwanese Patent Application No. 107146930, dated Nov. 10, 2022, 24 pages (with English translation).
Response to Office Action in U.S. Appl. No. 15/109,512, dated Aug. 16, 2017, 8 pages.
Response to Office Action in U.S. Appl. No. 15/841,652 dated Jul. 24, 2018, 5 pages.
Response to Oral Hearing in Indian Patent Application No. 201847045536, dated Sep. 6, 2021, 178 pages.
Response to Restriction Requirement in U.S. Appl. No. 15/109,512, dated May 10, 2017, 5 pages.
Response to Restriction Requirement in U.S. Appl. No. 15/841,652, dated Mar. 22, 2018, 5 pages.

(56) References Cited

OTHER PUBLICATIONS

Restriction Requirement in U.S. Appl. No. 15/109,512, dated Mar. 13, 2017, 10 pages.
Restriction Requirement in U.S. Appl. No. 15/841,652, dated Jan. 30, 2018, 8 pages.
Supplemental Notice of Allowability in U.S. Appl. No. 16/307,202, dated Nov. 6, 2019, 3 pages.
Suzuki et al., "Biodegradable lipid nanoparticles induce a prolonged RNA interference-mediated protein knockdown and show rapid hepatic clearance in mice and nonhuman primates," International Journal of Pharmaceutics, Jan. 9, 2017, 519(1-2):34-43.
Wan et al., "Lipid nanoparticle delivery systems for siRNA-based therapeutics," Drug Delivery and Translational Research, Jun. 28, 2013, 4(1):74-83.
Written Opinion in International Application No. PCT/JP2015/050295, dated Feb. 17, 2015, 6 pages (with English translation).
Written Opinion in International Application No. PCT/JP2015/085969, dated Mar. 15, 2016, 9 pages (with English translation).
Written Opinion in International Application No. PCT/JP2017/023051, dated Sep. 5, 2017, 9 pages (with English translation).
Written Opinion in International Application No. PCT/JP2018/047440, dated Feb. 19, 2019, 11 pages (with English translation).
International Search Report and Written Opinion PCT/JP2025/045237, dated Mar. 17, 2026, 24 pages (with English translation).

* cited by examiner

SEQUENCE LISTING

```
Sequence total quantity: 2
SEQ ID NO: 1            moltype = RNA  length = 1921
FEATURE                 Location/Qualifiers
source                  1..1921
                        mol_type = mRNA
                        note = Firefly Luciferase
                        organism = Photinus pyralis
SEQUENCE: 1
agggaaataa gagagaaaag aagagtaaga agaaatataa gagccaccat ggaggacgcc  60
aagaacatca agaagggccc cgccccctte tacccctgg aggacggcac cgccggcgag  120
cagctgcaca aggccatgaa gcggtacgcc ctggtgcccg gcaccatcgc cttcaccgac  180
gcccacatcg aggtggacat cacctacgcc gagtacttcg agatgagcgt gcggctggcc  240
gaggccatga agcggtacgg cctgaacacc aaccaccgga tcgtggtgtg cagcgagaac  300
agcctgcagt tcttcatgcc cgtgctgggc gccctgttca tcggcgtggc cgtggccccc  360
gccaacgaca tctacaacga gcgggagctg ctgaacagca tgggcatcag ccagcccacc  420
gtggtgttcg tgagcaagaa gggcctgcag aagatcctga acgtgcagaa gaagctgccc  480
atcatccaga agatcatcat catggacagc aagaccgact accagggctt ccagagcatg  540
tacaccttcg tgaccagcca cctgcccccc ggcttcaacg agtacgactt cgtgcccgag  600
agcttcgacc gggacaagac catcgccctg atcatgaaca gcagcggcag caccggcctg  660
cccaagggcg tggccctgcc ccaccggacc gcctgcgtgc ggttcagcca cgcccgggac  720
cccatcttcg gcaaccagat catccccgac accgccatcc tgagcgtggt gcccttccac  780
cacggcttcg gcatgttcac caccctgggc tacctgatct gcggcttccg ggtggtgctg  840
atgtaccggt tcgaggagga gctgttcctg cggagcctgc aggactacaa gatccagagc  900
gccctgctgg tgcccaccct gttcagcttc ttcgccaaga gcaccctgat cgacaagtac  960
gacctgagca acctgcacga gatcgccagc ggcggcgccc ccctgagcaa ggaggtgggc  1020
gaggccgtgg ccaagcggtt ccacctgccc ggcatccggc agggctacgg cctgaccgag  1080
accaccagcg ccatcctgat cacccccgag ggcgacgaca agcccggcgc cgtgggcaag  1140
gtggtgccct tcttcgaggc caaggtggtg gacctggaca ccggcaagac cctgggcgtg  1200
aaccagcggg gcgagctgtg cgtgcggggc cccatgatca tgagcggcta cgtgaacaac  1260
cccgaggcca ccaacgccct gatcgacaag gacggctggc tgcacagcgg cgacatcgcc  1320
tactgggacg aggacgagca cttcttcatc gtggaccggc tgaagagcct gatcaagtac  1380
aagggctacc aggtggcccc cgccgagctg gagagcatcc tgctgcagca ccccaacatc  1440
ttcgacgccg gcgtggccgg cctgcccgac gacgacgccg gcgagctgcc cgccgccgtg  1500
gtggtgctgg agcacggcaa gaccatgacc gagaaggaga tcgtggacta cgtggccagc  1560
caggtgacca ccgccaagaa gctgcggggc ggcgtggtgt tcgtggacga ggtgcccaag  1620
ggcctgaccg gcaagctgga cgcccggaag atccgggaga tcctgatcaa ggccaagaag  1680
ggcggcaaga tcgccgtgtg ataagctgcc ttctgcgggg cttgccttct ggccatgccc  1740
ttcttctctc ccttgcacct gtacctcttg gtctttgaat aaagcctgag taggaaggcg  1800
gaaaaaaaaa aaaaaaaaaa aaaaaaaaaa aaaaaaaaaa aaaaaaaaaa aaaaaaaaaa  1860
aaaaaaaaaa aaaaaaaaaa aaaaaaaaaa aaaaaaaaaa aaaaaaaaaa aaaaaaaaaa  1920
a                                                                  1921

SEQ ID NO: 2            moltype = RNA  length = 850
FEATURE                 Location/Qualifiers
source                  1..850
                        mol_type = mRNA
                        note = Human Erythropoietin
                        organism = Homo sapiens
SEQUENCE: 2
agggaaataa gagagaaaag aagagtaaga agaaatataa gagccaccat gggcgtgcac  60
gagtgccccg cctggctgtg gctgctgctg agcctgctga gcctgccct gggcctgccc  120
gtgctgggcg cccccccccg gctgatctgc gacagccggg tgctggagcg gtacctgctg  180
gaggccaagg aggccgagaa catcaccacc ggctgcgccg agcactgcag cctgaacgag  240
aacatcaccg tgcccgacac caaggtgaac ttctacgcct ggaagcggat ggaggtgggc  300
cagcaggccg tggaggtgtg gcagggcctg gccctgctga gcgaggccgt gctgcggggc  360
caggccctgc tggtgaacag cagccagccc tgggagcccc tgcagctgca cgtggacaag  420
gccgtgagcg gcctgcggag cctgaccacc ctgctgcggg ccctgggcgc ccagaaggag  480
gccatcagcc cccccgacgc cgccagcgcc gccccctgc ggaccatcac cgccgacacc  540
ttccggaagc tgttccgggt gtacagcaac ttcctgcggg gcaagctgaa gctgtacacc  600
ggcgaggcct gccggaccgg cgaccggtga taagctgcct tctgcggggc ttgccttctg  660
gccatgccct tcttctctcc cttgcacctg tacctcttgg tctttgaata aagcctgagt  720
aggaaggcgg aaaaaaaaaa aaaaaaaaaa aaaaaaaaaa aaaaaaaaaa aaaaaaaaaa  780
aaaaaaaaaa aaaaaaaaaa aaaaaaaaaa aaaaaaaaaa aaaaaaaaaa aaaaaaaaaa  840
aaaaaaaaaa                                                         850
```

IONIZABLE LIPIDS FOR NUCLEIC ACID DELIVERY

CROSS-REFERENCE TO RELATED APPLICATIONS

This application claims priority to Japanese Application No. 2024-231204, filed on Dec. 26, 2024. The disclosure of the above-referenced prior application is considered part of the disclosure of this application and is incorporated in its entirety into this application.

SEQUENCE LISTING

This application contains a Sequence Listing that has been submitted electronically as an XML file named "28637-0035001_SL_ST26.XML." The XML file, created on Dec. 16, 2025, is 5,874 bytes in size. The material in the XML file is hereby incorporated by reference in its entirety.

TECHNICAL FIELD

The present disclosure relates to an ionizable lipid for nucleic acid delivery.

BACKGROUND ART

In recent years, research and development of nucleic acid medicines containing nucleic acids as an active ingredient has been underway. These nucleic acids include nucleic acids inducing sequence-specific gene expression inhibition in vivo such as siRNA (small interfering RNA), miRNA (micro RNA), shRNA (short hairpin RNA or small hairpin RNA) expression vectors, and antisense oligonucleotides. In addition, research of nucleic acid medicines for expressing a protein of interest in cells such as mRNA that encodes a protein of interest is also underway.

Among these nucleic acid medicines, for example, nucleic acids are chemically stable but have a problem in therapeutic uses since nucleic acids are likely to be degraded by RNase (ribonuclease) in plasma and have a difficulty in permeating cell membranes alone. Regarding the above-mentioned problem, it is known that when nucleic acids such as siRNA and mRNA are encapsulated in particles (lipid particles, in particular, lipid nanoparticles; LNP) containing ionizable lipids, the encapsulated nucleic acids can be protected from degradation in plasma and permeated into lipophilic cell membranes.

For example, PTL 1 to 8 report ionizable lipids that are used for the delivery of nucleic acid medicines.

In recent years, taking the commercialization of mRNA vaccines against COVID-19 as an opportunity, development of nucleic acid medicines using LNP technology has accelerated, and development of not only vaccines but also LNP formulations for the treatment of various diseases have been underway.

CITATION LIST

Patent Literature

[PTL 1] WO 2010/144740
[PTL 2] WO 2011/153493
[PTL 3] WO 2013/086354
[PTL 4] WO 2013/158579
[PTL 5] WO 2015/095346
[PTL 6] WO 2016/104580
[PTL 7] WO 2014/089239
[PTL 8] WO 2017/222016
[PTL 9] Chinese Patent No. 114874106

SUMMARY OF INVENTION

Technical Problem

Despite the recent development, there is still a demand for ionizable lipids that can be used for nucleic acid delivery into cytoplasm.

Solution to Problem

The present disclosure is, for example, as follows.

[1]A compound represented by the following formula (I) or a pharmaceutically acceptable salt thereof:

(I)

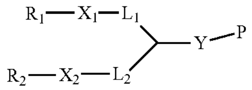

wherein $L_1$ represents $-(CH_2)_n-$, $L_2$ represents $-(CH_2)_m-$, n represents an integer of 1 to 5, m represents an integer of 1 to 5, $X_1$ and $X_2$ each independently represent $-OC(O)-$ or $-OC(O)O-$, Y represents $-OC(O)-$, or $-OC(O)O-$, $R_1$ and $R_2$ each independently represent an alkyl group having 2 to 25 carbon atoms or alkenyl group having 2 to 25 carbon atoms that is optionally substituted with one or more of alkoxy groups having 4 to 12 carbon atoms, $R_1$ or $R_2$ each have a total of 4 to 30 carbon atoms, and P is represented by the following formula P-1 or formula P-2, and

P-1

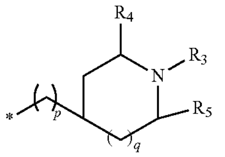

P-2

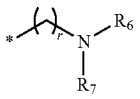

$R_3$ represents an alkyl group having 1 to 5 carbon atoms that is optionally substituted with a hydroxy group, $R_4$ and $R_5$ each independently represent a hydrogen atom or an alkyl group having 1 to 5 carbon atoms, or $R_4$ and $R_5$ are taken together to form an alkylene group having 2 to 5 carbon atoms, p represents 0 or 1, q represents an integer of 0 to 2, $R_6$ and $R_7$ each independently represent an alkyl group having 1 to 5 carbon atoms, r represents an integer of 1 to 5, and

* represents a linking site.

[2] The compound or pharmaceutically acceptable salt thereof according to [1], wherein n represents an integer of 2 to 4, and m represents an integer of 2 to 4.

[3] The compound or pharmaceutically acceptable salt thereof according to [1] or [2], wherein n represents 2 or 3, and m represents 2 or 3.

[4] The compound or pharmaceutically acceptable salt thereof according to any one of [1] to [3], wherein $R_1$ is represented by the following formula C-1, $R_2$ is represented by the following formula C-1 or represents a linear alkyl group having 4 to 12 carbon atoms, a linear alkenyl group having 4 to 12 carbon atoms, or a linear alkoxy group having 4 to 12 carbon atoms,

C-1

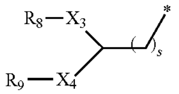

$X_3$ and $X_4$ each independently represent a single bond or —O—, $R_8$ and $R_9$ each independently represent an alkyl group having 4 to 12 carbon atoms or an alkenyl group having 4 to 12 carbon atoms, s represents an integer of 1 to 4, and

* represents a linking site.

[5] The compound or pharmaceutically acceptable salt thereof according to any one of [1] to [4], wherein P is represented by the formula P-1, n represents 2 or 3, m represents 2 or 3, $X_1$ and $X_2$ are identical to each other, $R_1$ and $R_2$ are identical to each other, $R_3$ represents an alkyl group having 1 to 4 carbon atoms that is optionally substituted with a hydroxy group, $R_4$ and $R_5$ each independently represent a hydrogen atom, or $R_4$ and $R_5$ are taken together to form an alkylene group having 2 or 3 carbon atoms, p represents 0 or 1, and q represents 1 or 2.

[6] The compound or pharmaceutically acceptable salt thereof according to any one of [1] to [5], wherein P is represented by the formula P-1, n represents 2 or 3, m represents 2 or 3, $X_1$ and $X_2$ are identical to each other, $R_1$ and $R_2$ are identical to each other, $R_3$ represents a methyl group, $R_4$ and $R_5$ each independently represent a hydrogen atom, p represents 0 or 1, and q represents 1 or 2.

[7] The compound or pharmaceutically acceptable salt thereof according to any one of [1] to [4], wherein the compound is selected from the group consisting of the following compounds:

(E1)

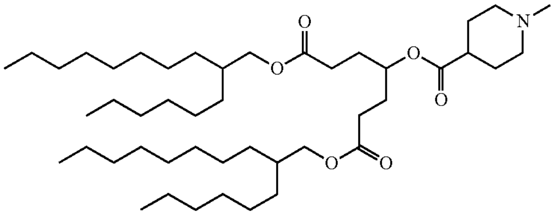

(E2)

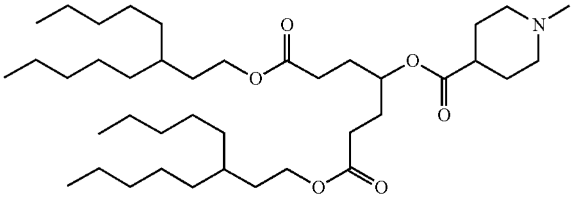

(E3)

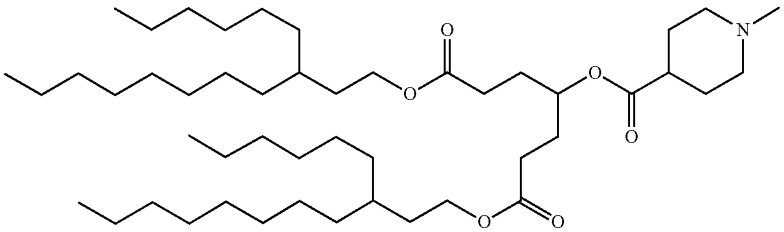

(E4)

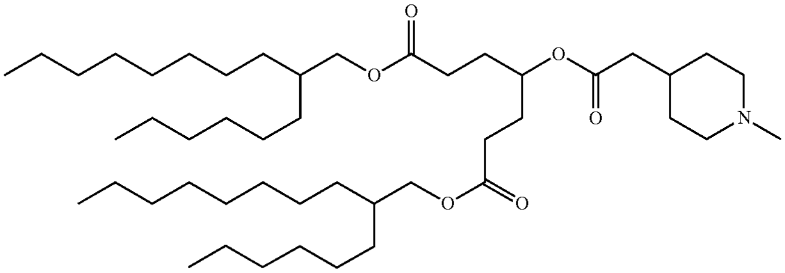

-continued
(E5)
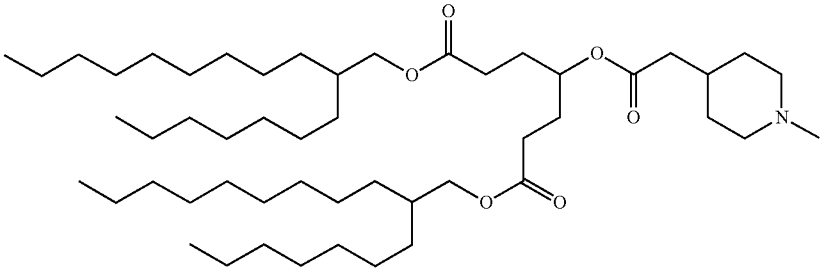
(E7)
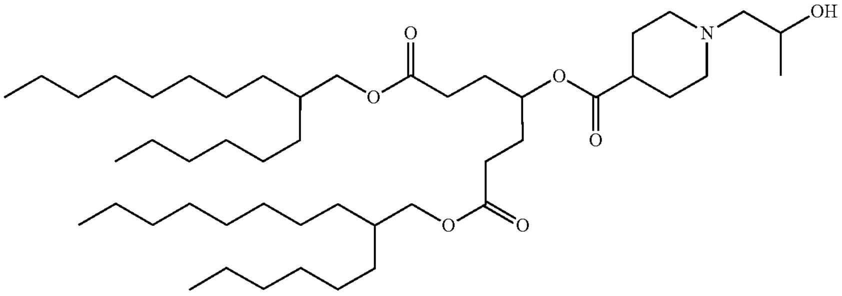
(E8)
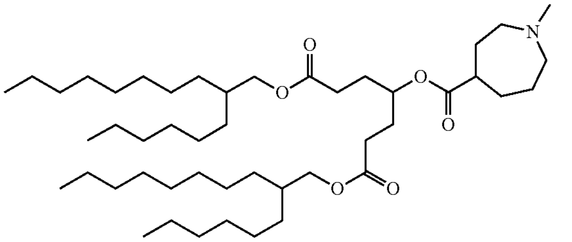
(E9)
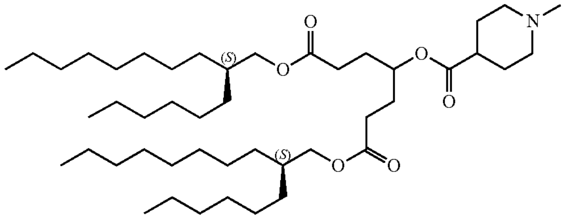
(E10)
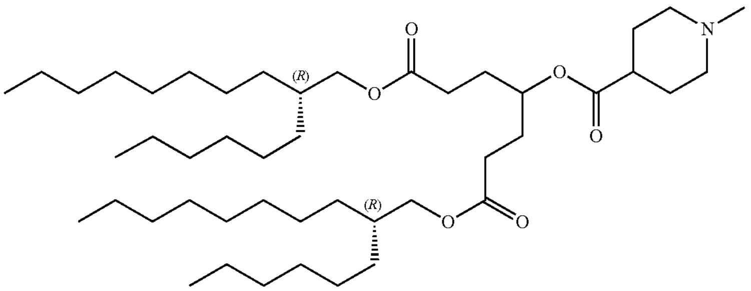
(E11)
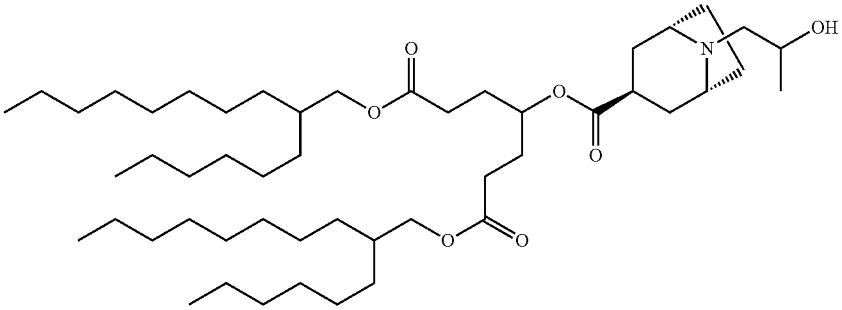

-continued
(E12)
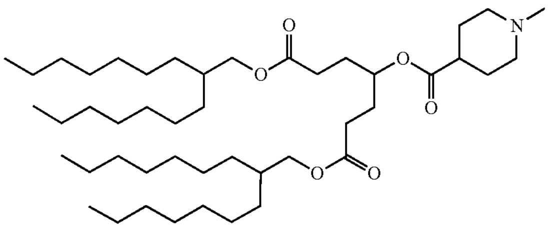
(E13)
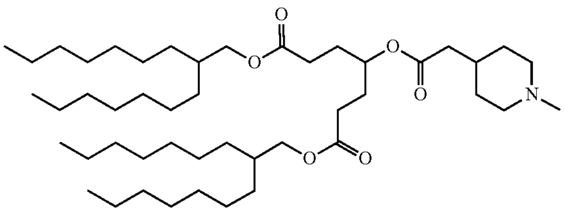
(E16)
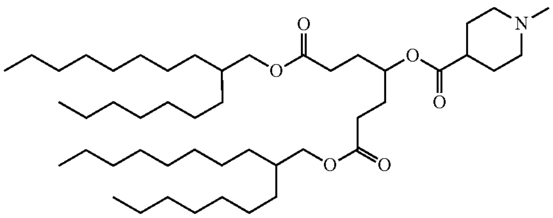
(E17)
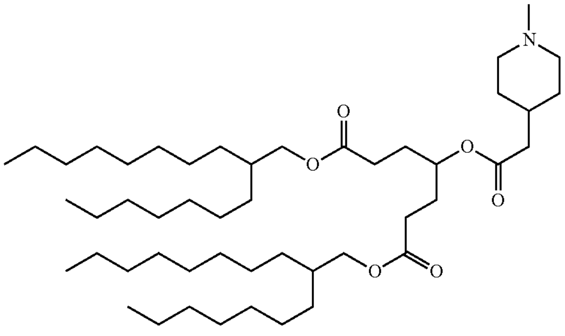
(E18)
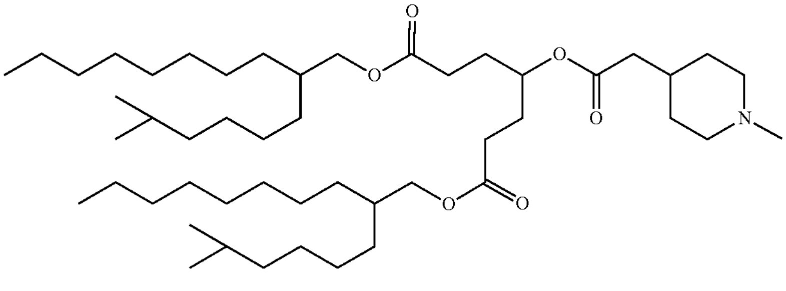
(E19)
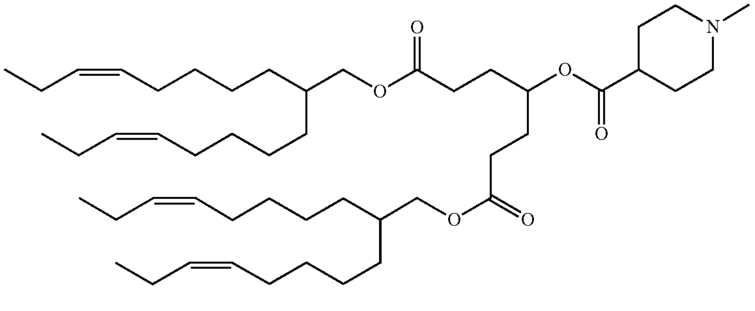
(E20)
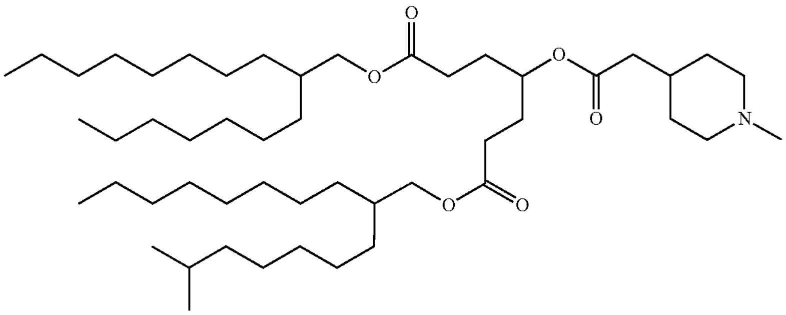

-continued
(E21)
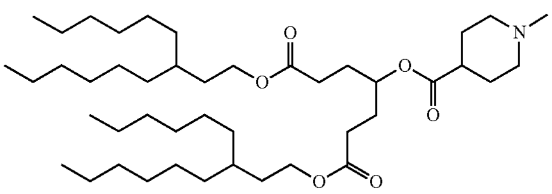
(E22)
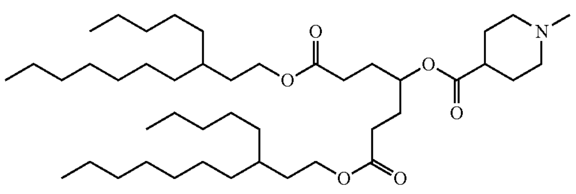
(E23)
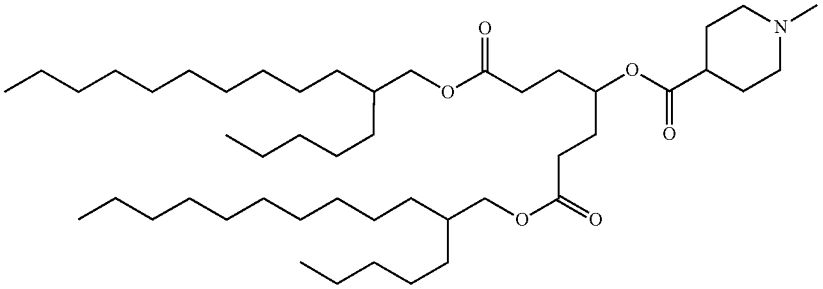
(E24)
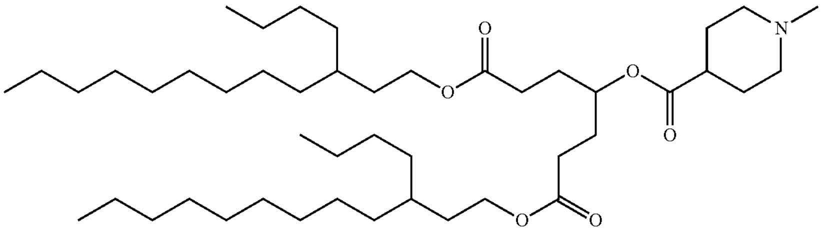
(E25)
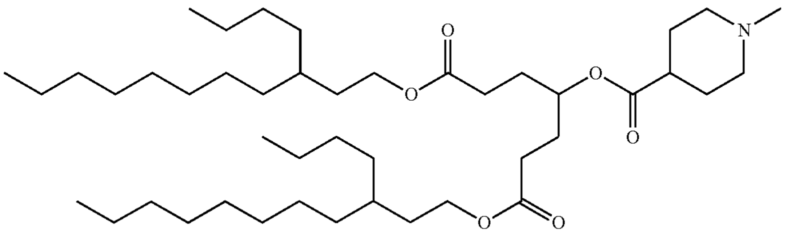
(E26)
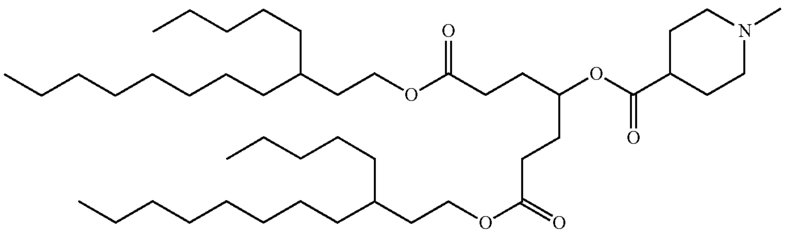
(E27)
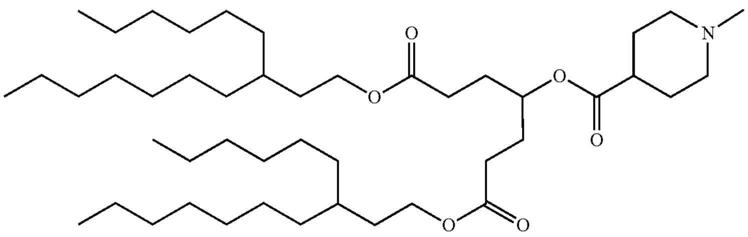

-continued
(E28)
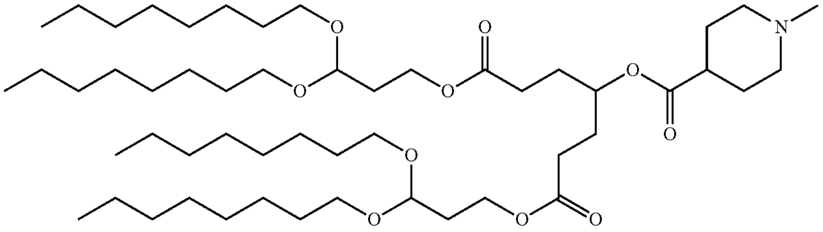
(E29)
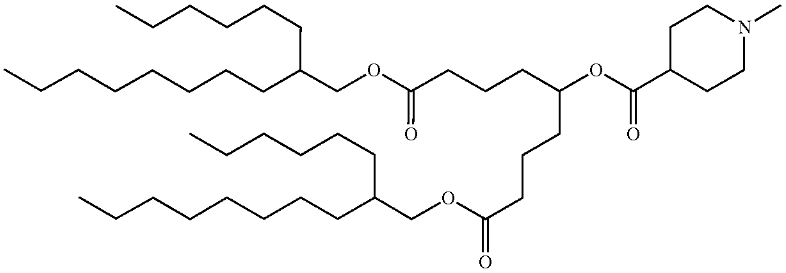
(E30)
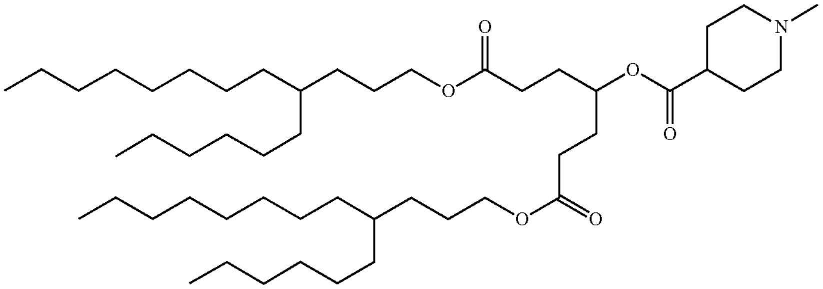
(E31)
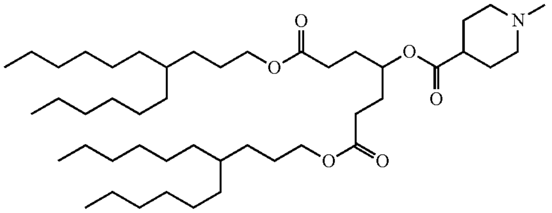
(E32)
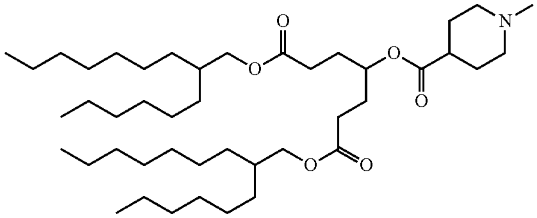
(E33)
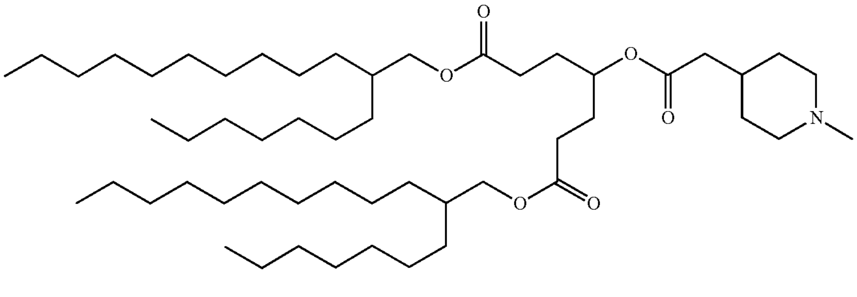
(E34)
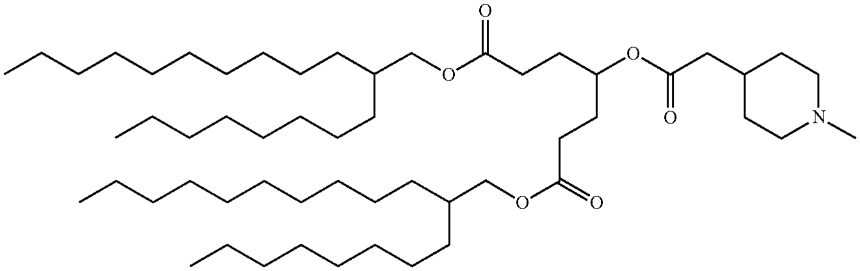

-continued
(E35)
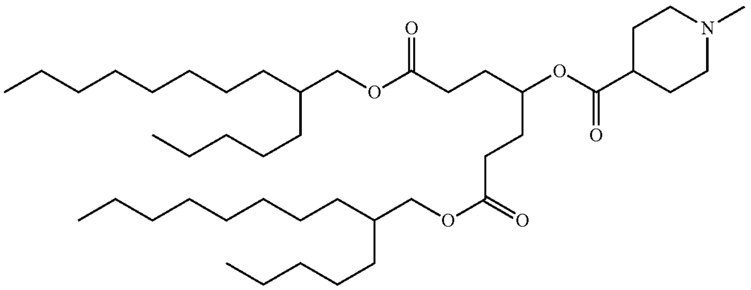
(E36)
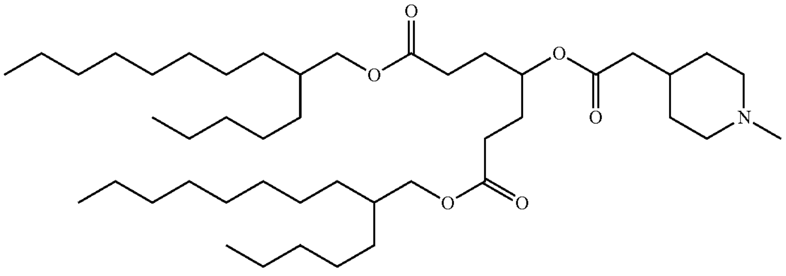
(E37)
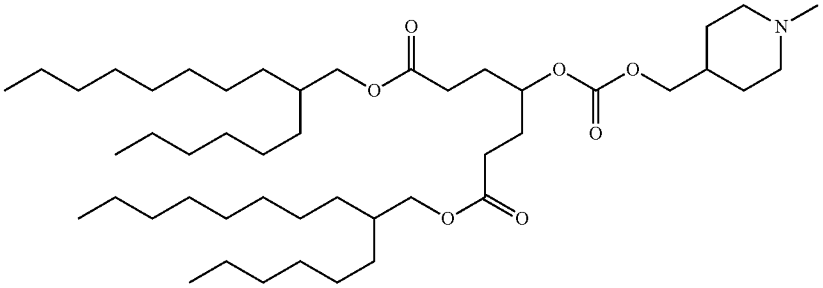
(E38)
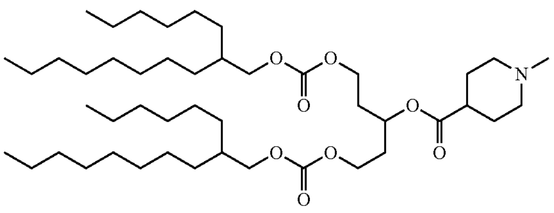
(E40)
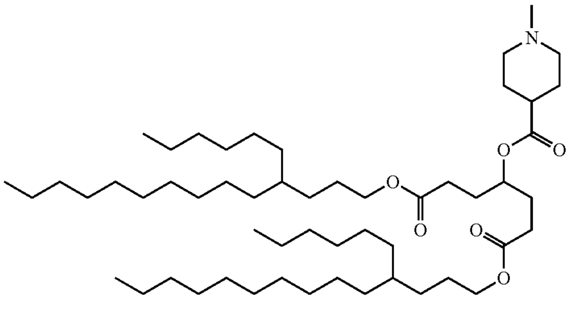
(E42)
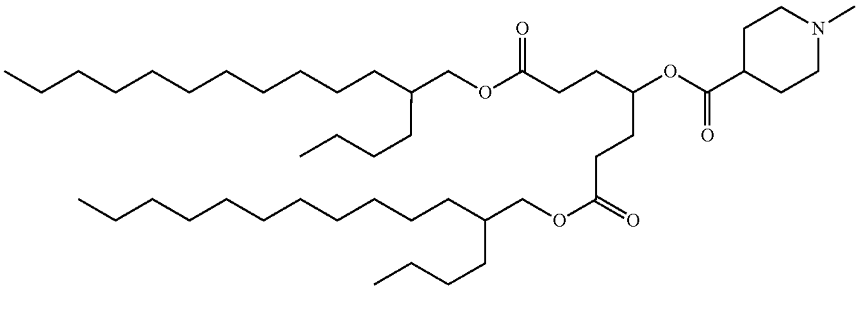

-continued
(E43)
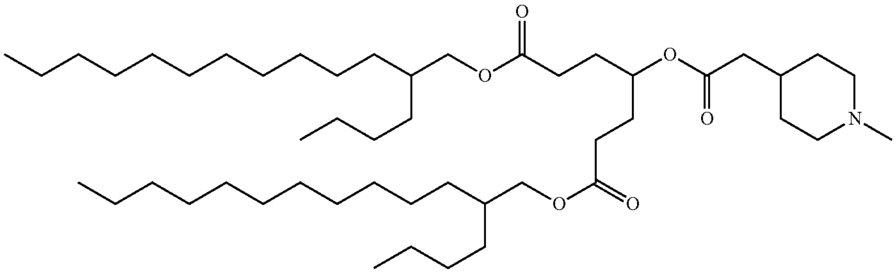
(E44)
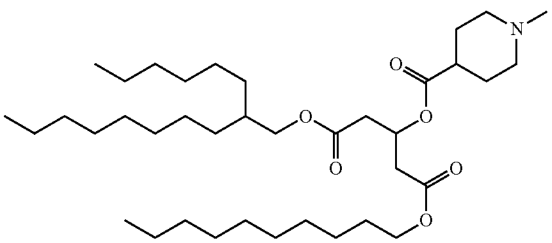
(E45)
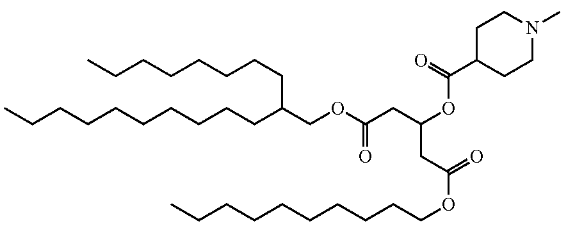
(E46)
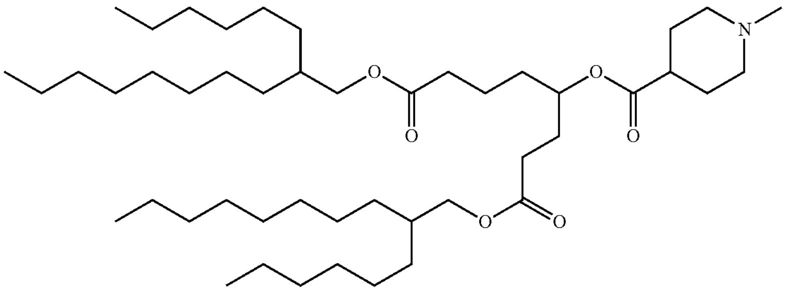
(E47)
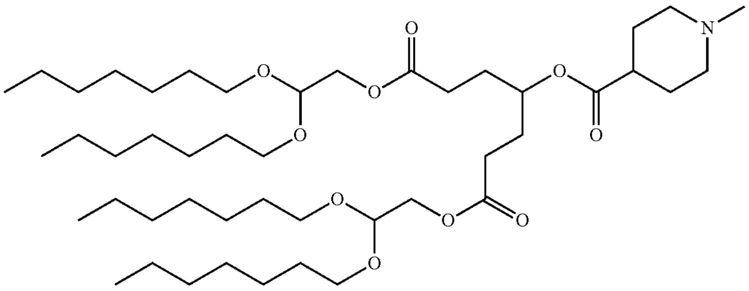
(E48)
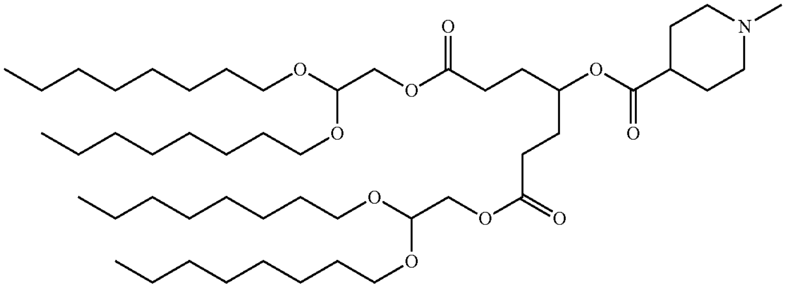

-continued
(E49)
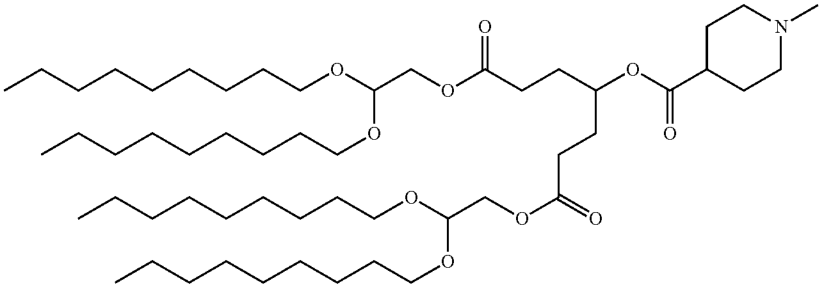
(E50)
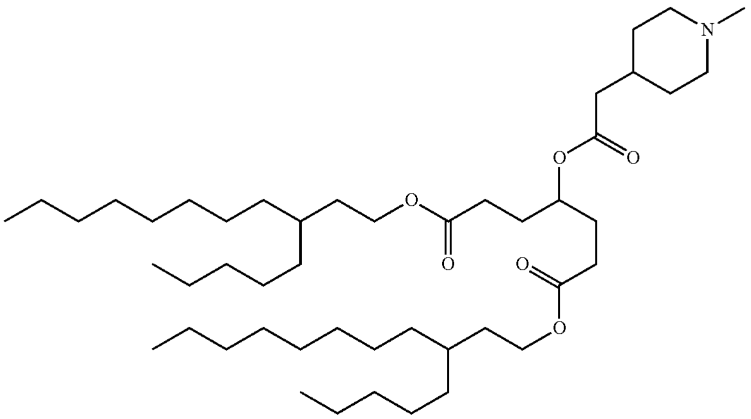
(E51)
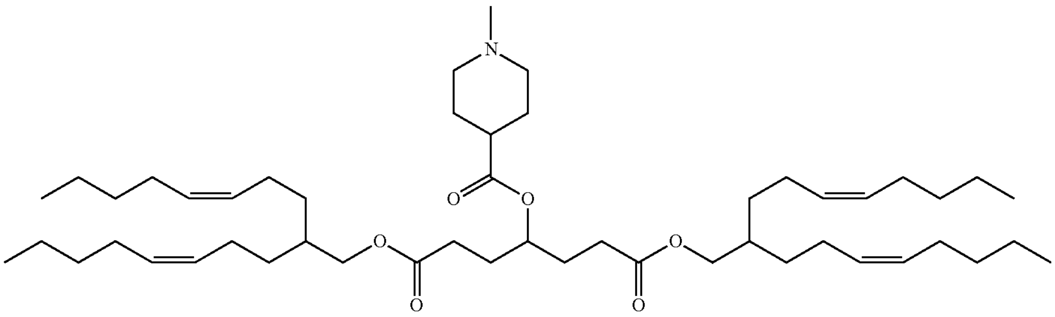
(E52)
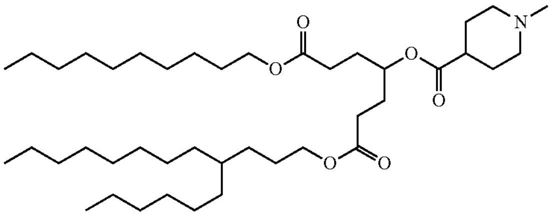
(E53)
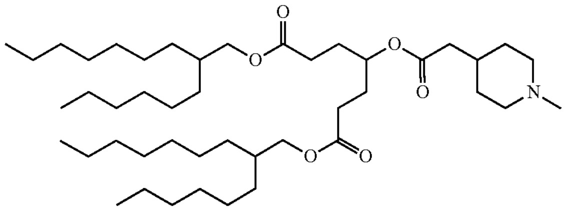
(E54)
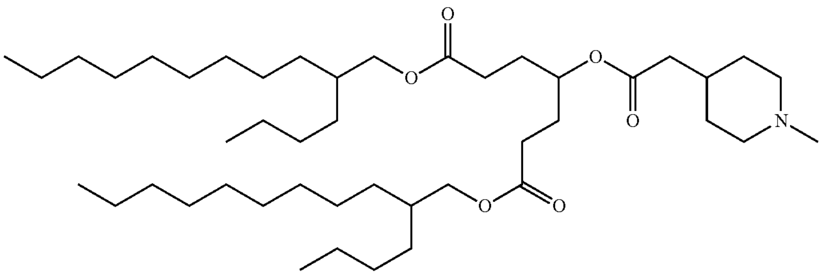

-continued
(E55)
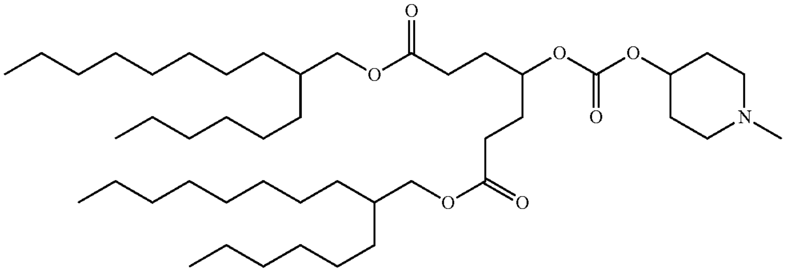
(E56)
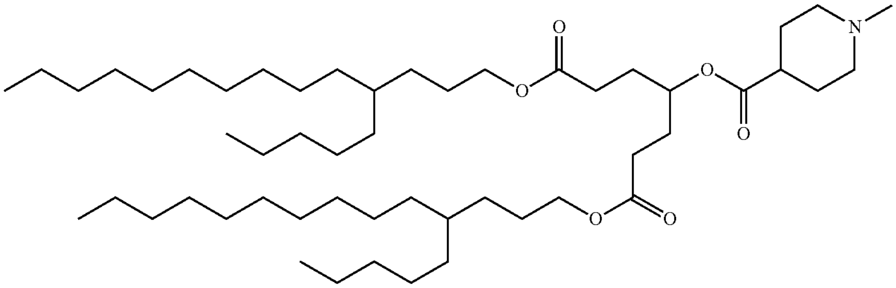
(E57)
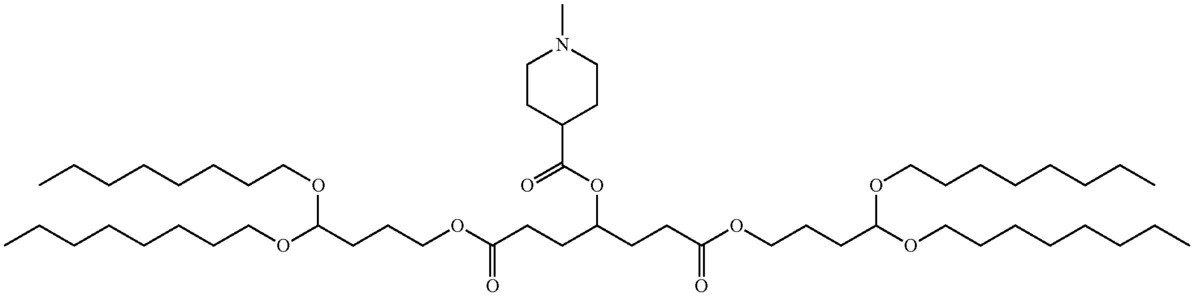
[8] The compound or pharmaceutically acceptable salt thereof according to any one of [1] to [6], wherein the compound is selected from the group consisting of the following compounds:
(E1)
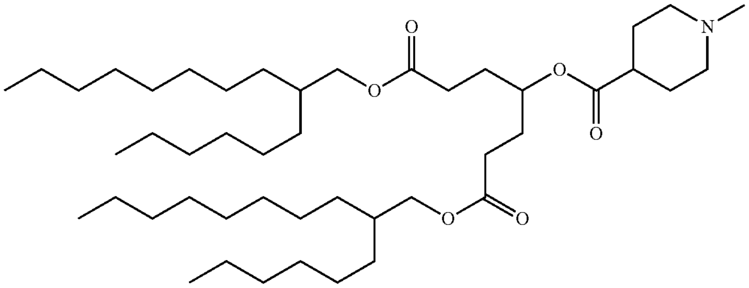

-continued
(E4)
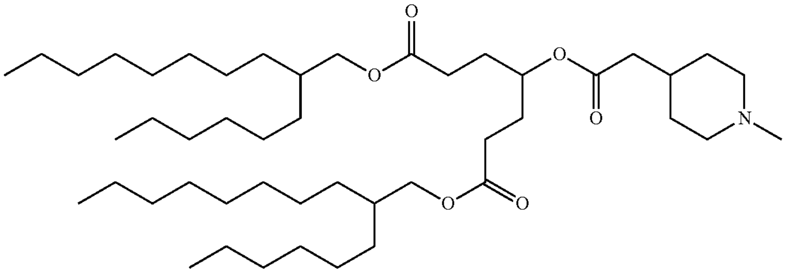
(E12)
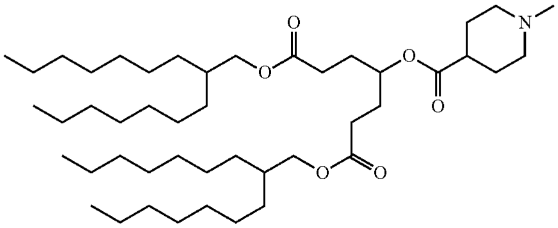
(E13)
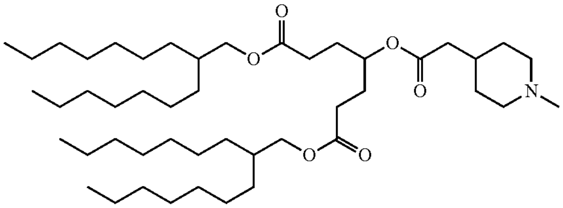
(E16)
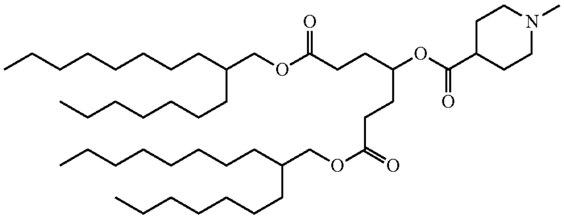
(E17)
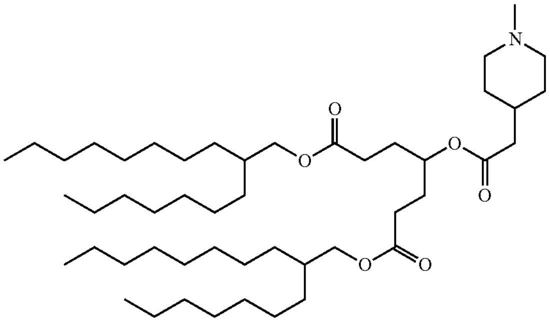
(E29)
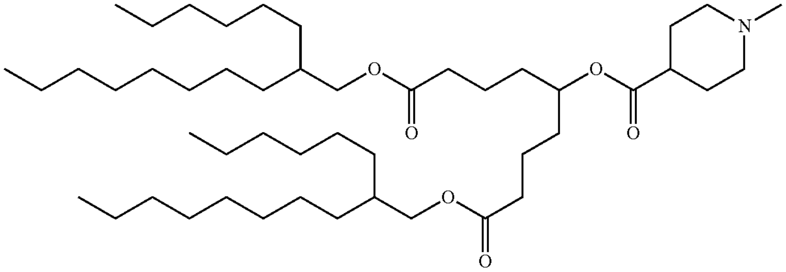
[9] The compound or pharmaceutically acceptable salt thereof according to any one of [1] to [5], wherein the compound is selected from the group consisting of the following compounds:
(E3)
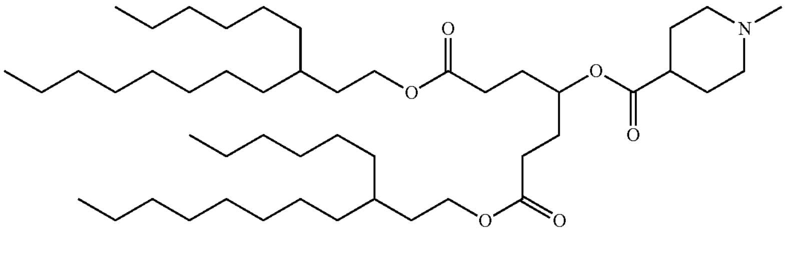

-continued
(E5)
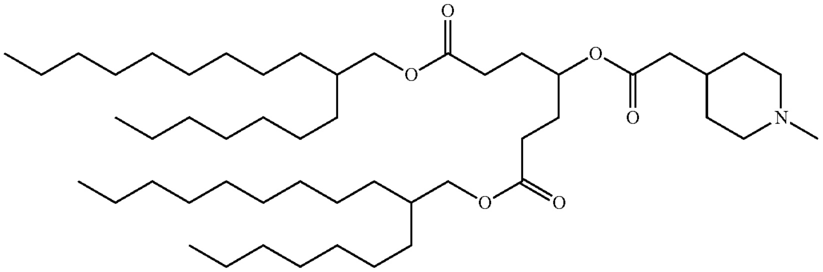
(E7)
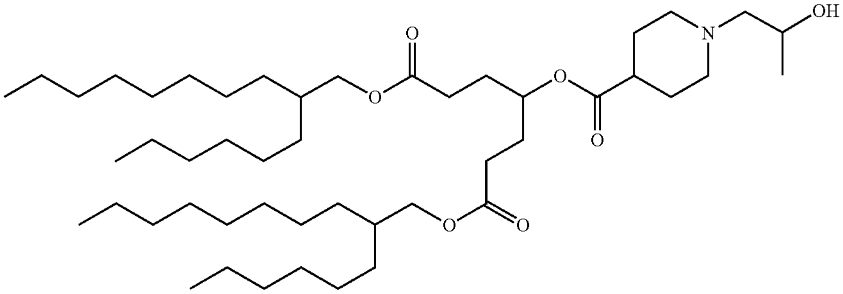
(E8)
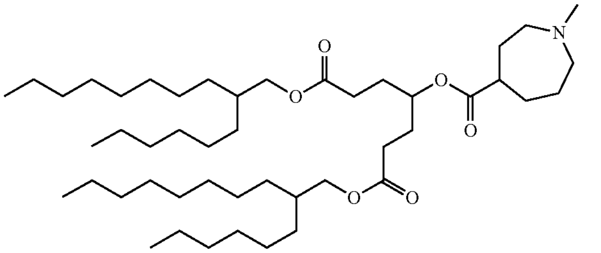
(E9)
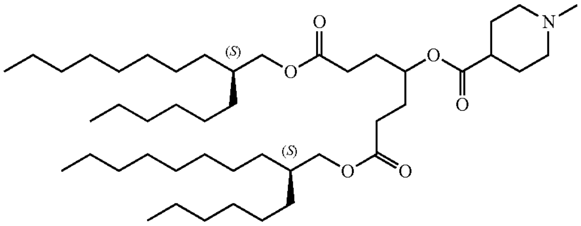
(E10)
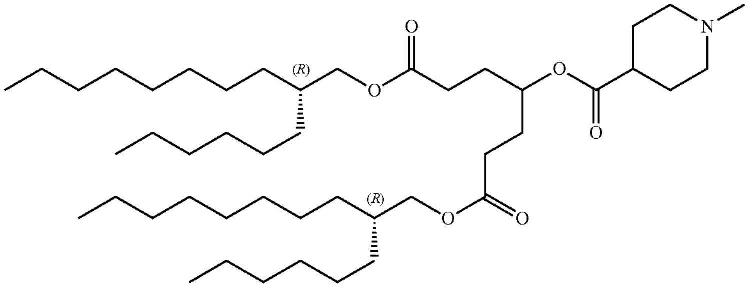
(E11)
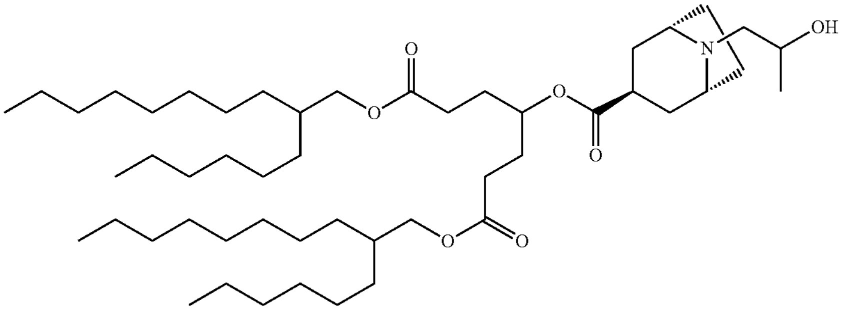

-continued
(E19)
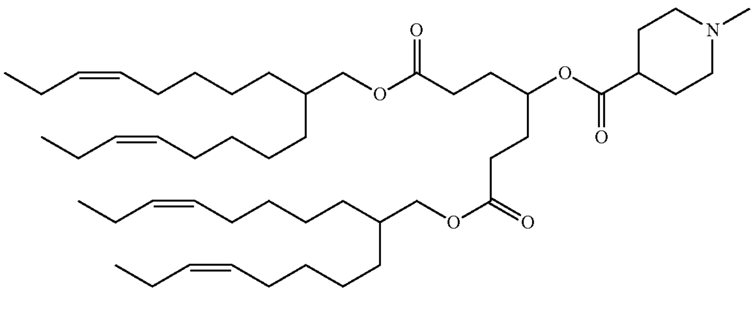
(E20)
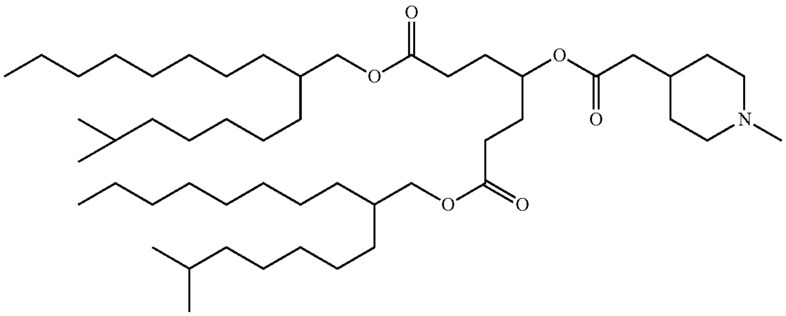
(E21)
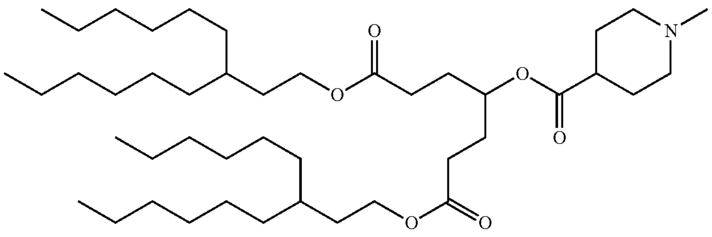
(E24)
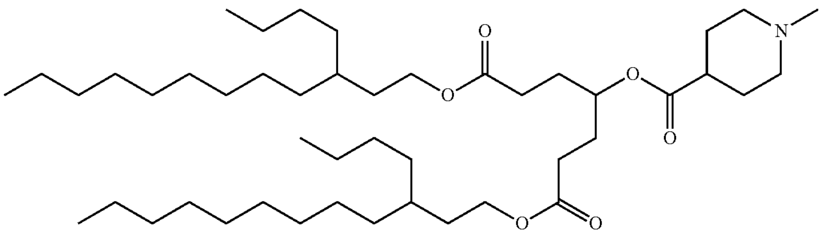
(E26)
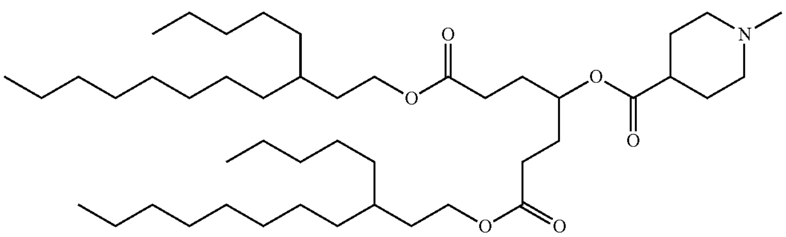
(E28)
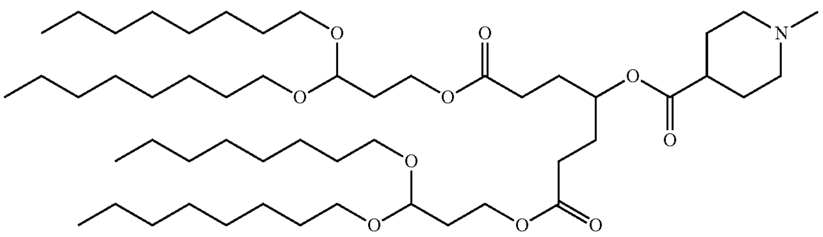

-continued (E30)

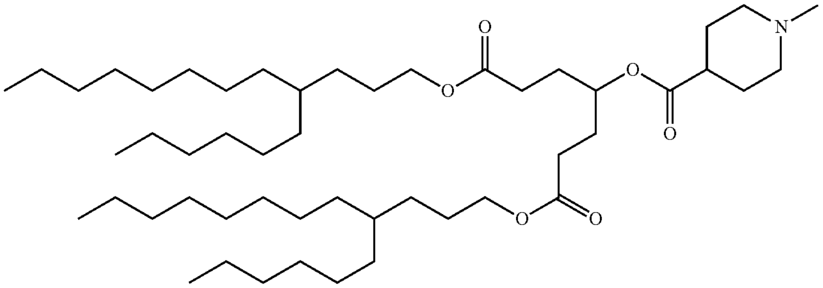

(E37)

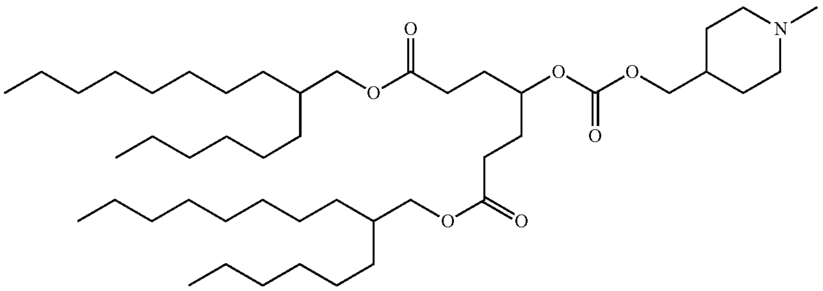

(E38)

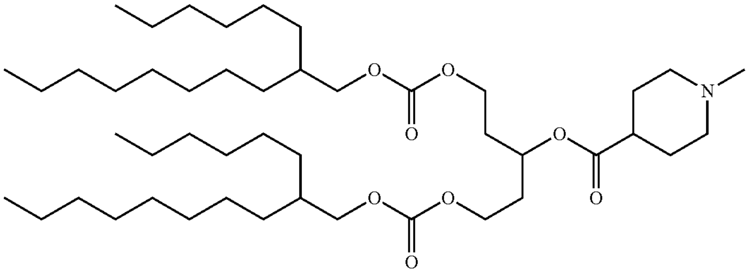

[10] The compound or pharmaceutically acceptable salt thereof according to any one of [1] to [4], wherein P is represented by the formula P-2, n represents 2 or 3, m represents 2 or 3, $X_1$ and $X_2$ are identical to each other, $R_1$ and $R_2$ are identical to each other, $R_6$ and $R_7$ each independently represent an alkyl group having 1 to 3 carbon atoms, and r represents an integer of 2 to 4.

[11] The compound or pharmaceutically acceptable salt thereof according to any one of [1] to [4] and [10], wherein P is represented by the formula P-2, n is 2, m is 2, $X_1$ and $X_2$ are —OC(O)—, $R_6$ and $R_7$ each independently represent an alkyl group having 1 to 3 carbon atoms, and r is 3.

[12] The compound or pharmaceutically acceptable salt thereof according to any one of [1] to [4], [10], and [11], wherein the compound is selected from the group consisting of the following compounds:

(E6)

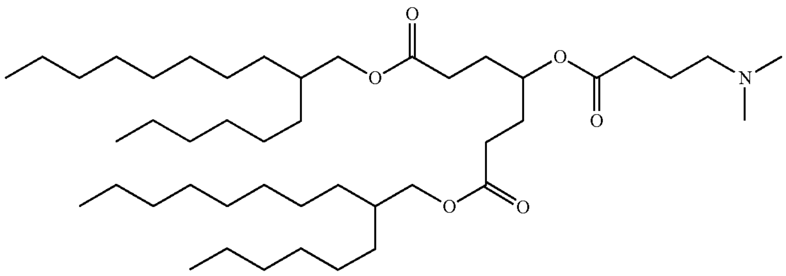

-continued
(E14)
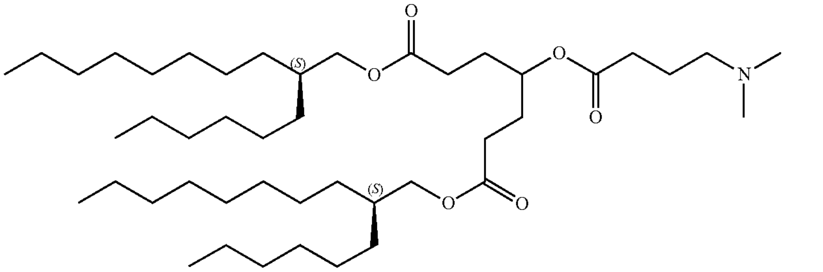
(E15)
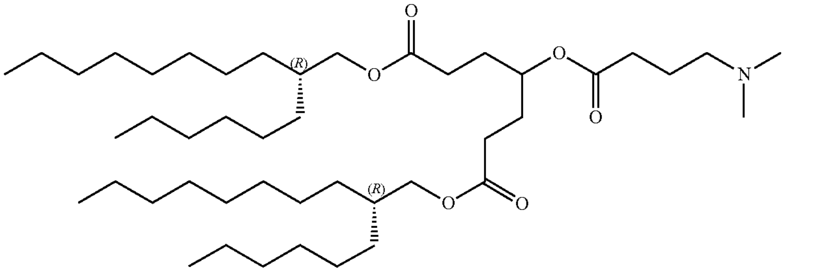
(E39)
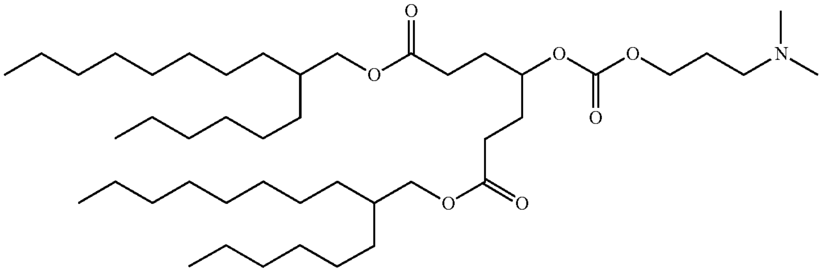
(E41)
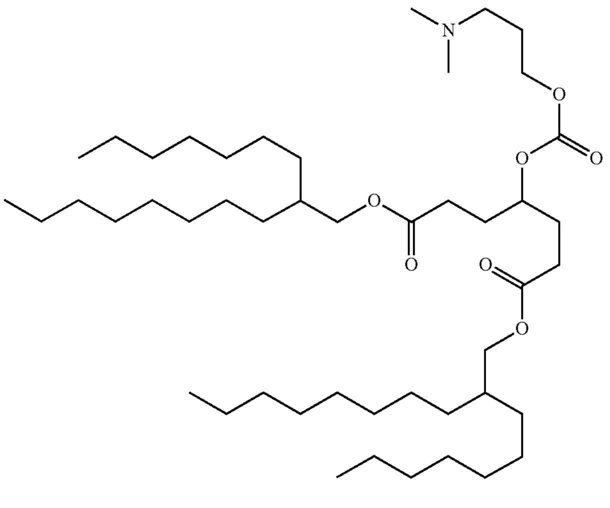

[13] The compound or pharmaceutically acceptable salt thereof according to any one of [1] to [4], [10], and [11] that is a compound represented by the following compound:

In the present specification, “alkyl” means linear, cyclic, or branched saturated aliphatic hydrocarbon groups having a specified number of carbon atoms.

(E6)

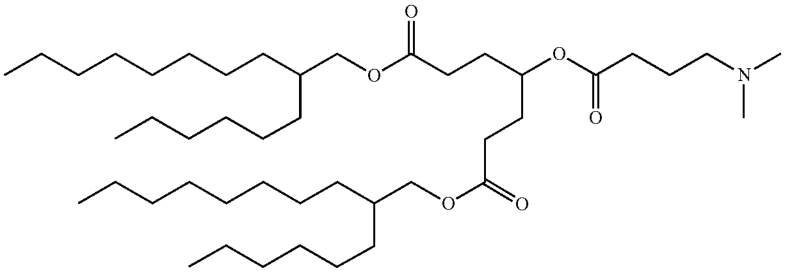

or a pharmaceutically acceptable salt thereof.

[14]A lipid complex comprising: (I) the compound or pharmaceutically acceptable salt thereof according to any one of [1] to [13]; and (II) at least one lipid selected from the group consisting of a neutral lipid, a polyethylene glycol-modified lipid, and a sterol.

[15]A composition comprising: (I) the compound or pharmaceutically acceptable salt thereof according to any one of [1] to [13]; (II) at least one lipid selected from the group consisting of a neutral lipid, a polyethylene glycol-modified lipid, and a sterol; and (III) a nucleic acid.

[16]A method for producing a composition, the method comprising: a step of mixing (I) the compound or pharmaceutically acceptable salt thereof according to any one of [1] to [13], a polar organic solvent-containing aqueous solution containing (II) at least one lipid selected from the group consisting of a neutral lipid, a polyethylene glycol-modified lipid, and a sterol, and an aqueous solution containing (III) a nucleic acid to obtain a liquid mixture; and a step of reducing a content of the polar organic solvent in the liquid mixture.

[17]A use of the compound or pharmaceutically acceptable salt thereof according to any one of [1] to [13], the lipid complex according to [14], or the composition according to [15] in the manufacture of a medicine.

Effects of Invention

The ionizable lipid of the present disclosure is capable of efficiently releasing a nucleic acid into cytoplasm. Therefore, the ionizable lipid of the present disclosure is available as a lipid for nucleic acid delivery into cytoplasm.

In addition, the ionizable lipid according to one aspect of the present disclosure is excellent in terms of retention of nucleic acid activity (storage stability of an active pharmaceutical ingredient).

DESCRIPTION OF EMBODIMENTS

Hereinafter, the present disclosure will be described in detail by showing embodiments, examples, and the like, but the present disclosure is not limited to the embodiments, examples, and the like shown below and can be implemented with any modification within a scope that does not depart from the gist of the present disclosure. All documents and publications mentioned in the present specification are incorporated herein by reference in their entirety regardless of the purpose thereof.

In the present specification, “alkoxy” refers to a group having the alkyl group bonding to an oxygen atom (O).

In the present specification, “alkenyl” means linear or branched hydrocarbon groups having a specified number of carbon atoms and at least one carbon-carbon double bond. Examples thereof include, but are not limited to, monoenes, dienes, trienes, tetraenes, and the like.

In the present specification, “alkylene” means linear, cyclic, or branched divalent saturated aliphatic hydrocarbon groups having a specified number of carbon atoms.

1. Ionizable Lipid

One aspect of the present disclosure is a compound represented by the following formula (I) or a pharmaceutically acceptable salt thereof, which can be used as an ionizable lipid. The ionizable lipid may be a hydrate of the salt or a solvate of the salt.

An asymmetric atom (for example, carbon or the like) in the compound of the present disclosure can be present in a form in which a racemic body or an enantiomer is concentrated, for example, an (R)-configuration, an (S)-configuration, or a mixture in which (R) and (S) are mixed in any proportions.

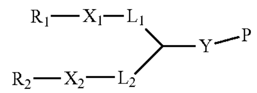

(I)

In the formula (I), P is represented by the following formula P-1 or formula P-2.

P-1

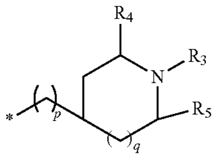

P-2

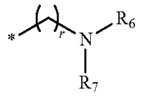

In the formula P-1, $R_3$ represents an alkyl group having 1 to 5 carbon atoms that is optionally substituted with a hydroxy group. $R_3$ is preferably an alkyl group having 1 to 3 carbon atoms that is optionally substituted with a hydroxy group. In several embodiments, $R_3$ is a methyl group. In several embodiments, $R_3$ is a propyl group substituted with a hydroxy group.

In the formula P-1, $R_4$ and $R_5$ each independently represent a hydrogen atom or an alkyl group having 1 to 5 carbon atoms, or $R_4$ and $R_5$ are taken together to form an alkylene group having 2 to 5 carbon atoms. $R_4$ and $R_5$ each independently preferably represent a hydrogen atom or are taken together to form an alkylene group having 2 to 3 carbon atoms. In several embodiments, $R_4$ and $R_5$ are hydrogen atoms. In several embodiments, $R_4$ and $R_5$ are taken together to form an ethylene group.

In the formula P-1, p represents 0 or 1. In several embodiments, p is 0. In several embodiments, p is 1.

In the formula P-1, q represents an integer of 0 to 2. q is preferably 1 or 2 and more preferably 1.

In the formula P-2, $R_6$ and $R_7$ each independently represent an alkyl group having 1 to 5 carbon atoms. $R_6$ and $R_7$ may be identical to or different from each other. In several embodiments, $R_6$ and $R_7$ are identical to each other. $R_6$ and $R_7$ are preferably alkyl groups having 1 to 3 carbon atoms and more preferably methyl groups.

In the formula P-2, r represents an integer of 1 to 5. r is preferably an integer of 2 to 4, more preferably an integer of 1 to 3, still more preferably 2 or 3, and particularly preferably 3.

In the formula P-1 and the formula P-2, * represents a linking site.

In several embodiments, P is a compound represented by the following formula P-1, and the ionizable lipid is a compound represented by the following formula (I-1) or a pharmaceutically acceptable salt thereof.

In several embodiments, P is a compound represented by the following formula P-2, and the ionizable lipid is a compound represented by the following formula (I-2) or a pharmaceutically acceptable salt thereof.

(I-1)

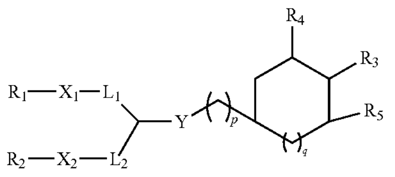

(I-2)

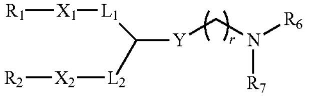

In the formula (I), the formula (I-1), and the formula (I-2), $L_1$ represents $-(CH_2)_n-$, and n represents an integer of 1 to 5. n is preferably 2 to 4 and more preferably 2 or 3 from the viewpoint of excellent nucleic acid release ability. In several embodiments, n is 2. In several embodiments, n is 3.

In the formula (I), the formula (I-1), and the formula (I-2), $L_2$ represents $-(CH_2)_m-$, and m represents an integer of 1 to 5. m is preferably 2 to 4 and more preferably 2 or 3 from the viewpoint of excellent nucleic acid release ability. In several embodiments, m is 2. In several embodiments, m is 3.

In the formula (I), the formula (I-1), and the formula (I-2), $L_1$ and $L_2$ can be identical to or different from each other. In several embodiments, $L_1$ and $L_2$ are identical to each other.

In the formula (I), the formula (I-1), and the formula (I-2), $X_1$ and $X_2$ each independently represent $-OC(O)-$ or $-OC(O)O-$. $X_1$ and $X_2$ may be identical to or different from each other. In several embodiments, $X_1$ and $X_2$ are identical to each other. In several embodiments, $X_1$ and $X_2$ are each independently $-OC(O)-$. In several embodiments, $X_1$ and $X_2$ are each independently $-OC(O)O-$.

In the formula (I), the formula (I-1), and the formula (I-2), Y represents $-OC(O)-$ or $-OC(O)O-$. In several embodiments, Y is $-OC(O)-$. In several embodiments, Y is $-OC(O)O-$.

In the formula (I), the formula (I-1), and the formula (I-2), $R_1$ and $R_2$ each independently represent an alkyl group having 2 to 25 carbon atoms or alkenyl group having 2 to 25 carbon atoms that is optionally substituted with one or more (preferably one or two) of alkoxy groups having 4 to 12 carbon atoms, and $R_1$ and $R_2$ each have a total of 4 to 30 carbon atoms. In the formula (I), the formula (I-1), and the formula (I-2), $R_1$ and $R_2$ may be identical to or different from each other.

In several embodiments, $R_1$ is represented by the following formula C-1, and $R_2$ is represented by the following formula C-1 or represents a linear alkyl group having 4 to 12 carbon atoms (preferably 6 to 10), a linear alkenyl group having 4 to 12 carbon atoms (preferably 6 to 10 carbon atoms), or a linear alkoxy group having 4 to 12 carbon atoms (preferably 6 to 10 carbon atoms).

C-1

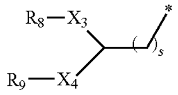

In the formula C-1, $X_3$ and $X_4$ each independently represent a single bond or $-O-$. $X_3$ and $X_4$ may be identical to or different from each other.

In the formula C-1, $R_8$ and $R_9$ each independently represent an alkyl group having 4 to 12 carbon atoms or an alkenyl group having 4 to 12 carbon atoms. $R_8$ and $R_9$ are preferably alkyl groups having 4 to 10 carbon atoms or alkenyl groups having 4 to 10 carbon atoms and more preferably alkyl groups or alkenyl groups having 6 to 8 carbon atoms.

In the formula C-1, s represents an integer of 1 to 4. s is preferably 1 or 2 and more preferably 1.

In the formula C-1, * represents a linking site.

In several embodiments, in the compound or the pharmaceutically acceptable salt thereof, P is represented by the formula (P-1), in the formula (I) and the formula (I-1), n represents 2 or 3, m represents 2 or 3, $X_1$ and $X_2$ are identical to each other, $R_1$ and $R_2$ are identical to each other and are preferably groups represented by the formula C-1 (the preferable aspects of the C-1 are as described above), $R_3$ represents an alkyl group having 1 to 4 carbon atoms that is optionally substituted with a hydroxy group (preferably an alkyl group having 1 to 3 carbon atoms that is optionally substituted with a hydroxy group, more preferably a methyl group or a propyl group substituted with a hydroxy group, and particularly preferably a methyl group), $R_4$ and $R_5$ each independently represent a hydrogen atom, or $R_4$ and $R_5$ are taken together to form an alkylene group having 2 or 3 carbon atoms, p represents 0 or 1, q represents 1 or 2. These may be hydrates of the salt or solvates of the salt.

In several embodiments, in the compound or the pharmaceutically acceptable salt thereof, P is represented by the formula (P-1), in the formula (I) and the formula (I-1), n represents 2 or 3, m represents 2 or 3, $X_1$ and $X_2$ are identical to each other, $R_1$ and $R_2$ are identical to each other and are preferably groups represented by the formula C-1 (the preferable aspects of the C-1 are as described above), $R_3$ represents a methyl group, $R_4$ and $R_5$ each independently represent a hydrogen atom, p represents 0 or 1, and q represents 1 or 2. These may be hydrates of the salt or solvates of the salt.

Hereinafter, examples of compounds of embodiments in which P is represented by the formula (P-1) will be shown. These compounds may be pharmaceutically acceptable salts thereof and can be used as ionizable lipids. The ionizable lipids may be hydrates of the salts or solvates of the salts.

(E1)

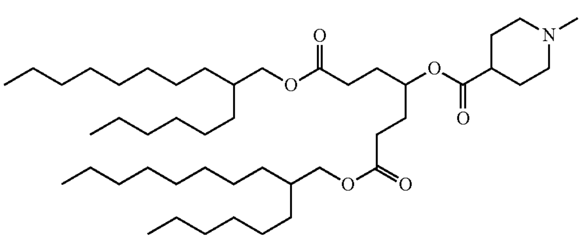

(E2)

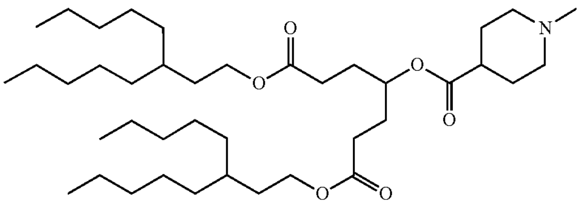

(E3)

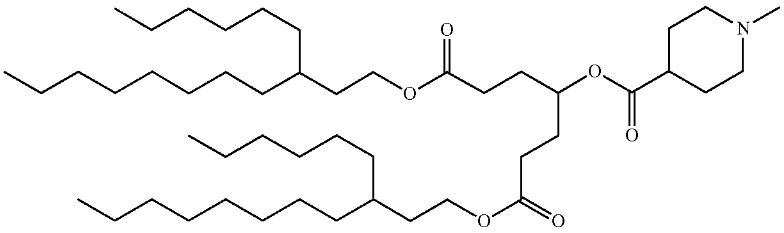

(E4)

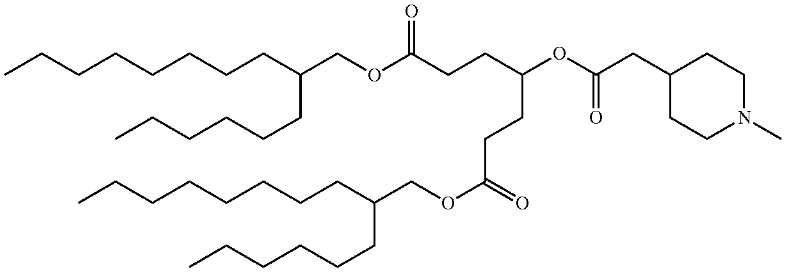

(E5)

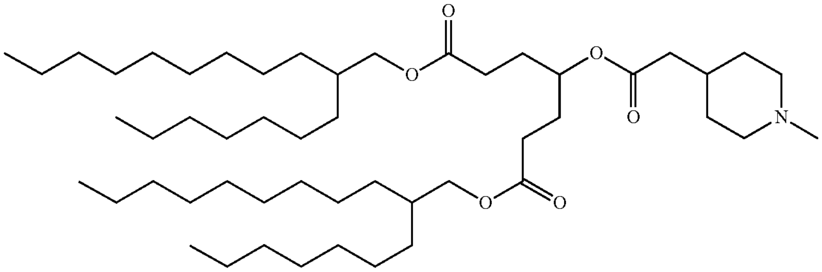

-continued
(E7)
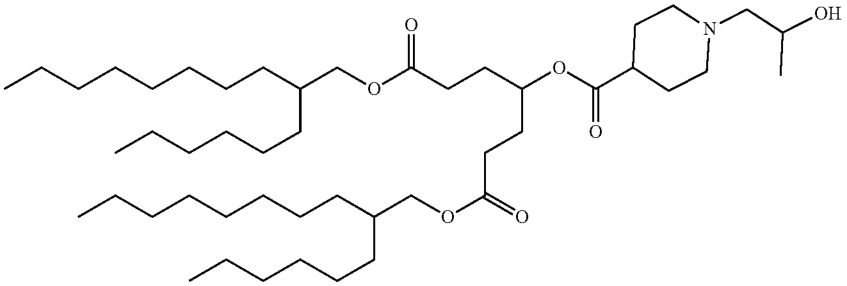
(E8)
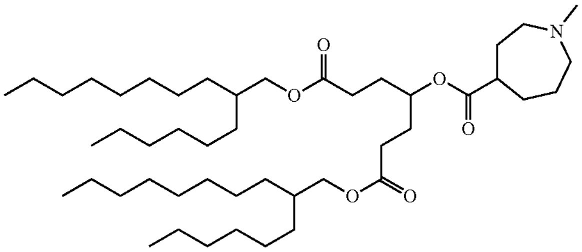
(E9)
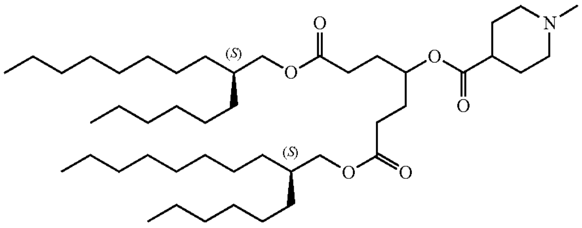
(E10)
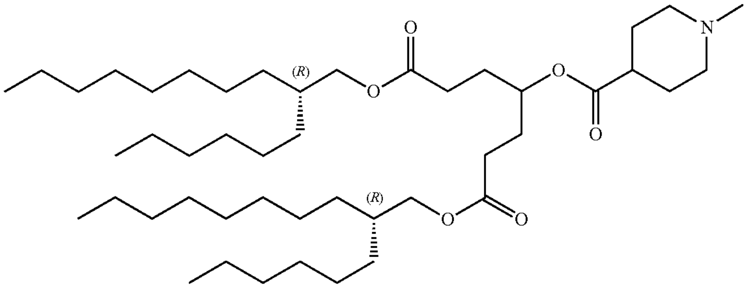
(E11)
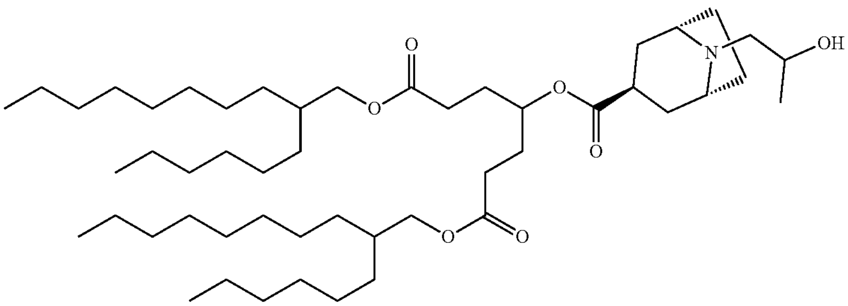
(E12)
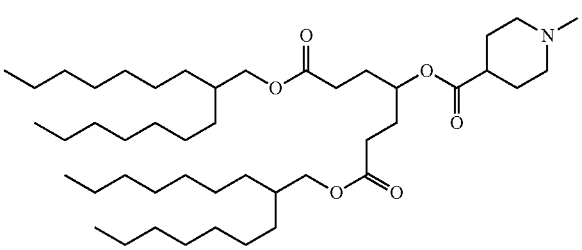
(E13)
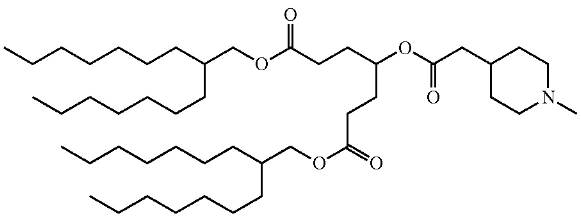

-continued
(E16)
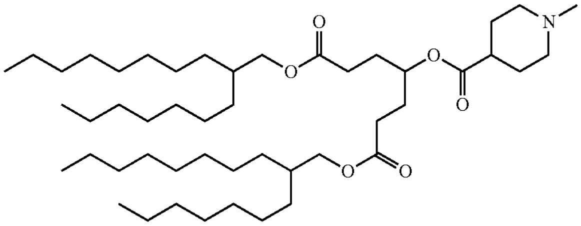
(E17)
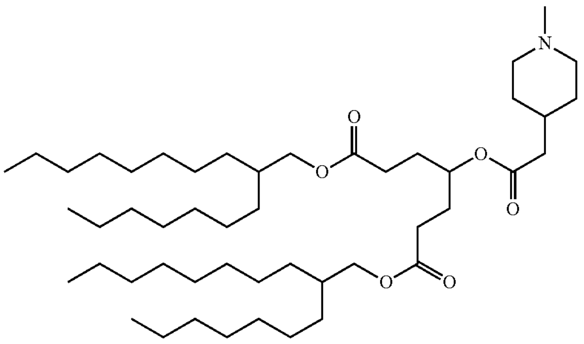
(E18)
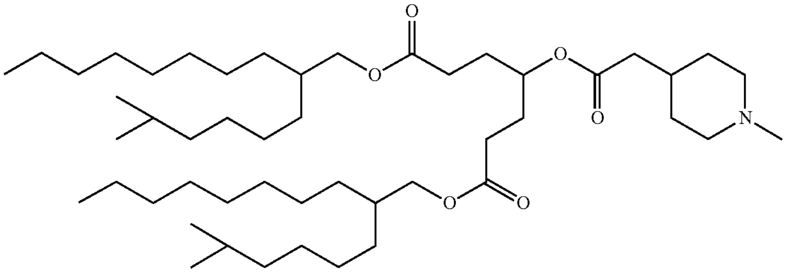
(E19)
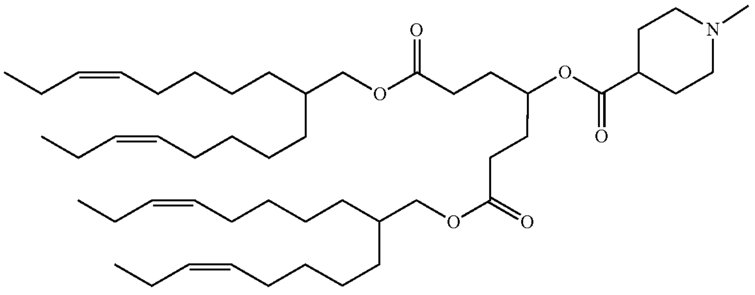
(E20)
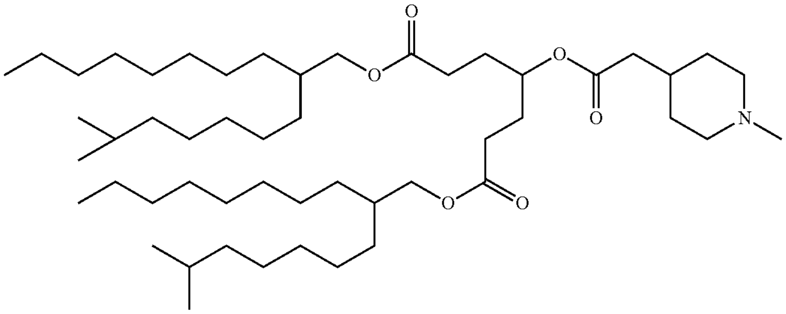
(E21)
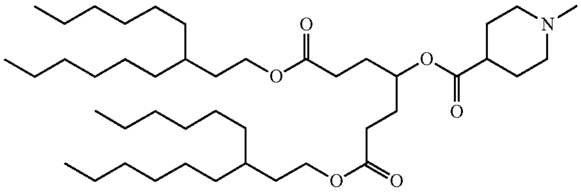
(E22)
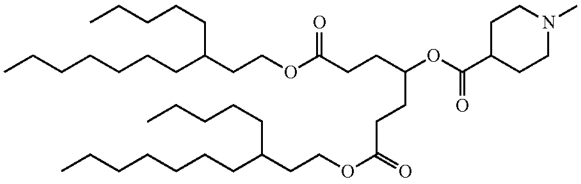

-continued
(E23)
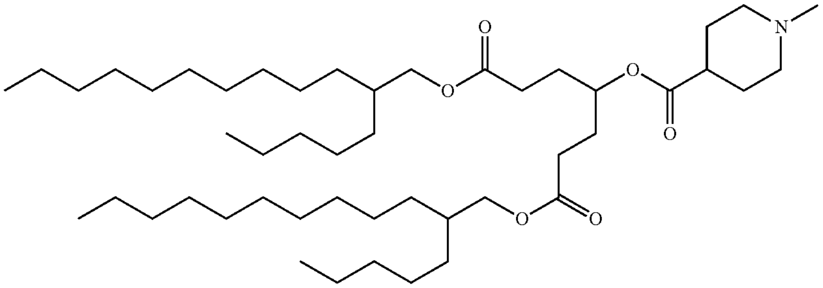
(E24)
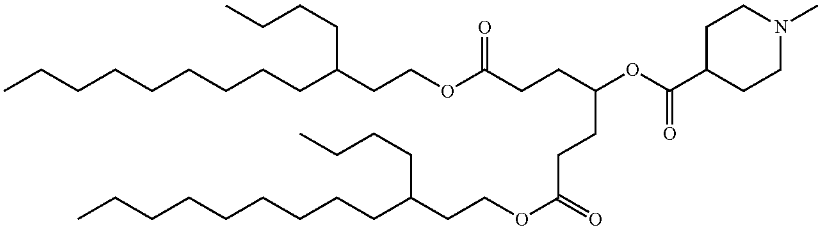
(E25)
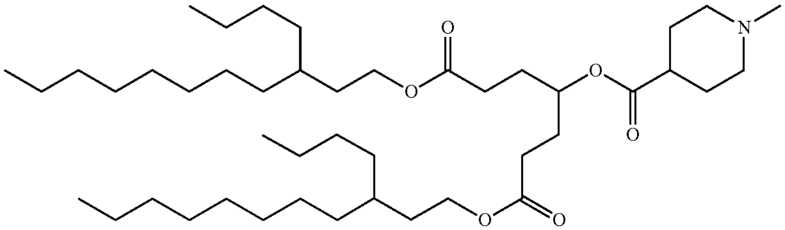
(E26)
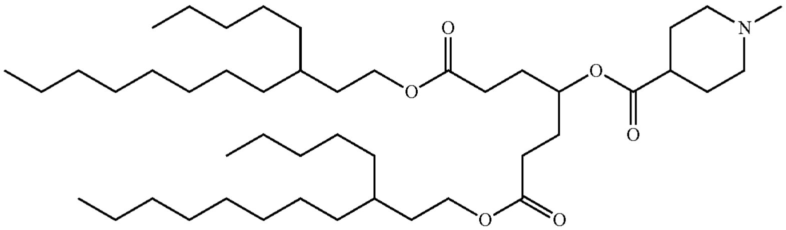
(E27)
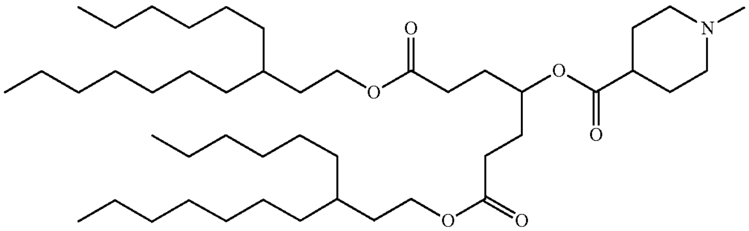
(E28)
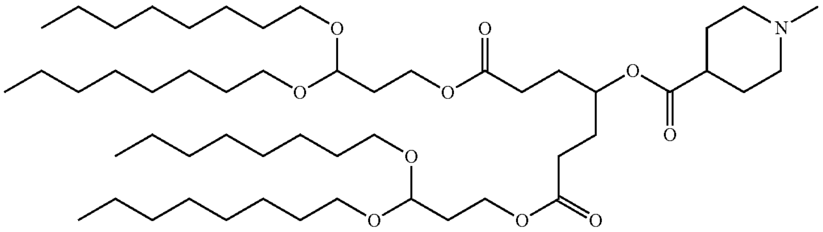

-continued
(E29)
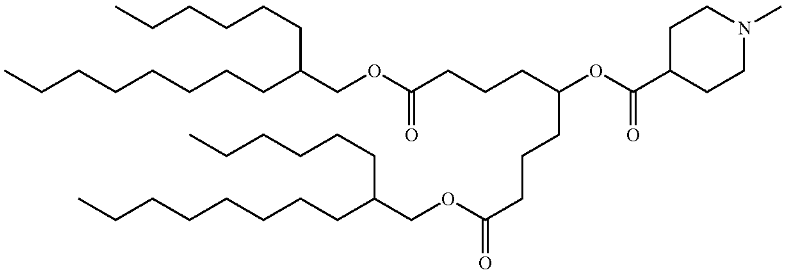
(E30)
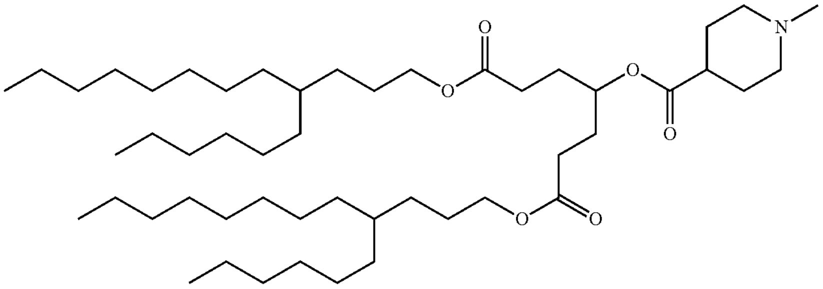
(E31)
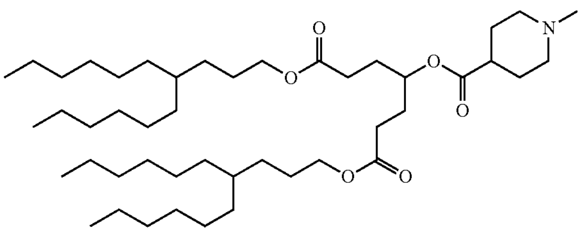
(E32)
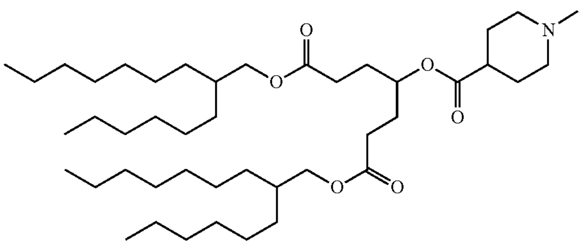
(E33)
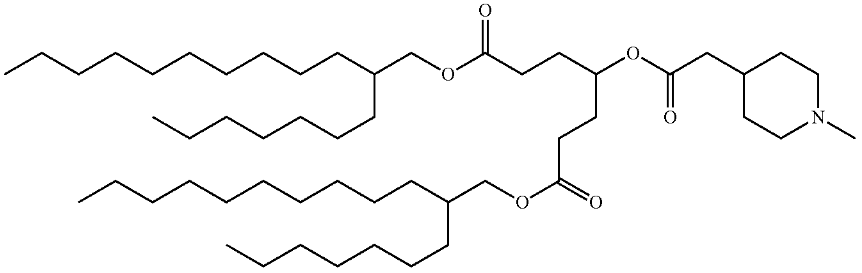
(E34)
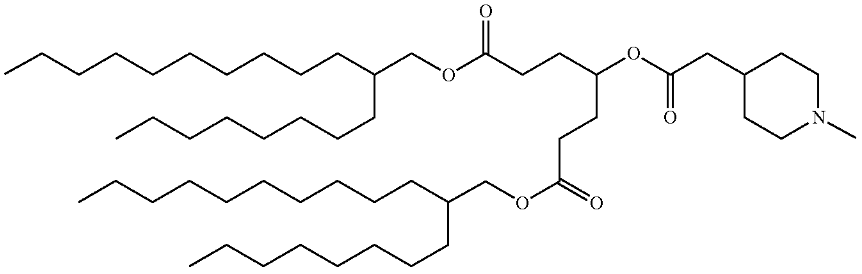

-continued
(E35)
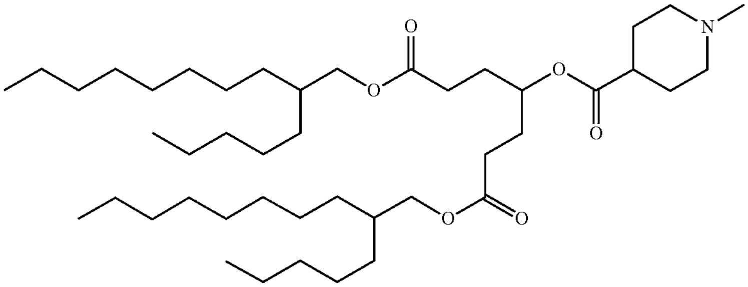
(E36)
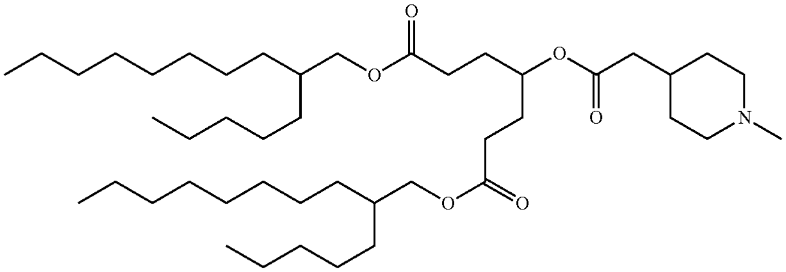
(E37)
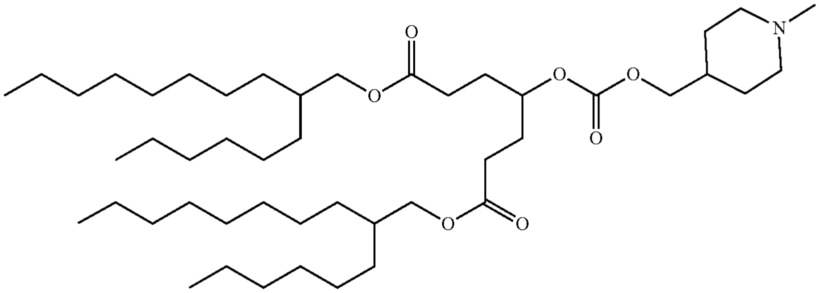
(E38)
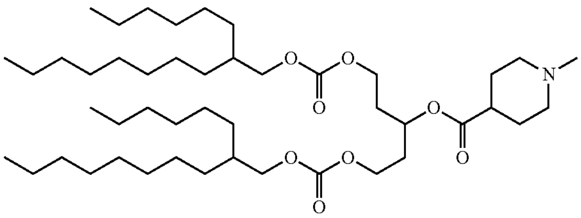
(E40)
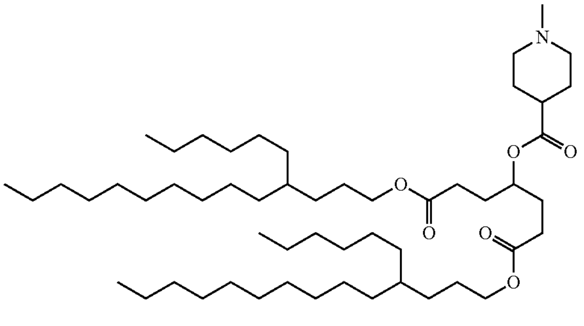
(E42)
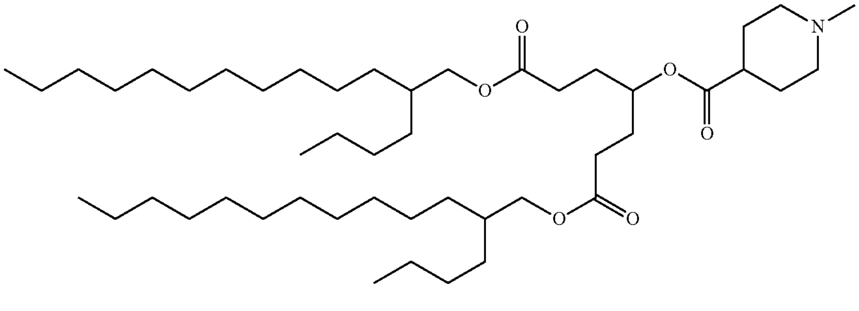

-continued
(E43)
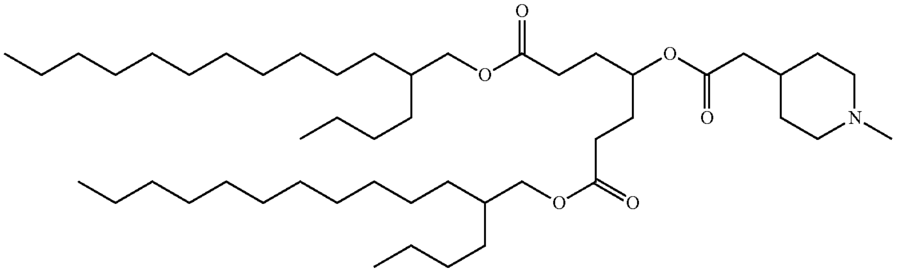
(E44)
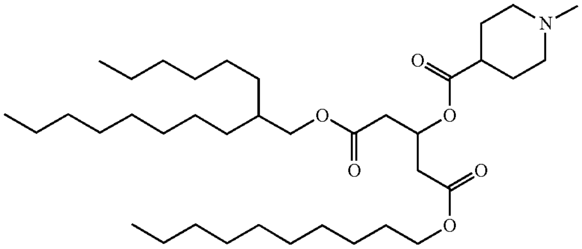
(E45)
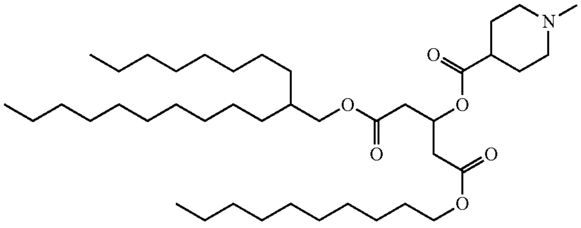
(E46)
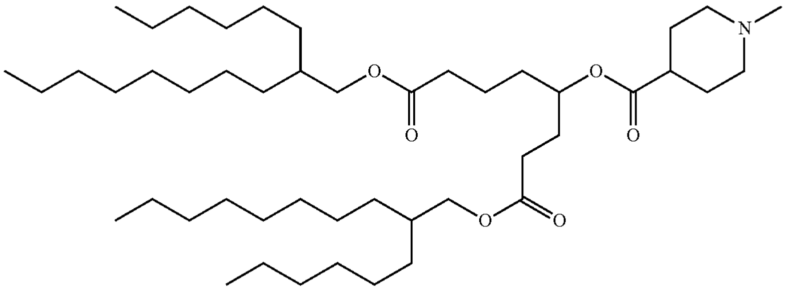
(E47)
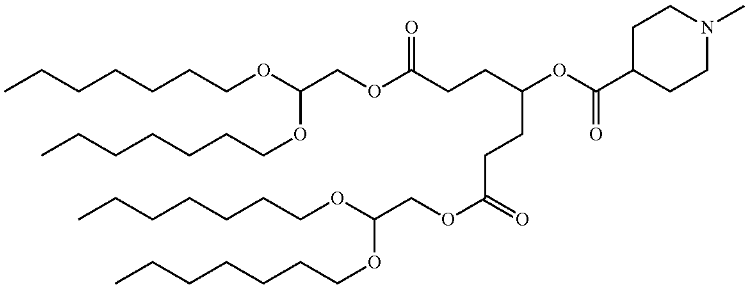
(E48)
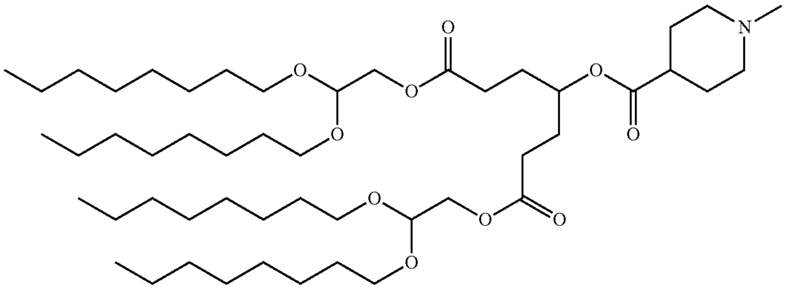

-continued
(E49)
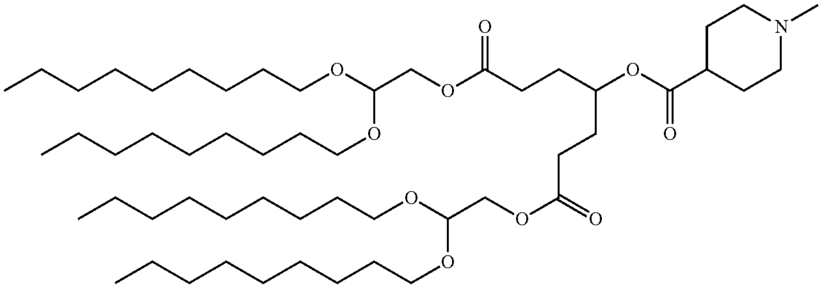
(E50)
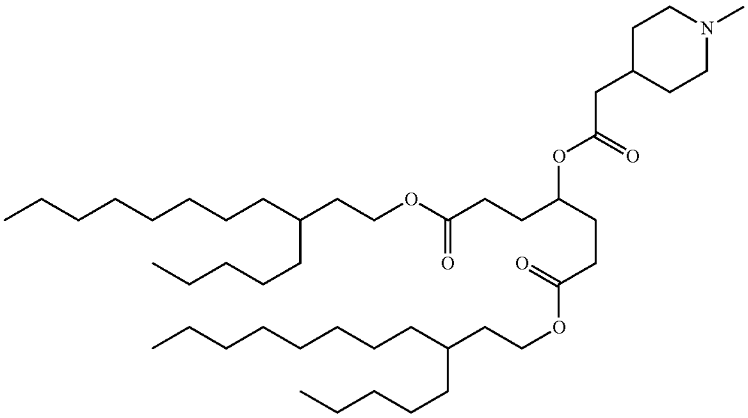
(E51)
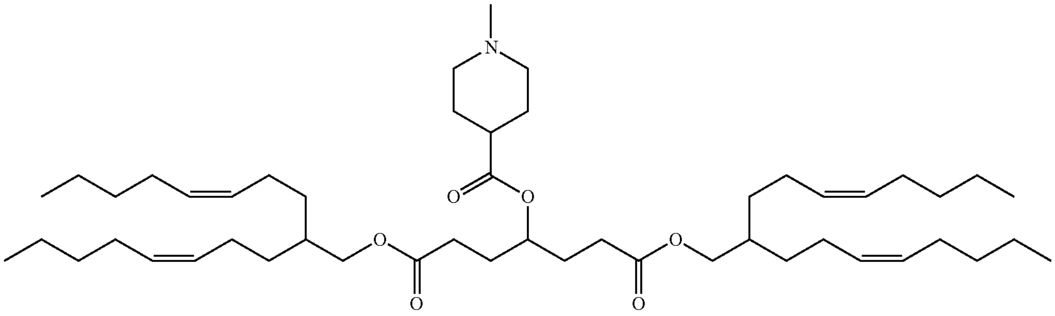
(E52)
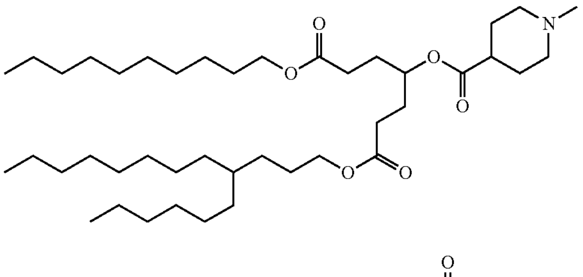
(E53)
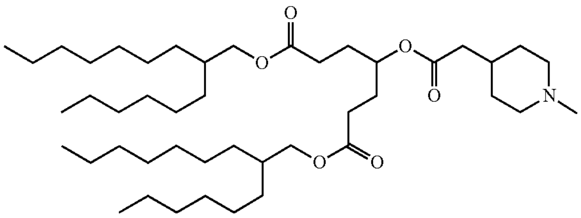
(E54)
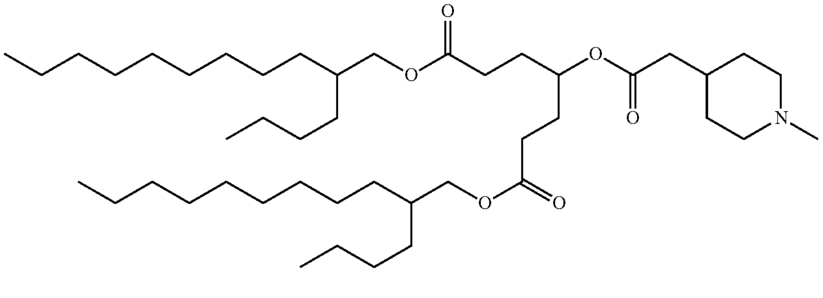

-continued (E55)

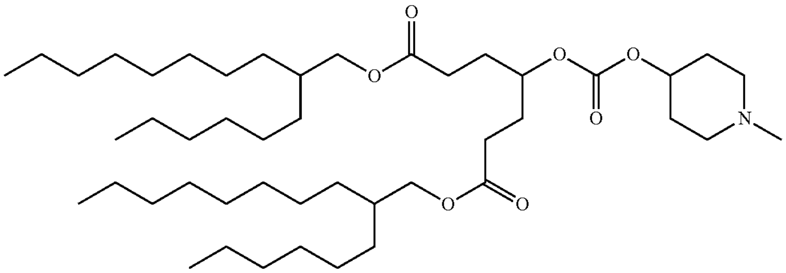

(E56)

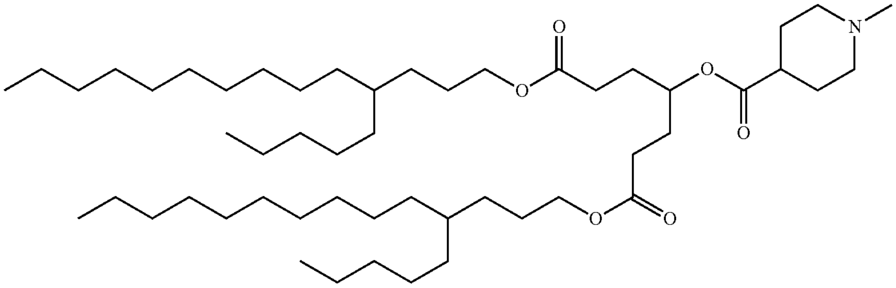

(E57)

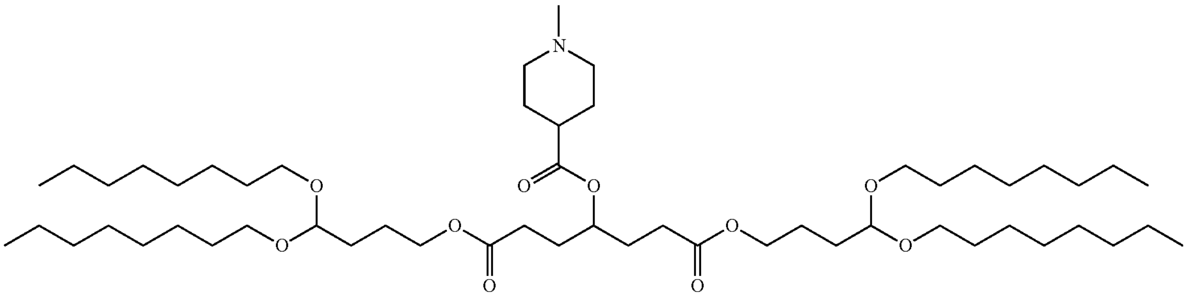

One embodiment of the present disclosure is a compound represented by any of the (E1), (E4), (E12), (E13), (E16), (E17), (E29), (E3), (E5), (E7), (E8), (E9), (E10), (E11), (E19), (E20), (E21), (E24), (E26), (E28), (E30), (E37), or (E38) or a pharmaceutically acceptable salt thereof and can be used as ionizable lipids. The ionizable lipids may be hydrates of the salts or solvates of the salts. These compounds are excellent in terms of nucleic acid release ability and retention of nucleic acid activity (storage stability of an active pharmaceutical ingredient).

One embodiment of the present disclosure is a compound represented by any of the (E1), (E4), (E12), (E13), (E16), (E17), or (E29) or a pharmaceutically acceptable salt thereof and can be used as ionizable lipids. The ionizable lipids may be hydrates of the salts or solvates of the salts. These compounds are excellent in terms of nucleic acid release ability and retention of nucleic acid activity (storage stability of an active pharmaceutical ingredient).

One embodiment of the present disclosure is a compound represented by any of the (E1), (E4), (E12), (E13), (E16), (E17), (E29), (E3), (E5), (E7), (E8), (E9), (E10), (E11), (E19), (E20), (E21), (E24), (E26), (E28), (E30), (E37), or (E38) or a pharmaceutically acceptable salt thereof and can be used as ionizable lipids. The ionizable lipids may be hydrates of the salts or solvates of the salts. These compounds are excellent in terms of nucleic acid release ability and retention of nucleic acid activity (storage stability of an active pharmaceutical ingredient).

One embodiment of the present disclosure is a compound represented by any of the (E1) or a pharmaceutically acceptable salt thereof and can be used as ionizable lipids. The ionizable lipids may be hydrates of the salts or solvates of the salts. These compounds are excellent in terms of nucleic acid release ability and retention of nucleic acid activity (storage stability of an active pharmaceutical ingredient).

One embodiment of the present disclosure is a compound represented by any of the (E1), (E2), (E4), (E5), (E8), (E9), (E10), (E11), (E12), (E13), (E16), (E17), (E18), (E19), (E20), (E21), (E22), (E24), (E26), (E27), (E28), (E29), (E30), (E31), (E32), (E33), (E34), (E35), (E36), (E37), (E38), (E40), (E43), (E45), (E46), (E47), (E49), (E50), (E53), (E54), (E55), (E56), or (E57) or a pharmaceutically acceptable salt thereof and can be used as ionizable lipids. The ionizable lipids may be hydrates of the salts or solvates of the salts. These compounds are excellent in terms of nucleic acid release ability.

One embodiment of the present disclosure is compounds represented by any of the (E1), (E2), (E4), (E8), (E9), (E10), (E11), (E12), (E16), (E17), (E18), (E19), (E20), (E21), (E22), (E24), (E26), (E27), (E28), (E29), (E30), (E31), (E32), (E33), (E34), (E35), (E36), (E37), (E38), (E43), (E46), (E47), (E49), (E53), (E54), (E55), (E56), or (E57) or pharmaceutically acceptable salts thereof and can be used as ionizable lipids. The ionizable lipids may be hydrates of the salts or solvates of the salts. These compounds are excellent in terms of nucleic acid release ability.

In several embodiments, in the compound or the pharmaceutically acceptable salt thereof, P is represented by the formula (P-2), in the formula (I) and the formula (I-2), n represents 2 or 3, m represents 2 or 3, $X_1$ and $X_2$ are identical to each other, $R_1$ and $R_2$ are identical to each other and are preferably group represented by the formula C-1 (the preferable aspects of the C-1 are as described above), $R_6$ and $R_7$ each independently represent an alkyl group having 1 to 3 carbon atoms (preferably a methyl group), and r represents an integer of 2 to 4 (more preferably an integer of 1 to 3, still more preferably 2 or 3, and particularly preferably 3). These may be hydrates of the salt or solvates of the salt.

In the embodiments, Y is —OC(O)— or —OC(O)O— and is preferably —OC(O)—.

In several embodiments, in the compound or the pharmaceutically acceptable salt thereof, P is represented by the formula (P-2), in the formula (I) and the formula (I-2), n is 2, m is 2, $X_1$ and $X_2$ are —OC(O)—, $R_1$ and $R_2$ are identical to each other and are preferably groups represented by the formula C-1 (the preferable aspects of the C-1 are as described above), $R_6$ and $R_7$ each independently represent an alkyl group having 1 to 3 carbon atoms (preferably a methyl group), and r is 3. These may be hydrates of the salt or solvates of the salt.

In the embodiments, Y is —OC(O)— or —OC(O)O— and is preferably —OC(O)—.

Hereinafter, examples of compounds of embodiments in which P is represented by the formula (P-2) will be shown. These compounds may be pharmaceutically acceptable salts thereof and can be used as ionizable lipids. The ionizable lipids may be hydrates of the salts or solvates of the salts.

(E6)

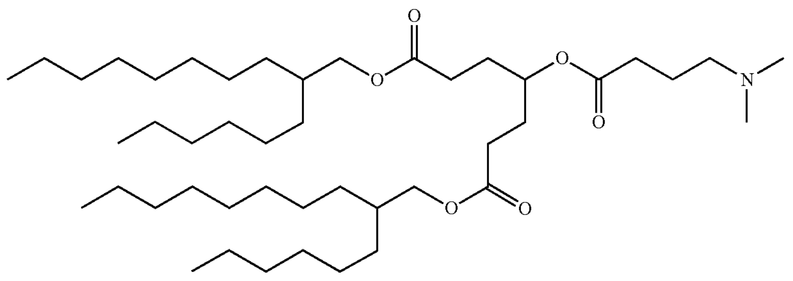

(E14)

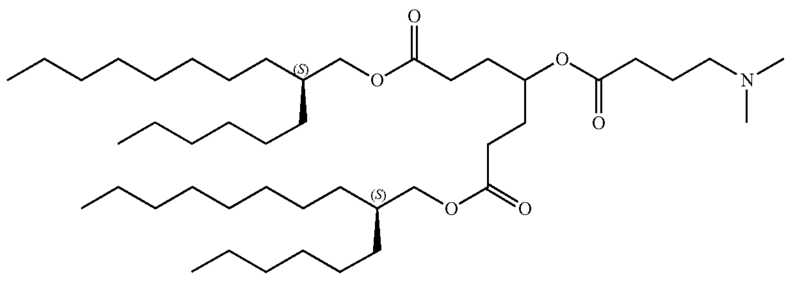

(E15)

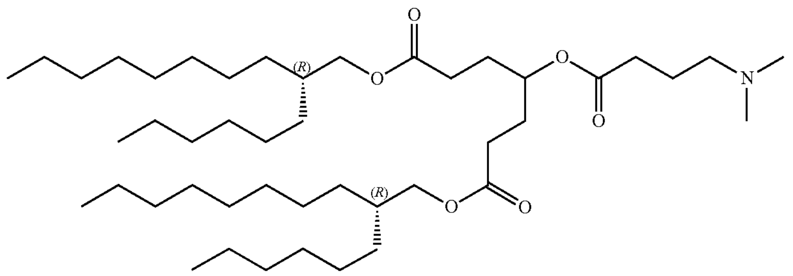

-continued (E39)

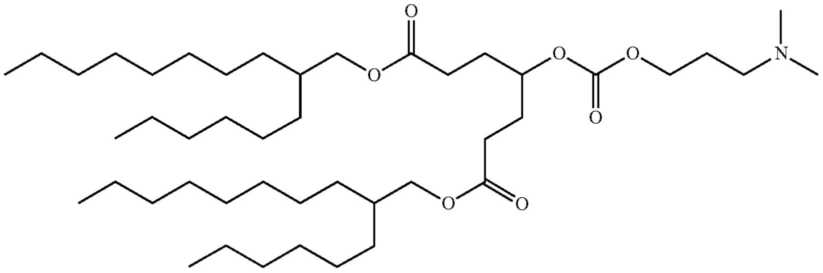

(E41)

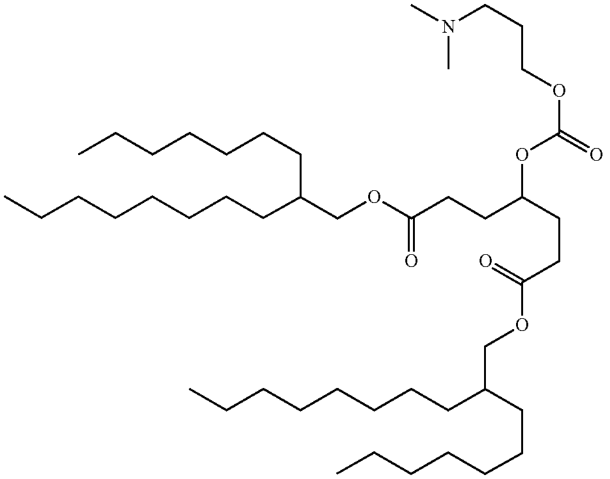

One embodiment of the present disclosure is a compound represented by the (E6) or a pharmaceutically acceptable salt thereof and can be used as an ionizable lipid. The ionizable lipid may be a hydrate of the salt or a solvate of the salt. The compound is excellent in terms of nucleic acid release ability and retention of nucleic acid activity (storage stability of an active pharmaceutical ingredient).

In the present specification, the ionizable lipid is an amphiphilic molecule having a lipid affinity region containing one or more hydrocarbon groups and a hydrophilic region containing a polar group that is neutral at physiological pH, but can be protonated in a low pH environment. That is, the ionizable lipid of the present disclosure is neutral at physiological pH, but can be protonated in a low pH environment (for example, a local low pH environment such as an endosome) to form a cation. For example, the compounds represented by the formulas (I-1) and (I-2) include compounds (cationic compounds) in which a hydrogen ion is coordinated to a lone pair on a nitrogen atom as shown in the following formulas (I-1)' and (I-2)'. The cationic compound is capable of forming salts indicated by the following formulae (I-1)' and (I-2)', and hydrates or solvates of the salts together with an anion.

(I-1)'

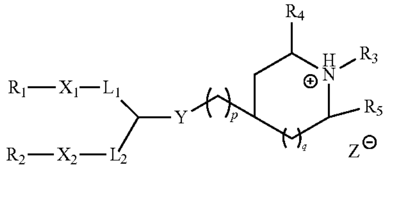

-continued (I-2)'

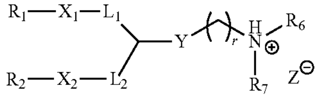

In the formulae (I-1)' and (I-2)', $L_1$ and $L_2$, $X_1$ and $X_2$, Y, $R_1$ to $R_7$, p, q and r are synonymous with the formulae (I-1) and (I-2). Z is an anion (counter ion). The compound of the present embodiment can be used as an ionizable lipid.

The anionic ion (Z in the formulas (I-1)' and (I-2)') that can be contained in the ionizable lipid of the present embodiment as a pair with the cationic compound is not particularly limited as long as the anionic ion is pharmaceutically acceptable, and examples thereof include inorganic ions such as chloride ions, bromide ions, nitrate ions, sulfate ions, and phosphate ions, organic acid ions such as acetate ions, oxalate ions, maleate ions, fumarate ions, citrate ions, benzoate ion, and methanesulfonate ion, and the like.

The ionizable lipid of the present disclosure can be present as a stereoisomer, such as a geometric isomer or an optical isomer, a tautomer, or the like, and the ionizable lipid of the present disclosure includes all possible isomers, including the above-described isomers, and mixtures thereof.

2. Method for Producing Ionizable Lipid

A method for producing an ionizable lipid of the present disclosure will be described. Hereinafter, one embodiment of a synthesis scheme of an ionizable lipid will be shown. All compounds described in the present specification are included in the present disclosure as compounds. The compound of the present disclosure can be synthesized according to at least one of the methods to be described in the following schemes. Since the ionizable lipid of the present disclosure may contain one or more asymmetric centers, synthesized compounds may be generated as (R)- or (S)-stereoisomers or mixtures thereof unless particularly otherwise described, the description of a specific compound in the present specification is intended to include both individual enantiomers and racemic mixtures thereof methods for the determination of stereochemistry and the separation of stereoisomers are well known to persons skilled in the art.

The ionizable lipid of the formula (I) can be synthesized, for example, as in the following schemes. Specifically, the ionizable lipid can be synthesized by, for example, a method in which an intermediate (a4) is obtained from an alcohol (a1) according to a scheme 1-1, a scheme 1-2, a scheme 1-3, or a scheme 1-4, and the compound of the formula (I) is obtained from the intermediate (a4) according to a scheme 2-1 or 2-2. Hereinafter, the following schemes will be described.

Scheme 1-1

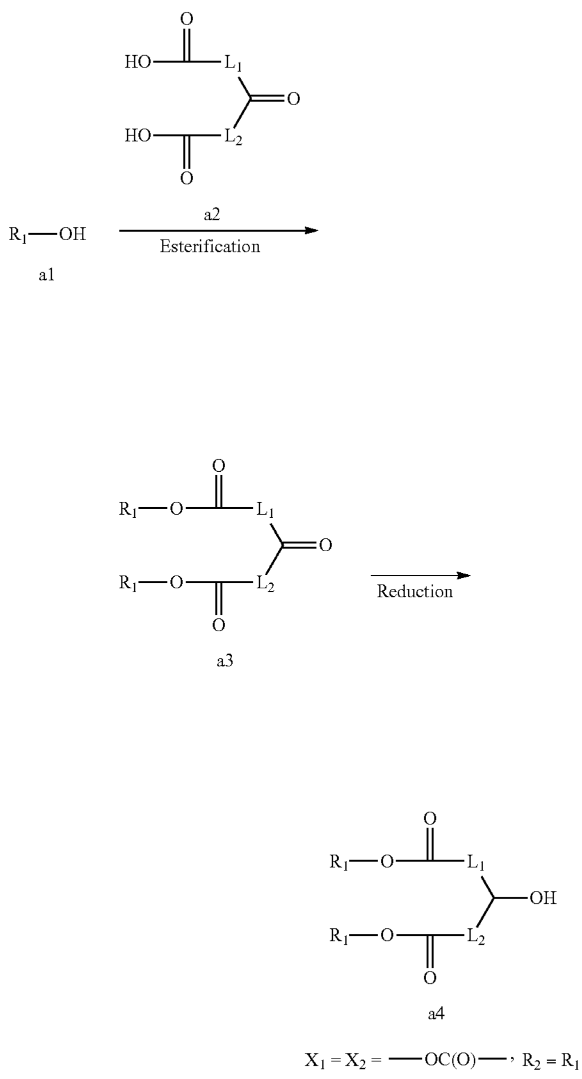

Scheme 1-2

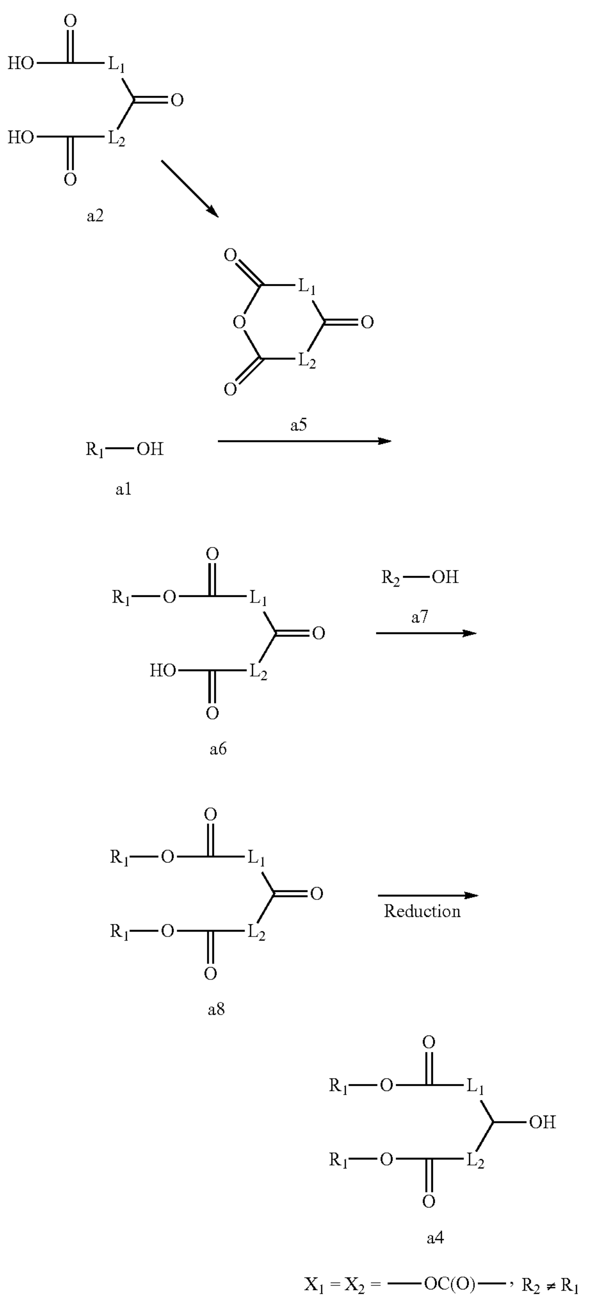

Scheme 1-3

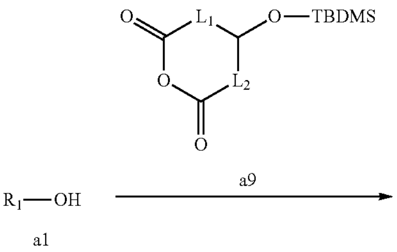

-continued

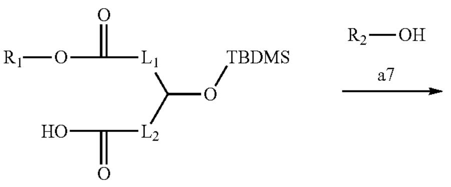

a10

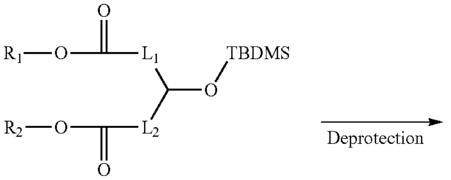

a11

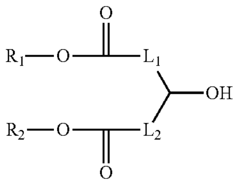

a4

$X_1 = X_2 =$ —OC(O)—, $R_2 \neq R_1$

Scheme 1-4

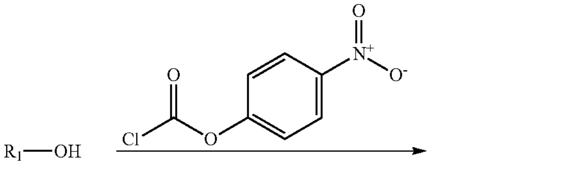

a1

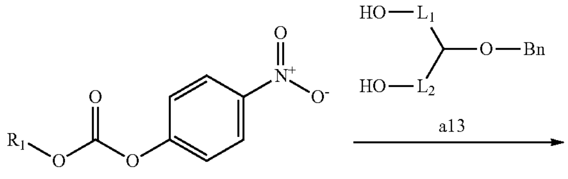

a12

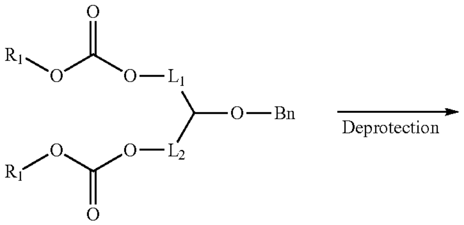

a14

-continued

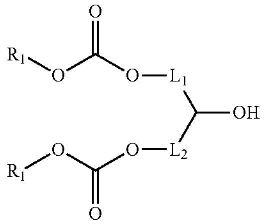

a4

$X_1 = X_2 =$ —OC(O)O—, $R_2 = R_1$

Scheme 2-1

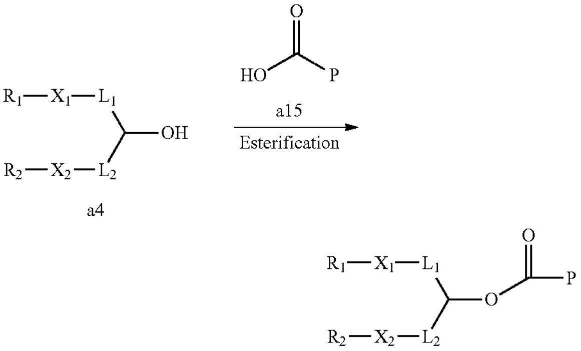

a4

(I)

Y = —OC(O)—

Scheme 2-2

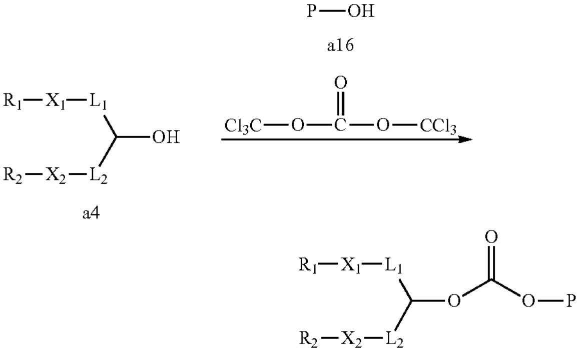

a4

Y = -OC(O)O—

(I)

In the schemes, $R_1$, $R_2$, $X_1$, $X_2$, $L_1$, $L_2$, and P are each synonymous with the formula (I). TBDMS indicates a tert-butyldimethylsilyl group, and Bn indicates a benzyl group.

[Scheme 1-1]

A scheme 1-1 is a reaction scheme by which an intermediate compound (a4) (diester alcohol) in a case where $X_1$ and $X_2$ are —OC(O)— and $R_1$ and $R_2$ are identical to each other is obtained from the alcohol (a1).

(Esterification)

First, the alcohol (a1) and an oxodicarboxylic acid (a2) are reacted in the presence of a condensing agent to obtain an oxodicarboxylic acid diester (a3). Examples of the condensing agent include 1-(bis(dimethylamino)methylene)-1H-1,2,3-triazolo(4,5-b)pyridinium 3-oxide hexafluorophosphate (HATU), 1-[3-(dimethylamino)propyl]-3-ethylcarbodiimide (EDC) hydrochloride, N,N'-dicyclohexylcarbodiimide (DCC), and the like. A base may be added, if necessary. Examples of the base include N-methylmorpholine (NMM), triethylamine (TEA), N,N-diisopropylethylamine (DIPEA), 4-(dimethylamino)pyridine (DMAP), pyridine, picoline, lutidine, and the like. Examples of a solvent include tetrahydrofuran (THF), methylene chloride, chloroform, toluene, hexane, ethyl acetate, N,N-dimethylformamide (DMF), and the like.

Commercially available products may be used as the alcohol (a1), and alcohols having a desired number of carbon atoms, a desired branched structure, a desired saturated structure, and/or a desired ether structure can be synthesized by, for example, production methods to be described in Examples below or appropriately modified methods thereof.

(Reduction)

Next, an oxo group (ketone) of the oxodicarboxylic acid diester (a3) is reduced to a hydroxyl group in the presence of a reducing agent to obtain a diester alcohol (a4). Examples of the reducing agent include sodium borohydride ($NaBH_4$) and the like. As the solvent, ethers such as diethyl ether, tetrahydrofuran, dioxane and methyl tert-butyl ether (MTBE), halogenated hydrocarbons such as chloroform, methylene chloride and dichloroethane, hydrocarbons such as hexane and toluene, and mixed solvents thereof, and the like can be used.

[Scheme 1-2]

A scheme 1-2 is a reaction scheme by which an intermediate compound (a4) (diester alcohol) in which $X_1$ and $X_2$ are —OC(O)— and $R_1$ and $R_2$ are different from each other is obtained from an alcohol (a1).

(Monoesterification)

First, the alcohol (a1) and an oxodicarboxylic anhydride (a5) are reacted by heating reflux to obtain an oxodicarboxylic acid monoester (a6). A base may be added, if necessary. Examples of the base include N-methylmorpholine (NMM), triethylamine (TEA), N,N-diisopropylethylamine (DIPEA), 4-(dimethylamino)pyridine (DMAP), pyridine, picoline, lutidine, and the like. Examples of a solvent include tetrahydrofuran (THF), methylene chloride, chloroform, toluene, hexane, ethyl acetate, N,N-dimethylformamide (DMF), and the like.

The oxodicarboxylic anhydride (a5) can be obtained by, for example, reacting the oxodicarboxylic acid (a2) in the presence of a dehydrating agent. The dehydrating agent is not particularly limited, and examples thereof include acetyl chloride, thionyl chloride, and the like.

(Esterification)

Next, an alcohol (a7) and the oxodicarboxylic acid monoester (a6) are reacted in the presence of a condensing agent to obtain an oxodicarboxylic acid diester (a7). Reaction conditions of the condensing agent, the base, and the like are similar to those in the (esterification) of the scheme 1-1.

(Reduction)

Next, an oxo group (ketone) of the oxodicarboxylic acid diester (a7) is reduced to a hydroxyl group in the presence of a reducing agent to obtain a diester alcohol (a4). Reaction conditions of the reducing agent, the solvent, and the like are similar to those in the (reduction) of the scheme 1-1.

[Scheme 1-3]

A scheme 1-3 is a reaction scheme by which an intermediate compound (a4) (diester alcohol) in which $X_1$ and $X_2$ are —OC(O)— and $R_1$ and $R_2$ are different from each other is obtained from the alcohol (a1).

(Monoesterification)

First, the alcohol (a1) and a dicarboxylic anhydride (a9) having a protecting group introduced into a hydroxy group are reacted by heating reflux to obtain a dicarboxylic acid monoester (a10). Examples of a solvent include tetrahydrofuran (THF), methylene chloride, chloroform, toluene, hexane, ethyl acetate, N,N-dimethylformamide (DMF), and the like. In the scheme 1-3, a tert-butyldimethylsilyl (TBDMS) group is used as a hydroxy protecting group in the compounds (a9) and (a10), but the protecting group is not limited to TBDMS, and hydroxy protecting groups that are conventionally well known to persons skilled in the art can be used.

(Esterification)

Next, an alcohol (a7) and the dicarboxylic acid monoester (a10) are reacted in the presence of a condensing agent to obtain a dicarboxylic acid diester (all). Reaction conditions of the condensing agent, the base, and the like are similar to those in the (esterification) of the scheme 1-1.

(Deprotection)

Subsequently, the hydroxy protecting group (TBDMS group) of the dicarboxylic acid diester (a1 1) is deprotected to obtain a diester alcohol (a4). Deprotection of the TBDMS group may be performed by, for example, making a fluoride salt such as tetra-n-butylammonium fluoride (TBAF) act in an organic solvent such as tetrahydrofuran.

[Scheme 1-4]

A scheme 1-4 is a reaction scheme by which an intermediate compound (a4) (dicarbonate alcohol) in which $X_1$ and $X_2$ are —OC(O)O— and $R_1$ and $R_2$ are identical to each other is obtained from the alcohol (a1).

(Carbonate Formation)

First, the alcohol (a1) and 4-nitrophenyl chloroformate are reacted in the presence of a base to obtain a nitrophenyl carbonate compound (a12). Examples of a solvent include tetrahydrofuran (THF), methylene chloride, chloroform, toluene, hexane, ethyl acetate, N,N-dimethylformamide (DMF), and the like. Examples of the base include N-methylmorpholine (NMM), triethylamine (TEA), N,N-diisopropylethylamine (DIPEA), 4-(dimethylamino)pyridine (DMAP), pyridine, picoline, lutidine, and the like.

Next, the nitrophenyl carbonate compound (a12) and a diol compound (a13) are reacted in the presence of a base to obtain a dicarbonate compound (a14). Reaction conditions of the base, the solvent, and the like are similar to those described above.

Alternatively, the carbonate may be formed by, similar to a method for (carbonate formation) in a scheme 2-2 to be described below, a method in which the alcohol (a1), the diol compound (a13), and phosgenes (for example, triphosgene) are reacted in the presence of a base.

(Deprotection)

Subsequently, a hydroxy protecting group (benzyl (Bn) group) of the dicarbonate compound (a14) is deprotected to obtain a dicarbonate alcohol (a4). Deprotection of the Bn group may be performed by, for example, a catalytic hydrogenation in the presence of a metal catalyst such as palladium/carbon.

In addition, in the present scheme 1-4, for example, in the case of producing a compound (a4) in which $R_1$ and $R_2$ are different from each other, it is possible to use, for example, a method in which, instead of the diol compound (a13), a compound in which one of the hydroxy groups of the diol compound (a13) has been protected with a protecting group is reacted with the nitrophenyl carbonate compound (a12) containing $R_1$ to form a carbonate, next, the protecting group is deprotected, and a carbonate formation reaction is then performed with the nitrophenyl carbonate compound (a12) containing $R_2$, which has been described regarding the method for producing the intermediate compound (a4) in which $R_1$ and $R_2$ are identical to each other.

[Scheme 2-1]

The scheme 2-1 is a reaction scheme by which a compound of the formula (I) in which Y is —OC(O)— is obtained from an intermediate (a4) (a diester alcohol or a dicarbonate alcohol).

(Esterification; Introduction of P)

An esterification reaction is performed between the intermediate (a4) (a diester alcohol or a dicarbonate alcohol) and P—COOH (carboxylic acid) or a derivative thereof (a halogen halide salt, an organic acid salt, or the like) (a15) in the presence of a condensing agent and a base to obtains a compound of the formula (I). As the condensing agent and the base, the same ones as those used in the (esterification) of the step 1-1 can be used.

[Scheme 2-2]

A scheme 2-2 is a reaction scheme by which a compound of the formula (I) in which Y is —OC(O)O— is obtained from an intermediate (a4) (a diester alcohol or a dicarbonate alcohol).

Introduction of P (Carbonate Formation)

The intermediate (a4) (a diester alcohol or a dicarbonate alcohol), P—OH (alcohol) or a derivative thereof (a16), and phosgenes (for example, triphosgene) are reacted in the presence of a base to obtain a compound of the formula (I), which is a final product. As the condensing agent and the base, the same ones as those used in the (esterification) of the step 1-1 can be used. Examples of a solvent include tetrahydrofuran (THF), methylene chloride, chloroform, toluene, hexane, ethyl acetate, N,N-dimethylformamide (DMF), and the like. Examples of the base include N-methylmorpholine (NMM), triethylamine (TEA), N,N-diisopropylethylamine (DIPEA), 4-(dimethylamino)pyridine (DMAP), pyridine, picoline, lutidine, and the like.

A method for carbonate formation is not limited to the above-described method, and for example, a reaction may be performed using a chloroformate derivative such as 4-nitrophenyl chloroformate as in the scheme 1-4.

In the schemes 2-1 and 2-2, it is possible to control the configuration of P in the compound of the formula (I) using a raw material having a controlled configuration (for example, the configuration of a carbon atom at the position 3 in a pyrrolidine ring) as P—COOH (carboxylic acid) or a derivative thereof (a15) or P—OH (alcohol) or a derivative thereof (a16).

In addition, it is possible to control the configuration of $R_1$ and $R_2$ using a raw material having a controlled configuration as the alcohols ($R_1$—OH and $R_2$—OH) used in the schemes 1-1 to 1-4.

In addition, after the introduction of P in the schemes 2-1 and 2-2, P may be modified (by, for example, the introduction of an alkyl group substituted with a hydroxy group).

In the schemes 1-1 to 1-4 and the scheme 2-1 and 2-2, P is introduced after the introduction of $R_1$ and $R_2$, but the ionizable lipid of the present disclosure may be synthesized by, for example, a method in which P is first introduced and $R_1$ and $R_2$ are then introduced as shown in the scheme 3.

Scheme 3

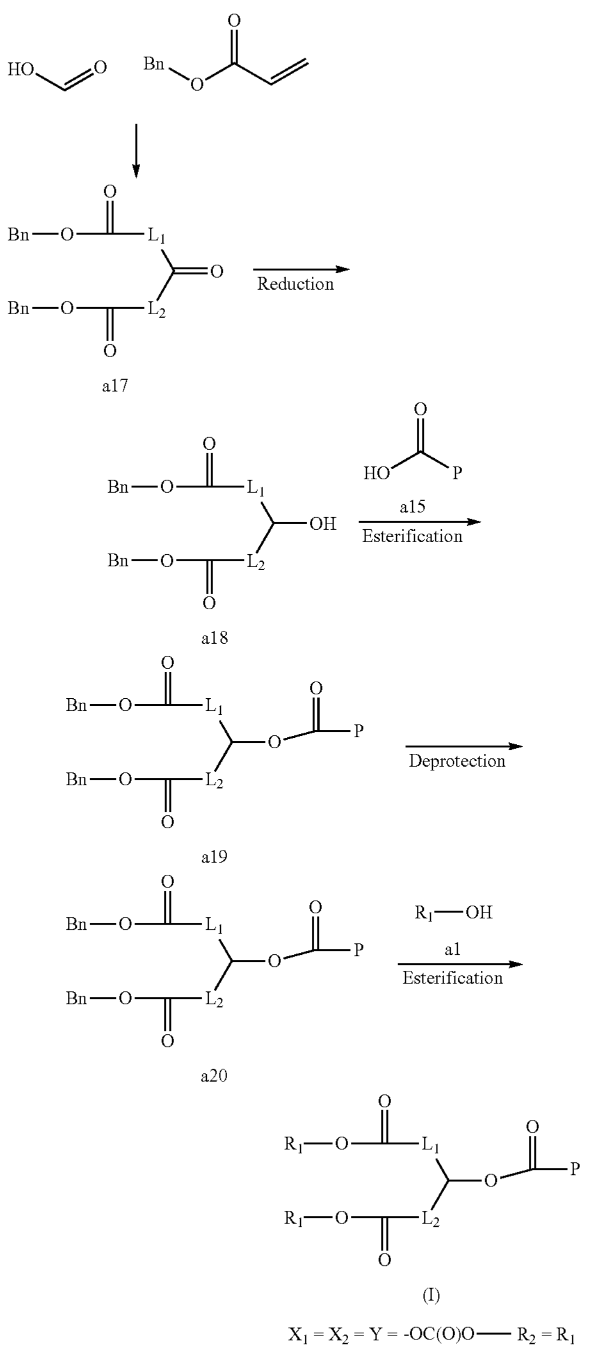

In the scheme, $R_1$, $R_2$, $L_1$, $L_2$, and P are each synonymous with the formula (I). Bn represents a benzyl group.

[Scheme 3]

A scheme 3 is a reaction scheme by which a compound of the formula (I) in which $X_1$ and $X_2$ are —OC(O)— and $R_1$ and $R_2$ are identical to each other is obtained from an oxodicarboxylic acid compound (a17) in which a carboxyl group has been protected.

The compound (a17) may be obtained by reacting formic acid and benzyl acrylate as in Example 9-1 to be described below or may be obtained by protecting the carboxyl group of the oxodicarboxylic acid (a2) with a protecting group (for example, Bn).

(Reduction)

First, an oxo group (ketone) of the compound (a17) is reduced to a hydroxyl group in the presence of a reducing agent to obtain an alcohol (a18). Reaction conditions of the reducing agent, a solvent, and the like are similar to those in the (reduction) of the scheme 1-1.

(Esterification: Introduction of P)

Next, an esterification reaction is performed between the alcohol (a18) and P—COOH (carboxylic acid) or a derivative thereof (a halogen halide salt or the like) (a15) in the presence of a condensing agent and a base to obtain an ester (a19). As the condensing agent and the base, the same ones as those used in the (esterification) of the step 1-1 can be used.

(Deprotection)

Subsequently, a carboxyl protecting group (benzyl (Bn) group) of the ester (a19) is deprotected to obtain an ester diol (a20). Deprotection of the Bn group may be performed by, for example, a catalytic hydrogenation in the presence of a metal catalyst such as palladium/carbon.

(Esterification: Introduction of $R_1$ and $R_2$)

Subsequently, the alcohol (a1) and the ester diol (a20) are reacted in the presence of a condensing agent to obtain a compound of the formula (I). As the condensing agent and the base, the same ones as those used in the (esterification) of the step 1-1 can be used.

In the synthesis of the compound of the present disclosure, unless the production of starting materials is described, the compounds are well known or can be produced by an analogous method well known in the art or as described in the Examples below. Persons skilled in the art can understand that the above-described schemes are simply representative methods for preparing the compound of the present disclosure and other well-known methods can also be used in the same manner.

For example, methods and intermediate compounds described in the prior art documents including WO 2015/105131, WO 2016/104580, WO 2017/222016, and WO 2019/131580 can be used to synthesize the compound of the present disclosure.

In the synthesis of the compound of the present disclosure, it may be necessary and/or desirable to protect a functional group of a molecule. The functional group can be protected with a conventional protecting group well known to persons skilled in the art. The protecting group can be removed at a convenient stage in the future using a method well known in the art. The protecting groups (the benzyl (Bn) protecting group and the tert-butyldimethylsilyl (TBDMS) protecting group) shown in the above-described schemes can also be substituted with other protecting groups well known to persons skilled in the art.

The compound according to the present disclosure may have crystal polymorphism, which is not limited to any, and the compound may be a single substance or mixture of any crystalline form. The compound according to the present disclosure also includes an amorphous form, and the compound according to the present disclosure includes an anhydride and a solvate (particularly a hydrate).

The term "pharmaceutically acceptable salt" in the present specification is not particularly limited as long as the salt is one that forms a salt with the compound according to the present disclosure, and specific examples thereof include acid addition salts such as inorganic acid salts, organic acid salts, or acidic amino acid salts.

In the "pharmaceutically acceptable salt" in the present specification, unless particularly otherwise described, the number of molecules of an acid with respect to one molecule of the compound in a formed salt is not particularly limited as long as the salt and the compound form the salt in an appropriate ratio, but about 0.5 to about 2 molecules of the acid is preferable per molecule of the compound, and about 0.5, about one, or about two molecules of the acid is more preferable per molecule of the compound.

Preferable examples of the inorganic acid salts include, for example, hydrochlorides, hydrobromides, sulfates, nitrates, phosphates, and the like, and preferable examples of the organic acid salts include, for example, acetates, succinates, fumarates, maleates, tartrates, citrates, lactates, stearates, benzoates, methanesulfonates, p-toluenesulfonates, benzene sulfonates, and the like.

Preferable examples of the acidic amino acid salts include, for example, aspartates, glutamates, and the like.

In a case where the compound according to the present disclosure is obtained as a free body, the compound can be converted to a state of a salt that the compound may form or a hydrate thereof according to a normal method.

In a case where the compound according to the present disclosure is obtained as a salt of the compound or a hydrate of the compound, the compound can be converted to a free body of the compound according to a normal method.

In addition, various isomers (for example, optical isomers, rotamers, stereoisomers, and the like) that can be obtained for the compound according to the present disclosure can be purified and isolated using usual separation means, for example, recrystallization, a diastereomeric salt method, enzymatic resolution, and various chromatography (for example, thin layer chromatography, column chromatography, gas chromatography, and the like).

3. Lipid Complex

One aspect of the present disclosure provides a lipid complex containing (I) the above-described ionizable lipid and (II) at least one lipid selected from the group consisting of a neutral lipid, a polyethylene glycol-modified lipid, and a sterol. In one embodiment of the present disclosure, the lipid complex contains (I) the above-described ionizable lipid, (II) at least one lipid selected from the group consisting of a neutral lipid, a polyethylene glycol-modified lipid, and a sterol, and (III) a nucleic acid. Therefore, the lipid complex of the present disclosure may or may not contain a nucleic acid. The lipid complex of the present embodiment enables efficient release of a nucleic acid into cytoplasm. In addition, the lipid complex of the present embodiment is excellent in terms of retention of nucleic acid activity (storage stability of an active pharmaceutical ingredient). In addition, the lipid complex of the present embodiment is capable of curbing an increase in particle size in the case of being stored for a certain period of time (for example, one month, 1.5 months, or three months) and of exhibiting excellent physical stability.

Examples of the form of the complex that is formed of a lipid containing an ionizable lipid and a nucleic acid include a complex of a nucleic acid and a membrane (reverse micelle) composed of a lipid monolayer of (single molecule), a complex of a nucleic acid and liposome, a complex of a nucleic acid and a micelle, and the like.

In several embodiments, the lipid complex has a structure in which the nucleic acid is encapsulated in a lipid containing an ionizable lipid.

In several embodiments, the lipid complex is a lipid particle. The lipid particle has a structure in which the nucleic acid is encapsulated in a particle composed of a lipid.

In several embodiments, the lipid complex is a lipid nanoparticle (LNP). The LNP has a structure in which the nucleic acid is encapsulated in particles comprised of lipids and having a nano-sized average particle size (for example, about 1 nm to 1000 nm).

(Nucleic Acid)

Examples of the nucleic acid include siRNA, miRNA, shRNA expression vectors, antisense oligonucleotides, mRNA, ribozyme, and the like. In one embodiment, the nucleic acid may be siRNA, miRNA, or mRNA.

(Lipid Components)

The lipid complex of the present embodiment contains, as lipid components, (I) the above-described ionizable lipid and (II) at least one lipid selected from the group consisting of a neutral lipid, a polyethylene glycol-modified lipid, and a sterol.

The neutral lipid means a lipid present in any form of a non-charged or neutral zwitterion at physiological pH. The neutral lipid is not particularly limited, and examples thereof include phospholipids such as dioleoyl phosphatidyl ethanolamine (DOPE), phosphatidyl ethanolamine (POPE), dioleoyl-phosphatidyl ethanolamine 4-(N-maleimidomethyl)-cy clohexane-1-carboxylate (DOPE-mal), palmitoyloleoyl phosphatidylcholine (POPC), egg phosphatidylcholine (EPC), dimyristoylphosphatidylcholine (DMPC), dipalmitoylphosphatidylcholine (DPPC), distearoylphosphatidylcholine (DSPC), diarachidoylphosphatidylcholine (DAPC), dibehenoyl phosphatidylcholine (DBPC), dilignoceroylphosphatidylcholine (DLPC), dioleoylphosphatidylcholine (DOPC), stearyl oleoyl phosphatidylcholine (SOPC), hydrogenated soybean phosphatidylcholine (HSPC), dioleoyl phosphatidylglycerol (DOPG), dipalmitoylphosphatidylglycerol (DPPG), distearoyl phosphatidylglycerol (DSPG), dioleoyl phosphatidylserine (DOPS), and sphingomyelin; ceramides (Cer); and the like. The neutral lipid can be used singly or as a mixture of two or more thereof.

In several embodiments, the neutral lipid contains at least one selected from DOPE, HSPC, DPPC, DSPC, and DAPC.

In a specific embodiment, the neutral lipid contains DSPC.

The polyethylene glycol-modified lipid is not particularly limited, and examples thereof include PEG2000-DMG (PEG2000-dimyristylglycerol), PEG2000-DPG (PEG2000-dipalmitoylglycerol), PEG2000-DSG (PEG2000-distearoylglycerol), PEG5000-DMG (PEG5000-dimyristylglycerol), PEG5000-DPG (PEG5000-dipalmitoylglycerol), PEG5000-DSG (PEG5000-distearoylglycerol), PEG-cDMA (N-[(methoxypoly (ethylene glycol)2000)carbamyl]-1,2-dimyristyloxylpropyl-3-amine), PEG-C-DOMG (R-3-[(ω-methoxy-poly(ethylene glycol)2000)carbamoyl)]-1,2-dimyristyloxylpropyl-3-amine), PEG-diacylglycerol (DAG), PEG-dialkyloxypropyl (DAA), PEG-phospholipid, PEG-ceramide (Cer), PEG-cholesterol, and the like. Examples of PEG-DAA includes PEG-dilauryloxypropyl, PEG-dimyristyloxypropyl, PEG-dipalmityloxypropyl, PEG-distearyloxypropyl, and the like.

The polyethylene glycol-modified lipid can be used singly or as a mixture of two or more thereof. In addition, the polyethylene glycol-modified lipid may have the ends of PEG (polyethylene glycol) methoxylated (MPEG; methoxy (polyethylene glycol)). For example, PEG2000-DMG includes MPEG2000-DMG.

In several embodiments, the polyethylene glycol-modified lipid contains at least one selected from PEG2000-DMG, PEG2000-DPG, PEG2000-DSG, PEG-cDMA, or PEG-C-DOMG.

In a specific embodiment, the polyethylene glycol-modified lipid contains PEG2000-DMG.

The sterol is an alcohol having a steroid skeleton. The sterol is not particularly limited, and examples thereof include cholesterol, dihydrocholesterol, lanosterol, β-sitosterol, campesterol, stigmasterol, brush casterol, ergocasterol, fucosterol, 3β-[N—(N',N'-dimethylaminoethyl)carbamoyl] cholesterol (DC-Chol), and the like. The sterols can be used singly or as a mixture of two or more thereof.

In several embodiments, the sterol contains at least one selected from cholesterol, dihydrocholesterol, lanosterol, or B3-sitosterol.

In a specific embodiment, the sterol contains cholesterol.

(Composition and Mixing Proportions)

The lipid complex of the present embodiment contains, for example, 50 to 100% by weight, for example, 50 to 9.99% by weight, for example, 70 to 99.97% by weight, or for example, 90 to 99.95% by weight of the lipid component relative to the total weight of the lipid complex.

The lipid complex of the present embodiment contains, for example, 10 to 100 mol %, for example, 20 to 90 mol %, or for example, 40 to 80 mol % of the above-described ionizable lipid based on all of the lipids contained in the lipid complex. The ionizable lipid can be used singly or as a mixture of two or more thereof.

The lipid complex of the present embodiment may contain, for example, 0 to 50 mol %, for example, 0 to 40 mol %, or for example, 0 to 30 mol % of the neutral lipid based on all of the lipids contained in the lipid complex.

The lipid complex of the present embodiment may contain, for example, 0 to 30 mol %, for example, 0 to 20 mol %, or for example, 0 to 10 mol % of the polyethylene glycol-modified lipid based on all of the lipids contained in the lipid complex.

The lipid complex of the present embodiment may contain, for example, 0 to 90 mol %, for example, 10 to 80 mol %, or for example, 20 to 50 mol % of the sterol based on all of the lipids contained in the lipid complex.

The combination of the lipid components in the lipid complex of the present embodiment is not particularly limited, and examples thereof include combinations of the ionizable lipids, the neutral lipid, and the sterol described above, the combinations of the ionizable lipid, the neutral lipid, the polyethylene glycol-modified lipid, and the sterol, and the like.

The ionizable lipid is necessary for encapsulation of the nucleic acid or for efficient delivery of the nucleic acid into cells of interest. The presence of the neutral lipid and the sterol in addition to the ionizable lipid makes it possible to form stable particles encapsulating the nucleic acid. Furthermore, since the polyethylene glycol-modified lipid is capable of curbing particle aggregation, the simultaneous presence of these four types of lipids makes it possible to form stable particles encapsulating the nucleic acid while curbing particle aggregation.

In several embodiments, the lipid complex is composed of the ionizable lipid/the neutral lipid/the polyethylene glycol-modified lipid/the sterol as the lipids, and the molar ratio proportions of the lipids may be, for example, 10 to 99/0 to 50/0 to 30/0 to 90, 20 to 90/0 to 40/0 to 20/10 to 80, or 30 to 70/0 to 30/0 to 10/20 to 50.

In several embodiments, the molar ratio proportions of the ionizable lipid/the neutral lipid/the polyethylene glycol-modified lipid/the sterol in the lipid complex may be 10 to 99/1 to 50/1 to 30/1 to 90, 20 to 90/1 to 40/1 to 20/10 to 80, or 30 to 70/1 to 30/1 to 10/20 to 50.

In a specific embodiment, the molar ratio proportions of the ionizable lipid/the neutral lipid/the polyethylene glycol-modified lipid/the sterol in the lipid complex is about 50/about 10/about 1.5/about 38.5.

The lipid complex of the present embodiment contains, for example, 0.01 to 50% by weight, for example, 0.03 to 30% by weight, or for example, 0.05 to 10% by weight of the nucleic acid relative to the total weight of the lipid complex.

(Properties)

The "average particle size" of the lipid complex of the present embodiment can be calculated by any method for the volume-average, number-average, or Z-average particle size. The average particle size (Z-average) of the lipid complex of the present embodiment may be, for example, 10 to 1000 nm, for example, 30 to 500 nm, or for example, 30 to 200 nm.

From the standpoint of curbing nonspecific adsorption and immune response, the lipid complex of the present embodiment is preferably almost free of surface charges in, for example, an environment of a pH of about 7.4 as in the blood. In addition, the lipid complex is preferably positively charged in a low pH (for example, 3.5 to 7.0) environment from the viewpoint of improving the fusion efficiency with endosomal membranes when incorporated into cells by endocytosis.

The encapsulation rate of the nucleic acid in the lipid complex was measured using, for example, Quant-iT RiboGreen RNA Reagent (Invitrogen, Cat #$R_{11491}$). Specifically, the encapsulation rate can be calculated using the concentration (A) of a nucleic acid measured after being diluted with RNase Free Water for the nucleic acid present in the external fluid of the lipid complex and the concentration (B) of a nucleic acid measured after being diluted with 1% Triton X-100 as the total concentration of the nucleic acid in the formulation.

$$\text{Encapsulation rate (\%)} = 100 - (A/B) \times 100$$

In several embodiments, the encapsulation rate (%) of the nucleic acid in the lipid complex calculated by the above-described method is higher than, for example, 80%, 85%, or 90%. In one embodiment, the encapsulation rate (%) of the nucleic acid in the lipid complex is higher than 90%.

In several embodiments, the lipid complex has a polydispersity index (PDI) of less than 0.3 (in particular, less than 0.2, or in particular, less than 0.1).

4. Compositions

One aspect of the present disclosure provides a composition containing (I) the above-described ionizable lipid, (II) at least one lipid selected from the group consisting of a neutral lipid, a polyethylene glycol-modified lipid, and a sterol, and (III) a nucleic acid.

In one embodiment of the present disclosure, the composition contains the above-described lipid complex containing a nucleic acid. The composition of the present embodiment enables efficient release of a nucleic acid into cytoplasm. The composition of the present embodiment may comprise the above-described lipid complex, a pharmaceutically acceptable medium, and an optional additive. The pharmaceutically acceptable medium and the additive will be described below.

(Nucleic Acid and Lipid Components)

The composition contains a nucleic acid. Examples of the nucleic acid include the same ones as those described in the "3. Lipid Complex."

The composition contains, as lipid components, (I) the above-described ionizable lipid and (II) at least one lipid selected from the group consisting of a neutral lipid, a polyethylene glycol-modified lipid, and a sterol. Examples of the ionizable lipid, the neutral lipid, the polyethylene glycol-modified lipid, and the sterol include the same ones as those described in the "3. Lipid Complex."

(Composition and Mixing Proportions)

The composition of the present embodiment contains, for example, 50 to 100% by weight, for example, 50 to 9.99% by weight, for example, 70 to 99.97% by weight, or for example, 90 to 99.95% by weight of the lipid component relative to the total weight of the composition.

The composition of the present embodiment contains, for example, 10 to 100 mol %, for example, 20 to 90 mol %, or for example, 40 to 80 mol % of the above-described ionizable lipid based on all of the lipids contained in the composition. The ionizable lipid can be used singly or as a mixture of two or more thereof.

The composition of the present embodiment may contain, for example, 0 to 50 mol %, for example, 0 to 40 mol %, or for example, 0 to 30 mol % of the neutral lipid based on all of the lipids contained in the composition.

The composition of the present embodiment may contain, for example, 0 to 30 mol %, for example, 0 to 20 mol %, or for example, 0 to 10 mol % of the polyethylene glycol-modified lipid based on all of the lipids contained in the composition.

The composition of the present embodiment may contain, for example, 0 to 90 mol %, for example, 10 to 80 mol %, or for example, 20 to 50 mol % of the sterol based on all of the lipids contained in the composition.

The combination of the lipid components in the composition of the present embodiment is not particularly limited, and examples thereof include combinations of the ionizable lipids, the neutral lipid, and the sterol described above, the combinations of the ionizable lipid, the neutral lipid, the polyethylene glycol-modified lipid, and the sterol, and the like.

The ionizable lipid is necessary for encapsulation of the nucleic acid or for efficient delivery of the nucleic acid into cells of interest. The presence of the neutral lipid and the sterol in addition to the ionizable lipid makes it possible to form stable particles encapsulating the nucleic acid. Furthermore, since the polyethylene glycol-modified lipid is capable of curbing particle aggregation, the simultaneous presence of these four types of lipids makes it possible to form stable particles encapsulating the nucleic acid while curbing particle aggregation.

In several embodiments, the composition is composed of the ionizable lipid/the neutral lipid/the polyethylene glycol-modified lipid/the sterol as the lipids, and the molar ratio proportions of the lipids may be, for example, 10 to 99/0 to 50/0 to 30/0 to 90, 20 to 90/0 to 40/0 to 20/10 to 80, or 30 to 70/0 to 30/0 to 10/20 to 50.

In several embodiments, the molar ratio proportions of the ionizable lipid/the neutral lipid/the polyethylene glycol-modified lipid/the sterol in the composition may be 10 to 99/1 to 50/1 to 30/1 to 90, 20 to 90/1 to 40/1 to 20/10 to 80, or 30 to 70/1 to 30/1 to 10/20 to 50.

In a specific embodiment, the molar ratio proportions of the ionizable lipid/the neutral lipid/the polyethylene glycol-modified lipid/the sterol in the composition is about 50/about 10/about 1.5/about 38.5.

The composition of the present embodiment contains, for example, 0.01 to 50% by weight, for example, 0.03 to 30% by weight, or for example, 0.05 to 10% by weight of the nucleic acid relative to the total weight of the composition.

(Pharmaceutically Acceptable Medium)

The composition of the present embodiment may contain a pharmaceutically acceptable medium.

Examples of the pharmaceutically acceptable medium include sterile water; saline; isotonic solutions containing an adjuvant such as glucose, D-sorbitol, D-mannose, D-mannitol, and sodium chloride; buffers such as a phosphate buffer, a citrate buffer, and an acetate buffer.

(Additive)

The composition of the present embodiment may further contain an additive such as a dissolution auxiliary such as an alcohol such as ethanol, propylene glycol, or polyethylene glycol, a stabilizer, an antioxidant, a preservative, an excipient that is commonly used in pharmaceutical production, a filler, an extender, a binder, a wetting agent, a disintegrant, a lubricant, a surfactant, a dispersant, a preservative, a flavoring agent, or a pain reliever.

The composition of the present embodiment may contain, as another additive, sugar such as sucrose, glucose, sorbitol, or lactose; an amino acid such as glutamine, glutamic acid, sodium glutamate, or histidine; a salt of an acid such as citric acid, phosphoric acid, acetic acid, lactic acid, carbonic acid, or tartaric acid.

The composition of the present disclosure may be formulated as a medical composition. In several embodiments, the medical composition may contain the above-described lipid complex, a pharmaceutically acceptable carrier, and an optional additive.

Examples of the dosage form of the medical composition include injections.

The composition of the present disclosure may be, for example, in a powder state where a solvent has been removed by lyophilization or the like or in a liquid state. A composition of one embodiment of the present disclosure is a powder composition containing the above-described lipid complex of the embodiment. The powder composition may be prepared by removing the solvent from the composition (dispersion) in a liquid state by, for example, filtration, centrifugation, or the like, or may be prepared by lyophilizing the dispersion. In a case where the composition is in a powder state, the composition can be used as an injection by being suspended or dissolved in a pharmaceutically acceptable medium prior to use. A composition of one embodiment of the present disclosure is a liquid composition containing the above-described lipid complex of the embodiment and a pharmaceutically acceptable medium. In a case where the composition is in a liquid state, the composition can be used as it is or as an injection by being suspended or dissolved in a pharmaceutically acceptable medium.

The composition can be administered to a patient by, for example, parenteral administration such as intra-arterial injection, intravenous injection, or subcutaneous injection. The dosage of the composition also varies with the target of administration, target organs, symptoms, and administration methods. The target of administration of the composition is not limited, and the composition can be applied to various animals, particularly to mammals, preferably human beings and experimental animals in clinical studies, screening, and experiment.

In a case where the nucleic acid that is encapsulated in the composition is a nucleic acid medicine, the composition can be used as a medical composition. For example, the composition of the present disclosure can be used in treatments (for example, gene therapies) in which a desired nucleic acid is introduced into target cytoplasm (for example, cytoplasm causing various diseases) in vivo or in vitro. Therefore, one embodiment of the present disclosure provides methods for treating various diseases (particularly, methods for gene therapy) in which a medical composition containing the above-described lipid complex is used. The target of administration and the method and conditions for administration are similar to those described above.

5. Methods for Producing Lipid Complex and Composition

Methods for producing the above-described lipid complex and composition are not particularly limited.

Examples of a method for encapsulating a molecule in the lipid complex include reverse-phase evaporation, Zwitterion (NaCl) hydration, cationic core hydration, and methods in which ethanol and calcium are used (also refer to Biomembr., 1468, 239 to 252 (2000)). The lipid complex encapsulating a nucleic acid of the present disclosure can be prepared by the above-described method well known in the art.

In several embodiments of the present disclosure, the composition is produced by, for example, a method including a step (a) of mixing (I) an ionizable lipid, a polar organic solvent-containing aqueous solution containing (II) at least one lipid selected from the group consisting of a neutral lipid, a polyethylene glycol-modified lipid, and a sterol, and (III) an aqueous solution containing a nucleic acid to obtain a liquid mixture, and a step (b) of reducing the content of a polar organic solvent in the liquid mixture. According to the production method of the present embodiment, it is possible to produce a composition capable of efficiently releasing a nucleic acid into cytoplasm.

A lipid complex containing a nucleic acid encapsulated in particles composed of a lipid can be formed by an electrostatic interaction between a water-soluble nucleic acid and the above-described ionizable lipid and a hydrophobic interaction between lipids. For example, when the content of the polar organic solvent in the liquid mixture is reduced, the solubility of (I) the above-described ionizable lipid and a lipid component containing (II) at least one lipid selected from the group consisting of a neutral lipid, a polyethylene glycol-modified lipid, and a sterol in the polar organic solvent-containing aqueous solution is changed, whereby a lipid complex is formed, and a lipid complex that is internally filled with the core of the nucleic acid and the lipid and a composition containing the lipid complex are obtained.

In the method of the present embodiment, first, in the step (a), (I) the above-described ionizable lipid, a polar organic solvent-containing aqueous solution containing (II) at least one lipid selected from the group consisting of a neutral lipid, a polyethylene glycol-modified lipid, and a sterol dissolved therein, and (III) an aqueous solution containing a nucleic acid are mixed to obtain a liquid mixture. The concentration of a polar organic solvent in the polar organic solvent-containing aqueous solution is not particularly limited as long as conditions for the lipid molecules to be dissolved are satisfied even after mixing with the aqueous solution of the nucleic acid. As an example, the concentration of the polar organic solvent in the polar organic solvent-containing aqueous solution in the step (a) can be 0.1 to 60% by weight. The aqueous solution containing a nucleic acid can be obtained by, for example, dissolving a nucleic acid in an acidic buffer.

Examples of the polar organic solvent that dissolves the lipids include polar organic solvents such as alcohols, and the polar organic solvent may be, for example, ethanol, isopropanol, chloroform, or tert-butanol.

Examples of the acidic buffer in which the nucleic acid is dissolved include a sulfate buffer, a phosphate buffer, a phthalate buffer, a tartrate buffer, a citrate buffer, a formate buffer, an oxalate buffer, an acetate buffer, and the like.

Subsequently, in the step (b), the content of the polar organic solvent is reduced by adding water or the like to the liquid mixture. This makes it possible to form the lipid complex. In order to efficiently form the lipid complex, it is preferable to rapidly lower the content of the polar organic solvent. As an example, the concentration of the polar organic solvent in the final polar organic solvent-containing aqueous solution in the step (b) can be 0 to 5% by weight.

In addition, the polar organic solvent may be removed from the liquid mixture obtained in the step (a) by dialysis, and the solvent may be substituted into a pharmaceutically acceptable medium. The content of the polar organic solvent in the solution decreases in the dialysis process, which makes it possible to form the lipid complex.

6. Kit

One aspect of the present disclosure can be a kit for nucleic acid medicine delivery containing the ionizable lipid. The kit can be preferably used for the treatment of various target cells (for example, gene therapy). In the kit of the present embodiment, the storage state of the ionizable lipid is not particularly limited and can be set to any state such as a solution state or a powder state in consideration of the stability (storability), ease of use, and the like. The kit of the present embodiment may contain, for example, aside from the above-described ionizable lipid, various nucleic acids, various media (pharmaceutically acceptable media and buffers), instructions for use (manuals for use), and the like. The kit of the present embodiment is used to prepare compositions or lipid complexes containing a desired nucleic acid to be introduced into target cells and a lipid containing the above-described ionizable lipid. The prepared compositions or lipid complexes can be effectively used for nucleic acid delivery to target cells. Furthermore, one embodiment of the present disclosure can be a kit for nucleic acid medicine delivery containing a medical composition containing the above-described ionizable lipid. In addition to the medical composition, the kit of the present embodiment may contain, for example, various media (pharmaceutically acceptable media), instructions for use (manuals for use), and the like.

EXAMPLES

The compound according to the present disclosure can be produced by, for example, methods to be described in the following Production Examples and Examples. However, these are exemplary, and the compound according to the present disclosure is not limited to the following specific examples in any cases. As the names of compounds to be shown below, those given in "E-Notebook" Version 23 (Revvity Signals Software) were used except for commonly used reagents.

In the Production Examples and the Examples, unless particularly otherwise described, as purification silica gel that was used in silica gel column chromatography, YMC GEL SILICA (YMC Co., Ltd., catalog code: SL06152W), Silica gel 60 (Kanto Chemicals), Silica gel spheres (Fuji Silysia Chemical Ltd., catalog code: PSQ60B), Silica gel 60 (Merck KGaA, catalog code: 1.07734), CHROMATREX BW (Fuji Silysia Chemical Ltd., catalog code: BW-300), Hi-Flash Column (YAMAZEN Corporation), or Presep Silica Gel (WAKO) was used, as purification silica gel that was used in NH silica gel column chromatography, NH silica gel (Fuji Silysia Chemical Ltd., catalog code: NH-DM2035), Hi-Flash Column Amino (YAMAZEN Corporation), or Presep NH2 HC (WAKO) was used, and as purification silica gel that was used in ODS silica gel column chromatography, Hi-Flash Column ODS (YAMAZEN Corporation) was used.

In the Production Examples and the Examples, unless particularly otherwise described, a fully automated preparative LC system (Waters MassLynx MS preparative system) was used for preparative purification. As columns used, Xbridge Prep C18 5 μm OBD (19 mm×100 mm) manufactured by Waters was used.

In the Production Examples and the Examples, unless particularly otherwise described, supercritical fluid chromatography (SFC) (Waters prep 100 SFC system) was used for chiral separation. As columns used, CHIRALPAK (registered trademark) IB (2 cm×25 cm), CHIRALPAK (registered trademark) IF (3 cm×25 cm), CHIRALPAK (registered trademark) IG (2 cm×25 cm) manufactured by Daicel Corporation were used.

For the determination of proton nuclear magnetic resonance spectra, Varian Mercury 400, Varian Mercury Plus 400, JEOL 400 (JMTC-400/54/SS, ECZ400S), JEOL 500 (JMTC-500/54/JJ, ECZ 500RS), or Bruker AVIII (600 MHz) were used. Chemical shifts in the proton nuclear magnetic resonance spectra are recorded in 6 units (ppm) relative to tetramethylsilane, and coupling constants are recorded in Hertz (Hz). The abbreviations for split patterns are as follows: s: singlet, d: doublet, t: triplet, q: quartet, quin: quintet, spt: septet, m: multiplet, brs: broad singlet, brd: broad doublet.

For the measurement of mass spectra, Waters UPLC™ was used. In an ionization method, measurement was performed using an electrospray ionization (ESI) method.

Abbreviations that were used in the Examples are conventional abbreviations well known to persons skilled in the art. Several abbreviations will be shown below.

Bn: Benzyl

DCC: N,N'-dicyclohexylcarbodiimide

DCM: Methylene chloride

DIPEA: Diisopropylethylamine

DMAP: 4-Dimethylaminopyridine

DMF: N,N-dimethylformamide

DMP: Dess-Martin periodinane

EDCI: 1-Ethyl-3-(3-dimethylaminopropyl)carbodiimide

ESI: Electrospray ionization method

HATU: 1-(Bis(dimethylamino)methylene)-1H-1,2,3-triazolo(4,5-b) pyridinium 3-oxide hexafluorophosphate Me: Methyl MTBE: Methyl tert-butyl ether MS: Mass spectrometry n-: Normal n-BuLi: n-Butyllithium NMR: Nuclear magnetic resonance PPTS: Pyridinium para-toluenesulfonate TBAF: Tetra-n-butylammonium fluoride tert-: Tertiary THF: Tetrahydrofuran "Room temperature" in the following Examples and Production Examples generally indicates about 10° C. to about 35° C. % indicates weight percent unless particularly otherwise described.

A. Synthesis of Ionizable Lipids

[Example1]

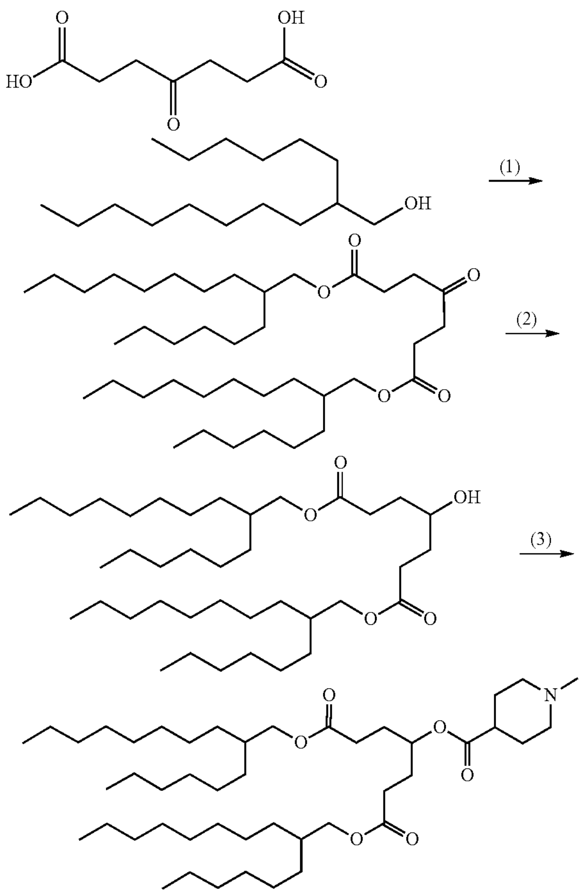

(1) Synthesis of Bis(2-hexyldecyl) 4-oxoheptanedioate

DMF (2 mL) was added to 4-oxoheptanedioic acid (100 mg) and 2-hexyl-1-decanol (348 mg), DIPEA (0.50 mL) and HATU (546 mg) were added at room temperature and stirred at 70° C. for four hours. Ethyl acetate (50 mL) and water (50 mL) were added to a mixture, organic layers were separated, and an aqueous layer was extracted with ethyl acetate. The combined organic layers were washed with water and a saturated saline solution, dried over anhydrous sodium sulfate, filtered, and then concentrated under reduced pressure. A residue was purified by silica gel column chromatography (n-heptane/ethyl acetate), and a title compound (199 mg) was obtained as a crude product.

(2) Synthesis of Bis(2-hexyldecyl) 4-hydroxyheptanedioate

The compound (304 mg) obtained in Example 1(1) was added to MTBE (2 mL) and methanol (2 mL), sodium borohydride (28.4 mg) was added at 0° C. and stirred at 0° C. for 10 minutes. MTBE (20 mL) and water (20 mL) were added to a mixture and stirred at 0° C. for 10 minutes, organic layers were then separated, and an aqueous layer was extracted with MTBE. The combined organic layers were washed with water and a saturated saline solution, dried over anhydrous sodium sulfate, filtered, and then concentrated under reduced pressure. A residue was purified by silica gel column chromatography (n-heptane/ethyl acetate), and a title compound (184 mg) was obtained.

(3) Synthesis of Bis(2-hexyldecyl) 4-((1-methylpiperidine-4-carbonyl)oxy)heptanedioate (Compound (E1))

The compound (430 mg) obtained in Example 1(2) and 1-methylpiperidine-4-carboxylic acid hydrochloride (371 mg) were added to DMF (6 mL), DIPEA (0.599 mL), EDCI (396 mg), and DMAP (25.2 mg) were added at room temperature and stirred at room temperature for 16 hours. Ethyl acetate (50 mL) and water (50 mL) were added to a mixture, an organic layer was washed with water and a saturated saline solution, dried over anhydrous sodium sulfate, filtered, and then concentrated under reduced pressure. A residue was purified by silica gel column chromatography (n-heptane/ethyl acetate, ethyl acetate/methanol), and a title compound (407 mg) was obtained. ESI-MS:772.5 ($[M+Na]^+$)

Example 2

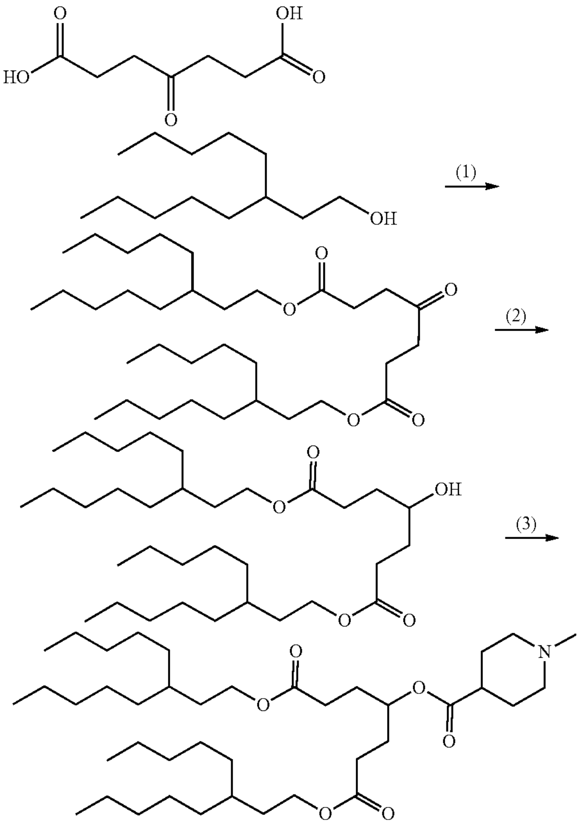

(1) Synthesis of Bis(3-pentyloctyl) 4-oxoheptanedioate

A title compound (120 mg) was obtained as a crude product by the same method as in Example 3(1) to be described below using 3-pentyl-octan-1-ol (115 mg) instead of 3-hexylundecan-1-ol.

(2) Synthesis of Bis(3-pentyloctyl) 4-hydroxyheptanedioate

A title compound (57 mg) was obtained by the same method as in Example 3(2) to be described below using the compound (120 mg) obtained in Example 2(1) instead of the compound obtained in Example 3(1).

(3) Synthesis of Bis(3-pentyloctyl) 4-((1-methylpiperidine-4-carbonyl)oxy)heptanedioate (Compound (E2))

A title compound (26 mg) was obtained by the same method as in Example 3(3) to be described below using the compound (57 mg) obtained in Example 2(2) instead of the compound obtained in Example 3(2) to be described below. ESI-MS:666.2 ([M+H]$^+$)

Example 3

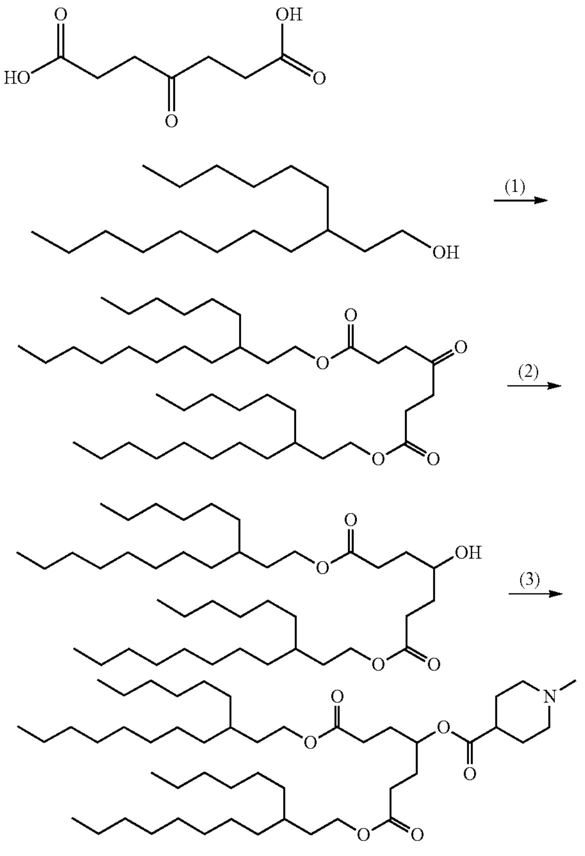

(1) Synthesis of Bis(3-hexylundecyl) 4-oxoheptanedioate 4-oxoheptanedioic acid (150 mg) and 3-hexylundecan-1-ol (552 mg) were added to DMF (5 mL), and DIPEA (0.75 mL) and HATU (819 mg) were added at room temperature and stirred at room temperature for 16 hours.

Ethyl acetate (50 mL) and water (50 mL) were added to a mixture, organic layers were separated, and an aqueous layer was extracted with ethyl acetate. The combined organic layers were washed with water and a saturated saline solution, dried over anhydrous sodium sulfate, filtered, and then concentrated under reduced pressure. A residue was purified by silica gel column chromatography (n-heptane/ethyl acetate), and a title compound (222 mg) was obtained as a crude product.

(2) Synthesis of Bis(3-hexylundecyl) 4-hydroxyheptanedioate

The compound (222 mg) obtained in Example 3(1) was added to MTBE (5 mL) and methanol (5 mL), and sodium borohydride (19.9 mg) was added at 0° C. and stirred at 0° C. for one hour.

MTBE (20 mL) and water (20 mL) were added to a mixture and stirred at 0° C. for 10 minutes, organic layers were separated, and an aqueous layer was extracted with MTBE. The combined organic layers were washed with water and a saturated saline solution, dried over anhydrous sodium sulfate, filtered, and then concentrated under reduced pressure. A residue was purified by silica gel column chromatography (n-heptane/ethyl acetate), and a title compound (130 mg) was obtained.

(3) Synthesis of Bis(3-hexylundecyl) 4-((1-methylpiperidine-4-carbonyl)oxy)heptanedioate (Compound (E3))

The compound (130 mg) obtained in Example 3(2) and 1-methylpiperidine-4-carboxylic acid hydrochloride (107 mg) were added to DMF (5 mL), DIPEA (0.17 mL), EDCI (114 mg), and DMAP (7.3 mg) were added at room temperature and stirred at room temperature for 16 hours.

n-heptane (50 mL) and water (50 mL) were added to a mixture, an organic layer was washed with water and a saturated saline solution, dried over anhydrous sodium sulfate, filtered, and then concentrated under reduced pressure. A residue was purified by NH silica gel column chromatography (n-heptane/ethyl acetate), and a title compound (135 mg) was obtained. ESI-MS:780.5 ([M+H]$^+$)

Example 4

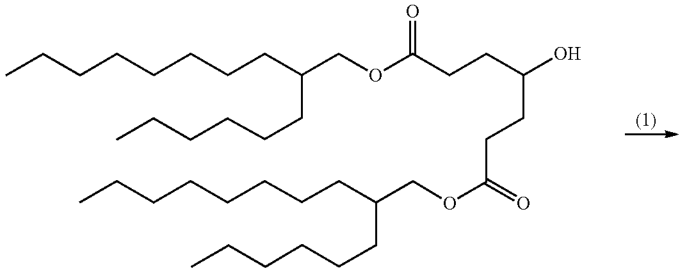

-continued
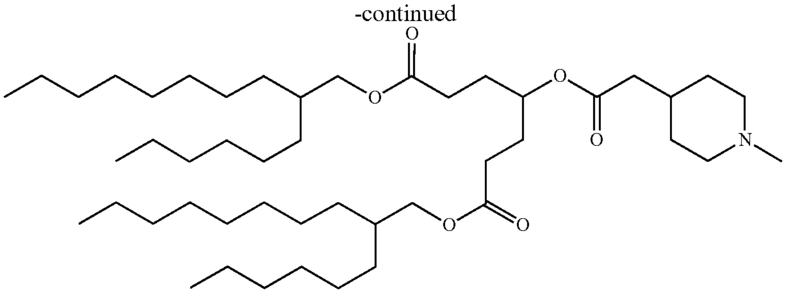
(1) Synthesis of Bis(2-hexyldecyl) 4-(2-(1-methylpiperidine-4-yl)acetoxy)heptanedioate (Compound (E4))
A title compound (17 mg) was obtained using the same procedure as in Example 1(3) and using 2-(1-methylpiperidine-4-yl)acetic acid (7.2 mg) as a raw material instead of 1-methylpiperidine-4-carboxylic acid hydrochloride. ESI-MS:786.7 ([M+Na]$^+$)
Example 5
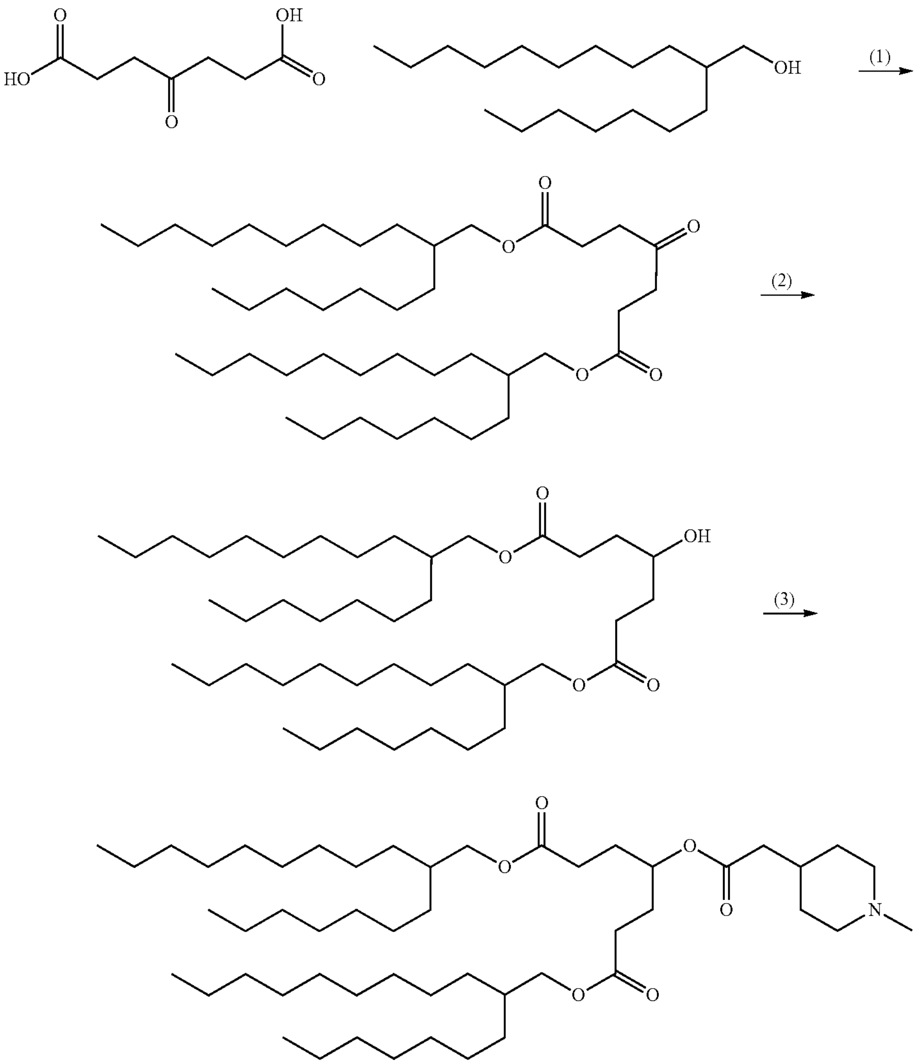

(1) Synthesis of Bis(2-heptylundecyl) 4-oxoheptanedioate

A title compound (690 mg) was obtained as a crude product by the same method as in Example 3(1) using 2-heptylundecan-1-ol (1.94 g) instead of 3-hexylundecan-1-ol.

(2) Synthesis of Bis(2-heptylundecyl) 4-hydroxyheptanedioate

A title compound (328 mg) was obtained by the same method as in Example 3(2) using the compound (690 mg) obtained in Example 5(1) instead of the compound obtained in Example 3(1).

(3) Synthesis of Bis(2-heptylundecyl) 4-(2-(1-methylpiperidin-4-yl)acetoxy)heptanedioate (Compound (E5))

A title compound (11.7 mg) was obtained by the same method as in Example 3(3) using the compound (15 mg) obtained in Example 5(2) instead of the compound obtained in Example 3(2) and 2-(1-methylpiperidin-4-yl)acetic acid (7.2 mg) instead of 1-methylpiperidine-4-carboxylic acid hydrochloride. ESI-MS:842.1 ([M+Na]+)

Example 6

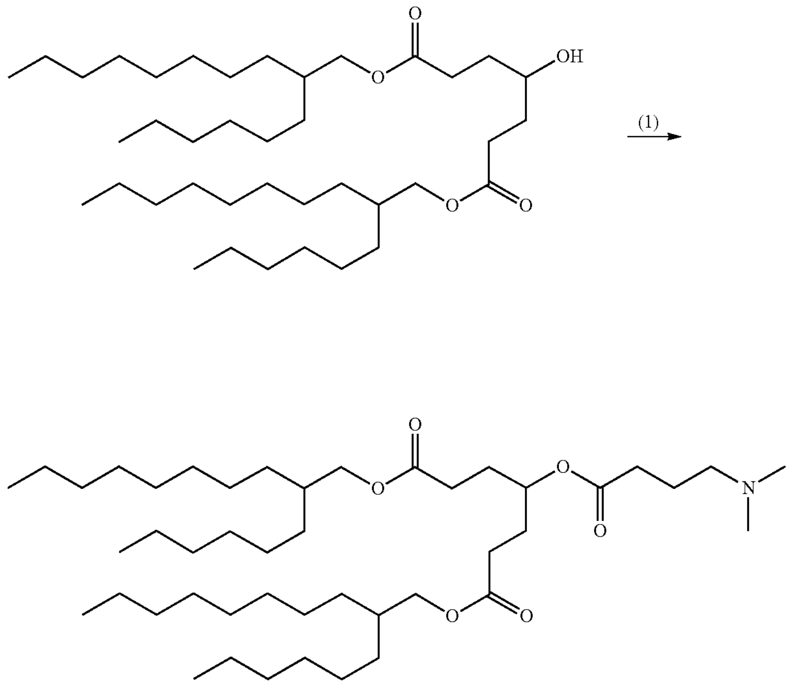 [SMILES: CCCCCCCCC(CCCCCC)COC(=O)CCC(O)CCC(=O)OCC(CCCCCC)CCCCCCCC ; CCCCCCCCC(CCCCCC)COC(=O)CCC(CCC(=O)OCC(CCCCCC)CCCCCCCC)OC(=O)CCCN(C)C]

(1) Synthesis of Bis(2-hexyldecyl) 4-((4-(dimethylamino)butanoyl)oxy)heptanedioate (Compound (E6))

A title compound (35.6 mg) was obtained using the same method as in Example 1(3) and using 4-dimethylaminobutyric acid hydrochloride (26.8 mg) as a raw material instead of 1-methylpiperidine-4-carboxylic acid hydrochloride. ESI-MS:760.3 ([M+Na]+)

Example 7

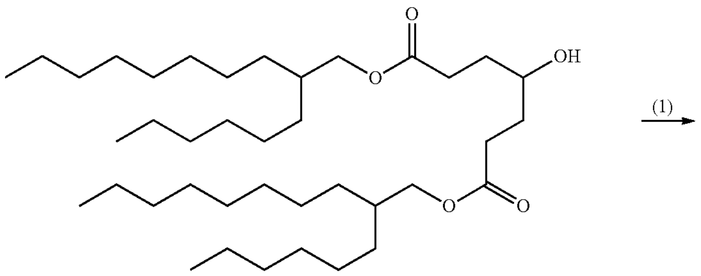

-continued

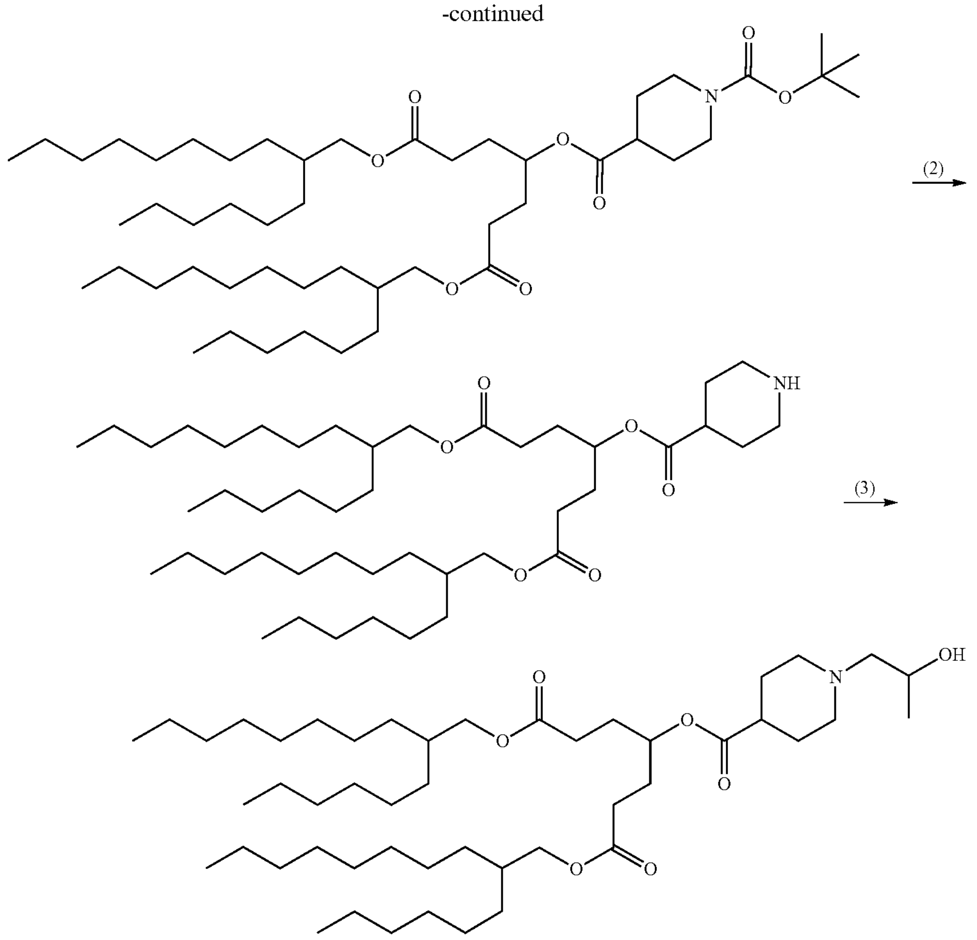

(1) Synthesis of 4-(1,7-Bis((2-hexyldecyl)oxy)-1,7-dioxoheptane-4-yl) 1-(tert-butyl)piperidine-1,4-dicarboxylate A title compound (131 mg) was obtained using the same method as in Example 1(3) and using 1-((tert-butoxy)carbonyl)piperidine-4-carboxylic acid (97 mg) as a raw material instead of 1-methylpiperidine-4-carboxylic acid hydrochloride.

(2) Synthesis of Bis(2-hexyldecyl) 4-((piperidine-4-carbonyl)oxy)heptanedioate

The compound (131 mg) obtained in Example 7(1) was dissolved in DCM (5 mL), trifluoroacetic acid (0.36 mL) was added at room temperature, and the components were stirred for four hours. A mixture was cooled to 0° C., and the mixture was adjusted to pH=10 with a 5N sodium hydroxide aqueous solution. An aqueous layer was extracted with DCM, combined organic layers were washed with water and a saturated saline solution, then, dried over anhydrous sodium sulfate, filtered, and then concentrated under reduced pressure, and a title compound (129 mg) was obtained as a crude product.

(3) Synthesis of Bis(2-hexyldecyl) 4-((1-(2-hydroxypropyl)piperidine-4-carbonyl)oxy)heptanedioate (Compound (E7))

The compound (20 mg) obtained in Example 7(2) was dissolved in ethanol (1 mL), and propylene oxide (19 μL) was added at room temperature. A mixture was stirred at 70° C. for two hours. The mixture was cooled to room temperature and then directly purified by NH silica gel column chromatography (heptane/ethyl acetate), and a title compound (10.7 mg) was obtained. ESI-MS:816.4 ([M+Na]$^+$)

Example 8

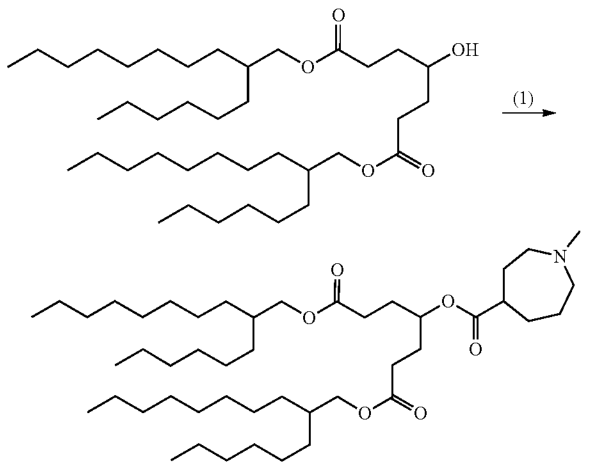

(1) Synthesis of Bis(2-hexyldecyl) 4-((1-methylazepane-4-carbonyl)oxy)heptanedioate (Compound (E8))

A title compound (19.1 mg) was obtained using the same method as in Example 1(3) and using 1-methylazepane-4-carboxylic acid (10.1 mg) as a raw material instead of 1-methylpiperidine-4-carboxylic acid hydrochloride. ESI-MS:786.8 ([M+Na]$^+$)

Example 9-1

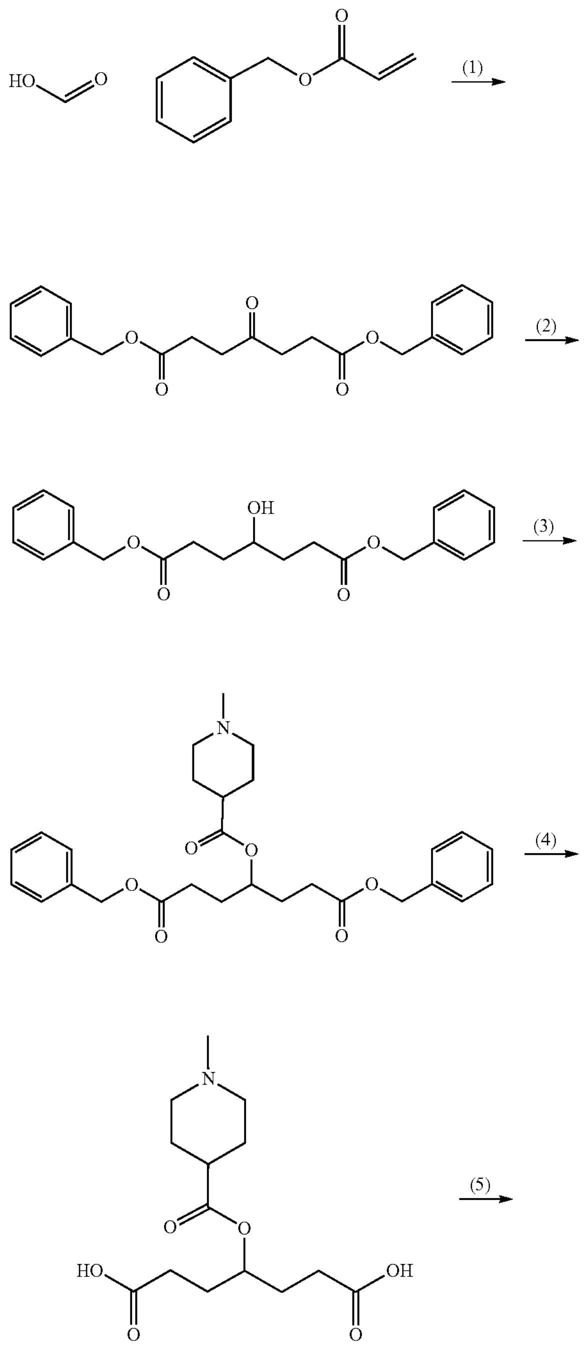

-continued

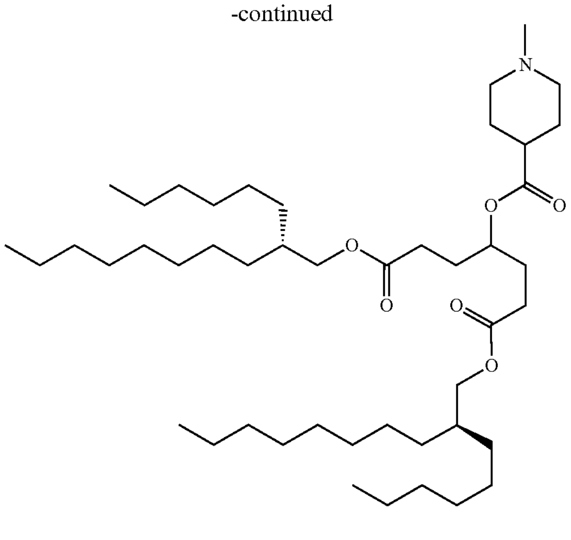

(1) Synthesis of Dibenzyl 4-oxoheptanedioate

Palladium trifluoroacetate (83 mg) and 1,3-bis(diphenylphosphino)propane (206 mg) were suspended in acetonitrile (522 μL), benzyl acrylate (1.53 mL), formic acid (575 μL) and acetic anhydride (708 μL) were added at room temperature, a reaction vessel was sealed and substituted with nitrogen, and the components were stirred at 90° C. for 20 hours. A mixture was cooled to room temperature and then directly purified by silica gel column chromatography (cyclohexane/diethyl ether), and a title compound (446 mg) was obtained.

(2) Synthesis of Dibenzyl 4-hydroxyheptanedioate

Diethyl ether (20 mL) and methanol (5 mL) were added to the compound (446 mg) obtained in Example 9-1(1), sodium borohydride (57.1 mg) was added at −20° C., and the components were stirred for two hours.

Diethyl ether (100 mL) and a saturated ammonium chloride aqueous solution (10 mL) were added to a mixture, and an aqueous layer was extracted with diethyl ether. Combined organic layers were washed with a saturated saline solution, dried over anhydrous sodium sulfate, filtered, and then concentrated under reduced pressure. A residue was purified by silica gel column chromatography (cyclohexane/diethylether), and a title compound (338 mg) was obtained.

(3) Synthesis of Dibenzyl 4-((1-methylpiperidine-4-carbonyl)oxy)heptanedioate

The compound (350 mg) obtained in Example 9-1(2) and 1-methylpiperidine-4-carboxylic acid (337 mg) were added to DMF (10 mL), EDCI (489 mg) and DMAP (288 mg) were added at room temperature, and the components were stirred at 50° C. for 18 hours. MTBE (50 mL) and water (20 mL) were added to a mixture, and an aqueous layer was extracted with MTBE. Combined organic layers were washed with a saturated saline solution, dried over sodium sulfate, filtered, and then concentrated under reduced pressure. A residue was purified by silica gel column chromatography (DCM/methanol), and a title compound (272 mg) was obtained.

(4) Synthesis of 4-((1-methylpiperidine-4-carbonyl)oxy)heptanedioic acid

The compound (336 mg) obtained in Example 9-1(3) was added to ethyl acetate (75 mL) and methanol (75 mL), and palladium on carbon (10%, 300 mg) was added. The inside of a reaction vessel was substituted with a hydrogen gas, and the components were stirred for 40 hours. A mixture was filtered with CELITE (registered trademark), and the CELITE was washed with methanol (50 mL) and ethyl acetate (50 mL). An obtained solution was concentrated under reduced pressure, and a title compound (214 mg) was obtained.

(5) Synthesis of Bis((S)-2-hexyldecyl) 4-((1-methylpiperidine-4-carbonyl)oxy)heptanedioate (Compound (E9))

The compound (100 mg) obtained in Example 9-1(4) was added to DMF (5 mL), (S)-2-hexyldecan-1-ol (177 mg), DMAP (24 mg), and EDCI (153 mg) were added, and the components were stirred at room temperature for 18 hours. MTBE (5 mL) and water (2 mL) were added to a mixture, and an aqueous layer was extracted twice with MTBE (5 mL). Combined organic layers were dried over anhydrous sodium sulfate, filtered, and then concentrated under reduced pressure. A residue was purified by silica gel column chromatography (cyclohexane/MTBE), and a title compound (103 mg) was obtained. ESI-MS:750.8 ([M+H]$^+$)

Example 9-2

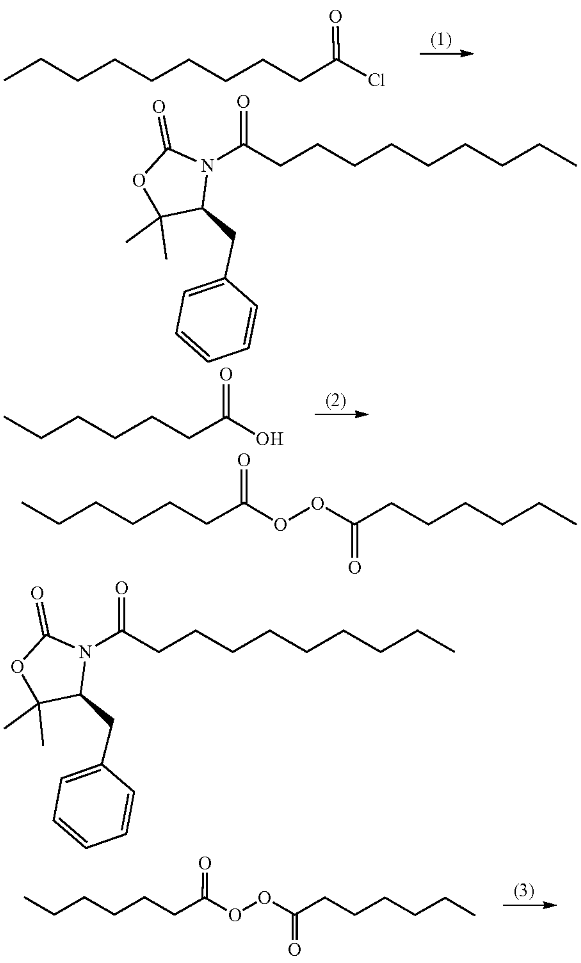

-continued

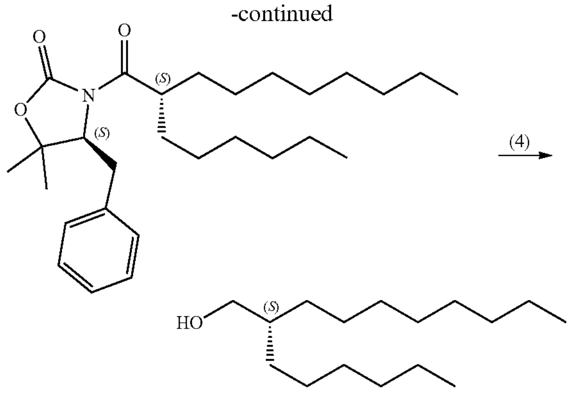

(1) Synthesis of (S)-4-Benzyl-3-decanoyl-5,5-dimethyloxazolidin-2-one (S)-4-Benzyl-5,5-dimethyloxazolidin-2-one (500 mg) was added to THF (10 mL) and cooled to −78° C., n-BuLi (2.5M hexane solution, 1.07 mL) was then added over 15 minutes, and a THF (2 mL) solution of decanoyl chloride (604 mg) was added over 20 minutes. A mixture was stirred at room temperature for two hours. A saturated ammonium chloride aqueous solution (2 mL) was added to the mixture, and ethyl acetate (5 mL) was further added. An aqueous layer was extracted with ethyl acetate (5 mL) twice, and combined organic layers were washed with a saturated sodium bicarbonate aqueous solution (2 mL) and a saturated saline solution (2 mL), dried over sodium sulfate, filtered, and then concentrated under reduced pressure. A residue was purified by silica gel column chromatography (cyclohexane/ethyl acetate), and a title compound (710 mg) was obtained.

(2) Synthesis of Heptanoic peroxyanhydride

Heptanoic acid (4.15 mL) was added to DCM (80 mL), a 30% hydrogen peroxide aqueous solution (800 μL) was added at 0° C., the components were stirred for 10 minutes, DMAP (0.358 g) and DCC (6.58 g) were then added, and the components were stirred for two hours. A mixture was diluted with hexane (400 mL), a solid was removed by filtration, and the mixture was dried over magnesium sulfate and then concentrated. A residue was purified by silica gel column chromatography (cyclohexane/ethyl acetate), and a title compound (2.03 g) was obtained.

(3) Synthesis of (S)-4-benzyl-3-((S)-2-hexyldecanoyl)-5,5-dimethyloxazolidin-2-one The compound (709 mg) obtained in Example 9-2(1) was dissolved in 1,2-dichloroethane, and titanium tetrachloride (0.239 mL) was added dropwise at 0° C. After five minutes, triethylamine (0.825 mL) was added, and the components were further stirred at 0° C. for 40 minutes. A 1,2-dichloroethane solution (4 mL) of the compound (764 mg) obtained in Example 9-2(2) was added dropwise to a mixture, and the mixture was stirred at room temperature for two hours. A saturated ammonium chloride aqueous solution (12 mL) was added to the mixture, and an aqueous layer was extracted with DCM (40 mL) twice. Combined organic layers were dried over anhydrous sodium sulfate, filtered, and then concentrated under reduced pressure. A residue was purified by silica gel column chromatography, and a title compound (527 mg) was obtained.

(4) Synthesis of (S)-2-hexyldecan-1-ol

The compound (469 mg) obtained in Example 9-2(3) was added to THF (10 mL) and methanol (342 μL), and lithium borohydride (2.0 M THF solution, 4.22 mL) was added dropwise at 0° C. A mixture was stirred at 0° C. for 30 min and then stirred at room temperature overnight. The mixture was cooled to 0° C., MTBE (5 mL) and a saturated saline solution (1 mL) were added, and an aqueous layer was extracted with MTBE (5 mL) three times. Combined organic layers were dried over anhydrous sodium sulfate, filtered, and then concentrated under reduced pressure. A residue was purified by silica gel column chromatography (cyclohexane/MTBE), and a title compound (243 mg) was obtained.

Example 10

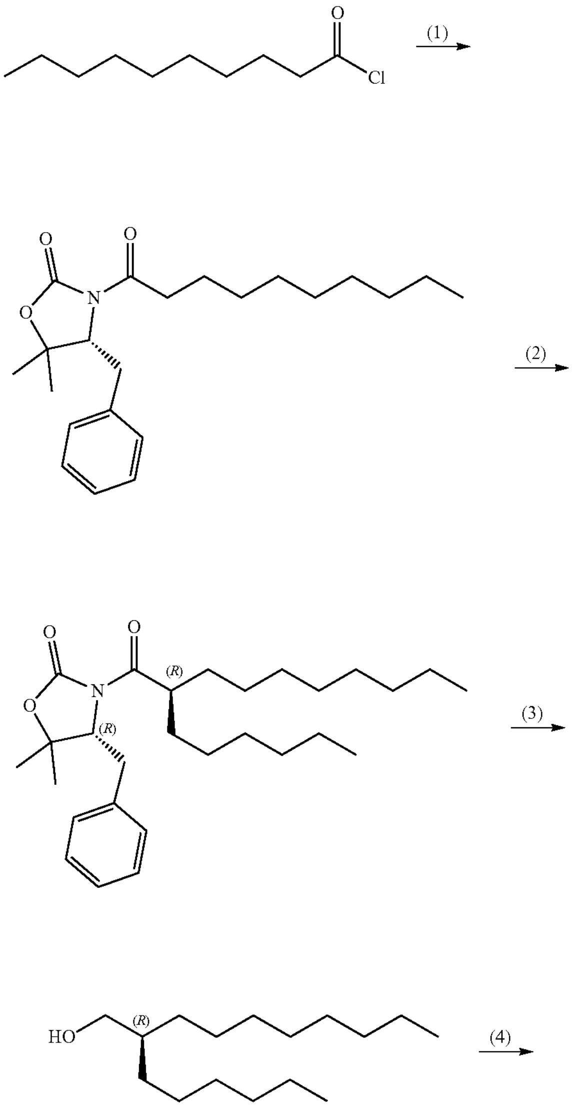

-continued

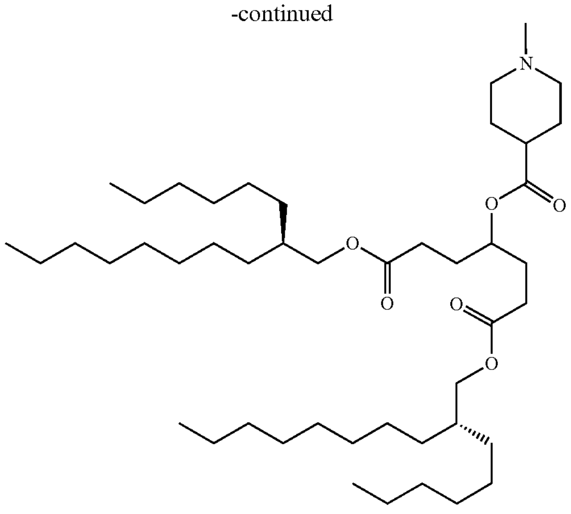

(1) Synthesis of (R)-4-benzyl-3-decanoyl-5,5-dimethyloxazolidin-2-one

A title compound (711 mg) was obtained by the same method as in Example 9-2(1) using (R)-4-benzyl-5,5-dimethyloxazolidin-2-one (500 mg) instead of (S)-4-benzyl-5,5-dimethyloxazolidin-2-one.

(2) Synthesis of (R)-4-benzyl-3-((R)-2-hexyldecanoyl)-5,5-dimethyloxazolidin-2-one A title compound (610 mg) was obtained by the same method as in Example 9-2(3) using the compound (710 mg) obtained in Example 10(1) as a raw material instead of the compound obtained in Example 9-2(1).

(3) Synthesis of (R)-2-hexyldecan-1-ol

A title compound (304 mg) was obtained by the same method as in Example 9-2(4) using the compound (610 mg) obtained in Example 10(2) as a raw material instead of the compound obtained in Example 9-2(3).

(4) Synthesis of Bis((R)-2-hexyldecyl) 4-((1-methylpiperidine-4-carbonyl)oxy)heptanedioate (Compound (E10))

A title compound (90 mg) was obtained by the same method as in Example 9-1(5) using the compound (177 mg) obtained in Example 10(3) instead of (S)-2-hexyldecan-1-ol. ESI-MS:750.8 ([M+H]$^+$)

Example 11

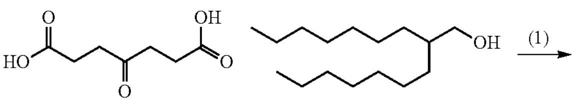

-continued

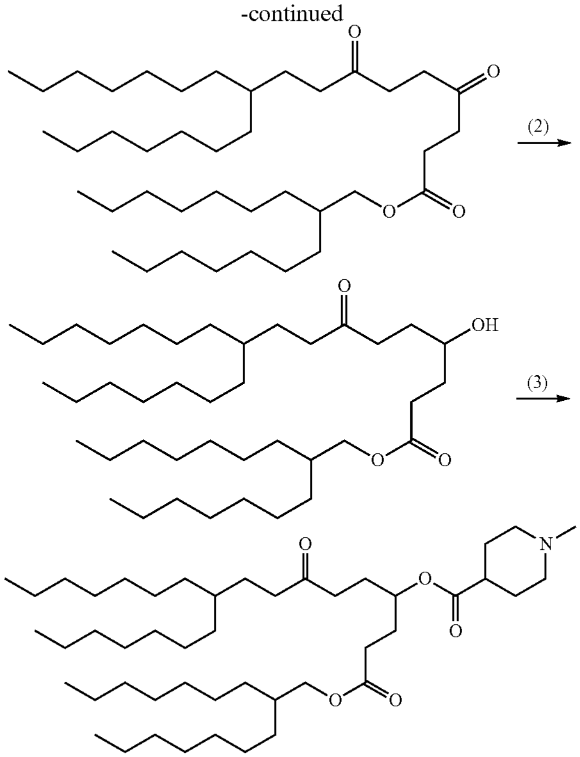

(1) Synthesis of 3-(1,7-Bis((2-hexyldecyl)oxy)-1,7-dioxoheptane-4-yl) 8-(tert-butyl) (1R,3s,5S)-8-azabicyclo[3.2.1]octane-3,8-dicarboxylate A title compound (410 mg) was obtained using the same method as in Example 1(3) and using (1R,3s,5S)-8-((tert-butoxy)carbonyl)-8-azabicyclo[3.2.1]octane-3-carboxylic acid (184 mg) instead of 1-methylpiperidine-4-carboxylic acid hydrochloride. ESI-MS:885.4 ([M+Na]$^+$)

(2) and (3) Synthesis of Bis(2-hexyldecyl) 4-(((1R,3s,5S)-8-(2-hydroxypropyl)-8-azabicyclo[3.2.1]octane-3-carbonyl)oxy)heptanedioate (Compound (E11))

A title compound (216 mg) was obtained using the same method as in Example 7(2) and (3) and using the compound (410 mg) obtained in Example 11(1) instead of the compound obtained in Example 7(1). ESI-MS:842.4 ([M+Na]$^+$)

Example 12

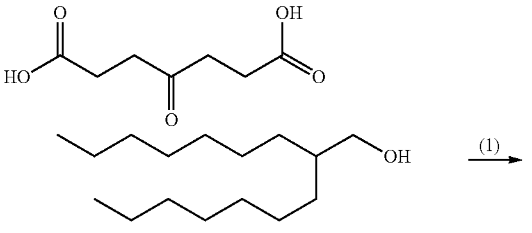

-continued

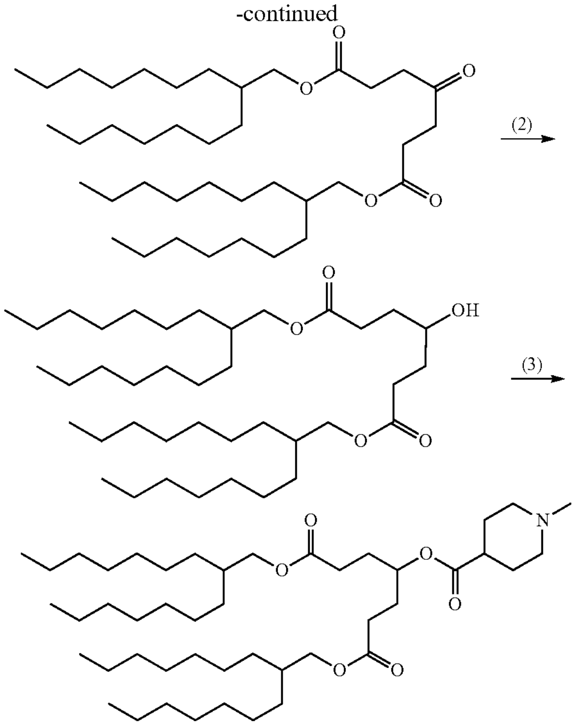

(1) Synthesis of Bis(2-heptylnonyl) 4-oxoheptanedioate

A title compound (195 mg) was obtained as a crude product by the same method as in Example 3(1) using 2-heptylnonan-1-ol (522 mg) instead of 3-hexylundecan-1-ol.

(2) Synthesis of Bis(2-heptylnonyl) 4-hydroxyheptanedioate

A title compound (95 mg) was obtained by the same method as in Example 3(2) using the compound (195 mg) obtained in Example 12(1) instead of the compound obtained in Example 3(1).

(3) Synthesis of Bis(2-heptylnonyl) 4-((1-methylpiperidine-4-carbonyl)oxy)heptanedioate (Compound (E12))

A title compound (15.4 mg) was obtained by the same method as in Example 3(3) using the compound (15 mg) obtained in Example 12(2) instead of the compound obtained in Example 3(2). ESI:772.5 ([M+Na]$^+$)

Example 13

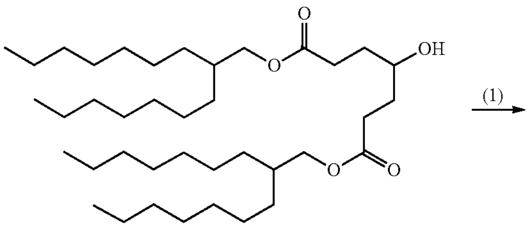

-continued

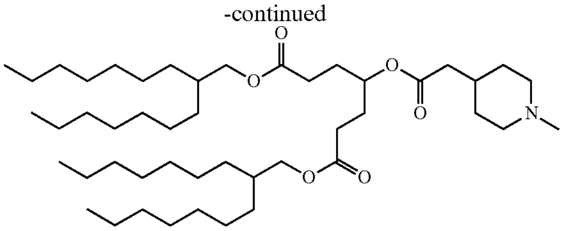

(1) Synthesis of Bis(2-heptylnonyl) 4-((1-methylpiperidin-4-yl)acetoxy)heptanedioate (Compound (E13))

A title compound (18.5 mg) was obtained using the same method as in Example 5(3) using the compound (15 mg) obtained in Example 12(2) as a raw material instead of the compound obtained in Example 5(2). ESI:1550.9 ([2M+Na]$^+$)

Example 14

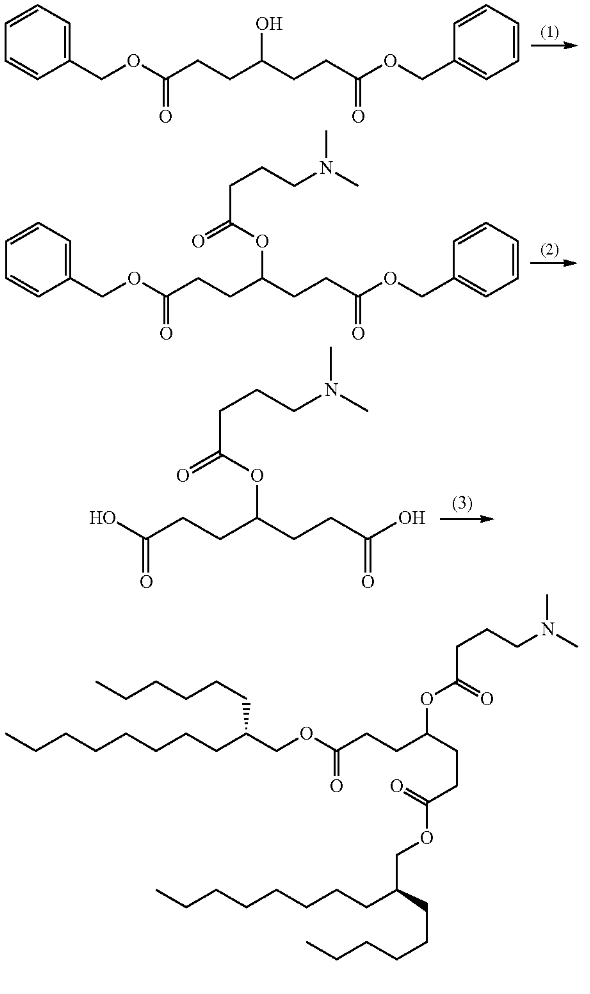

(1) Synthesis of Dibenzyl 4-((4-dimethylamino)butanoyl)oxy)heptanedioate

The compound (700 mg) obtained in Example 9-1(2), 4-(dimethylamino)butyric acid hydrochloride (494 mg), and DMAP (120 mg) were added to DMF (7.6 mL), EDCI (527 mg) was added at room temperature, and the components were stirred at room temperature for 18 hours. Ethyl acetate (50 mL) and water (20 mL) were added to a mixture, and an aqueous layer was extracted with acetic acid three times. Combined organic layers were dried over anhydrous sodium sulfate, filtered, and then concentrated under reduced pressure. A residue was purified by silica gel column chromatography (DCM/methanol), and a title compound (758 mg) was obtained.

(2) Synthesis of 4-((4-(Dimethylamino)butanoyl)oxy)heptanedioic acid

The compound (223 mg) obtained in Example 14(1) was added to methanol (120 mL) and reduced with H-Cube (registered trademark) (10% palladium on carbon, Full $H_2$, 0-3 Bar), an obtained solution was concentrated under reduced pressure, and a title compound (116 mg) was obtained.

(3) Synthesis of Bis((S)-2-hexyldecyl) 4-((4-dimethylamino)butanoyl)oxy)heptanedioate (Compound (E14))

The compound (115 mg) obtained in Example 14(2), the compound (202 mg) obtained in Example 9-2(4), and DMAP (24 mg) were added to DMF (1.5 mL), EDCI (190 mg) was added, and the components were stirred for 17 hours. A mixture was concentrated under reduced pressure, a residue was purified by silica gel column chromatography (diethyl ether/methanol), and a title compound (141 mg) was obtained. ESI-MS:738.8 ([M+H]$^+$)

Example 15

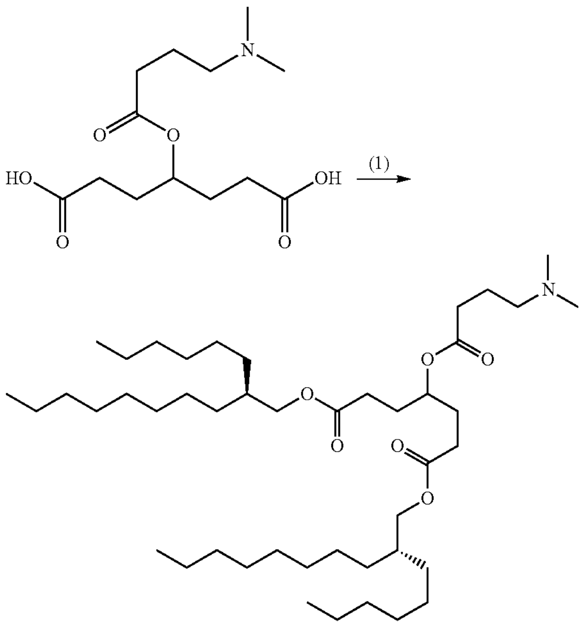

(1) Synthesis of Bis((R)-2-hexyldecyl) 4-((4-(dimethylamino)butanoyl)oxy) heptanedioate (Compound (E15))

The compound (135 mg) obtained in Example 14(2), (R)-2-hexyldecan-1-ol (238 mg), and DMAP (28.5 mg) were added to DMF (1.8 mL), EDCI (224 mg) was added, and the components were stirred for 17 hours. A mixture was purified by silica gel column chromatography (MTBE/methanol), and a title compound (220 mg) was obtained. ESI-MS:738.8 ($[M+H]^+$)

Example 16

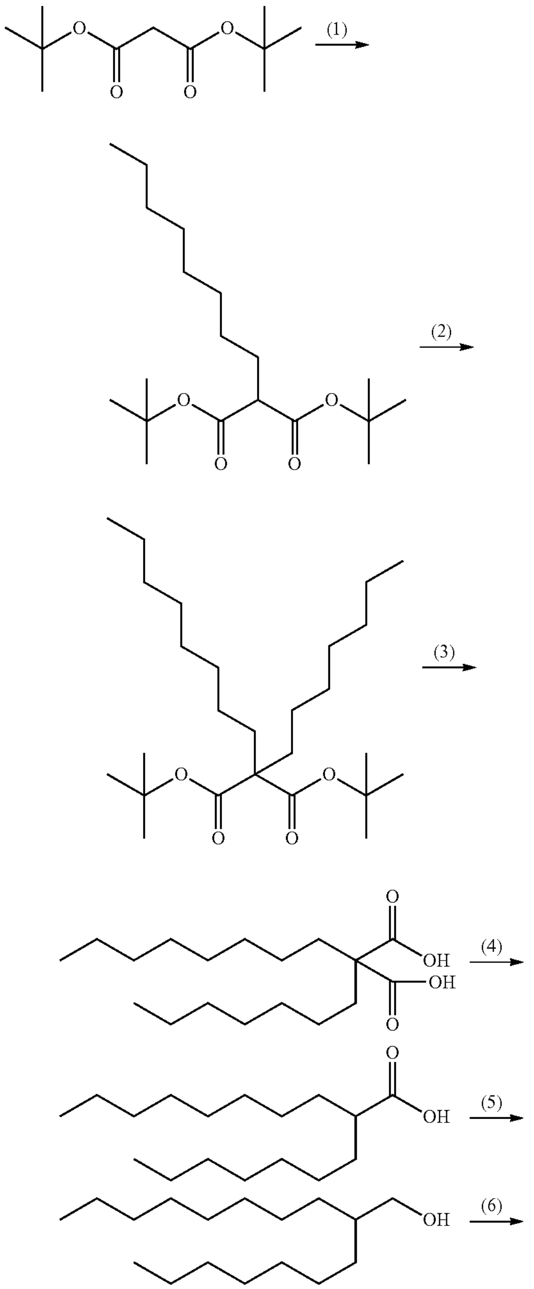

-continued

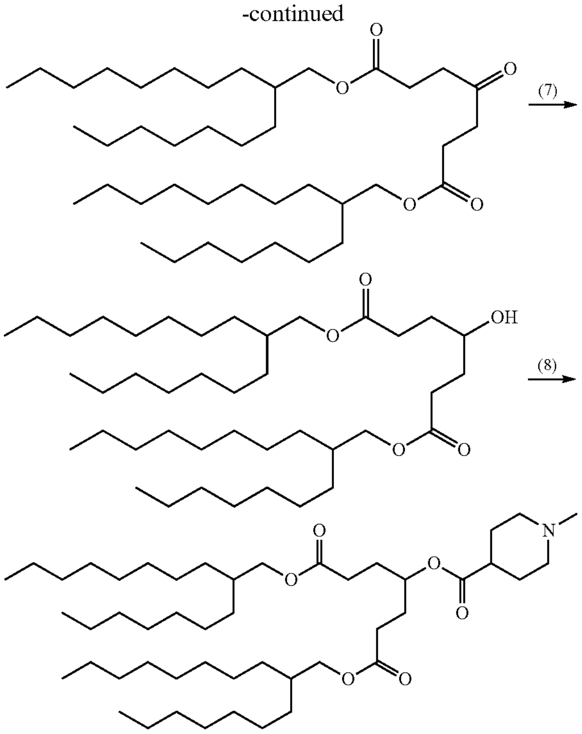

(1) Synthesis of di-tert-Butyl 2-octylmalonate

A title compound (1.20 g) was obtained by the same method as in Example 18(1) to be described below.

(2) Synthesis of di-tert-Butyl 2-heptyl-2-octylmalonate

A title compound (1.11 g) was obtained by the same method as in Example 18(2) to be described below using 1-bromoheptane (1.19 g) instead of 1-bromo-5-methylhexane. ESI-MS:449.2 ($[M+Na]^+$)

(3) Synthesis of 2-Heptyl-2-octylmalonic acid

A title compound (0.80 g) was obtained by the same method as in Example 18(3) to be described below using the compound (1.10 g) obtained in Example 16(2) instead of a compound obtained in Example 18(2) to be described below. ESI-MS:313.1 ($[M-H]^-$)

(4) Synthesis of 2-Heptyldecanoic acid

A title compound (0.58 g) was obtained by the same method as in Example 18(4) using the compound (0.80 g) obtained in Example 16(3) instead of the compound obtained in Example 18(3).

(5) Synthesis of 2-Heptyldecan-1-ol

A title compound (0.56 g) was obtained by the same method as in Example 18(5) using the compound (0.58 g) obtained in Example 16(4) instead of the compound obtained in Example 18(4).

(6) Synthesis of Bis(2-heptyldecyl) 4-oxoheptanedioate

A title compound (500 mg) was obtained by the same method as in Example 3(1) using the compound (589 mg)

obtained in Example 16(5) instead of 3-hexylundecan-1-ol. The title compound contained 2-heptyldecan-1-ol, which was a raw material, but no further purification was performed, and the next reaction was used.

(7) Synthesis of Bis(2-heptyldecyl) 4-hydroxyheptanedioate

A title compound (260 mg) was obtained by the same method as in Example 3(2) using the compound (500 mg) obtained in Example 16(6) instead of the compound obtained in Example 3(1).

(8) Synthesis of Bis(2-heptyldecyl) 4-((1-methylpiperidine-4-carbonyl)oxy)heptanedioate (Compound (E16))

A title compound (6.62 mg) was obtained by the same method as in Example 3(3) using the compound (40 mg) obtained in Example 16(7) instead of the compound obtained in Example 3(2). ESI-MS:779.4 ([M+H]$^+$)[0164] [Example 17]

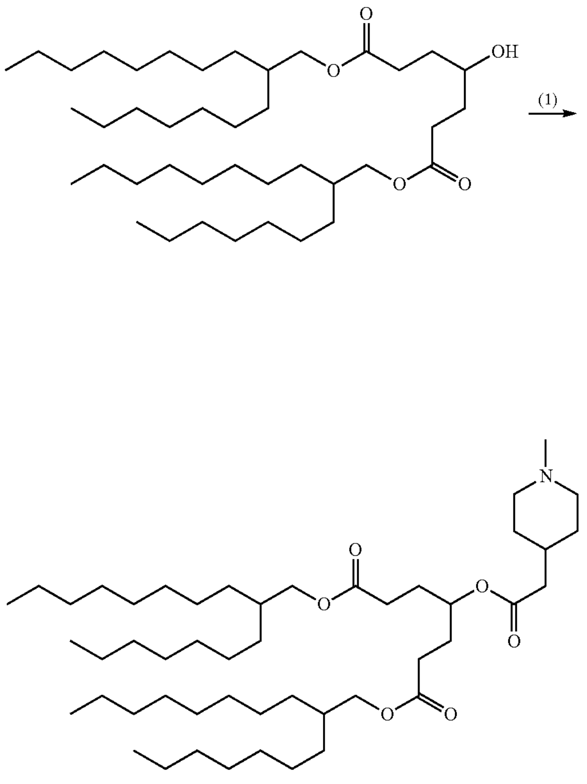

(1) Synthesis of Bis(2-heptyldecyl) 4-(2-(1-methylpiperidin-4-yl)acetoxy)heptanedioate (Compound (E17))

A title compound (13.8 mg) was obtained by the same method as in Example 5(3) using the compound (40 mg) obtained in Example 16(7) instead of the compound obtained in Example 5(2). ESI-MS:814.7 ([M+Na]$^+$)

Example 18

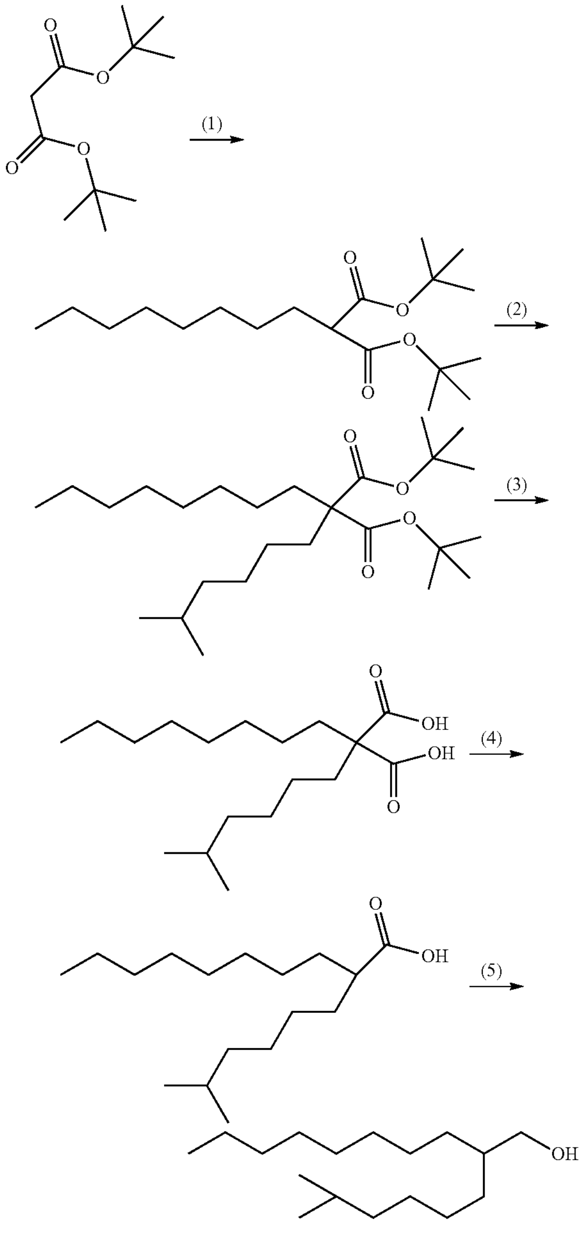

(1) Synthesis of di-tert-Butyl 2-octylmalonate

Sodium hydride (60%, 911 mg) was added to DMF (70 mL) and a DMF (20 mL) solution of di-tert-butyl malonate (5.38 g) was added at 0° C. A mixture was stirred at 0° C. for 30 minutes, and a DMF (10 mL) solution of sodium iodide (3.10 g) and 1-bromooctane (3.60 mL) was added. The mixture was stirred at 0° C. for 30 minutes and then stirred at room temperature for four hours. The mixture was cooled to 0° C., and a saturated ammonium chloride aqueous solution (50 mL) was then added. Furthermore, the mixture was diluted with ethyl acetate (100 mL) and water (50 mL). An aqueous layer was extracted with ethyl acetate, and combined organic layers were washed with water and a saturated saline solution, dried over anhydrous sodium sulfate, filtered, and then concentrated under reduced pressure. A residue was purified by silica gel column chromatography (n-heptane/ethyl acetate) twice, and a title compound (3.70 g) was obtained.

(2) Synthesis of di-tert-Butyl 2-(5-methylhexyl)-2-octylmalonate

Sodium hydride (60%, 308 mg) was added to DMF (70 mL) and a DMF (20 mL) solution of the compound (2.30 g) obtained in Example 18(1) was added dropwise at 0° C. A mixture was stirred at 0° C. for 30 minutes, and a DMF (10 mL) solution of sodium iodide (1.05 g) and 1-bromo-5-methylhexane (1.38 g) was added. The mixture was stirred at 0° C. for 30 minutes and then stirred at room temperature for four hours. The mixture was cooled to 0° C. and a saturated ammonium chloride aqueous solution (50 mL) was then added. The mixture was further diluted with ethyl acetate (100 mL) and water (50 mL). An aqueous layer was extracted with ethyl acetate, and combined organic layers were washed with water and a saturated saline solution, dried over anhydrous sodium sulfate, filtered, and then concentrated under reduced pressure. A residue was purified by silica gel column chromatography (n-heptane/ethyl acetate) twice, and a title compound (2.29 g) was obtained.

(3) Synthesis of 2-(5-Methylhexyl)-2-octylmalonic acid

4M HCl (1,4-dioxane solution, 30 mL) was added to the compound (2.29 g) obtained in Example 18(2), stirred at room temperature for 16 hours, and then concentrated under reduced pressure to obtain a title compound (2.71 g) as a crude product.

(4) Synthesis of 2-(5-Methylhexyl)decanoic acid

Ortho-xylene (30 mL) was added to the compound (2.71 g) obtained in Example 18(3) and stirred at 160° C. for three hours. A mixture was concentrated under reduced pressure to obtain a title compound (1.62 g).

(5) Synthesis of 2-(5-Methylhexyl)decan-1-ol

THF (20 mL) was added to the compound (1.62 g) obtained in Example 18(4), lithium aluminum hydride (1.0 M THF solution, 11.9 mL) was added at 0° C., the components were stirred at 0° C. for four hours and then stirred at room temperature for two hours. A mixture was cooled to 0° C., ethyl acetate (10 mL) was then added, water (0.45 mL), a 15% sodium hydroxide aqueous solution (0.48 mL), and water (1.35 mL) were added in order, the components were stirred at room temperature for 10 minutes, a generated precipitate was filtered with CELITE, and an obtained solution was concentrated under reduced pressure. A residue was purified by silica gel column chromatography (n-heptane/ethyl acetate), and a title compound (994 mg) was obtained.

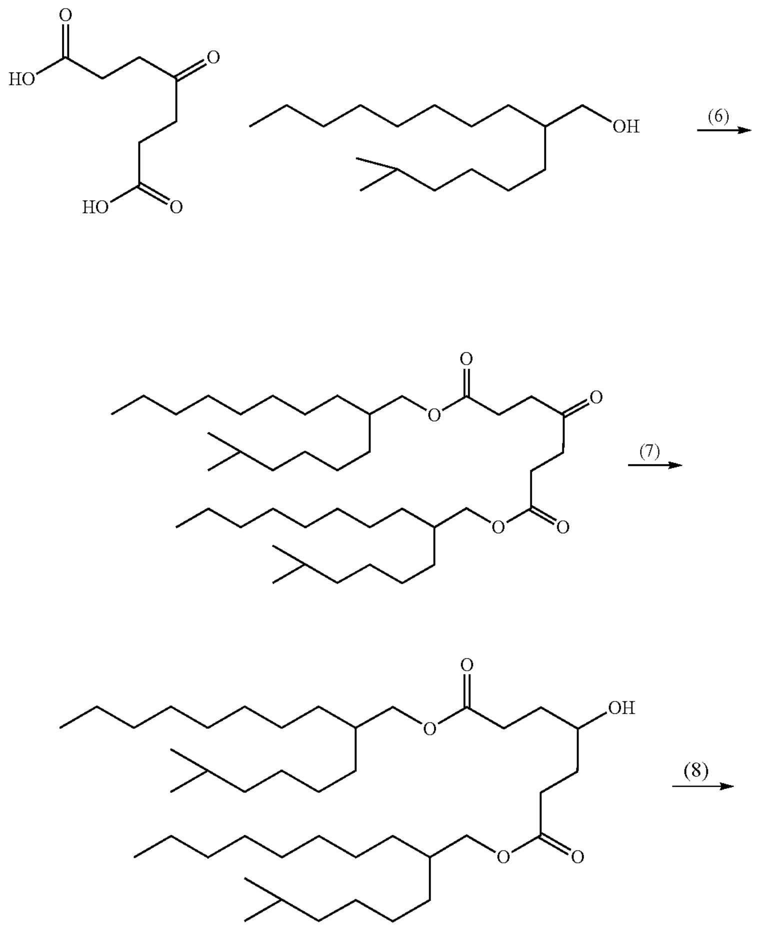

-continued

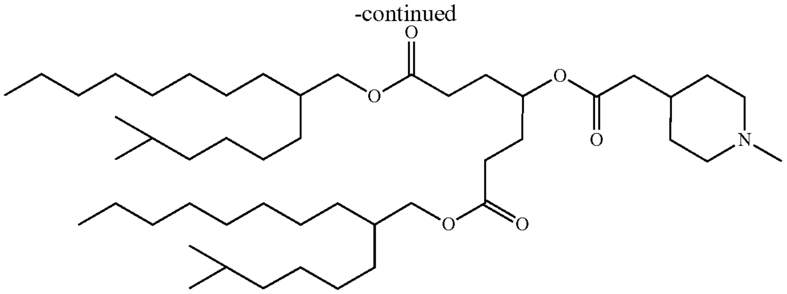

(6) Synthesis of Bis(2-(5-methylhexyl)decyl) 4-oxoheptanedioate

A title compound (241 mg) was obtained as a crude product by the same method as in Example 3(1) using the compound obtained in Example 18(5) instead of 3-hexylundecan-1-ol.

(7) Synthesis of Bis(2-(5-methylhexyl)decyl) 4-hydroxyheptanedioate

A title compound (34 mg) was obtained by the same method as in Example 3(2) using the compound (241 mg) obtained in Example 18(6) as a raw material instead of the compound obtained in Example 3(1).

(8) Synthesis of Bis(2-(5-methylhexyl)decyl) 4-(2-(1-methylpiperidin-4-yl)acetoxy)heptanedioate (Compound (E18))

A title compound (10.2 mg) was obtained by the same method as in Example 5(3) using the compound (13 mg) obtained in Example 18(7) instead of the compound obtained in Example 5(2). ESI-MS:792.9 ([M+H]+)

Example 19

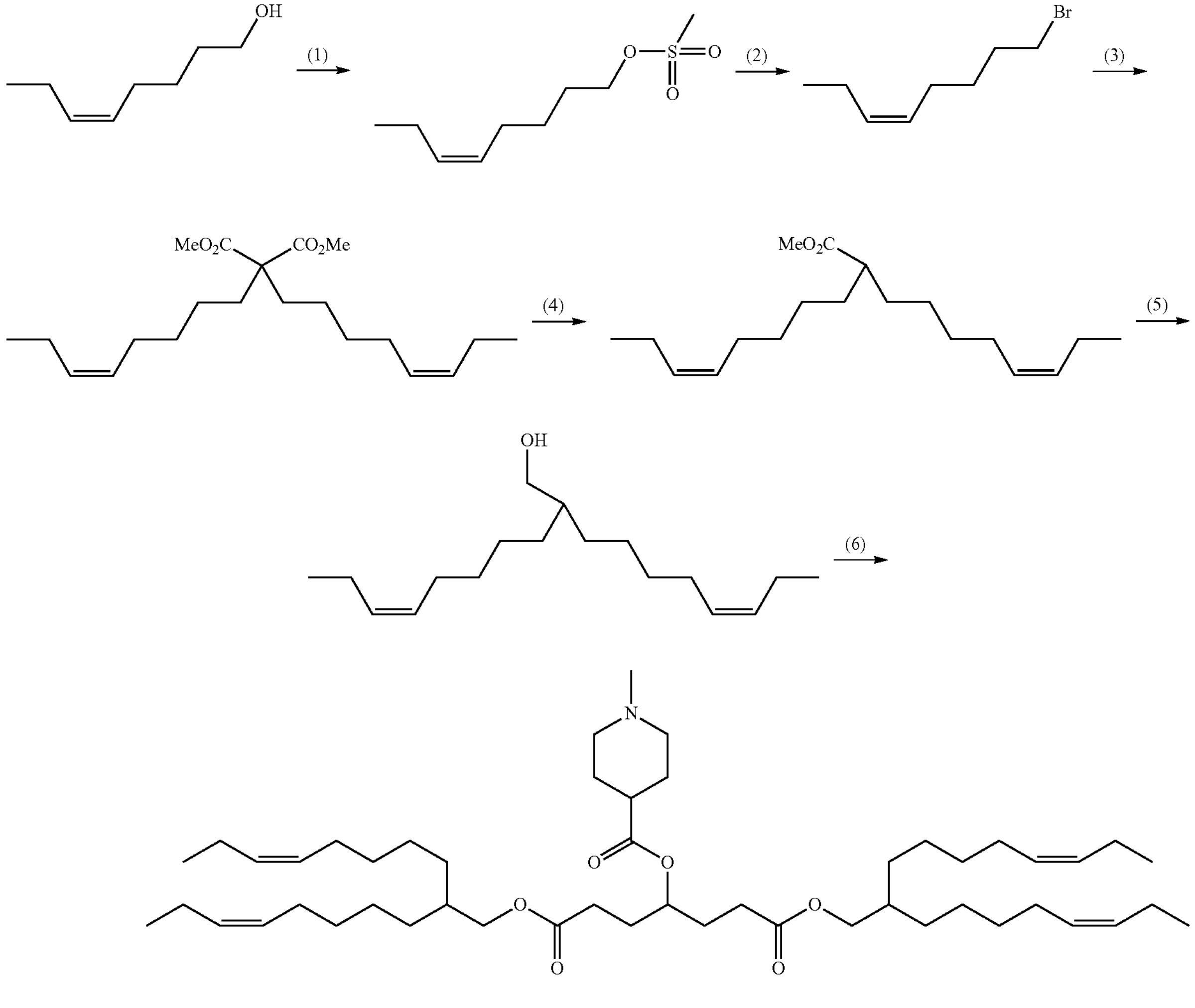

(1) Synthesis of (Z)-Oct-5-en-1-yl methanesulfonate (Z)-Oct-5-en-1-ol (4.46 g) and triethylamine (7.28 mL) were added to DCM (50 mL), and methanesulfonic chloride (3.25 mL) was added at 3° C. over four minutes. A mixture was stirred at 3° C. for 15 minutes and then stirred at room temperature for 105 minutes. Ethyl acetate (200 mL) was added to the mixture, and the mixture was washed with a mixture of water (100 mL) and a saturated saline solution (10 mL). An aqueous layer was extracted with ethyl acetate (100 mL), combined organic layers were washed with a saturated saline solution (100 mL) and then dried over sodium sulfate, a solid was removed by filtration, the organic layers were dried under reduced pressure, and a title compound (7.03 g) was obtained.

(2) Synthesis of (Z)-8-Bromooct-3-ene

Anhydrous THF (140 mL) was added to the compound (7.03 g) obtained in Example 19(1), tetra-n-butylammonium bromide (13.18 g) was added under a nitrogen atmosphere, and a mixture was heating-refluxed at 80° C. under a nitrogen atmosphere for one hour. The mixture was washed away under reduced pressure, and a residue was diluted with water (75 mL) and then extracted with cyclohexane (75 mL) twice. An organic layer was washed with a saturated saline solution (50 mL), dried over sodium sulfate, filtered, and then concentrated under reduced pressure, and a title compound (5.58 g) was obtained.

(3) Synthesis of Dimethyl 2,2-di((Z)-oct-5-en-1-yl) malonate

Anhydrous THF (15 mL) was added to dimethyl malonate (0.439 mL), sodium hydride (60%, 382 mg) was added under a nitrogen atmosphere and stirred for 30 minutes, an anhydrous THF solution (2 mL, washed 1 mL) of the compound (1.83 g) obtained in Example 19(2) was added and stirred at room temperature for 44 and a half hours, sodium iodide (57.3 mg) was added, and a mixture was heating-refluxed at 70° C. for three days. The mixture was cooled to room temperature, water (20 mL) was added, and extraction with ethyl acetate (25 mL) was performed twice. Combined organic layers were washed with a saturated saline solution (20 mL), dried over sodium sulfate, filtered, and then concentrated under reduced pressure. A residue was purified by silica gel column chromatography (cyclohexane/ethyl acetate), and a title compound (704 mg) was obtained.

(4) Synthesis of Methyl (Z)-2-((Z)-oct-5-en-1-yl) dec-7-enoate

Anhydrous DMF (2 mL) was added to the compound (66 mg) obtained in Example 19(3) and lithium chloride (80 mg), and the components were heated at 120° C. under a nitrogen atmosphere for 18 hours. Water (20 mL) and a saturated saline solution (5 mL) were added to the mixture, extraction was performed with ethyl acetate (20 mL) twice, and combined organic layers were then washed with a saturated saline solution (20 mL), dried over sodium sulfate, filtered, and then concentrated under reduced pressure. A residue was purified by silica gel column chromatography (cyclohexane/ethyl acetate), and a title compound (45.7 mg) was obtained.

(5) Synthesis of (Z)-2-((Z)-oct-5-en-1-yl)dec-7-en-1-ol

Anhydrous THF (1 mL) was added to the compound (42.5 mg) obtained in Example 19(4), and lithium aluminum hydride (2M THF solution, 0.144 mL) was added at room temperature under a nitrogen atmosphere. A mixture was stirred at 70° C. for two hours and cooled to room temperature, sodium sulfate decahydrate (93 mg) was then added, and the components were stirred for 37 minutes. A mixture was diluted with ethyl acetate, and a solid was removed by filtration. The solid was washed with ethyl acetate, combined organic layers were concentrated under reduced pressure, a residue was purified by silica gel column chromatography (cyclohexane/ethyl acetate), and a title compound (29.1 mg) was obtained.

(6) Synthesis of Bis((Z)-2-((Z)-oct-5-en-1-yl)dec-7-en-1-yl) 4-((1-methylpiperidine-4-carbonyl)oxy) heptanedioate (Compound (E19))

A title compound (31 mg) was obtained by the same method as in Example 9-1(5) using the compound (42.7 mg) obtained in Example 19(5) as a raw material instead of the compound obtained in Example 9-2(4). ESI-MS:798.8 ([M+H]$^+$)

Example 20

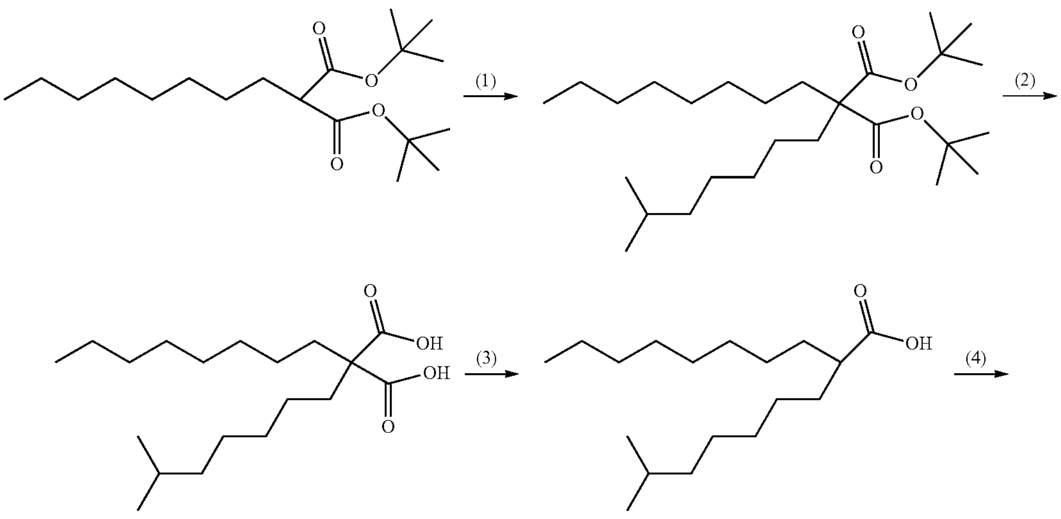

-continued

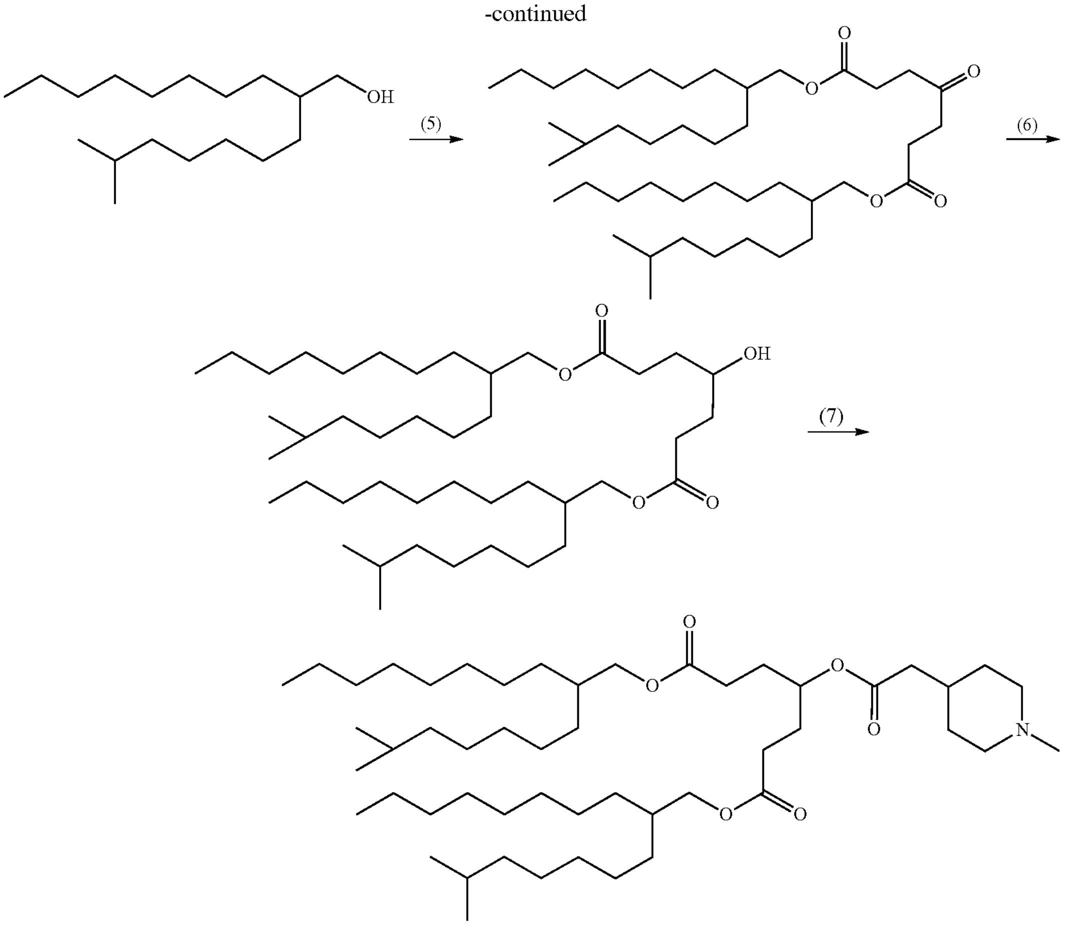

(1) Synthesis of di-tert-Butyl 2-(6-methylheptyl)-2-octylmalonate

A title compound (2.37 g) was obtained by the same method as in Example 18(2) using 1-bromo-6-methylheptane (1.29 g) as a raw material instead of 1-bromo-5-methylhexane.

(2) Synthesis of 2-(6-Methylheptyl)-2-octylmalonic acid

A title compound (2.45 g) was obtained as a crude product by the same method as in Example 18(3) using the compound (2.37 g) obtained in Example 20(1) instead of the compound obtained in Example 18(2) as raw material. ESI-MS:329.1 ([M+H]$^+$)

(3) Synthesis of 2-(6-Methylheptyl)decanoic acid

A title compound (1.67 g) was obtained by the same method as in Example 18(4) using the compound (2.45 g) obtained in Example 20(2) as a raw material instead of the compound obtained in Example 18(3).

(4) Synthesis of 2-(6-Methylheptyl)decan-1-ol

A title compound (1.15 g) was obtained by the same method as in Example 18(5) using the compound (1.67 g) obtained in Example 20(3) as a raw material instead of the compound obtained in Example 18(4).

(5) Synthesis of Bis(2-(6-methylheptyl)decyl) 4-oxoheptanedioate

A title compound (384 mg) was obtained as a crude product by the same method as in Example 18(6) using the compound (582 mg) obtained in Example 20(4) instead of the compound obtained in Example 18(5) as raw material.

(6) Synthesis of Bis(2-(6-methylheptyl)decyl) 4-hydroxyheptanedioate

A title compound (201 mg) was obtained by the same method as in Example 18(7) using the compound (384 mg) obtained in Example 20(5) as a raw material instead of the compound obtained in Example 18(6).

(7) Synthesis of Bis(2-(6-methylheptyl)decyl) 4-(2-(1-methylpiperidin-4-yl)acetoxy)heptanedioate (Compound (E20))

A title compound (10.2 mg) was obtained by the same method as in Example 18(8) using the compound (12 mg) obtained in Example 20(6) as a raw material instead of the compound obtained in Example 18(7). ESI-MS:820.9 ([M+H]$^+$)

Example 21

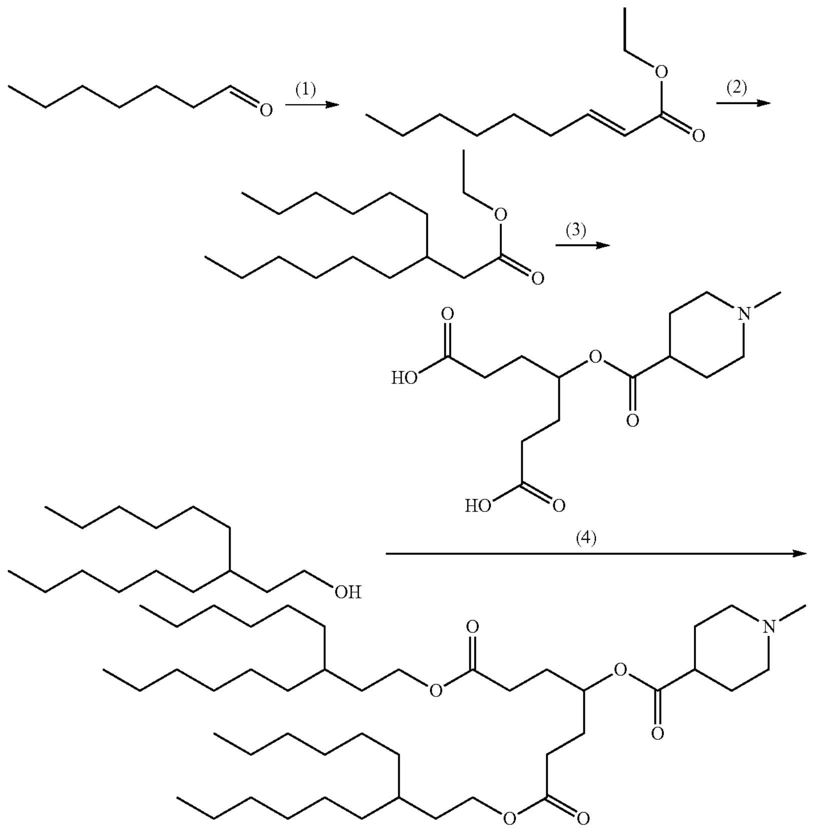

(1) Synthesis of Ethyl (E)-non-2-enoate

Sodium hydride (2.10 g) was added to THF (50 mL), ethyl 2-(diethoxyphosphoryl)acetate (13.74 g) was added, and the components were stirred for one hour. A THF solution (10 ml) of heptanal (6.09 ml) was added to a mixture over one hour, and the mixture was stirred for 16 hours. A saturated ammonium chloride aqueous solution (5 ml) and water (25 ml) were added to the mixture and stirred for five minutes, and ethyl acetate (100 ml) was then added. An aqueous layer was extracted with ethyl acetate (25 ml) twice and combined organic layers were then dried over anhydrous sodium sulfate. Filtration was performed, a filtrate was concentrated under reduced pressure, a residue was purified by silica gel column chromatography (cyclohexane/ether), and a title compound (4.65 g) was obtained.

(2) Synthesis of Ethyl 3-hexylnonanoate

Copper bromide (0.078 g) and lithium chloride (0.023 g) were added to THF (10 mL) and stirred at room temperature for 10 minutes. A mixture was cooled to 0° C., and the compound (1.0 g) obtained in Example 21(1) and trimethylsilyl chloride (0.832 ml) were added and stirred for 20 minutes. Hexylmagnesium bromide (2M diethyl ether solution, 3.26 ml) was added at the same temperature, and the components were stirred for one hour and warmed up to room temperature. A saturated ammonium chloride aqueous solution (10 mL) and water (20 mL) were added to the mixture, and extraction was then performed twice with diethyl ether (20 mL). Combined organic layers were dried over anhydrous sodium sulfate. Filtration was performed, a filtrate was concentrated under reduced pressure, a residue was purified by silica gel column chromatography (cyclohexane/ether), and a title compound (1.14 g) was obtained.

(3) Synthesis of 3-Hexylnonan-1-ol

The compound (1.14 g) obtained in Example 21(3) was dissolved in THF (20 mL), lithium aluminum hydride (2.0M THF solution, 6.32 mL) was added at 0° C., and the components were warmed up to room temperature and stirred for 16 hours. A mixture was cooled to 0° C., MTBE (20 mL) and water (0.5 mL) were then added and a 2N-sodium hydroxide aqueous solution (1 mL) and water (2 mL) were added in order. A generated solid was removed by CELITE filtration, and a filtrate was concentrated under reduced pressure. A residue was purified by silica gel column chromatography (cyclohexane/diethylether), and a title compound (671 mg) was obtained.

(4) Synthesis of Bis(3-hexylnonyl) 4-((1-methylpiperidine-4-carbonyl)oxy)heptanedioate (Compound (E21))

The compound (15 mg) obtained in Example 9-1(4) was added to DMF (1 mL), 3-hexylnonan-1-ol (56.9 mg), DMAP (3.04 mg), and EDCI (28.6 mg) were added and stirred at room temperature for 16 hours. MTBE (10 mL) and water (1 mL) were added to a mixture, and an organic layer was separated. The organic layer was concentrated under reduced pressure, a residue was purified by silica gel column chromatography (MTBE/methanol), and a title compound (12 mg) was obtained. ESI-MS:722.8 ([M+H]$^+$)

Example 22

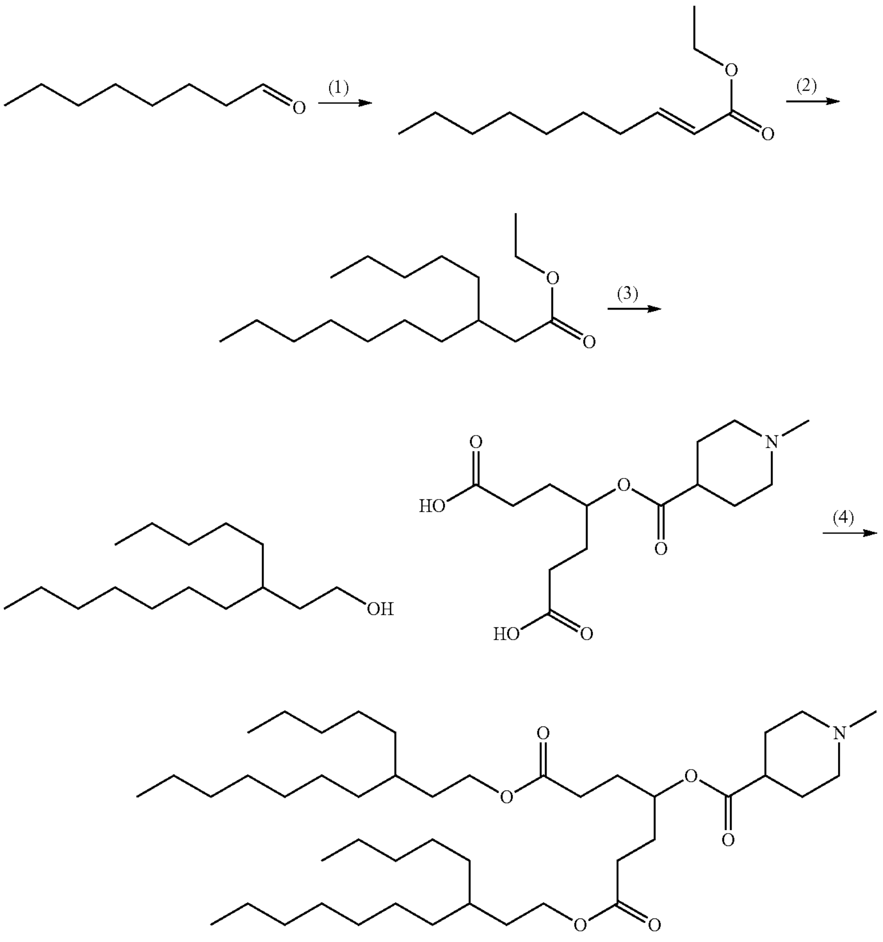

(1) Synthesis of Ethyl (E)-dec-2-enoate

A title compound (6.8 g) was obtained by the same method as in Example 21(1) using octanal (5 g) as a raw material instead of heptanal.

(2) Synthesis of Ethyl 3-pentyldecanoate

A title compound (1.08 g) was obtained by the same method as in Example 21(2) using the compound (1.0 g) obtained in Example 22(1) and pentyl magnesium bromide (2M diethyl ether solution, 3.03 ml) instead of the compound obtained in Example 21(1).

(3) Synthesis of 3-Pentyldecan-1-ol

A title compound (0.70 g) was obtained by the same method as in Example 21(3) using the compound (1.08 g) obtained in Example 22(2) instead of the compound obtained in Example 21(2).

(4) Synthesis of Bis(3-pentyldecyl) 4-((1-methylpiperidine-4-carbonyl)oxy)heptanedioate (Compound (E22))

A title compound (17.6 mg) was obtained by the same method as in Example 21(4) using the compound (56.9 mg) obtained in Example 22(3) instead of the compound obtained in Example 21(3). ESI-MS:722.8 ([M+H]$^+$)

Example 23

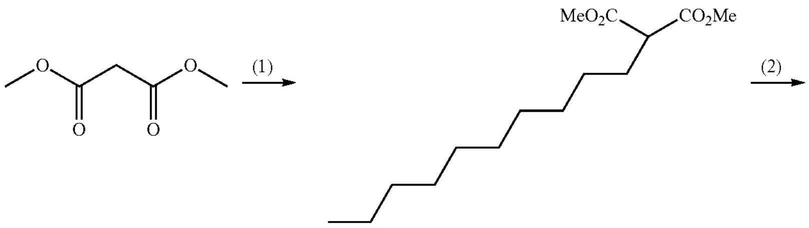

-continued

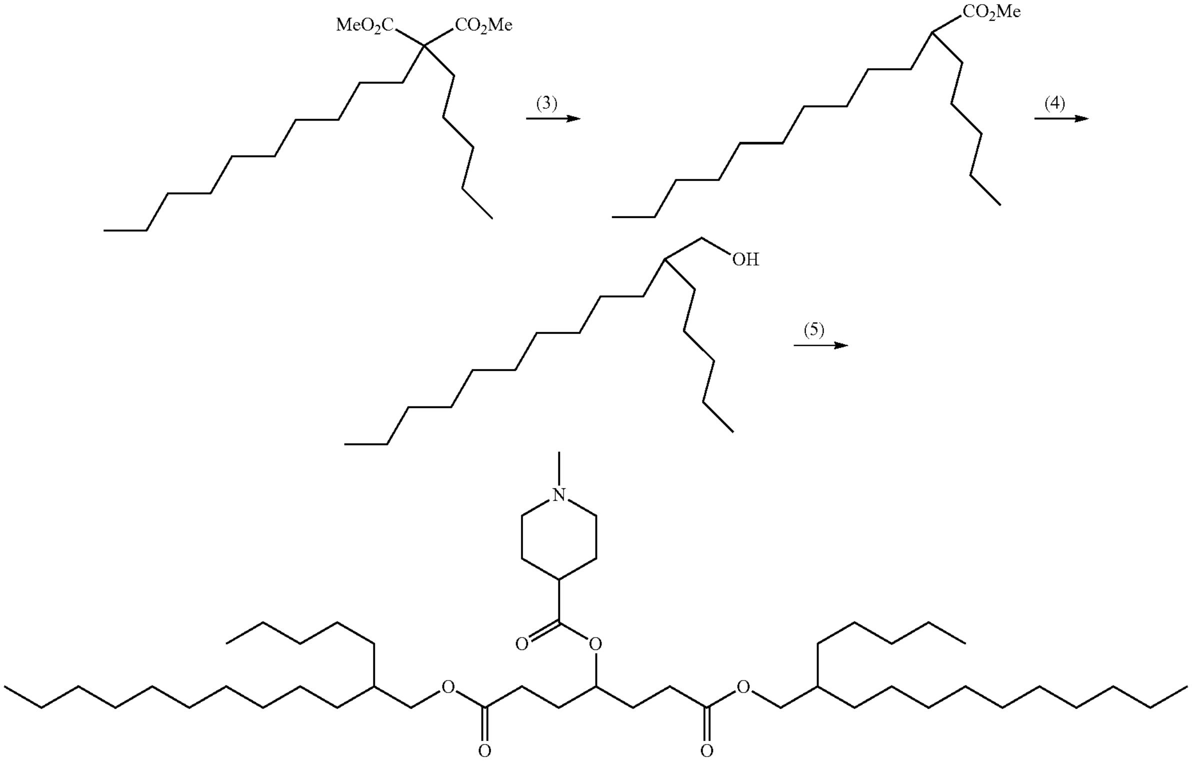

(1) Synthesis of Dimethyl 2-decylmalonate

Anhydrous THF (20 mL) was added to dimethyl malonate (1.00 g), sodium hydride (60%, 303 mg) was added at 3° C. under a nitrogen atmosphere, the components were stirred at room temperature for 37 minutes, 1-iododecane (1.62 mL) was added dropwise over four minutes and stirred at room temperature for 23 hours. Water (30 mL) and a saturated saline solution (5 mL) were added to a mixture, and extraction was performed with ethyl acetate (30 mL). An organic layer was washed with a saturated saline solution (30 mL), dried over sodium sulfate, filtered, and then concentrated under reduced pressure. A residue was purified by silica gel column chromatography (cyclohexane/ethyl acetate), and a title compound (1.48 g) was obtained.

(2) Synthesis of Dimethyl 2-decyl-2-pentylmalonate

Anhydrous THF (15 mL) was added to the compound (746 mg) obtained in Example 23(1), sodium hydride (60%, 164 mg) was added at 2° C. under a nitrogen atmosphere, the components were stirred at room temperature for 35 minutes, and 1-iodopentane (0.715 mL) was added dropwise over 3 minutes, and the components were stirred at room temperature for 17 and a half hours. Water (30 mL) and a saturated saline solution (5 mL) were added to a mixture, and extraction was performed with ethyl acetate (30 mL). An organic layer was washed with a saturated saline solution (30 mL), dried over sodium sulfate, filtered, and then concentrated under reduced pressure. A residue was purified by silica gel column chromatography (cyclohexane/ethyl acetate), and a title compound (561 mg) was obtained.

(3) Synthesis of Methyl 2-pentyldodecanoate

Anhydrous DMF (11 mL) was added to the compound (561 mg) obtained in Example 23(2) and lithium chloride (694 mg), and the components were heated at 120° C. under a nitrogen atmosphere for 43.5 hours. Water (100 mL) was added to a mixture, extraction was then performed with ethyl acetate (100 mL), an organic layer was then washed with a saturated saline solution (50 mL) and washed away under reduced pressure, a residue was purified by silica gel column chromatography (cyclohexane/ethyl acetate), and a title compound (398 mg) was obtained.

(4) Synthesis of 2-Pentyldodecan-1-ol

Anhydrous THF (8 mL) was added to the compound (395 mg) obtained in Example 23(3), and lithium aluminum hydride (2M THF solution, 1.39 mL) was added at room temperature under a nitrogen atmosphere. A mixture was stirred at 70° C. for two hours and cooled to room temperature, sodium sulfate decahydrate (894 mg) was added, and the components were stirred for 45 minutes. The mixture was diluted with ethyl acetate, and a solid was removed by filtration. The solid was washed with ethyl acetate, combined organic layers were concentrated under reduced pressure, a residue was purified by silica gel column chromatography (cyclohexane/ethyl acetate), and a title compound (347 mg) was obtained.

(5) Synthesis of Bis(2-pentyldodecyl) 4-((1-methylpiperidine-4-carbonyl)oxy)heptanedioate (Compound (E23))

A title compound (30.6 mg) was obtained by the same method as in Example 9-1(5) using the compound (41 mg) obtained in Example 23(4) as a raw material instead of the compound obtained in Example 9-2(5). ESI-MS:778.9 ([M+H]$^+$)

Example 24

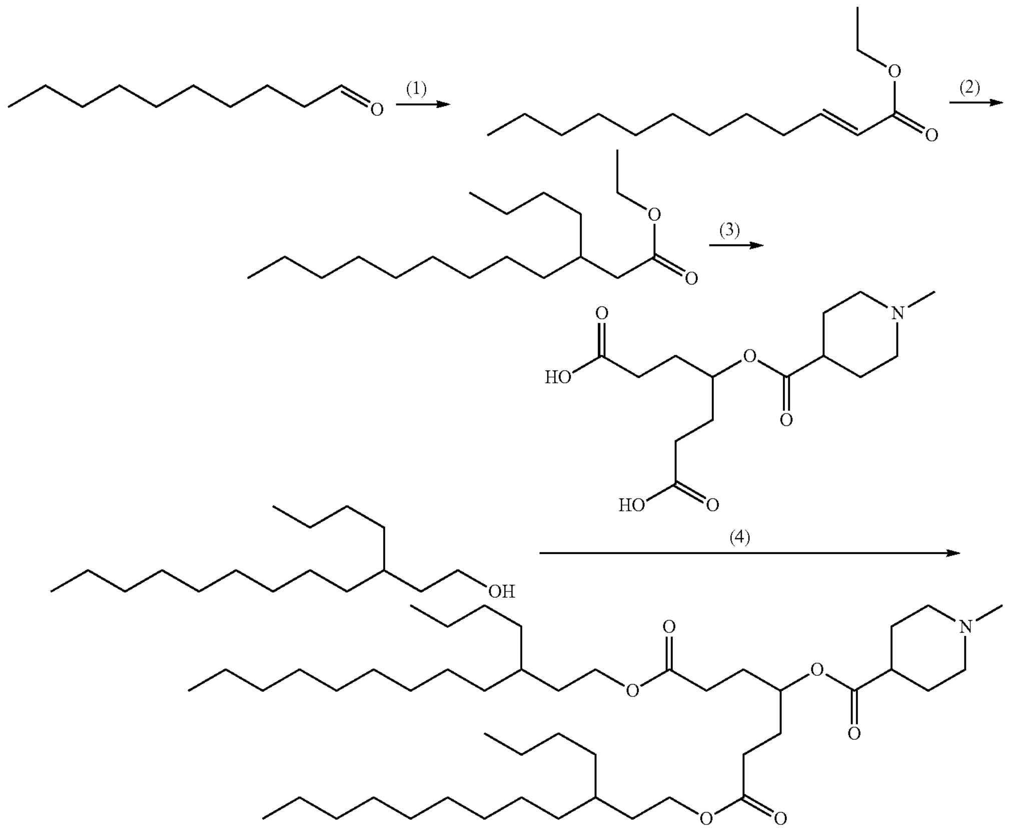

(1) Synthesis of Ethyl (E)-dodec-2-enoate

A title compound (5.7 g) was obtained by the same method as in Example 21(1) using decanal (5 g) a raw material instead of heptanal.

(2) Synthesis of Ethyl 3-butyldodecanoate

A title compound (1.01 g) was obtained by the same method as in Example 21(2) using the compound (1.0 g) obtained in Example 24(1) instead of the compound obtained in Example 21(1) and butylmagnesium bromide (2M THF solution, 2.65 ml) instead of hexylmagnesium bromide.

(3) Synthesis of 3-Butyldodecan-1-ol

A title compound (0.716 g) was obtained by the same method as in Example 21(3) using the compound (1.01 g) obtained in Example 24(2) instead of the compound obtained in Example 21(2).

(4) Synthesis of Bis(3-butyldodecyl) 4-((1-methylpiperidine-4-carbonyl)oxy)heptanedioate (Compound (E24))

A title compound (17.9 mg) was obtained by the same method as in Example 21(4) using the compound (60.3 mg) obtained in Example 24(3) instead of the compound obtained in Example 21(3). ESI-MS:750.9 ([M+H]$^+$)

Example 25

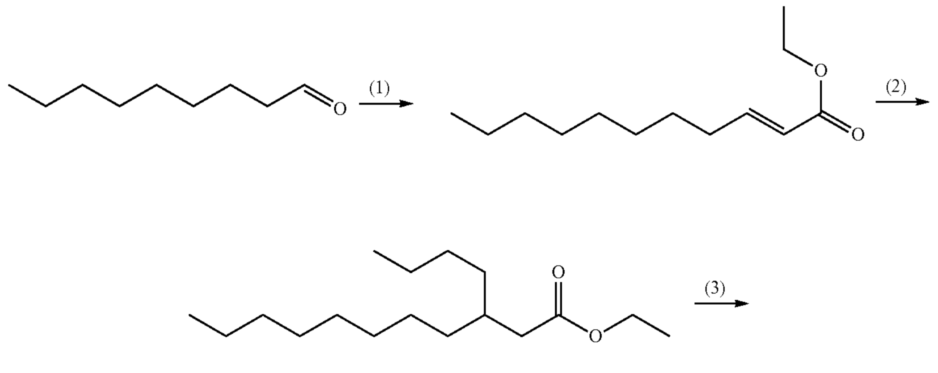

-continued

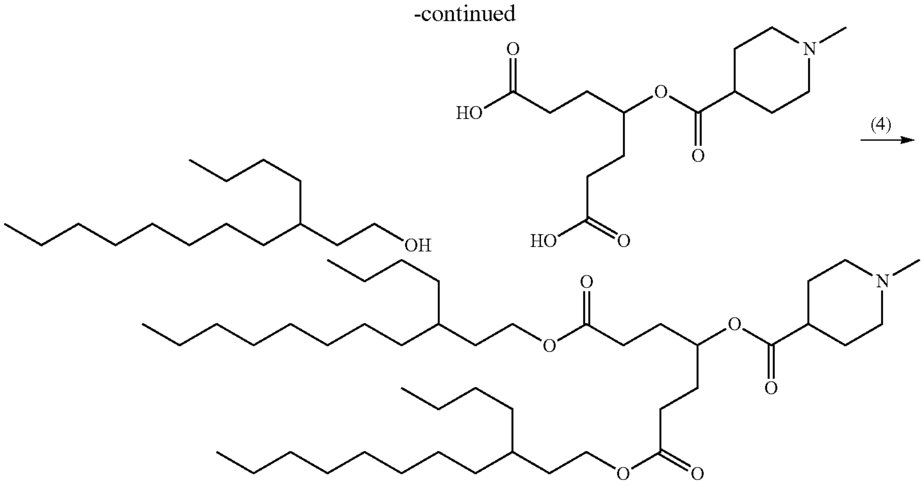

(1) Synthesis of Ethyl (E)-undec-2-enoate

THF (30 mL) was added to ethyl 2-(diethoxyphosphoryl) acetate (4.76 mL) and cooled to −78° C., n-BuLi (2.5M hexane solution, 9.6 mL) was then added, the components were stirred for 30 minutes, a THF (30 mL) solution of nonanal (3.44 mL) was added over one hour, and the components were stirred for 30 minutes. A saturated ammonium chloride aqueous solution (10 ml) was added to a mixture and warmed up to room temperature, water (10 ml) and ethyl acetate (50 mL) were then added, and phase separation was performed. An aqueous layer was extracted with ethyl acetate (50 ml), combined organic layers were washed with a saturated sodium bicarbonate aqueous solution (20 mL) and a saturated saline solution (10 mL), dried over sodium sulfate, and filtered, a filtrate was concentrated under reduced pressure, a residue was purified by silica gel column chromatography (cyclohexane/diethylether), and a title compound (1.55 g) was obtained.

(2) Synthesis of Ethyl 3-butylundecanoate

A title compound (610 mg) was obtained by the same method as in Example 21(2) using the compound (450 mg) obtained in Example 25(1) instead of the compound obtained in Example 21(1) and using butylmagnesium bromide (2M THF solution, 1.27 mL) instead of hexylmagnesium bromide.

(3) Synthesis of 3-Butylundecan-1-ol

A title compound (366 mg) was obtained by the same method as in Example 23(4) using the compound (600 mg) obtained in Example 25(2) instead of the compound obtained in Example 23(3).

(4) Synthesis of Bis(3-butylundecyl) 4-((1-methylpiperidine-4-carbonyl)oxy)heptanedioate (Compound (E25))

A title compound (16.7 mg) was obtained by the same method as in Example 9-1(5) using the compound (45.5 mg) obtained in Example 25(3) as a raw material instead of the compound obtained in Example 9-2(4). ESI-MS:722.9 ([M+H]$^+$)

Example 26

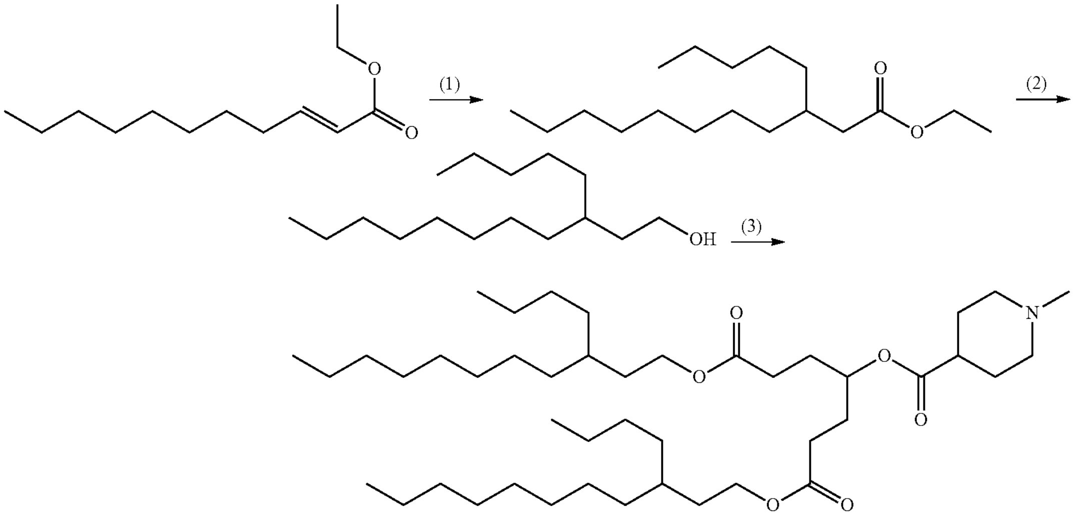

(1) Synthesis of Ethyl 3-pentylundecanoate

A title compound (610 mg) was obtained by the same method as in Example 25(2) using pentyl magnesium bromide (1.27 mL, 2M diethyl ether solution) instead of butyl magnesium bromide.

(2) Synthesis of 3-Pentylundecan-1-ol

A title compound (381 mg) was obtained by the same method as in Example 23(4) using the compound (600 mg) obtained in Example 26(1) instead of the compound obtained in Example 23(3).

(3) Synthesis of Bis(3-pentylundecyl) 4-((1-methylpiperidine-4-carbonyl)oxy)heptanedioate (Compound (E26))

A title compound (14.3 mg) was obtained by the same method as in Example 9-1(5) using the compound (48.3 mg) obtained in Example 26(2) as a raw material instead of the compound obtained in Example 9-2(4). ESI-MS:750.9 ([M+H]$^+$)

Example 27

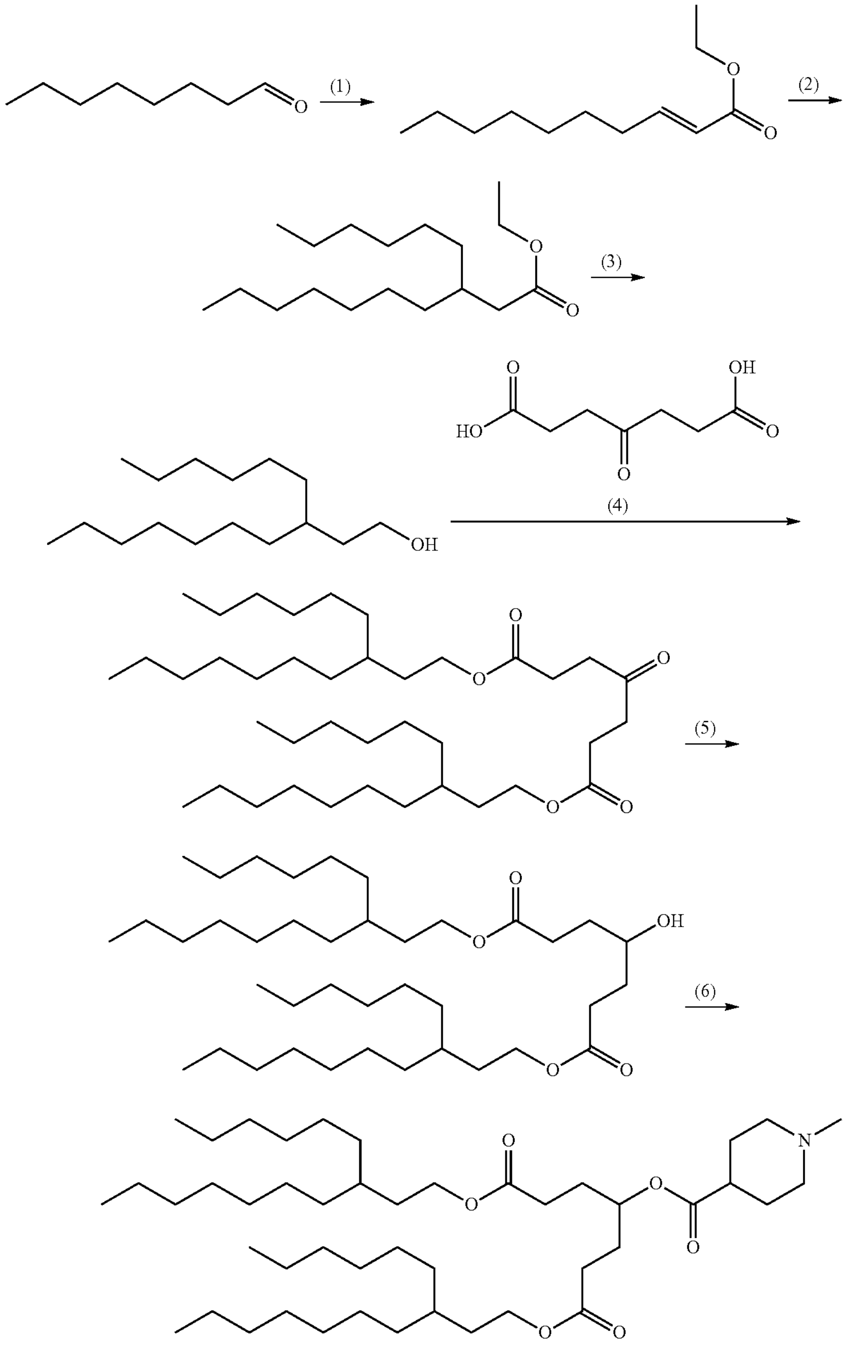

(1) Synthesis of Ethyl (E)-dec-2-enoate

A title compound (1.60 g) was obtained by the same method as in Example 21(1) using octanal (1.8 g) as a raw material instead of heptanal.

(2) Synthesis of Ethyl 3-hexyldecanoate

A title compound (770 mg) was obtained by the same method as in Example 21(2) using the compound (1000 mg) obtained in Example 27(1) instead of the compound obtained in Example 21(1). ESI-MS:285.2 ($[M+H]^+$)

(3) Synthesis of 3-Hexyldecan-1-ol

A title compound (390 mg) was obtained by the same method as in Example 21(3) using the compound (770 mg) obtained in Example 27(2) instead of the compound obtained in Example 21(2).

$^1$H NMR (400 MHz, $CDCl_3$) δ ppm 0.87 (s, 6H) 1.24 (s, 20H) 1.26-1.34 (m, 1H) 1.35-1.45 (m, 1H) 1.48-1.55 (m, 2H) 1.55-1.61 (m, 1H) 3.65 (s, 2H)

(4) Synthesis of Bis(3-hexyldecyl) 4-oxoheptanedioate

A title compound (130 mg) was obtained by the same method as in Example 3(1) using the compound (140 mg) obtained in Example 27(3) instead of 3-hexylundecan-1-ol.

(5) Synthesis of Bis(3-hexyldecyl) 4-hydroxyheptanedioate

A title compound (45 mg) was obtained by the same method as in Example 3(2) using the compound (130 mg) obtained in Example 27(4) instead of the compound obtained in Example 3(1). ESI-MS:625.2 ($[M+H]^+$)

(6) Synthesis of Bis(3-hexyldecyl) 4-((1-methylpiperidine-4-carbonyl)oxy)heptanedioate (Compound (E27))

A title compound (9.97 mg) was obtained by the same method as in Example 3(3) using the compound (15 mg) obtained in Example 27(5) instead of the compound obtained in Example 3(2). ESI-MS:750.5 ($[M+H]^+$)

Example 28

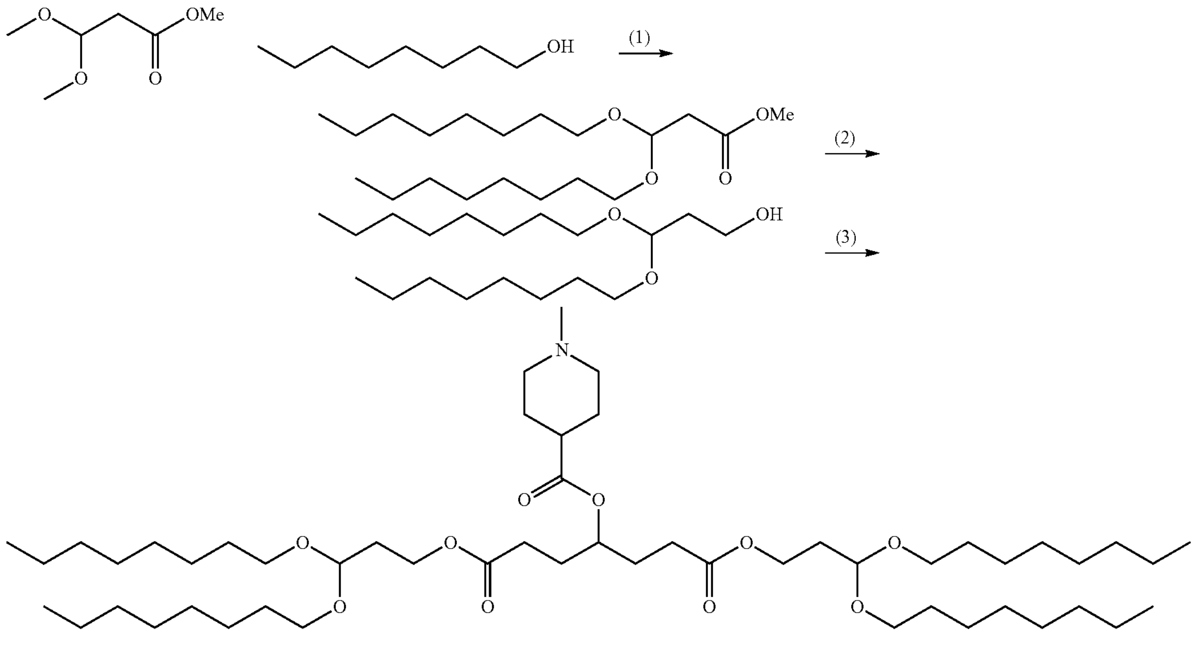

(1) Synthesis of Methyl 3,3-bis(octyloxy)propanoate

Octan-1-ol (1.59 mL) was added to methyl 3,3-dimethoxypropanoate (500 mg) and PPTS (42 mg) and stirred at 105° C. for four hours. A mixture was purified by silica gel column chromatography (cyclohexane/ethyl acetate), and a title compound (843 mg) was obtained as a crude product.

(2) Synthesis of 3,3-Bis(octyloxy)propan-1-ol

An anhydrous THF (4 mL) solution of the compound (851 mg) obtained in Example 28(1) was added to lithium aluminum hydride (1M THF solution, 2.96 mL) at −1° C. under a nitrogen atmosphere over two minutes. A mixture was stirred at room temperature for two and a half hours, sodium sulfate decahydrate (1 g) was then added, and the components were stirred for 30 minutes. A solid was removed by filtration from the mixture, and the solid was washed with THF (5 mL) four times. Combined organic layers were concentrated under reduced pressure, and a title compound (613 mg) was obtained.

(3) Synthesis of Bis(3,3-bis(octyloxy)propyl) 4-((1-methylpiperidine-4-carbonyl)oxy)heptanedioate (Compound (E28))

A title compound (26.5 mg) was obtained by the same method as in Example 9-1(5) using the compound (45.6 mg)

obtained in Example 28(2) as a raw material instead of the compound obtained in Example 9-2(4). ESI-MS:899.0 ([M+H]+)

Example 29

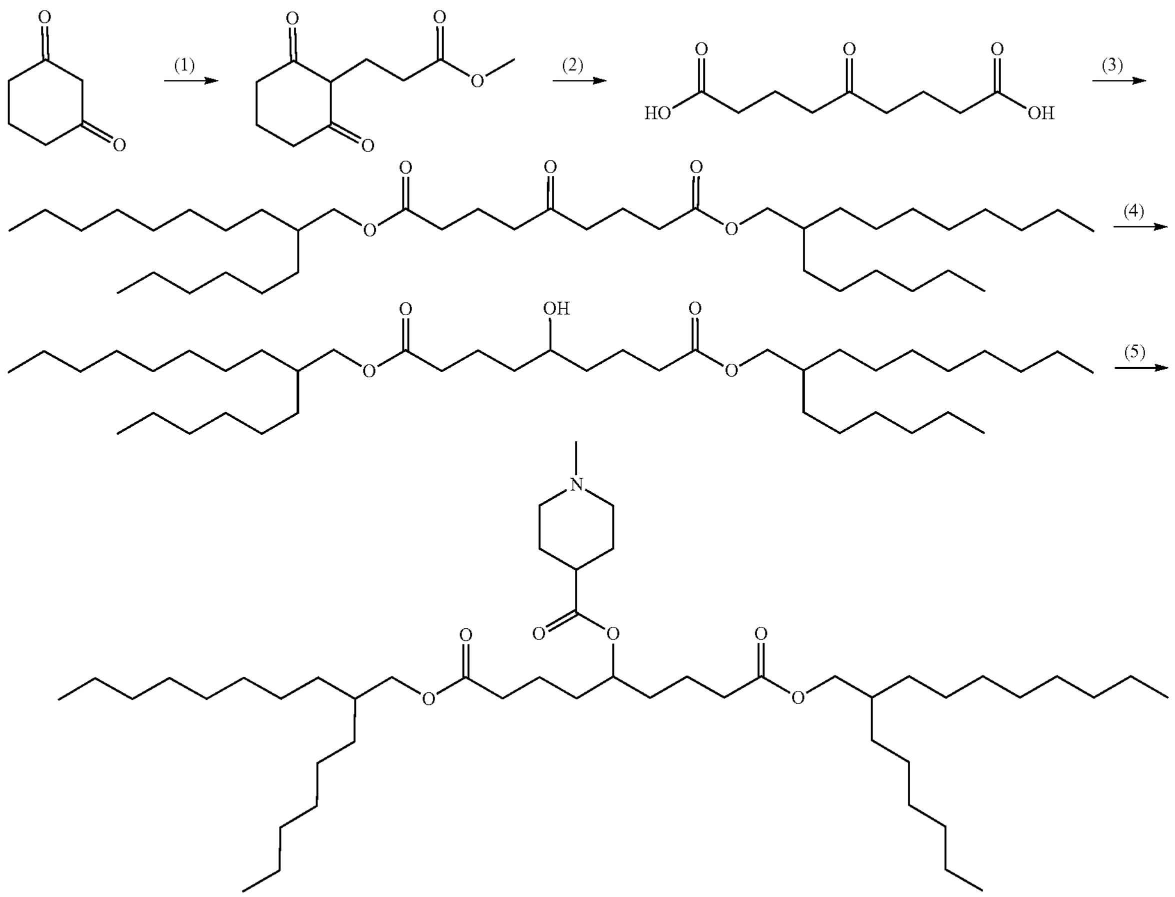

(3) Synthesis of Bis(2-hexyldecyl) 5-oxononanedioate

2-Hexyldecan-1-ol (5.38 mL) was added to the compound (150 mg) obtained in Example 29(2), sulfuric acid (20 μL) was further added, and the components were heated at 100° C. for 17 hours. A mixture was cooled to room temperature, then, diluted with cyclohexane (50 mL), washed with a saturated sodium bicarbonate aqueous solution (20 mL), water (10 mL), and a saturated saline solution (10 mL), dried over sodium sulfate, and distilled with a Kugelrohr (1 mbar, 190° C. to 220° C.) to obtain a title compound (278 mg).

(1) Synthesis of Methyl 3-(2,6-dioxocyclohexyl)propanoate

DMF (50 mL) was added to cyclohexane-1,3-dione (2.5 g), furthermore, methyl acrylate (2.43 mL) and cesium carbonate (4.36 g) were added, and the components were stirred at 75° C. for 20 hours. Methyl acrylate (2.43 mL) was further added to a mixture, the components were stirred at 75° C. for 17 hours, the mixture was then added to 150 mL of ice water, and the pH was adjusted to six with dilute hydrochloric acid. The mixture was extracted with ethyl acetate (250 mL) twice. Combined organic layers were washed twice with a saturated saline solution (250 mL), dried over magnesium sulfate, and filtered, a filtrate was concentrated under reduced pressure, a residue was purified by silica gel column chromatography (cyclohexane/ethyl acetate), and a title compound (1.35 g) was obtained.

(2) Synthesis of 5-Oxononanedioic Acid

10% Hydrochloric acid (40 mL) was added to the compound (1.35 g) obtained in Example 29(1), and the compound was heating-refluxed for 17 hours. A mixture was concentrated under reduced pressure, and a title compound (1.44 g) was obtained.

(4) Synthesis of Bis(2-hexyldecyl) 5-hydroxynonanedioate

Diethyl ether (3 mL) and methanol (0.9 mL) were added to the compound (189 mg) obtained in Example 29(3), sodium borohydride (11.5 mg) was added at −20° C., and the components were stirred for one hour. A mixture was diluted with diethyl ether (10 mL), and a saturated ammonium chloride aqueous solution (2 mL) was added. An aqueous layer was extracted with diethyl ether (5 mL) twice, combined organic layers were dried over sodium sulfate and filtered, a filtrate was concentrated under reduced pressure, a residue was purified by silica gel column chromatography (cyclohexane/diethyl ether), and a title compound (98 mg) was obtained.

(5) Synthesis of Bis(2-hexyldecyl) 5-((1-methylpiperidine-4-carbonyl)oxy)nonanedioate (Compound (E29))

DMF (0.5 mL) was added to the compound (32.2 mg) obtained in Example 29(4), 1-methylpiperidine-4-carboxylic acid (17.7 mg), and DMAP (3 mg), EDCI (22.7 mg) was added at room temperature, and the components were stirred for 18 hours. A mixture was concentrated under reduced pressure, a residue was purified by silica gel column chromatography (MTBE/methanol), and a title compound (18.3 mg) was obtained. ESI-MS:779.0 ([M+H]$^+$)

Example 30

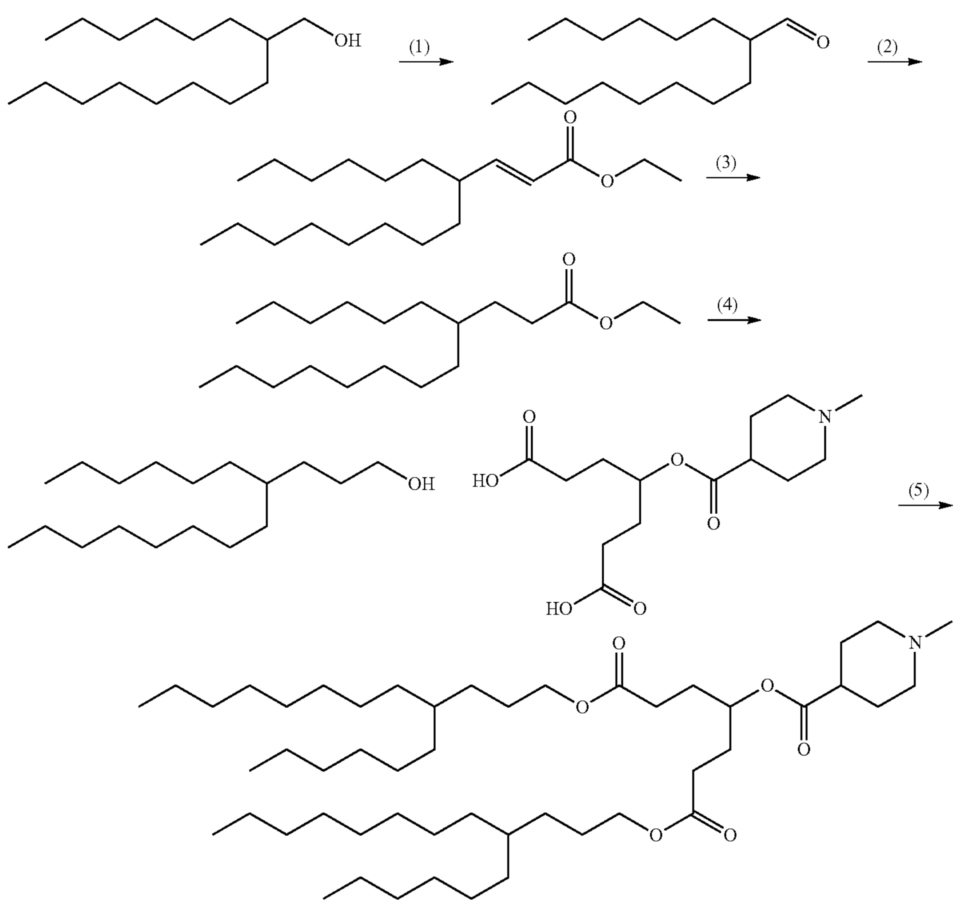

(1) Synthesis of 2-Hexyldecanal

2-Hexyldecan-1-ol (4.5 g) was added to DCM (100 mL), DMP (9.84 g) was added, and the components were stirred for two hours. A saturated sodium bicarbonate aqueous solution (10 mL) and a saturated sodium thiosulfate solution (10 mL) were added, and a mixture was stirred for one hour. DCM (50 ml) was added to the mixture, filtration was performed, a filtrate was concentrated under reduced pressure, and a title compound (4.0 g) was obtained.

(2) Synthesis of Ethyl (E)-4-Hexyldodec-2-enoate

Sodium hydride (60%, 0.798 g) was added to THF (50 mL), ethyl 2-(diethoxyphosphoryl)acetate (5.22 g) was added, and the components were stirred for one hour. A THF solution (10 ml) of the compound (4 g) obtained as in Example 30(1) was added, and the components were then stirred for 16 hours. A saturated ammonium chloride aqueous solution (5 ml) and water (25 ml) were added, the components were stirred for five minutes, and ethyl acetate (100 ml) was then added. An aqueous layer was extracted with ethyl acetate (25 ml) twice, and combined organic phases were dried over anhydrous sodium sulfate. Filtration was performed, a filtrate was concentrated under reduced pressure, a residue was purified by silica gel column chromatography (cyclohexane/diethylether), and a title compound (4.0 g) was obtained.

(3) Synthesis of Ethyl 4-hexyldodecanoate

The compound (1.0 g) obtained in Example 30(2) and palladium on carbon (0.685 g) were added to ethyl acetate (50 mL) under a nitrogen atmosphere. The atmosphere was substituted with a hydrogen atmosphere, the components were then stirred for 16 hours. The inside of a flask was substituted with a nitrogen atmosphere, filtration was then performed, a filtrate was concentrated under reduced pressure, and a title compound (1.28 g) was obtained.

(4) Synthesis of 4-Hexyldodecan-1-ol

The compound (1.00 g) obtained in Example 30(3) was dissolved in THF (20 mL), lithium aluminum hydride (2.0M THF solution, 6.32 mL) was added at 0° C., the components were warmed up to room temperature and stirred for 16 hours. MTBE (20 mL) was added, a reaction solution was cooled to 0° C., and water (0.5 mL), a 2N sodium hydroxide aqueous solution (1 mL), and water (2 mL) were added in order. A generated solid was removed by CELITE filtration, and a filtrate was concentrated under reduced pressure. A residue was purified by silica gel column chromatography (cyclohexane/diethylether), and a title compound (645 mg) was obtained.

(5) Synthesis of Bis(4-hexyldodecyl) 4-((1-methylpiperidine-4-carbonyl)oxy)heptanedioate (Compound (E30))

The compound (12 mg) obtained in Example 30(4) was added to DMF (1 mL), 4-hexyldodecan-1-ol (53.9 mg), DMAP (2.43 mg), and EDCI (22.90 mg) were added, and the components were stirred for 16 hours.

MTBE (10 mL), water (10 mL), a saturated saline solution (1 mL) were added to a mixture, and an organic layer was separated. The organic layer was concentrated under reduced pressure, and a residue was purified by silica gel column chromatography (MTBE/methanol), and a title compound (16.6 mg) was obtained. ESI-MS:806.9 ([M+H]$^+$)

Example 31

(1) Synthesis of 2-Hexyloctanal

A title compound (780 mg) was obtained by the same method as in Example 30(1) using 2-hexyloctan-1-ol (0.9 g) as a raw material instead of 2-hexyldecan-1-ol.

(2) Synthesis of Ethyl (E)-4-hexyldec-2-enoate

A title compound (970 mg) was obtained by the same method as in Example 30(2) using the compound (780 mg) obtained in Example 31(1) instead of the compound obtained in Example 30(1).

(3) Synthesis of Ethyl 4-hexyl decanoate

A title compound (0.977 g) was obtained by the same method as in Example 30(3) using the compound (0.97 g) obtained in Example 31(2) instead of the compound obtained in Example 30(2).

(4) Synthesis of 4-Hexyldecan-1-ol

A title compound (697 mg) was obtained by the same method as in Example 30(4) using the compound (1 g) obtained in Example 31(3) instead of the compound obtained in Example 30(3).

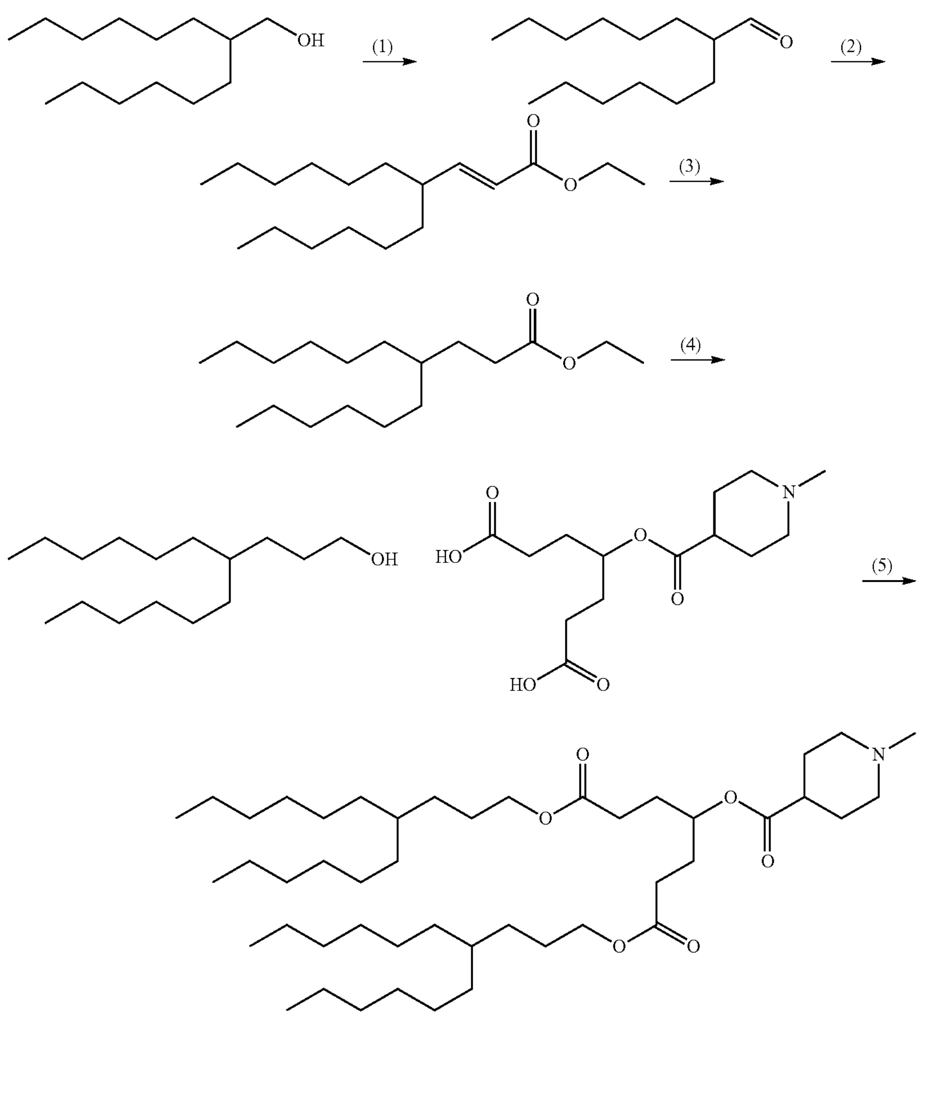

(5) Synthesis of Bis(4-hexyldecyl) 4-((1-methylpiperidine-4-carbonyl)oxy)heptanedioate (Compound (E31))
A title compound (11.5 mg) was obtained by the same method as in Example 30(5) using the compound (15 mg) obtained in Example 31(4) instead of the compound obtained in Example 30(4). ESI-MS:750.9 ([M+H]+)
Example 32
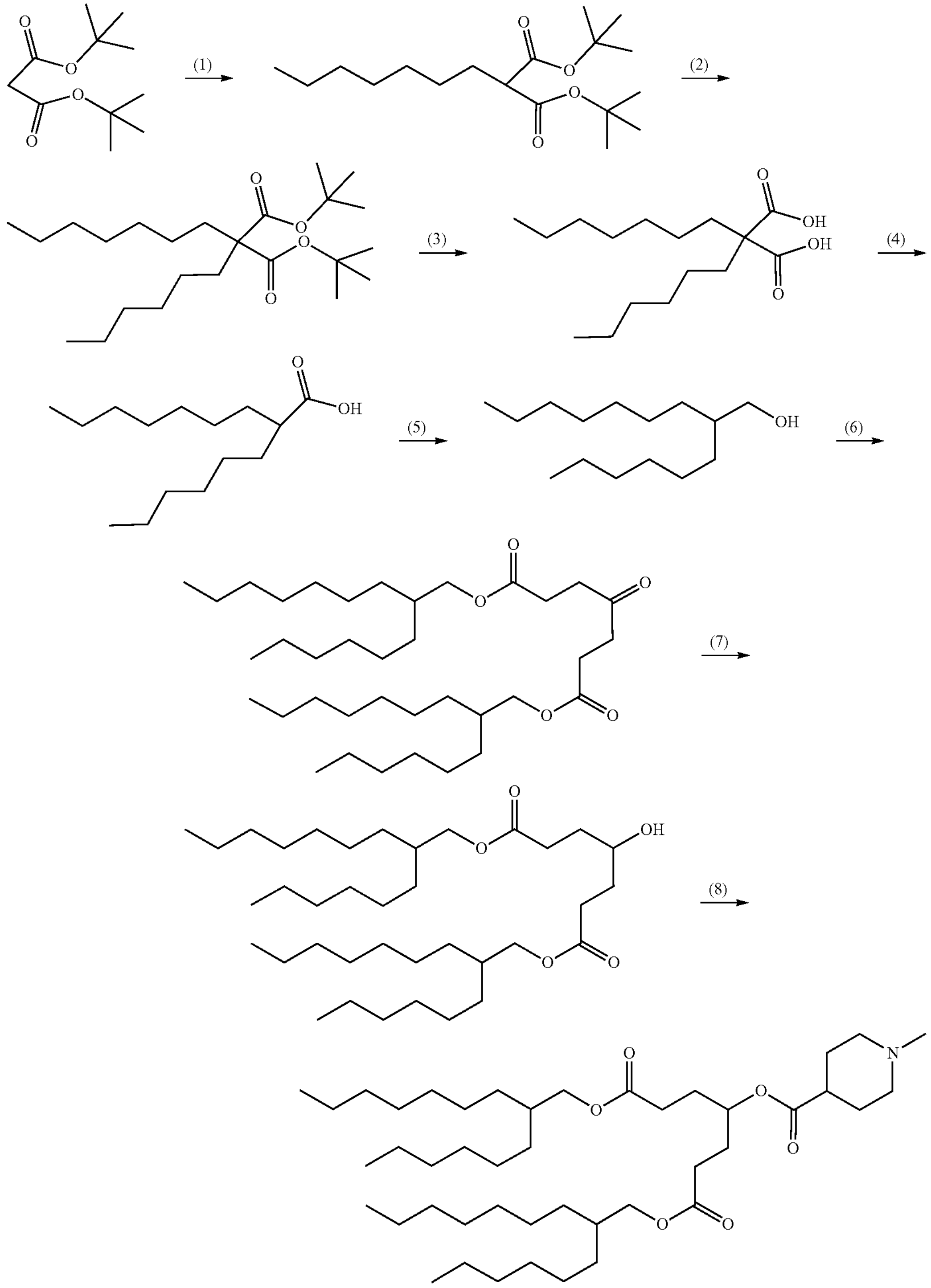

(1) Synthesis of di-tert-Butyl 2-heptylmalonate

A title compound (5.90 g) was obtained by the same method as in Example 18(1) using 1-bromoheptane (3.86 mL) as a raw material instead of 1-bromooctane.

(2) Synthesis of di-tert-Butyl 2-heptyl-2-hexylmalonate

A title compound (2.95 g) was obtained by the same method as in Example 18(2) using the compound (2.50 g) obtained in Example 32(1) as a raw material instead of the compound obtained in Example 18(1) and 1-bromohexane (1.34 mL) instead of 1-bromo-5-methylhexane, respectively.

(3) Synthesis of 2-Heptyl-2-hexylmalonic acid

A title compound (3.21 g) was obtained as a crude product by the same method as in Example 18(3) using the compound (2.95 g) obtained in Example 32(2) as a raw material instead of the compound obtained in Example 18(2).

(4) Synthesis of 2-Hexylnonanoic acid

A title compound (2.13 g) was obtained by the same method as in Example 18(4) using the compound (3.21 g) obtained in Example 32(3) as a raw material instead of the compound obtained in Example 18(3).

(5) Synthesis of 2-Hexylnonan-1-ol

A title compound (1.26 g) was obtained by the same method as in Example 18(5) using the compound (2.13 g) obtained in Example 32(4) as a raw material instead of the compound obtained in Example 18(4).

(6) Synthesis of Bis(2-hexylnonyl) 4-oxoheptanedioate

A title compound (345 mg) was obtained as a crude product by the same method as in Example 18(6) using the compound (492 mg) obtained in Example 32(5) as a raw material instead of the compound obtained in Example 18(5).

(7) Synthesis of Bis(2-hexylnonyl) 4-hydroxyheptanedioate

A title compound (159 mg) was obtained by the same method as in Example 18(7) using the compound (345 mg) obtained in Example 32(6) as a raw material instead of the compound obtained in Example 18(6).

(8) Synthesis of Bis(2-hexylnonyl) 4-((1-methylpiperidine-4-carbonyl)oxy)heptanedioate (Compound (E32))

A title compound (6.8 mg) was obtained by the same method as in Example 3(3) using the compound (12 mg) obtained in Example 32(7) as a raw material instead of the compound obtained in Example 3(2). ESI-MS:744.6 ([M+Na]+)

Example 33

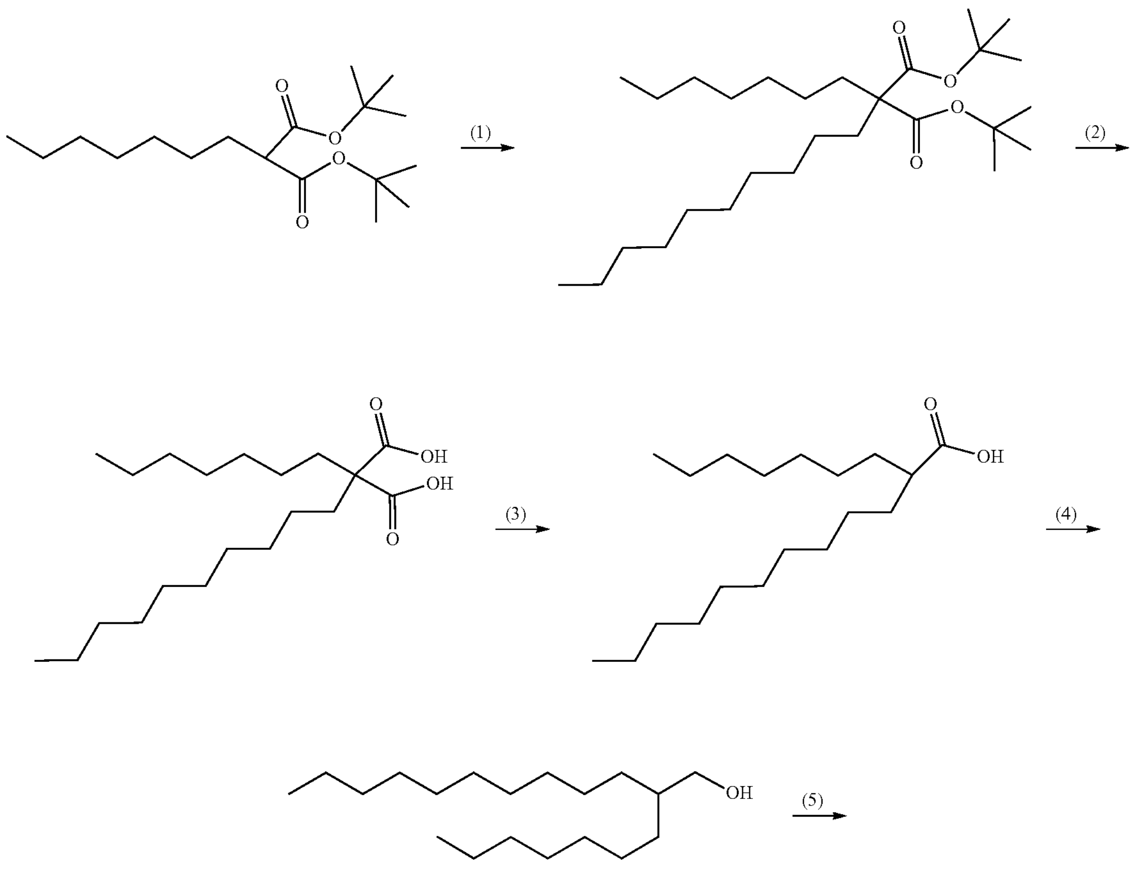

-continued

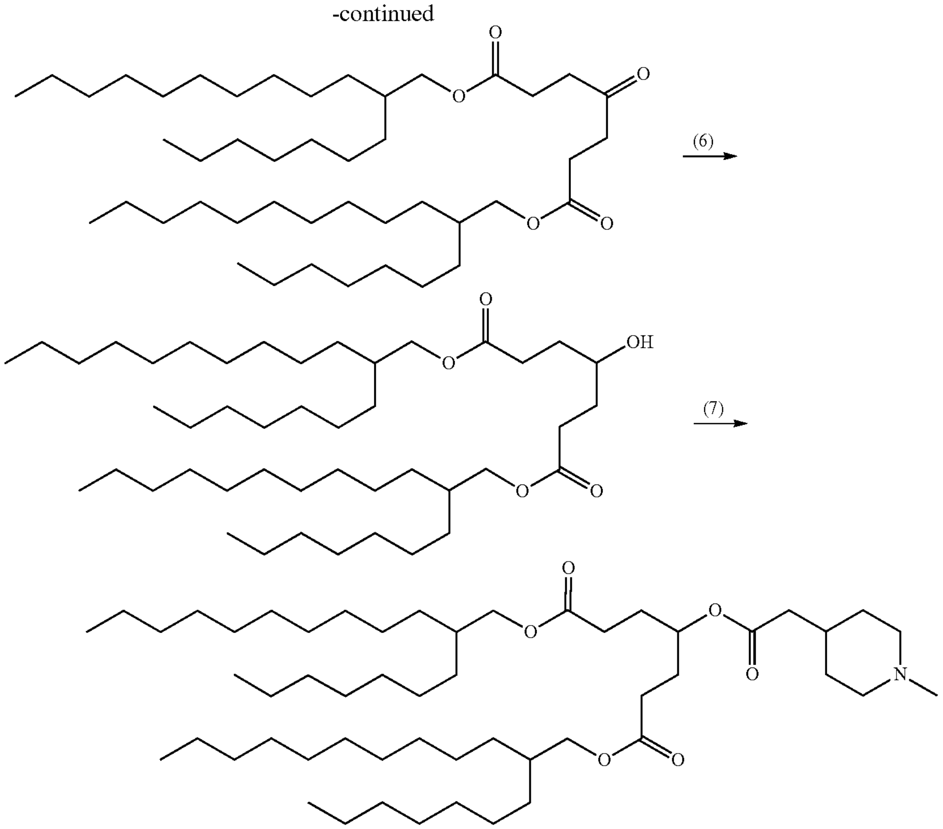

(1) Synthesis of di-tert-Butyl 2-decyl-2-heptylmalonate

Sodium hydride (60%, 350 mg) was added to DMF (20 mL) and a DMF (5 mL) solution of the compound (2.50 g) obtained in Example 32(1) was added dropwise at 0° C. A mixture was stirred at 0° C. for 30 minutes, and a DMF (5 mL) solution of 1-iododecane (2.04 mL) was added. A mixture was stirred at 0° C. for 30 minutes and then stirred at room temperature for two hours. The mixture was cooled to 0° C., and a saturated ammonium chloride aqueous solution (50 mL) was then added. Furthermore, the mixture was diluted with ethyl acetate (100 mL) and water (50 mL). An aqueous layer was extracted with ethyl acetate, combined organic layers were washed with water and a saturated saline solution, dried over anhydrous sodium sulfate, filtered, and then concentrated under reduced pressure.

A residue was purified by silica gel column chromatography (n-heptane/ethyl acetate), and a title compound (2.63 g) was obtained.

(2) Synthesis of 2-Decyl-2-heptylmalonic acid

A title compound (2.56 g) was obtained as a crude product by the same method as in Example 18(3) using the compound (2.63 g) obtained in Example 33(1) as a raw material instead of the compound obtained in Example 18(2).

(3) Synthesis of 2-Heptyldodecanoic acid

A title compound (1.85 g) was obtained by the same method as in Example 18(4) using the compound (2.56 g) obtained in Example 33(2) as a raw material instead of the compound obtained in Example 18(3).

(4) Synthesis of 2-Heptyldodecan-1-ol

A title compound (1.19 g) was obtained by the same method as in Example 18(5) using the compound (1.85 g) obtained in Example 33(3) as a raw material instead of the compound obtained in Example 18(4).

(5) Synthesis of Bis(2-heptyldodecyl) 4-oxoheptanedioate

A title compound (304 mg) was obtained as a crude product by the same method as in Example 18(6) using the compound (613 mg) obtained in Example 33(4) as a raw material instead of the compound obtained in Example 18(5).

(6) Synthesis of Bis(2-heptyldodecyl) 4-hydroxyheptanedioate

A title compound (213 mg) was obtained by the same method as in Example 18(7) using the compound (304 mg) obtained in Example 33(5) as a raw material instead of the compound obtained in Example 18(6).

(7) Synthesis of Bis(2-heptyldodecyl) 4-(2-(1-methylpiperidin-4-yl)acetoxy)heptanedioate (Compound (E33))

A title compound (11.9 mg) was obtained by the same method as in Example 18(8) using the compound (12 mg) obtained in Example 33(6) as a raw material instead of the compound obtained in Example 18(7). ESI-MS:870.2 ([M+Na]$^+$)

Example 34
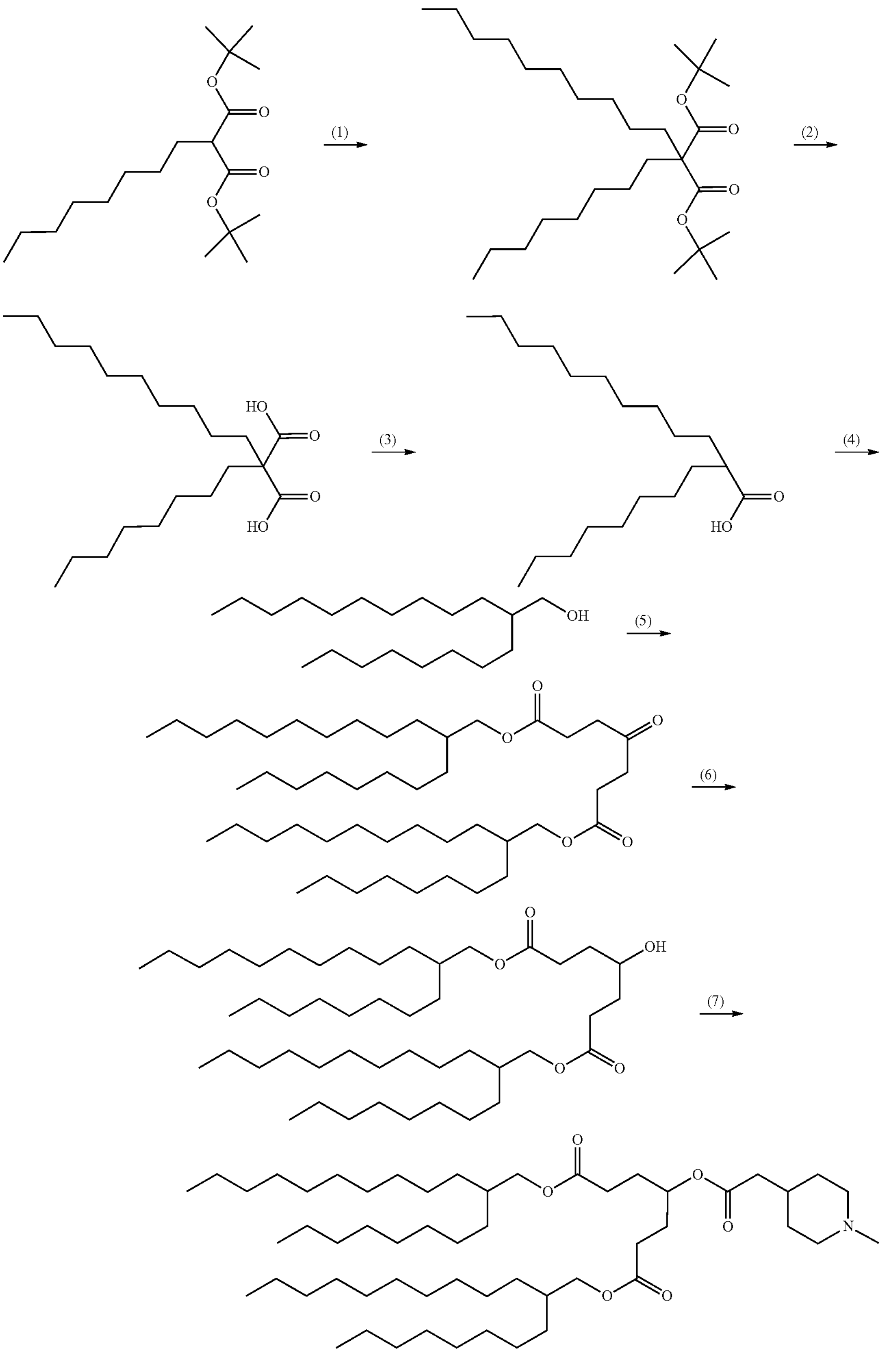

(1) Synthesis of di-tert-Butyl 2-decyl-2-octylmalonate

A title compound (3.44 g) was obtained by the same method as in Example 33(1) using the compound (2.50 g) obtained in Example 18(1) as a raw material instead of the compound obtained in Example 32(1).

(2) Synthesis of 2-Decyl-2-octylmalonic acid

A title compound (2.57 g) was obtained by the same method as in Example 18(3) using the compound (3.44 g) obtained in Example 34(1) as a raw material instead of the compound obtained in Example 18(2).

(3) Synthesis of 2-Octyldodecanoic acid

A title compound (2.31 g) was obtained by the same method as in Example 18(4) using the compound (2.57 g) obtained in Example 34(2) as a raw material instead of the compound obtained in Example 18(3).

(4) Synthesis of 2-Octyldodecan-1-ol

A title compound (2.04 g) was obtained by the same method as in Example 18(5) using the compound (2.28 g) obtained in Example 34(3) as a raw material instead of the compound obtained in Example 18(4).

(5) Synthesis of Bis(2-octyldodecyl) 4-oxoheptanedioate

A title compound (168 mg) was obtained as a crude product by the same method as in Example 18(6) using the compound (643 mg) obtained in Example 34(4) instead of the compound obtained in Example 18(5).

(6) Synthesis of Bis(2-octyldodecyl) 4-hydroxyheptanedioate

A title compound (145 mg) was obtained by the same method as in Example 18(7) using the compound (168 mg) obtained in Example 34(5) as a raw material instead of the compound obtained in Example 18(6).

(7) Synthesis of Bis(2-octyldodecyl) 4-(2-(1-methylpiperidin-4-yl)acetoxy)heptanedioate (Compound (E34))

A title compound (8.5 mg) was obtained by the same method as in Example 18(8) using the compound (12 mg) obtained in Example 34(6) instead of the compound obtained in Example 18(7). ESI-MS:898.4 ([M+Na]$^+$)

Example 35

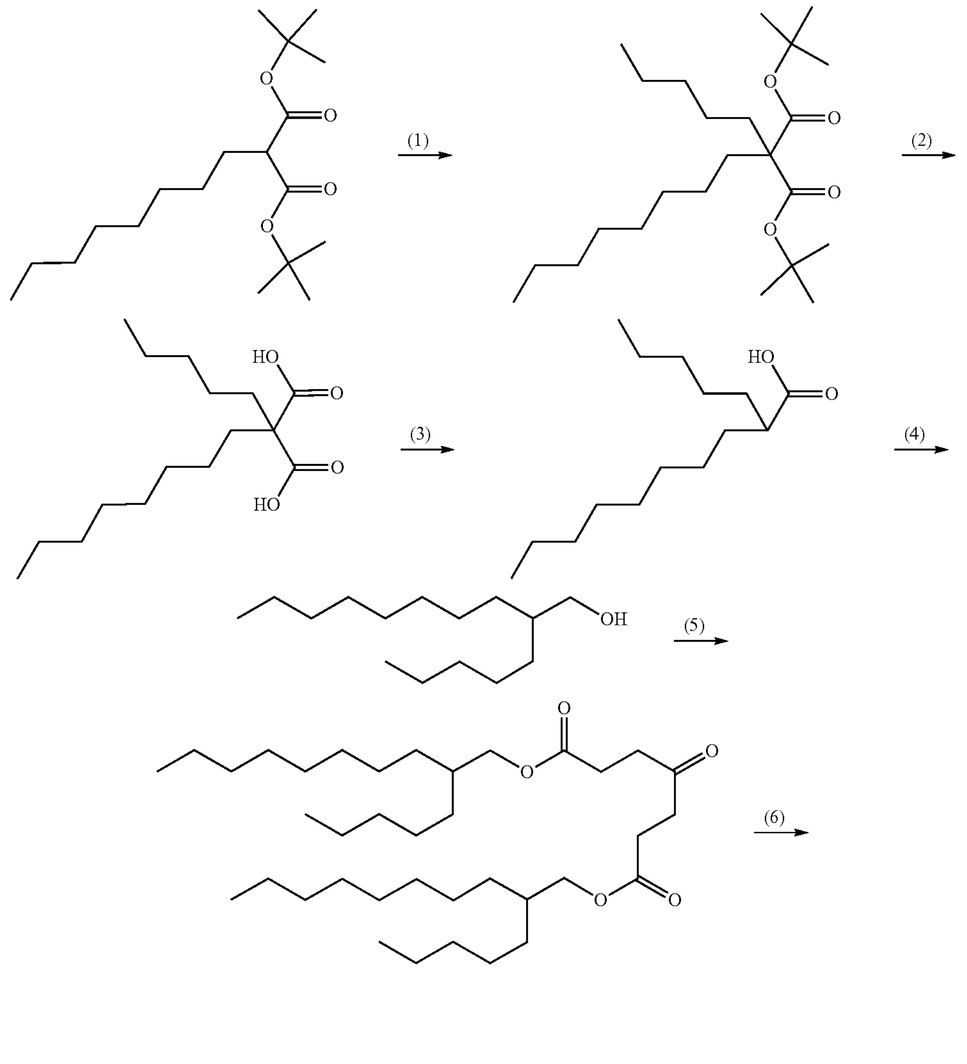

-continued

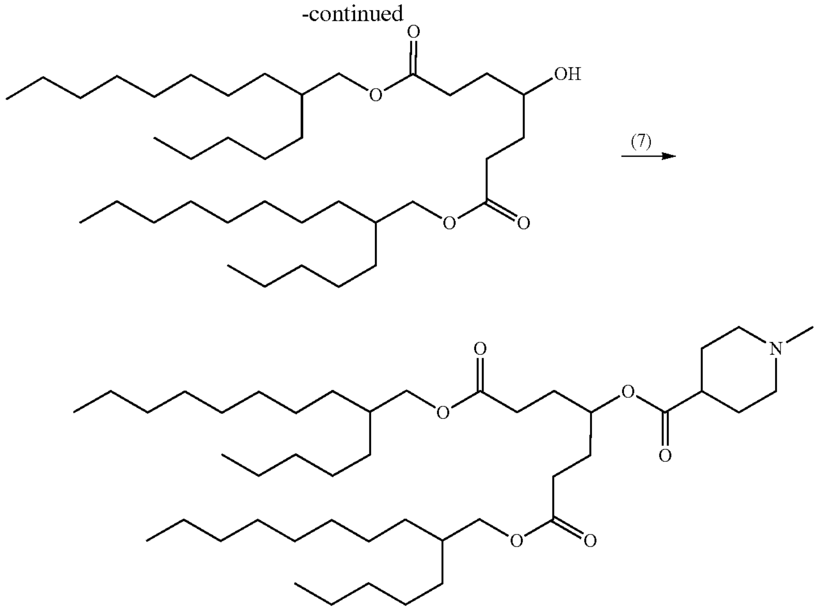

(1) Synthesis of di-tert-Butyl 2-octyl-2-pentylmalonate

A title compound (2.93 g) was obtained by the same method as in Example 33(1) using the compound (2.50 g) obtained in Example 18(1) instead of the compound obtained in Example 32(1) and 1-iodopentane (1.09 mL) instead of 1-iodododecane as raw materials.

(2) Synthesis of 2-Octyl-2-pentylmalonic acid

A title compound (2.11 g) was obtained by the same method as in Example 18(3) using the compound (2.93 g) obtained in Example 35(1) as a raw material instead of the compound obtained in Example 18(2).

(3) Synthesis of 2-Pentyldodecanoic acid

A title compound (1.85 g) was obtained by the same method as in Example 18(4) using the compound (2.02 g) obtained in Example 35(2) as a raw material instead of the compound obtained in Example 18(3).

(4) Synthesis of 2-Pentyldecan-1-ol

A title compound (841 mg) was obtained by the same method as in Example 18(5) using the compound (1.85 g) obtained in Example 35(3) as a raw material instead of the compound obtained in Example 18(4).

(5) Synthesis of Bis(2-pentyldecyl) 4-oxoheptanedioate

A title compound (286 mg) was obtained as a crude product by the same method as in Example 18(6) using the compound (492 mg) obtained in Example 35(4) as a raw material instead of the compound obtained in Example 18(5).

(6) Synthesis of Bis(2-pentyldecyl) 4-hydroxyheptanedioate

A title compound (136 mg) was obtained by the same method as in Example 18(7) using the compound (286 mg) obtained in Example 35(5) as a raw material instead of the compound obtained in Example 18(6).

(7) Synthesis of Bis(2-pentyldecyl) 4-((1-methylpiperidine-4-carbonyl)oxy)heptanedioate (Compound (E35))

A title compound (8.8 mg) was obtained by the same method as in Example 3(3) using the compound (12 mg) obtained in Example 35 (6) as a raw material instead of the compound obtained in Example 3(2). ESI-MS:744.5 ([M+Na]$^+$)

Example 36

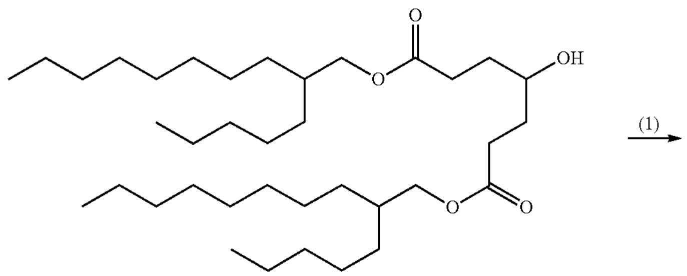

-continued

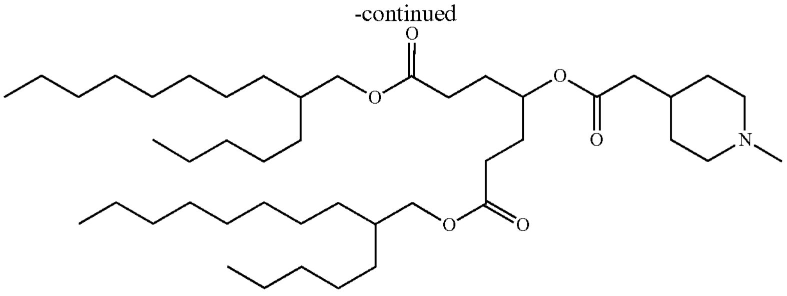

(1) Synthesis of Bis(2-pentyldecyl) 4-(2-(1-methylpiperidin-4-yl)acetoxy)heptanedioate (Compound (E36))

A title compound (8.5 mg) was obtained by the same method as in Example 18(8) using the compound (12 mg) obtained in Example 35(6) instead of the compound obtained in Example 18(7). ESI-MS:758.2 ([M+Na]$^+$)

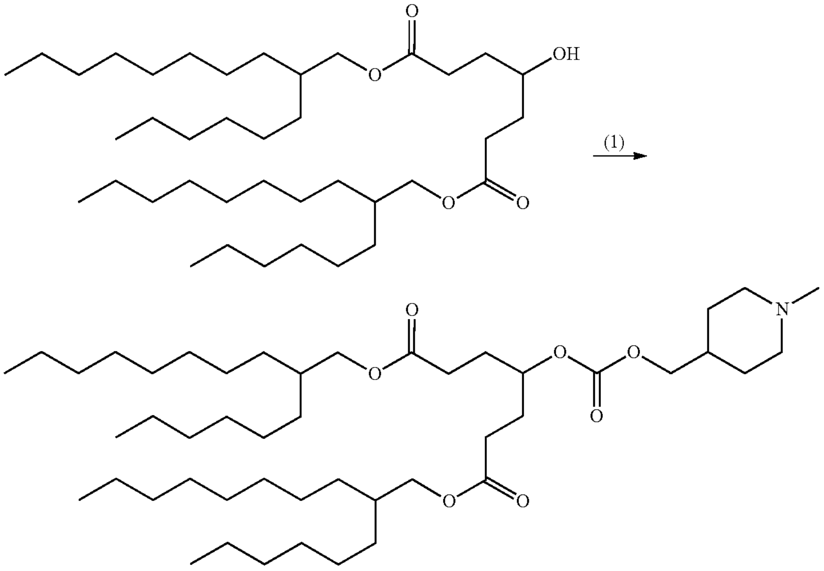

(1) Synthesis of Bis(2-hexyldecyl) 4-((((1-methylpiperidin-4-yl)methoxy)carbonyl)oxy)heptanedioate (Compound (E37))

Bis(2-hexyldecyl) 4-hydroxyheptanedioate (50 mg) was dissolved in toluene (1000 μL), and pyridine (39 μL) and triphosgene (14.2 mg) were added at 0° C. A mixture was stirred at 0° C. for one hour, and (1-methylpiperidin-4-yl) methanol (17.6 mg) was then added. After the mixture was stirred at room temperature overnight, a saturated sodium bicarbonate aqueous solution (1 mL) was added to the mixture, and extraction was performed with n-heptane (1 mL) three times. Combined organic layers were concentrated under reduced pressure, a residue was purified by silica gel column chromatography (ethyl acetate/methanol),l and a title compound (9.15 mg) was obtained. ESI-MS: 780.1 ([M+H]$^+$)

Example 38

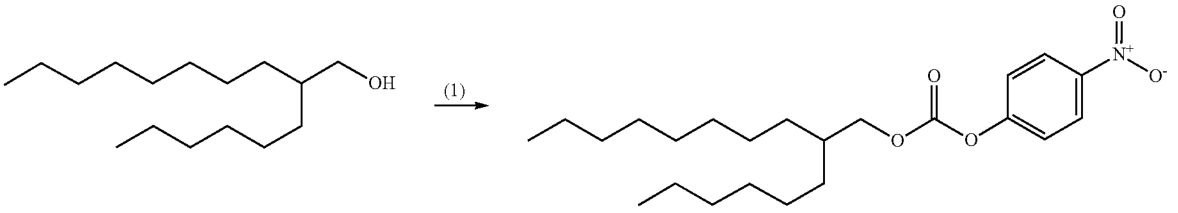

-continued
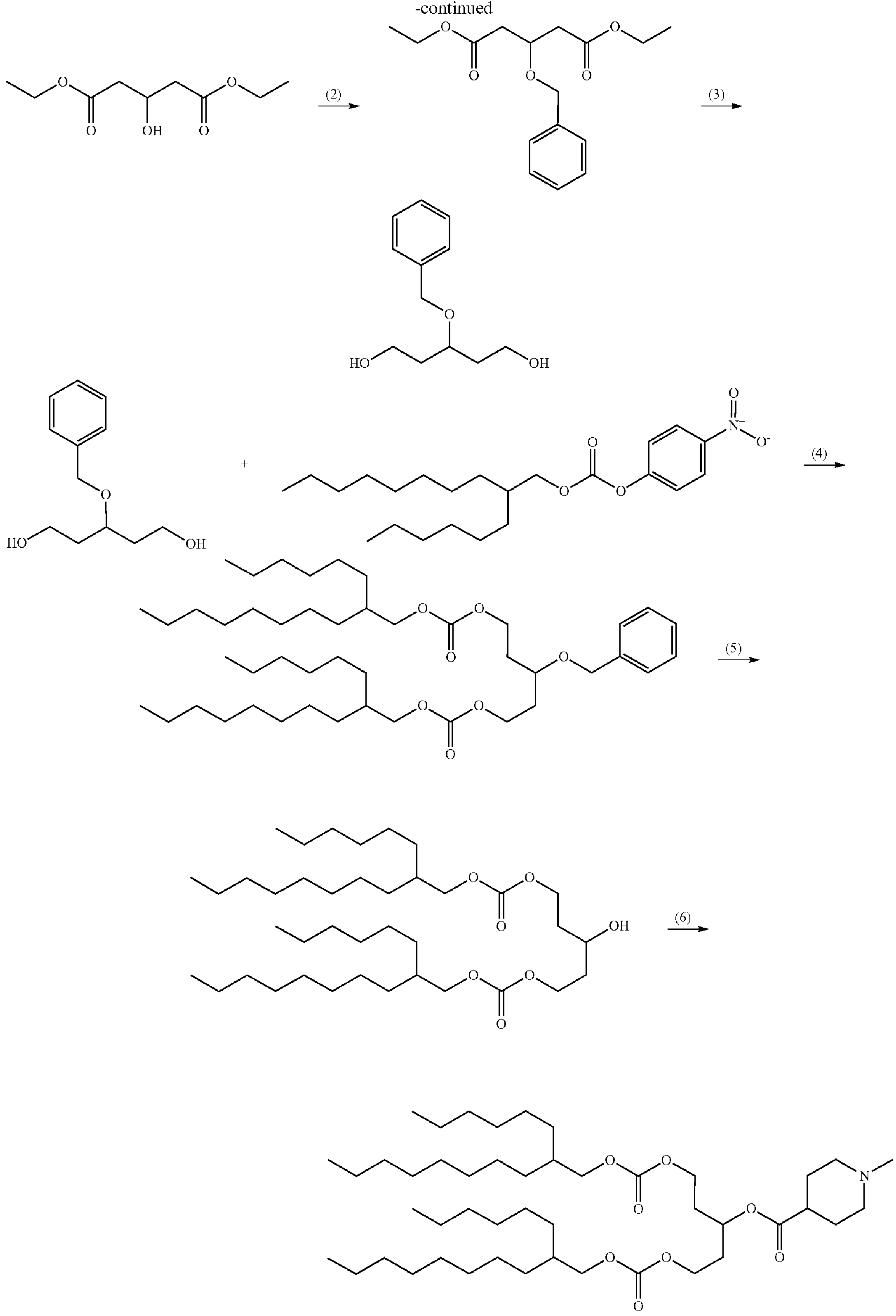

(1) Synthesis of 2-Hexyldecyl (4-nitrophenyl) carbonate

2-Hexyl-1-decanol (630 mg) and triethylamine (1.09 mL) were added to THF (10 mL), 4-nitrophenyl chloroformate (786 mg) was added at room temperature, and the components were stirred for 30 minutes. A mixture was diluted with ethyl acetate (30 mL), washed with water and a saturated saline solution, and dried over sodium sulfate, a solid was removed by filtration and then concentrated under reduced pressure. A residue was purified by silica gel column chromatography (n-heptane/ethyl acetate), and a title compound (973 mg) was obtained.

(2) Synthesis of Diethyl 3-(benzyloxy)pentanedioate

DCM (30 mL) was added to diethyl 3-hydroxyglutarate (1.80 mL), benzyl 2,2,2-trichloroacetoimidate (2.00 mL) and trifluoromethanesulfonic acid (86 μL) were added at room temperature, and the components were stirred at room temperature for 16 hours. A mixture was concentrated under reduced pressure, an obtained residue was purified by silica gel column chromatography (n-heptane/ethyl acetate), and a title compound (2.05 g) was obtained.

(3) Synthesis of 3-(Benzyloxy)pentane-1,5-diol

THF (10 mL) was added to the compound (300 mg) obtained in Example 38(2), lithium aluminum hydride (2.0M THF solution, 1.53 mL) was added at 0° C., and the components were stirred at room temperature for two hours. A mixture was cooled to 0° C., ethyl acetate (5 mL) was then added, water (0.12 mL), a 15% sodium hydroxide aqueous solution (0.12 mL), and water (0.36 mL) were then added in order, the components were stirred at room temperature for 10 minutes, a generated precipitate was filtered with CELITE, an obtained solution was concentrated under reduced pressure, and a title compound (208 mg) was obtained as a crude product.

(4) Synthesis of 3-(Benzyloxy)pentane-1,5-diyl bis (2-hexyldecyl) bis(carbonate)

THF (5 mL) was added to the compound (100 mg) obtained in Example 38(3), the compound (485 mg) obtained in Example 38(1), and triethylamine (0.20 mL), DMAP (174 mg) was added at room temperature, and the components were then stirred at 80° C. for one hour. A mixture was concentrated under reduced pressure, an obtained residue was purified by silica gel column chromatography (n-heptane/ethyl acetate), and a title compound (150 mg) was obtained as a crude product.

(5) Synthesis of Bis(2-hexyldecyl) (3-hydroxypentan-1,5-diyl) bis(carbonate)

Ethanol (3 mL) was added to the compound (150 mg) obtained in Example 38(4), 10% palladium on carbon (50% wet, 43 mg) was added, the components were then stirred at room temperature under a hydrogen atmosphere for two hours, hydrochloric acid (1M, 0.5 mL) was then added, and the components were further stirred for two hours. A solid was removed by CELITE filtration and washed with ethanol, an organic layer was concentrated under reduced pressure, and a title compound (128 mg) was obtained as a crude product.

(6) Synthesis of 9,23-Dihexyl-12,20-dioxo-11,13,19,21-tetraoxahentriacontane-16-yl 1-methylpiperidine-4-carboxylate (Compound (E38))

A title compound (9.8 mg) was obtained by the same method as in Example 3(3) using the compound (24 mg) obtained in Example 38(5) as a raw material instead of the compound obtained in Example 3(2). ESI-MS:804.5 ([M+Na]$^+$)

Example 39

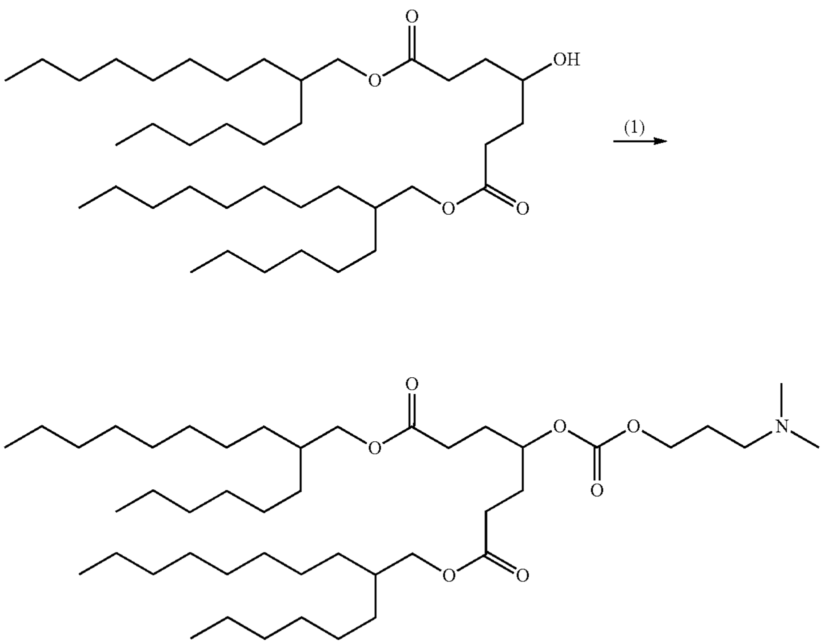

(1) Synthesis of Bis(2-hexyldecyl) 4-(((3-(dimethylamino)propoxy)carbonyl)oxy)heptanedioate (Compound (E39))
A title compound (36.56 mg) was obtained by the same method as in Example 37(1) using 3-dimethylamino-1-propanol (8.25 mg) instead of (1-methylpiperidin-4-yl) methanol. ESI-MS:776.9 ($[M+Na]^+$)
Example 40
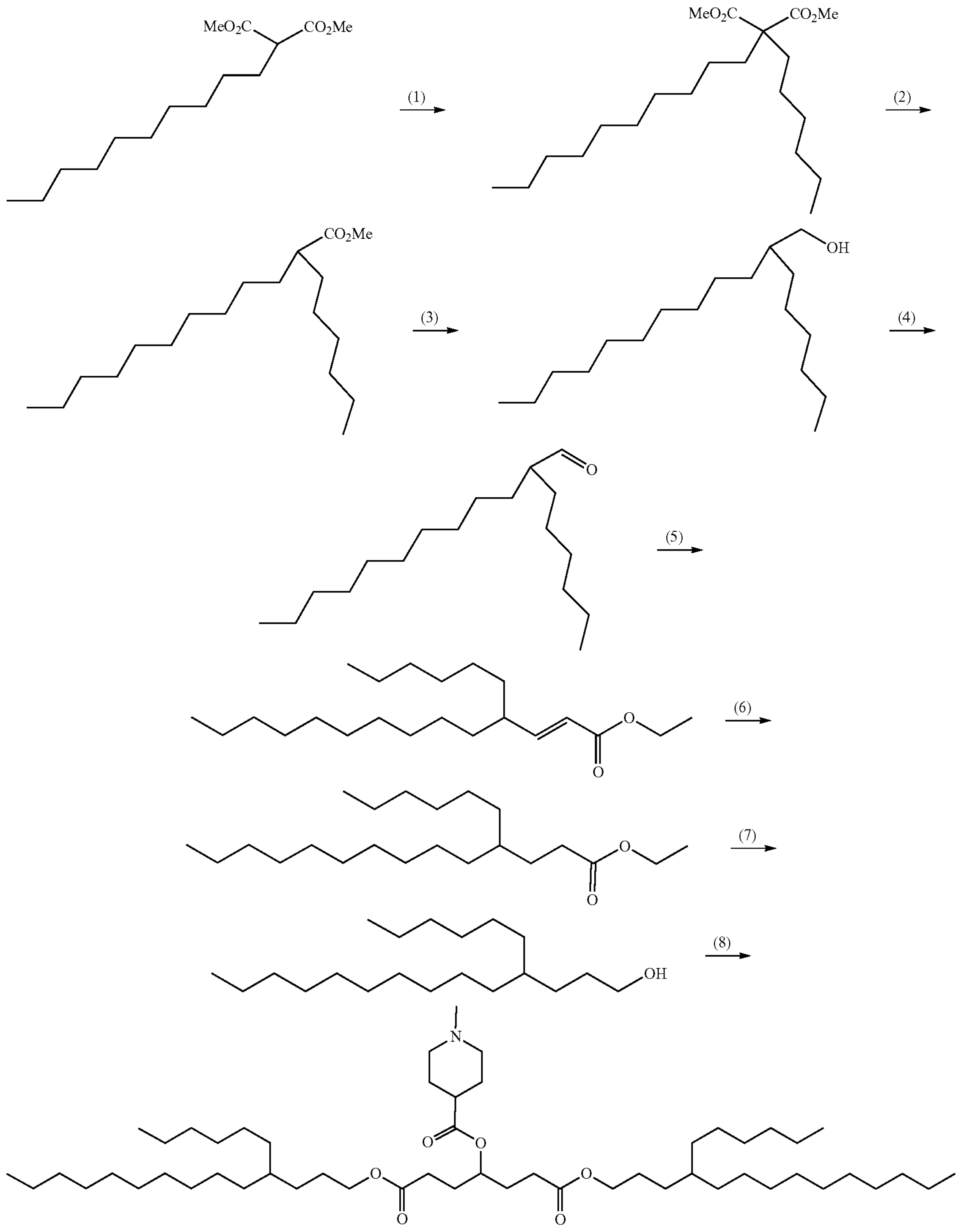

(1) Synthesis of Dimethyl 2-decyl-2-hexylmalonate

A title compound (0.609 g) was obtained by the same method as in Example 23(2) using 1-iodohexane (0.788 mL) instead of 1-iodopentane obtained in Example 23(1).

(2) Synthesis of Methyl 2-hexyldodecanoate

A title compound (0.445 g) was obtained by the same method as in Example 23(3) using the compound (0.605 g) obtained in Example 40(1) instead of the compound obtained in Example 23(2).

(3) Synthesis of 2-Hexyldodecan-1-ol

A title compound (0.387 g) was obtained by the same method as in Example 23(4) using the compound (0.441 g) obtained in Example 40(2) instead of the compound obtained in Example 23(3).

(4) Synthesis of 2-Hexyldodecanal

A title compound was obtained as a crude product (55 mg) by the same method as in Example 30(1) using the compound (120 mg) obtained in Example 40(3) instead of 2-hexyldecan-1-ol.

(5) Synthesis of Ethyl (E)-4-hexyltetradec-2-enoate

A title compound (30 mg) was obtained as a crude product by the same method as in Example 30(2) using the compound (60 mg) obtained in Example 40(4) instead of the compound obtained in Example 30(1).

(6) Synthesis of Ethyl 4-hexyltetradecanoate

A title compound (31 mg) was obtained as a crude product by the same method as in Example 30(3) using the compound (30 mg) obtained in Example 40(5) instead of the compound obtained in Example 30(2).

(7) Synthesis of 4-Hexyltetradecan-1-ol

A title compound (15 mg) was obtained by the same method as in Example 30(4) using the compound (30 mg) obtained in Example 40(6) instead of the compound obtained in Example 30(3).

(8) Synthesis of Bis(4-hexyltetradecyl) 4-((1-methylpiperidine-4-carbonyl)oxy)heptanedioate (Compound (E40))

A title compound (2.9 mg) was obtained by the same method as in Example 23(5) using the compound (14.9 mg) obtained in Example 40(7) instead of the compound obtained in Example 30(4). ESI-MS:862.9 ([M+H]+)

Example 41

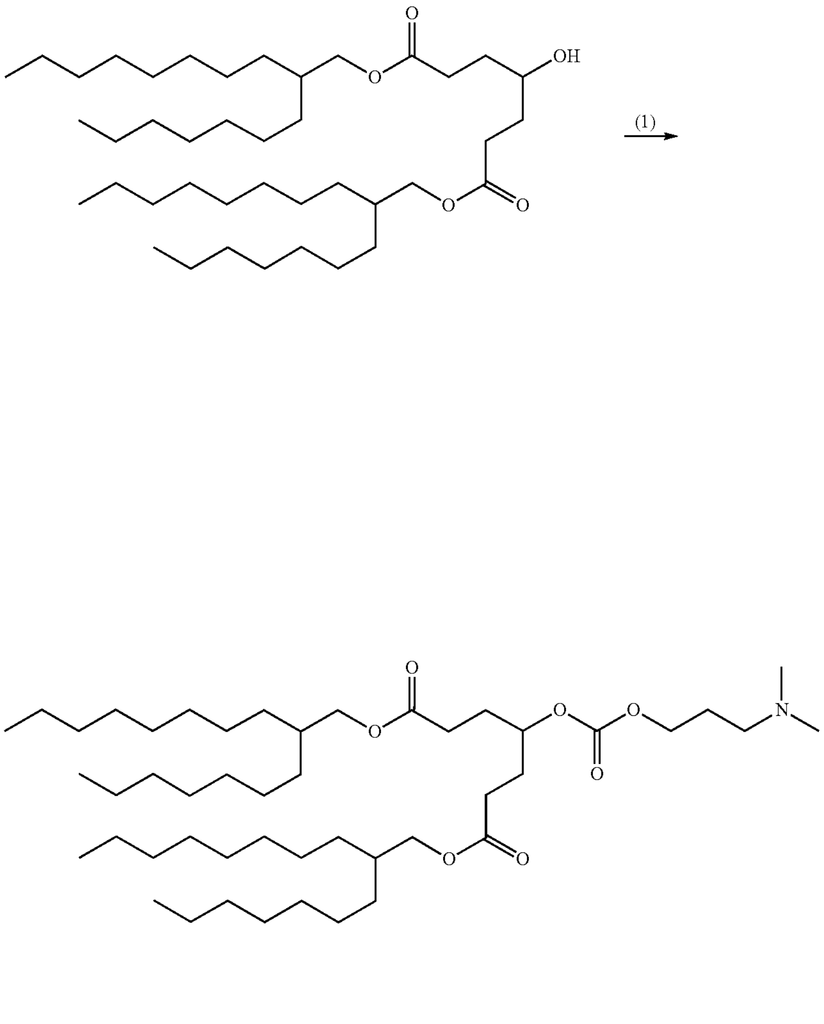

(1) Synthesis of Bis(2-heptyldecyl) 4-(((3-(dimethylamino)propoxy)carbonyl)oxy)heptanedioate (Compound (E41))
A title compound (7.44 mg) was obtained by the same method as in Example 37(1) using bis(2-heptyldecyl) 4-hydroxyheptanedioate (50 mg) instead of bis(2-hexyldecyl) 4-hydroxyheptanedioate and 3-dimethylamino-1-propanol (7.90 mg) instead of 1-methylpiperidinemethanol. ESI-MS.783.5 ($[M+H]^+$)
Example 42
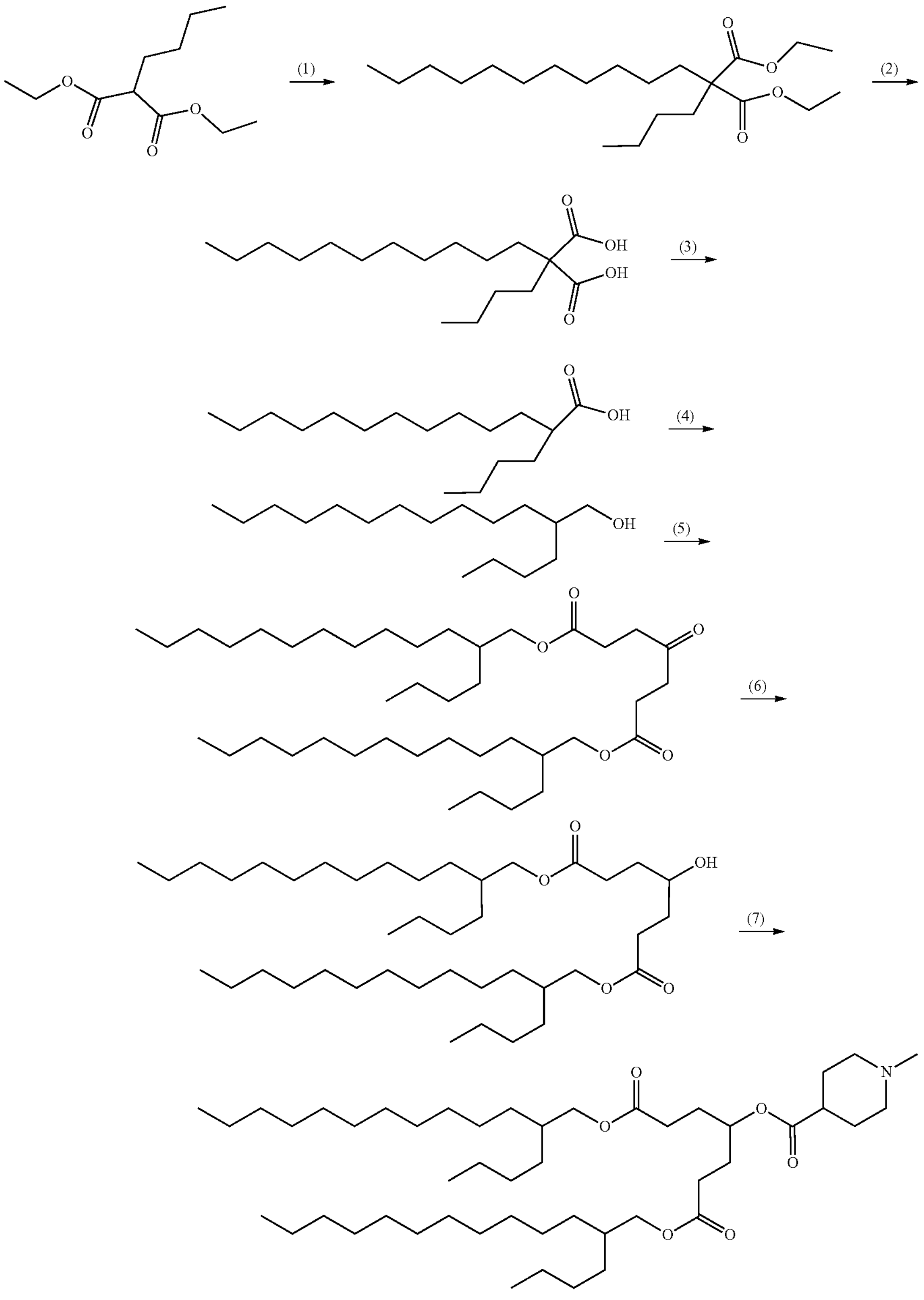

(1) Synthesis of Diethyl 2-butyl-2-undecylmalonate

DMF (20 mL) was added to sodium hydride (60%, 494 mg), a DMF (5 mL) solution of diethyl butylmalonate (2.73 mL) was added at 0° C., and the components were stirred at 0° C. for 30 minutes. After that, a DMF (5 mL) solution of sodium iodide (1.85 g) and 1-bromodecane (3.29 mL) was added, and the components were stirred at 0° C. for 30 minutes and then stirred at room temperature for two hours. A saturated ammonium chloride aqueous solution (50 mL), ethyl acetate (100 mL), and water (50 mL) were added to a mixture, phase separation was performed, and an aqueous layer was then extracted with ethyl acetate. An organic layer was washed with water and a saturated saline solution, dried over sodium sulfate, filtered, and then concentrated under reduced pressure. A residue was purified by silica gel column chromatography (n-heptane/ethyl acetate), and a title compound (3.52 g) was obtained.

(2) Synthesis of 2-Butyl-2-undecylmalonic acid

Ethanol (20 mL) and water were added to the compound (3.65 g) obtained in Example 42(1), a sodium hydroxide aqueous solution (50%, 1.94 mL) was further added at room temperature, and the components were stirred at 100° C. for 16 hours. A mixture was cooled to 0° C., made acidic with 4N hydrochloric acid, and then extracted with MTBE. An organic layer was washed with 0.1N hydrochloric acid and saturated saline solution/0.1N hydrochloric acid (10/1), dried over sodium sulfate, filtered, and then concentrated under reduced pressure, and a title compound (2.70 g) was obtained.

(3) Synthesis of 2-Butyltridecanoic acid

Ortho-xylene (30 mL) was added to the compound (2.70 g) obtained in Example 42(2) and the components were stirred at 160° C. for five hours. A mixture was concentrated under reduced pressure, and a title compound (2.39 g) was obtained.

(4) Synthesis of 2-Butyltridecan-1-ol

A title compound (1.91 g) was obtained by the same method as in Example 18(5) using the compound (2.39 g) obtained in Example 42(3) instead of the compound obtained in Example 18(4).

(5) Synthesis of Bis(2-butyltridecyl) 4-oxoheptanedioate

Sulfuric acid (9.2 μL) was added to 4-oxoheptanedioic acid (150 mg) and the compound (486 mg) obtained in Example 42(4), and the components were stirred at 90° C. for three hours. A mixture was directly purified by silica gel column chromatography (n-heptane/ethyl acetate), and a title compound (473 mg) was obtained as a crude product.

(6) Synthesis of Bis(2-butyltridecyl) 4-hydroxyheptanedioate

A title compound (322 mg) was obtained using the same method as in Example 3(2) and using the compound (473 mg) obtained in Example 42(5) instead of the compound obtained in Example 3(1).

(7) Synthesis of Bis(2-butyltridecyl) 4-((1-methylpiperidine-4-carbonyl)oxy)heptanedioate (Compound (E42))

A title compound (10.5 mg) was obtained using the same method as in Example 3(3) and using the compound (12 mg) obtained in Example 42(6) instead of the compound obtained in Example 3(2). ESI-MS:800.3 ([M+Na]$^+$)

Example 43

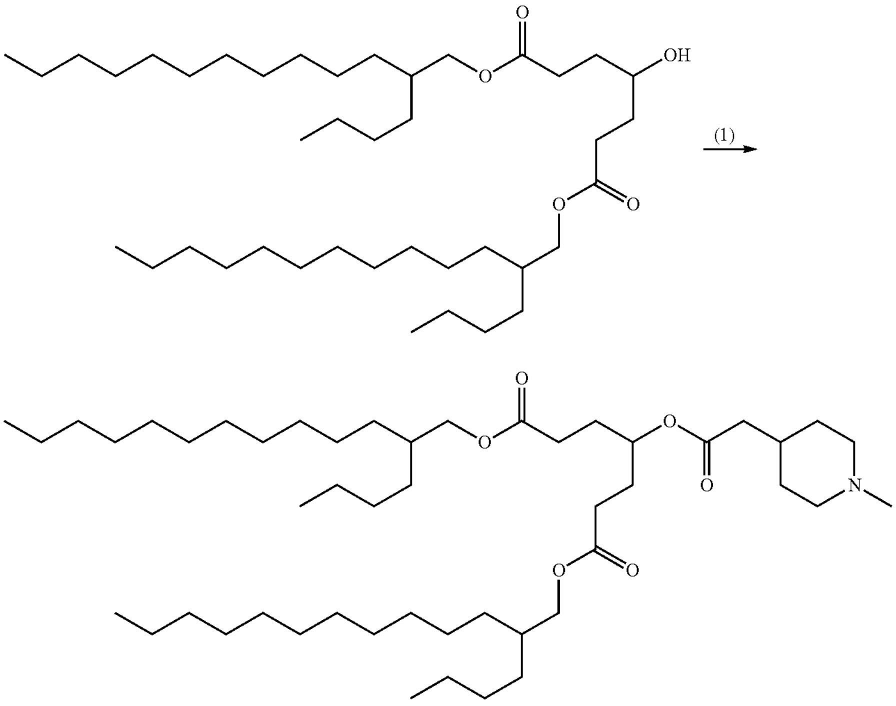

(1) Synthesis of Bis(2-butyltridecyl) 4-(2-(1-methylpiperidin-4-yl)acetoxy)heptanedioate (Compound (E43))

A title compound (11.7 mg) was obtained using the same method as in Example 4(1) and using the compound (12 mg) obtained in Example 42(6) instead of the compound obtained in Example 3(2). ESI-MS:814.5 ([M+Na]+)

Example 44

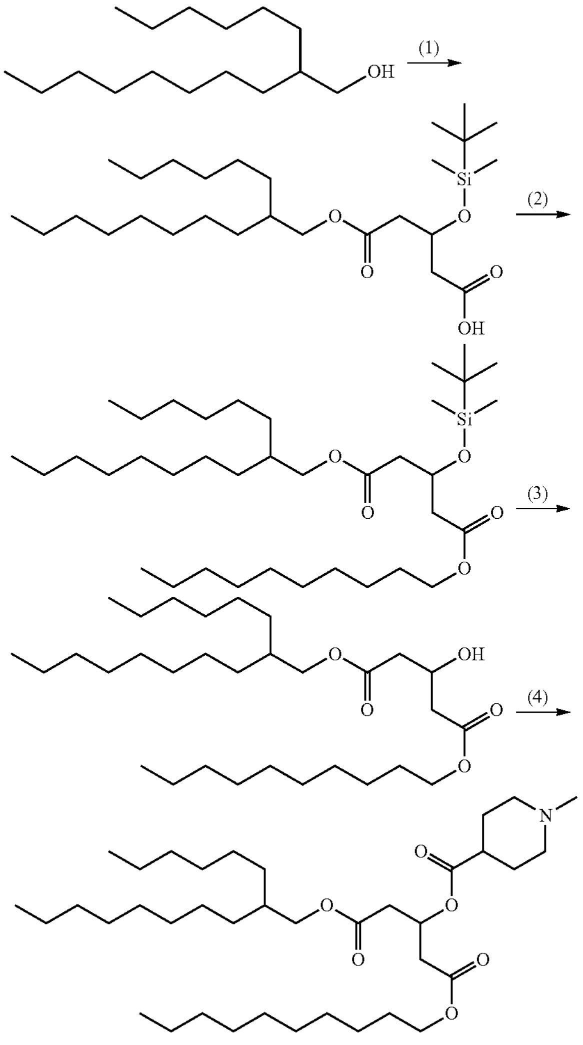

(1) Synthesis of 3-((tert-Butyldimethylsilyl)oxy)-5-((2-hexyldecyl)oxy)-5-oxopentanoic acid 4-((tert-Butyldimethylsilyl)oxy)dihydro-2H-pyran-2,6(3H)-dione (0.529 g) and 2-hexyldecan-1-ol (0.5 g) were added to toluene (5 ml) and heating-refluxed during 16 hours. A mixture was concentrated under reduced pressure, a residue was purified by silica gel column chromatography (cyclohexane/ethyl acetate), and a title compound (144 mg) was obtained.

(2) Synthesis of 1-Decyl 5-(2-hexyldecyl) 3-((tert-butyldimethylsilyl)oxy)pentanedioate The compound (140 mg) obtained in Example 44(1), decan-1-ol (68.3 mg), EDCI (83 mg), and DMAP (10.5 mg) were added to toluene (2 mL), and a mixture was concentrated under reduced pressure. Toluene (1 mL) was added to a residue, and concentration of the mixture under reduced pressure was repeated twice. DIPEA (0.151 mL) and THF (3 mL) were added to the obtained residue and stirred at room temperature for 16 hours. The mixture was concentrated under reduced pressure, a residue was purified by silica gel column chromatography (cyclohexane/diethylether), and a title compound (153 mg) was obtained.

(3) Synthesis of 1-Decyl 5-(2-hexyldecyl) 3-hydroxypentanedioate

The compound (153 mg) obtained in Example 44(2) was added to THF (5 mL), and TBAF (1 M, 0.732 mL) was added at 0° C. A mixture was stirred at room temperature for two hours. The mixture was concentrated under reduced pressure, a residue was purified by silica gel column chromatography (cyclohexane/diethylether), and a title compound (110 mg) was obtained.

(4) Synthesis of 1-Decyl 5-(2-hexyldecyl) 3-((1-methylpiperidine-4-carbonyl)oxy)pentanedioate (Compound (E44))

The compound (20 mg) obtained in Example 44(3), 1-methylpiperidine-4-carboxylic acid (11.2 mg), EDCI (22.4 mg), and DMAP (2.4 mg) were added to toluene, and a mixture was concentrated under reduced pressure. Toluene (1 mL) was added to the residue, and concentration of the mixture under reduced pressure was repeated twice. DIPEA (0.034 mL) and DMF (1 mL) were added to the obtained residue and stirred at room temperature for 16 hours. Water (10 mL), MTBE (10 mL), and a saturated saline solution (1 mL) were added. An organic layer was concentrated under reduced pressure, a residue was purified by silica gel column chromatography (methanol/MTBE), and a title compound (8 mg) was obtained. ESI-MS:638.9 ([M+H]+)

Example 45

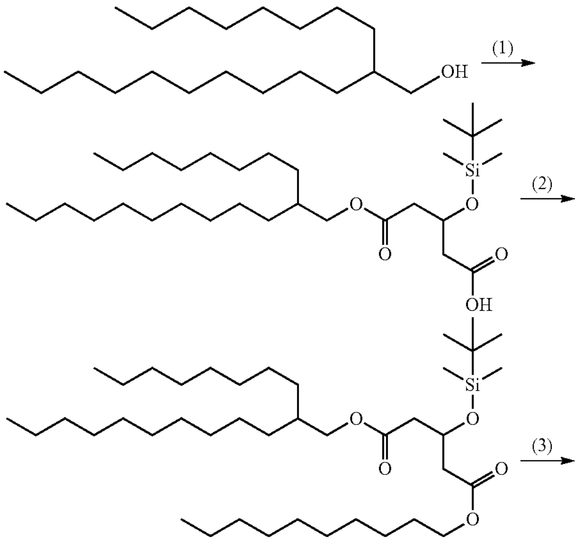

-continued

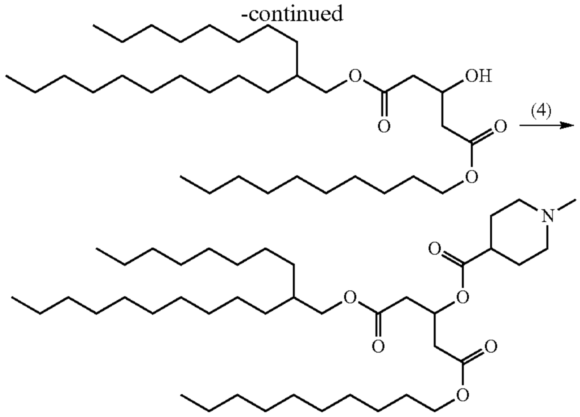

(1) Synthesis of 3-((tert-Butyldimethylsilyl)oxy)-5-((2-octyldodecyl)oxy)-5-oxopentanoic acid A title compound (140 mg) was obtained by the same method as in Example 44(1) using 2-octyldodecan-1-ol (0.5 g) instead of 2-hexyldecan-1-ol.

(2) Synthesis of 1-Decyl 5-(2-octyldodecyl) 3-((tert-butyldimethylsilyl)oxy)pentanedioate A title compound (128 mg) was obtained by the same method as in Example 44(2) using the compound (157 mg) obtained in Example 45(1) instead of the compound obtained in Example 44(1).

(3) Synthesis of 1-Decyl 5-(2-octyldodecyl) 3-hydroxypentanedioate

A title compound (93 mg) was obtained by the same method as in Example 44(3) using the compound (128 mg) obtained in Example 45(2) instead of the compound obtained in Example 44(2).

(4) Synthesis of 1-Decyl 5-(2-octyldodecyl) 3-((1-methylpiperidine-4-carbonyl)oxy)pentanedioate (Compound (E45))

A title compound (7.4 mg) was obtained by the same method as in Example 44(4) using the compound (20 mg) obtained in Example 45(3) instead of the compound obtained in Example 44(3). ESI-MS:695.0 ([M+H]$^+$)

Example 46

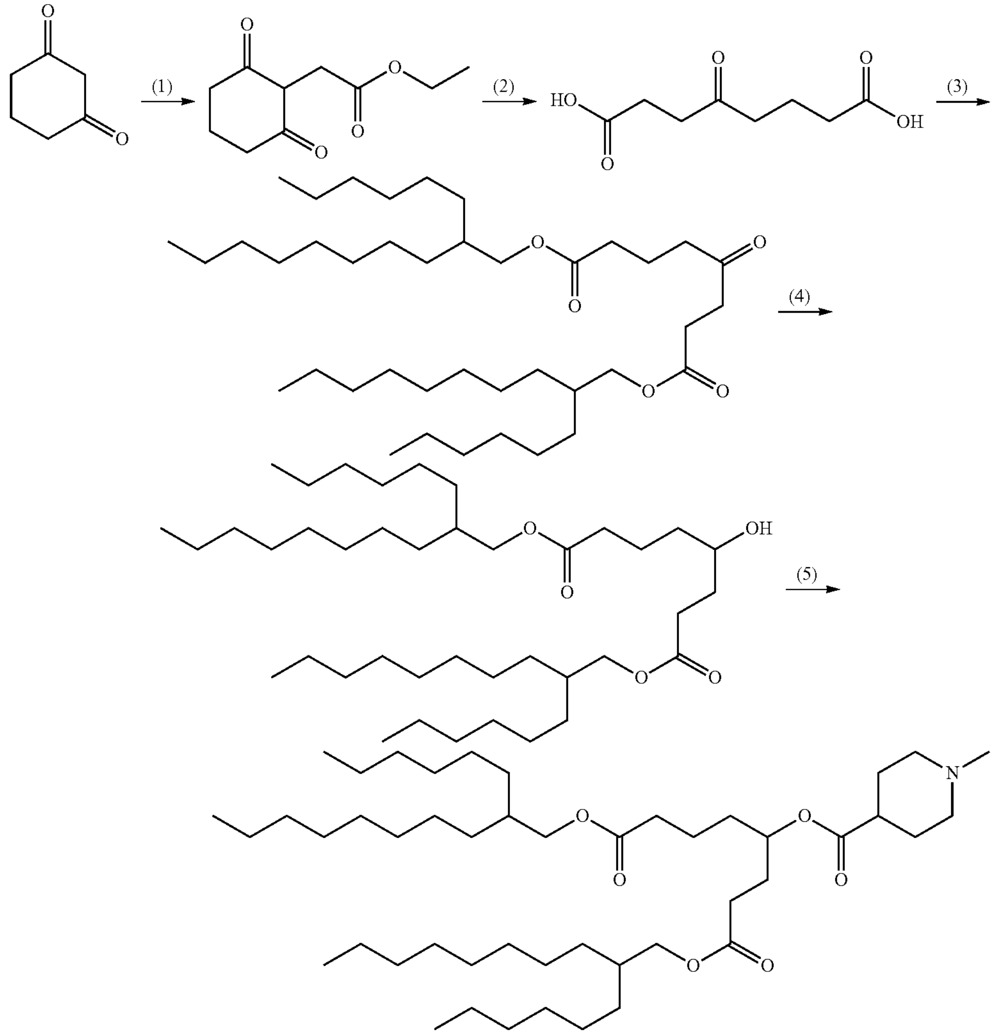

(1) Synthesis of Ethyl 2-(2,6-dioxocyclohexyl)acetate

A 5N sodium hydroxide aqueous solution (2.0 mL) was added to cyclohexane-1,3-dione (1.12 g), and ethyl bromoacetate (2.23 mL) was further added at 0° C. A mixture was warmed at 90° C. and stirred overnight. An aqueous layer was separated and extracted with DCM, combined organic layers were washed with a saturated saline solution, dried over sodium sulfate, and then purified by silica gel chromatography (cyclohexane/ethyl acetate), and a title compound (280 mg) was obtained.

(2) Synthesis of 4-Oxooctanedioic acid

10% hydrochloric acid (8 mL) was added to the compound (280 mg) obtained in Example 46(1) and heating-refluxed for 17 hours. A mixture was concentrated and purified by reverse phase silica gel chromatography (C18 column, water/acetonitrile/formic acid) to obtain a title compound (114 mg).

(3) Synthesis of Bis(2-hexyldecyl) 4-oxooctanedioate

Toluene (2.8 mL), sulfuric acid (16.1 μL), and a molecular sieve 4A (100 mg) were added to the compound (114 mg) obtained in Example 46(2) and 2-hexyl-1-decanol (425 μL) and heated at 90° C. for three days. A mixture was concentrated, purified by silica gel chromatography (cyclohexane/ethyl acetate), and obtained as a crude product (78 mg).

(4) Synthesis of Bis(2-hexyldecyl) 4-hydroxyoctanedioate

The compound (33.8 mg) obtained in Example 46(3) was added to methanol (0.2 mL) and diethyl ether (0.8 mL), sodium borohydride (2.11 mg) was added at −20° C., and the components were stirred for one hour. A saturated ammonium chloride aqueous solution (1 mL) was added to a mixture, the mixture was stirred at room temperature for 20 minutes and then concentrated, and MTBE (5 mL) and water (5 mL) were added. An aqueous layer was separated and extracted with MTBE, combined organic layers were dried over sodium sulfate, concentrated, and purified by silica gel chromatography (cyclohexane/diethyl ether), and a title compound (30 mg) was obtained.

(5) Synthesis of Bis(2-hexyldecyl) 4-((1-methylpiperidine-4-carbonyl)oxy)octanedioate (Compound (E46))

The compound (30 mg) obtained in Example 46(4), 1-methylpiperidine-4-carboxylic acid (16.8 mg), and DMAP (3 mg) were added to DMF (0.5 mL), EDCI (21.6 mg) was added, and the components were stirred for 18 hours. A mixture was purified by silica gel chromatography (MTBE/methanol), and a title compound (23.4 mg) was obtained.

Example 47

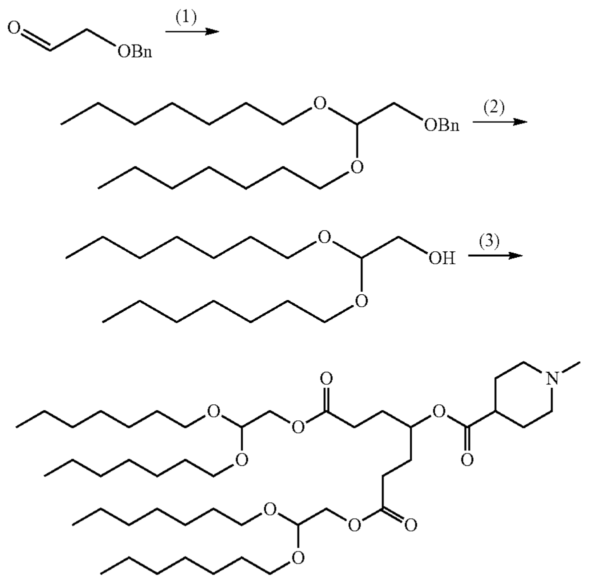

(1) Synthesis of ((2,2-Bis(heptyloxy)ethoxy)methyl)benzene 2-(Benzyloxy)acetaldehyde (203 mg) and PPTS (17.0 mg) were added to heptan-1-ol (573 μL) and stirred at 105° C. for two hours and 10 minutes. A mixture was purified by silica gel chromatography (cyclohexane/ethyl acetate), and a title compound (274 mg) was obtained.

(2) Synthesis of 2,2-Bis(heptyloxy)ethan-1-ol

An industrial modified alcohol (3 mL) and ethyl acetate (3 mL) were added to the compound (271 mg) obtained in Example 47(1), 10% palladium on carbon (50% wet, 158 mg) was further added, and the components were stirred under a hydrogen atmosphere for five hours. A reactant was filtered with CELITE, washed with 35 mL of an industrial modified alcohol, and then concentrated. An obtained mixture was purified by silica gel chromatography (cyclohexane/diethyl ether), and a title compound (161 mg) was obtained.

(3) Synthesis of Bis(2,2-bis(heptyloxy)ethyl) 4-((1-methylpiperidine-4-carbonyl)oxy)heptanedioate (compound (E47))

A title compound (25.6 mg) was obtained by the same method as in Example 9-1(5) using the compound (33.9 mg) obtained in Example 47(2) instead of the compound obtained in Example 9-2(4). ESI-MS:815.6 ([M+H]$^+$)

Example 48

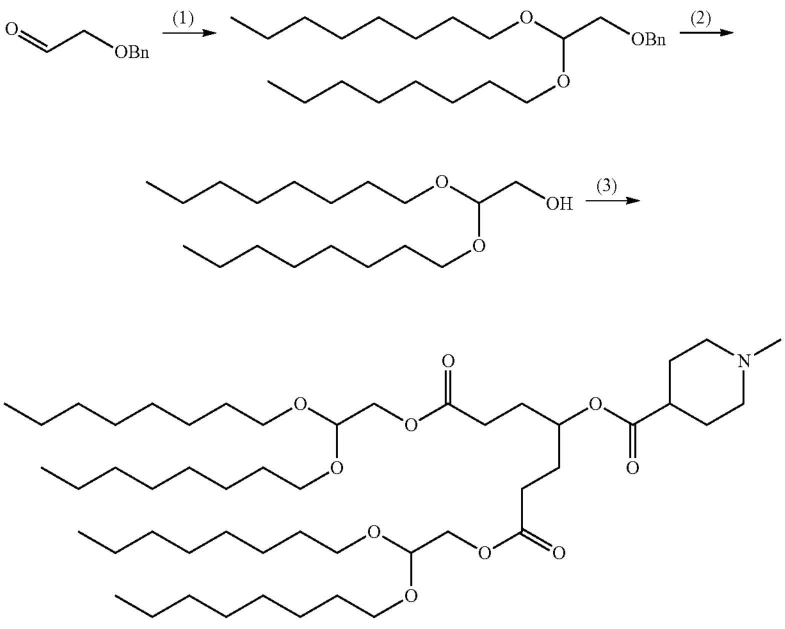

(1) Synthesis of ((2,2-Bis(octyloxy)ethoxy)methyl)benzene

A title compound (324 mg) was obtained by the same method as in Example 47(1) using octan-1-ol (661 μL) instead of heptan-1-ol.

(2) Synthesis of 2,2-Bis(octyloxy)ethan-1-ol

A title compound (183 mg) was obtained by the same method as in Example 47(2) using the compound (321 mg) obtained in Example 48(1) instead of the compound obtained in Example 47(1).

(3) Synthesis of Bis(2,2-bis(octyloxy)ethyl) 4-((1-methylpiperidine-4-carbonyl)oxy)heptanedioate (Compound (E48))

A title compound (25.6 mg) was obtained by the same method as in Example 47(3) using the compound (36.4 mg) obtained in Example 48(2) instead of the compound obtained in Example 47(2). ESI-MS:871.2 ([M+H]$^+$)

Example 49

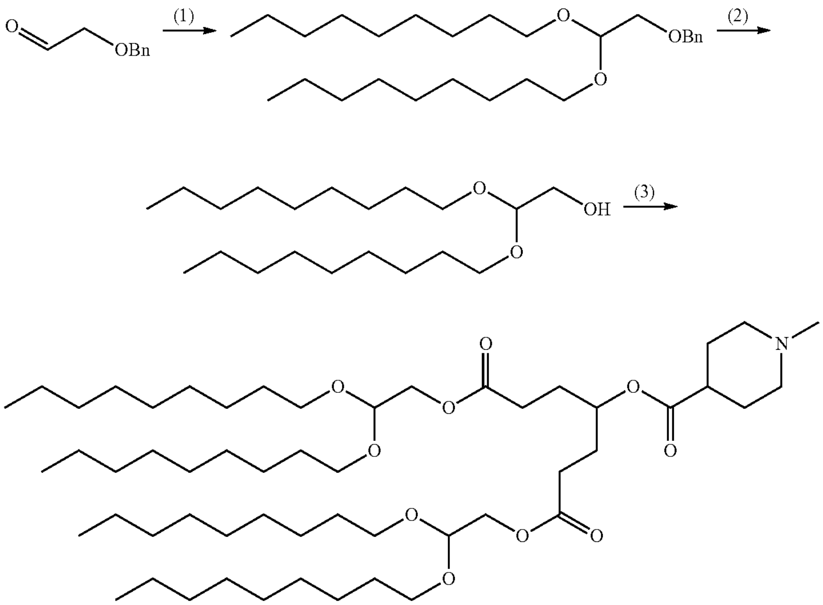

(1) Synthesis of ((2,2-Bis(nonyloxy)ethoxy)methyl)benzene

A title compound (336 mg) was obtained by the same method as in Example 47(1) using nonan-1-ol (710 μL) instead of heptan-1-ol.

(2) Synthesis of 2,2-Bis(nonyloxy)ethan-1-ol

A title compound (201 mg) was obtained by the same method as in Example 47(2) using the compound (334 mg) obtained in Example 49(1) instead of the compound obtained in Example 47(1).

(3) Synthesis of Bis(2,2-bis(nonyloxy)ethyl) 4-((1-methylpiperidine-4-carbonyl)oxy)heptanedioate (Compound (E49))

A title compound (25.6 mg) was obtained by the same method as in Example 47(3) using the compound (36.4 mg) obtained in Example 48(2) instead of the compound obtained in Example 47(2). ESI-MS:927.0 ([M+H]+)

Example 50

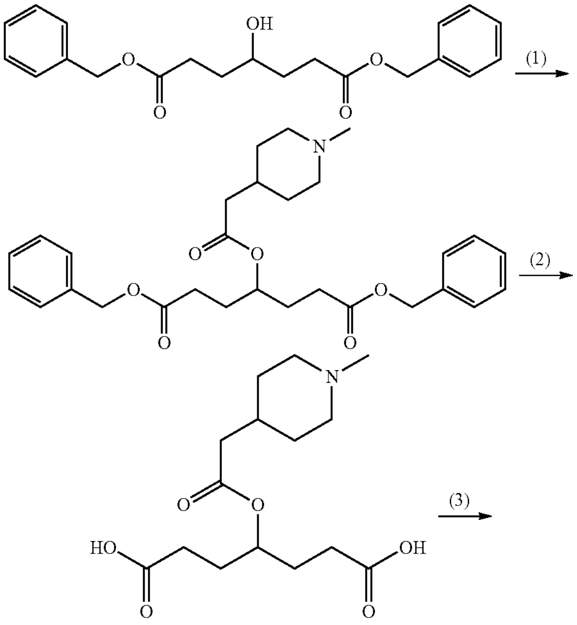

-continued

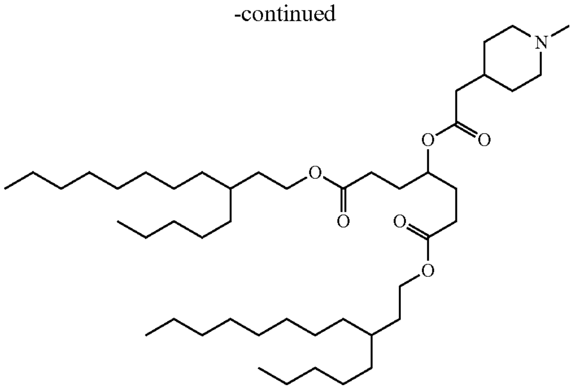

(1) Synthesis of Dibenzyl 4-(2-(1-methylpiperidin-4-yl)acetoxy)heptanedioate

A title compound (209 mg) was obtained by the same method as in Example 9-1(3) using 2-(1-methylpiperidin-4-yl)acetic acid (221 mg) instead of the compound (200 mg) obtained in Example 9-1(2) and piperidine-4-carboxylic acid hydrochloride.

(2) Synthesis of 4-(2-(1-Methylpiperidin-4-yl)acetoxy)heptanedioic acid

A title compound (119 mg) was obtained by the same method as in Example 9-1(4) using the compound (204 mg) obtained in Example 50(1) instead of the compound obtained in Example 9-1(3).

(3) Synthesis of Bis(3-pentylundecyl) 4-(2-(1-methylpiperidin-4-yl)acetoxy)heptanedioate (Compound (E50))

A title compound (24 mg) was obtained by the same method as in Example 9-1(5) using the compound (20 mg) obtained in Example 50(2) instead of the compound obtained in example 9-1(4) and 3-pentylundecan-1-ol (38.4 mg) instead of (S)-2-hexyldecan-1-ol. ESI-MS:765.0 ([M+H]+)

Example 51

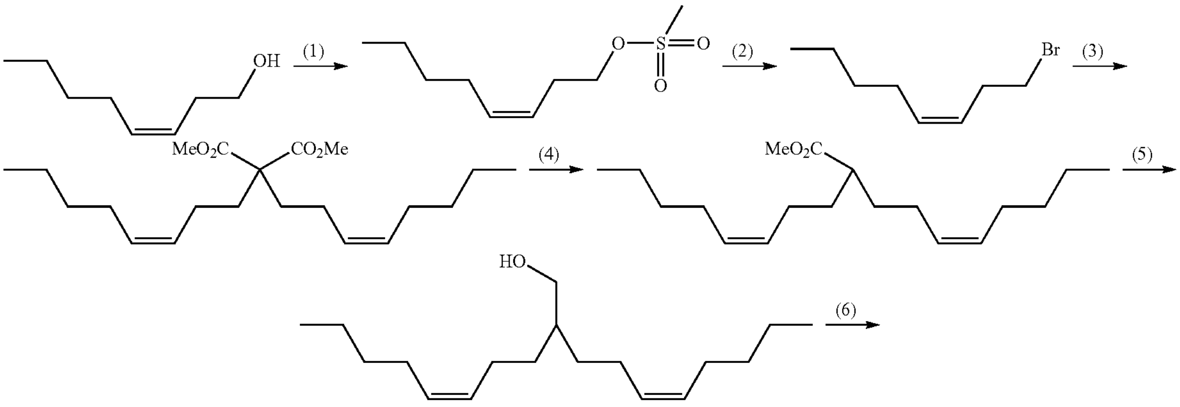

-continued

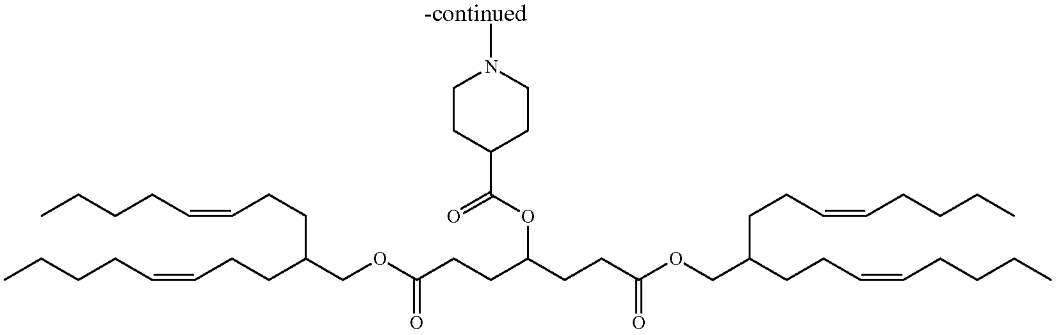

(1) Synthesis of (Z)-Oct-3-en-1-yl methanesulfonate

A title compound (3.23 g) was obtained by the same method as in Example 19(1) using (Z)-oct-3-en-1-ol (2.0 g) instead of (Z)-oct-5-en-1-ol.

(2) Synthesis of (Z)-1-Bromooct-3-ene

A title compound (2.64 g) was obtained by the same method as in Example 19(2) using the compound (3.23 g) obtained in Example 51(1) instead of the compound obtained in Example 19(1).

(3) Synthesis of Dimethyl 2,2-di((Z)-oct-3-en-1-yl) malonate

THF (10 mL) was added to dimethyl malonate (504 mg), and sodium hydride (60%, 160 mg) was added at 3° C. The components were stirred at room temperature for 30 minutes, a THF (1.5 mL) solution of the compound (802 mg) obtained in Example 51(2) was then added, and the components were stirred at room temperature for 44 hours. A mixture was immersed in an ice bath, sodium hydride (60%, 160 mg) was added, a THF (1.5 mL) solution of the compound (802 mg) obtained in Example 51(2) and potassium iodide (127 mg) were further added, and the components were stirred at room temperature for 23 hours. Sodium hydride (60%, 81 mg) was further added to the mixture and stirred for three days. Water (50 mL) and ethyl acetate (100 mL) were added to the mixture, an organic layer was washed with a saturated saline solution (30 mL) and then dried over sodium sulfate, a solid was removed by filtration and dried under reduced pressure. A residue was purified by silica gel column chromatography (cyclohexane/ethyl acetate), and a title compound (126 mg) was obtained.

(4) Synthesis of Methyl (Z)-2-((Z)-oct-3-en-1-yl) dec-5-enoate

A title compound (44 mg) was obtained by the same method as in Example 19(4) using the compound (126 mg) obtained in Example 51(3) instead of the compound obtained in Example 19(3).

(5) Synthesis of (Z)-2-((Z)-oct-3-en-1-yl)dec-5-en-1-ol

A title compound (34.1 mg) was obtained by the same method as in Example 19(5) using the compound (41.8 mg) obtained in Example 51(4) instead of the compound obtained in Example 19(4).

(6) Synthesis of Bis((Z)-2-((Z)-oct-3-en-1-yl)dec-5-en-1-yl) 4-((1-methylpiperidine-4-carbonyl)oxy) heptanedioate (Compound (E51))

A title compound (26.94 mg) was obtained by the same method as in Example 19(6) using the compound (33.7 mg) obtained in Example 51(5) instead of the compound obtained in Example 19(5).

ESI-MS:798.9 ([M+H]$^+$)

Example 52

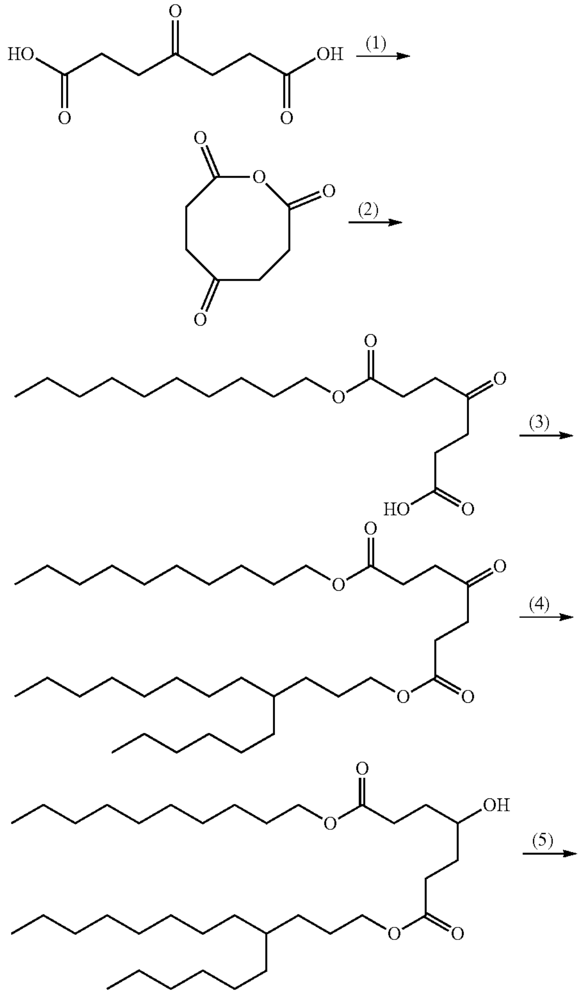

-continued

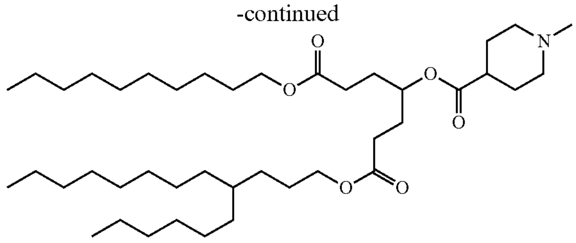

(1) Synthesis of Oxocane-2,5,8-trione

Acetyl chloride (20 mL) was added to 4-oxoheptanedioic acid (1.7 g). A mixture was heating-refluxed for 16 hours. The mixture was cooled to room temperature and then concentrated under reduced pressure. Xylene (30 mL) was added and concentrated again under reduced pressure, and a title compound (1.5 g) was obtained.

(2) Synthesis of 7-(Decyloxy)-4,7-dioxoheptanoic acid

Pyridine (90 μL) was added to the compound (227 mg) obtained in Example 52(1) and decan-1-ol (177 mg). A mixture was heating-refluxed for 16 hours and then concentrated under reduced pressure. Ethyl acetate (10 mL) and hydrochloric acid (1N, 10 mL) were added, and an organic layer was then separated. The obtained organic layer was washed with water (10 mL) twice and then washed with a saturated saline solution (10 mL). The organic layer was concentrated under reduced pressure and purified by silica gel chromatography (ethyl acetate/cyclohexane) to obtain a title compound (143 mg).

(3) Synthesis of 1-Decyl 7-(4-hexyldodecyl) 4-oxoheptanedioate

Toluene (1 mL) was added to 4-hexyldodecan-1-ol (83 mg) and concentrated under reduced pressure. The compound (114 mg) obtained in Example 52(2), EDCI (146 mg), DMAP (62.2 mg), and DMF (1 mL) were added to an obtained residue. A mixture was stirred for 16 hours, and MTBE (20 mL), water (10 mL), and a saturated saline solution (1 mL) were then added. After a separation operation was performed, an aqueous layer was extracted with MTBE (10 mL) twice. Combined organic layers were washed with a saturated saline solution and dried over sodium sulfate. An obtained mixture was concentrated under reduced pressure and purified by silica gel chromatography (cyclohexane/ethyl acetate), and a title compound (120 mg) was obtained.

(4) Synthesis of 1-decyl 7-(4-hexyldodecyl) 4-hydroxyheptanedioate

A title compound (43 mg) was obtained by the same method as in Example 46(4) using the compound (120 mg) obtained in Example 52(3) instead of the compound obtained in Example 46(3).

(5) Synthesis of 1-Decyl 7-(4-hexyldodecyl) 4-((1-methylpiperidine-4-carbonyl)oxy)heptanedioate (Compound (E52))

A title compound (22 mg) was obtained by the same method as in Example 46(5) using the compound (43 mg) obtained in Example 52(4) instead of the compound obtained in Example 46(4).

ESI-MS:695.0 ([M+H]$^+$)

Example 53

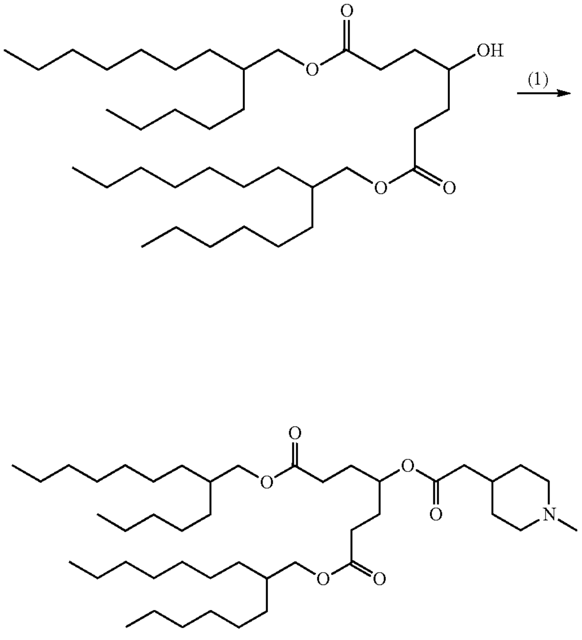

(1) Synthesis of Bis(2-hexylnonyl) 4-(2-(1-methylpiperidin-4-yl)acetoxy)heptanedioate (Compound (E53))

A title compound (13.7 mg) was obtained by the same method as in Example 4(1) using the compound (12 mg) obtained in Example 32(6) instead of the compound obtained in Example 3(2). ESI-MS:736.7 ([M+H]$^+$)

Example 54

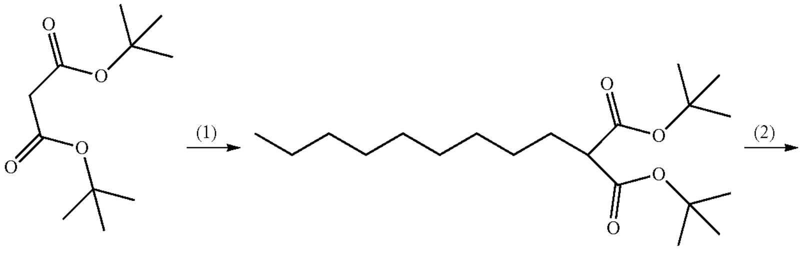

-continued

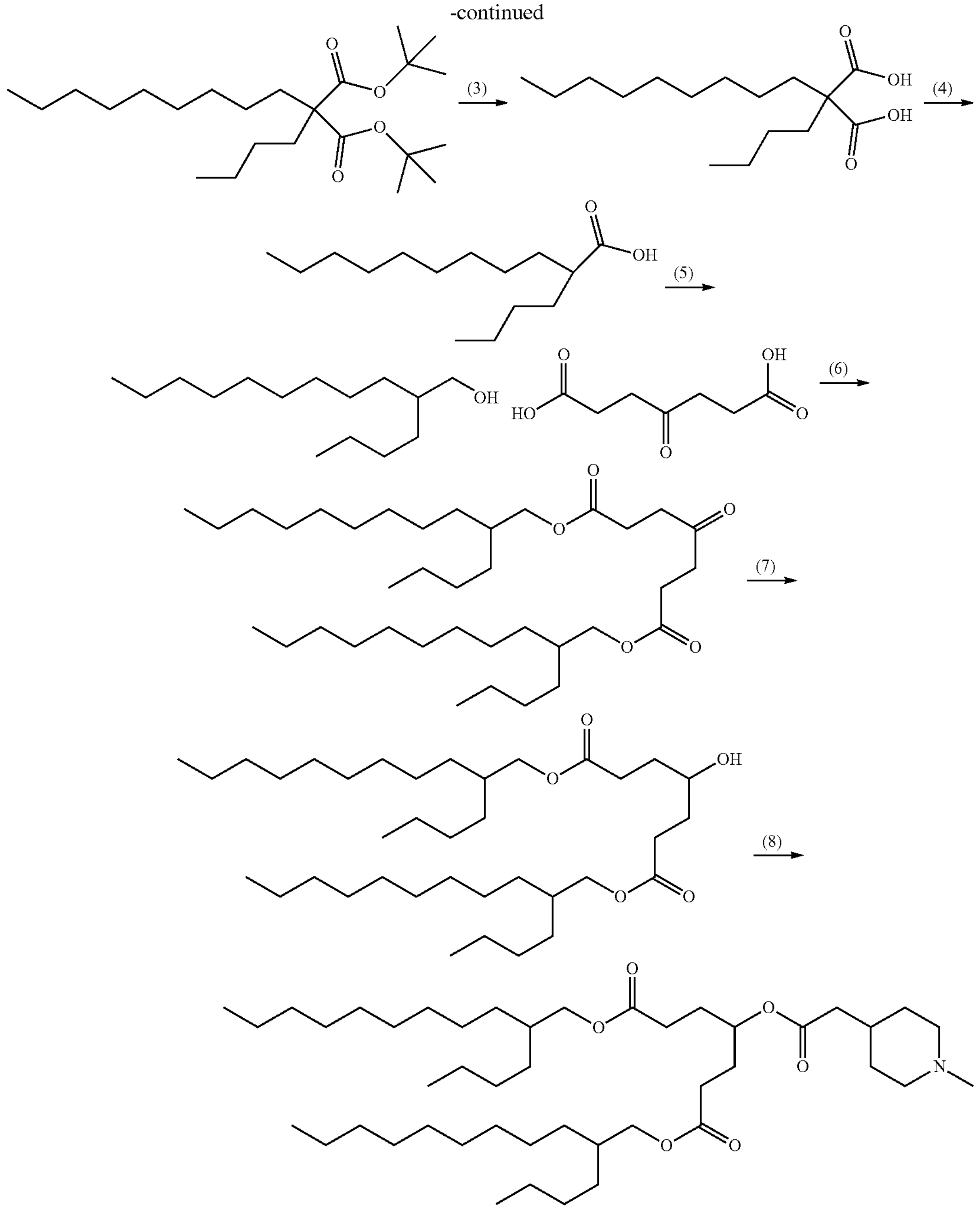

(1) Synthesis of di-tert-Butyl 2-nonylmalonate

A title compound (5.39 g) was obtained by the same method as in Example 18(1) using 1-iodononane (4.65 mL) instead of 1-bromooctane.

(2) Synthesis of di-tert-Butyl 2-butyl-2-nonylmalonate

A title compound (2.72 g) was obtained by the same method as in Example 18(2) using the compound (2.5 g) obtained in Example 54(1) instead of the compound obtained in Example 18(1).

(3) Synthesis of 2-Butyl-2-nonylmalonic acid

A title compound was obtained as a crude product (2.56 g) by the same method as in Example 18(3) using the compound (2.72 g) obtained in Example 54(2) instead of the compound obtained in Example 18(2).

(4) Synthesis of 2-Butylundecanoic acid

A title compound (1.71 g) was obtained by the same method as in Example 18(4) using the compound (2.56 g) obtained in Example 54(3) instead of the compound obtained in Example 18(3).

(5) Synthesis of 2-Butylundecan-1-ol

A title compound (1.32 g) was obtained by the same method as in Example 18(5) using the compound (1.71 g) obtained in Example 54(4) instead of the compound obtained in Example 18(4).

(6) Synthesis of Bis(2-butylundecyl) 4-oxoheptanedioate

A title compound (470 mg) was obtained by the same method as in Example 3(1) using the compound (525 mg) obtained in Example 54(5) instead of 3-hexylundecanol. ESI-MS:595.2 ([M+H]$^+$)

(7) Synthesis of Bis(2-butylundecyl) 4-hydroxyheptanedioate

A title compound (100 mg) was obtained by the same method as in Example 3(2) using the compound (470 mg) obtained in Example 54(6) instead of the compound obtained in Example 3(1). ESI-MS:597.3 ([M+H]$^+$)

(8) Synthesis of Bis(2-butylundecyl) 4-(2-(1-methylpiperidin-4-yl)acetoxy)heptanedioate (Compound (E54))

A title compound (2.36 mg) was obtained by the same method as in Example 5(3) using the compound (20 mg) obtained in Example 54(7) instead of the compound obtained in Example 5(2). ESI-MS:736.5 ([M+H]$^+$)

Example 55

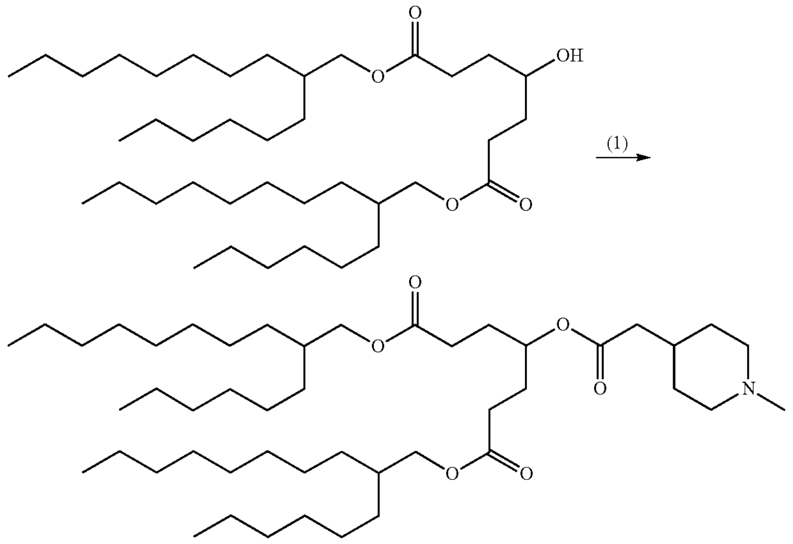

(1) Synthesis of Bis(2-hexyldecyl) 4-((((1-methylpiperidin-4-yl)oxy)carbonyl)oxy)heptanedioate (Compound (E55))

A title compound (18.58 mg) was obtained by the same method as in Example 37(1) using 4-hydroxy-1-methylpiperidine (18.43 mg) instead of (1-methylpiperidin-4-yl) methanol. ESI-MS:766.4 ([M+H]$^+$)

Example 56

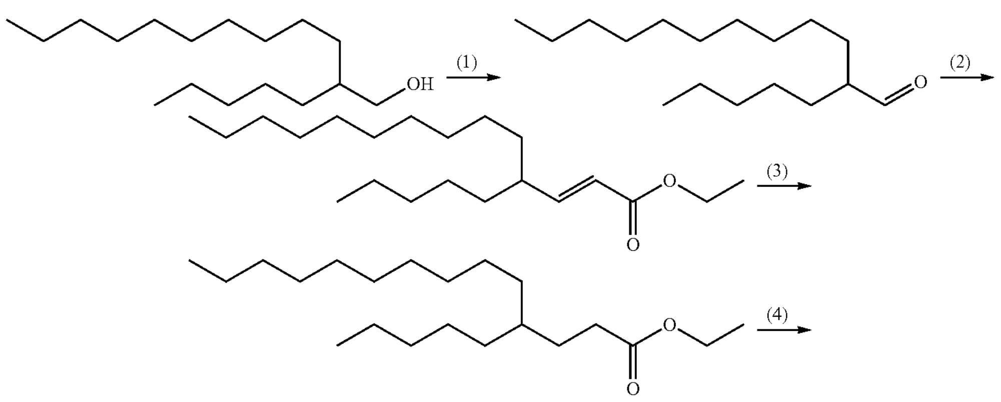

-continued

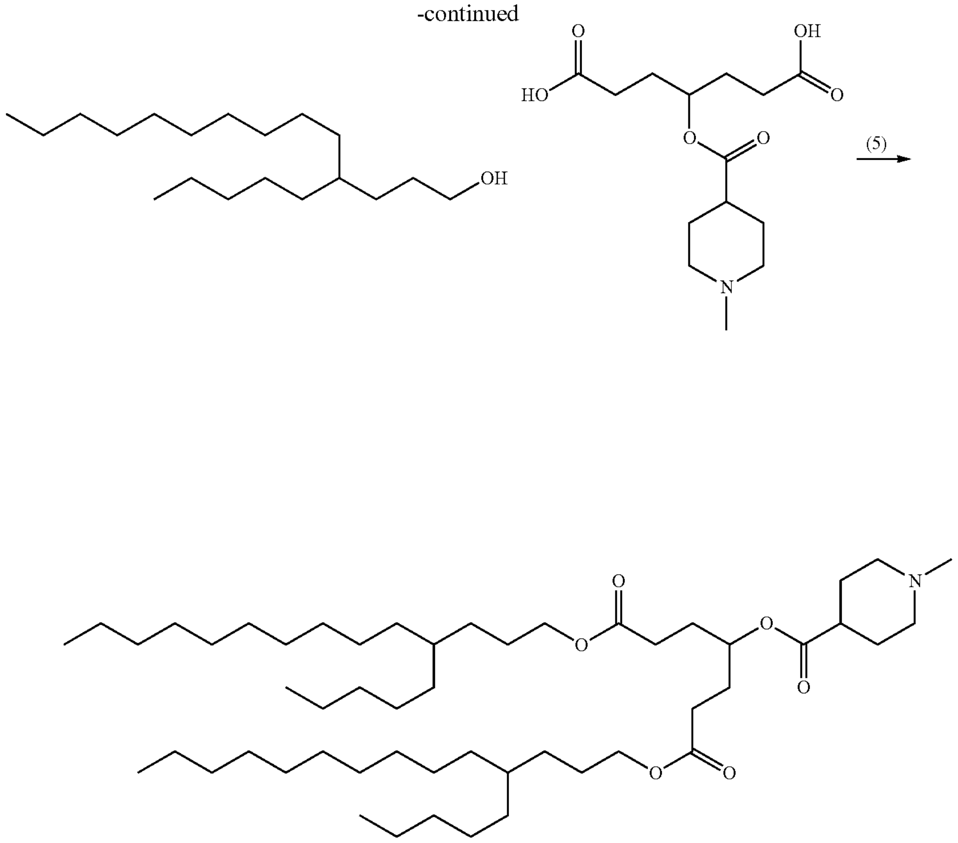

(1) Synthesis of 2-Pentyldodecanal

The compound (90 mg) obtained in Example 23(4) was added to DCM (5 mL), DMP (186 mg) was then added at 0° C., and the components were stirred for three hours. A saturated sodium thiosulfate aqueous solution (2 mL) and a saturated sodium bicarbonate aqueous solution (2 mL) were added and stirred for 10 minutes. A mixture was diluted by adding DCM (20 mL) and then filtered, and a filtrate was concentrated under reduced pressure. A residue was purified by silica gel column chromatography (diethylether/cyclohexane), and a title compound (50 mg) was obtained.

(2) Synthesis of Ethyl (E)-4-pentyltetradec-2-enoate

A title compound (50 mg) was obtained by the same method as in Example 21(1) using the compound (60 mg) obtained in Example 56(1) instead of heptanal.

(3) Synthesis of Ethyl 4-pentyltetradecanoate

Ethyl acetate (5 mL) was added to the compound (50 mg) obtained in Example 56(2) and palladium on carbon (32.8 mg), and the components were stirred for 16 hours in a hydrogen atmosphere. The inside of a flask was substituted with nitrogen, and filtration was then performed. A filtrate was concentrated under reduced pressure, and a title compound (44 mg) was obtained.

(4) Synthesis of 4-Pentyltetradecan-1-ol

A title compound (30 mg) was obtained by the same method as in Example 21(3) using the compound (44 mg) obtained in Example 56(3) instead of the compound obtained in Example 21(2).

(5) Synthesis of Bis(4-pentyltetradecyl) 4-((1-methylpiperidine-4-carbonyl)oxy)heptanedioate (Compound (E56))

A title compound (6.3 mg) was obtained by the same method as in Example 9-1(5) using the compound (30.2 mg) obtained in Example 56(4) instead of the compound obtained in Example 9-2(4). ESI-MS:835.0 ([M+H]$^+$)

Example 57

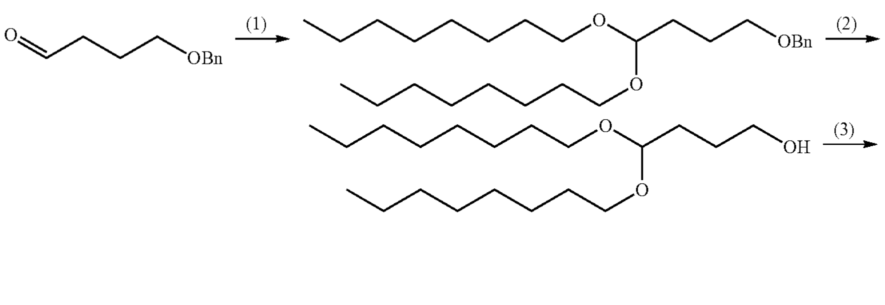

-continued

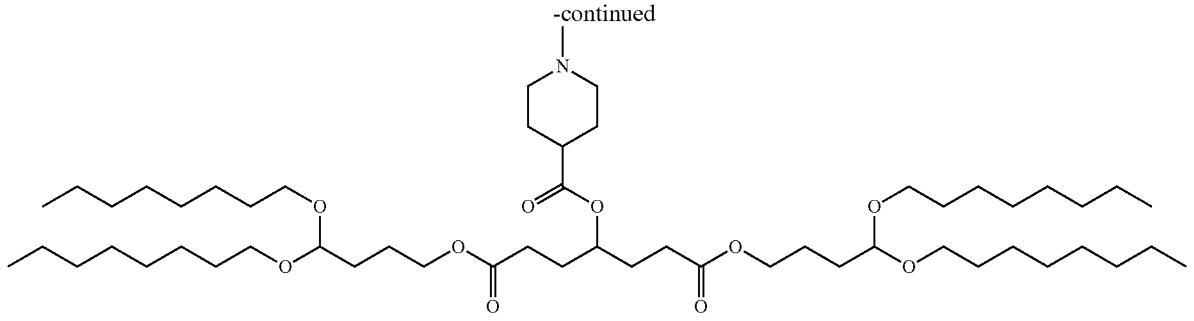

(1) Synthesis of ((4,4-Bis(octyloxy)butoxy)methyl)benzene

A title compound (283 mg) was obtained by the same method as in Example 47(1) using 4-(benzyloxy)butanal (200 mg) instead of 2-(benzyloxy)acetaldehyde and octan-1-ol (530 μL) instead of heptan-1-ol, respectively.

(2) Synthesis of 4,4-Bis(octyloxy)butan-1-ol

A title compound (168 mg) was obtained by the same method as in Example 47(2) using the compound (281 mg) obtained in Example 57(1) instead of the compound obtained in Example 47(1).

(3) Synthesis of Bis(4,4-bis(octyloxy)butyl) 4-((1-methylpiperidine-4-carbonyl)oxy)heptanedioate (Compound (E57))

A title compound (28.1 mg) was obtained by the same method as in Example 47(3) using the compound (40.8 mg) obtained in Example 57(2) instead of the compound obtained in Example 47(2). ESI-MS:927.0 ($[M+H]^+$)

Comparative Compounds

The following three comparative compounds were used as ionizable lipids.

Comparative Example 1

2-{9-Oxo-9-[(3-pentyloctyl)oxy]nonyl}dodecyl 1-methylpiperidine-4-carboxylate (Compound (C1))

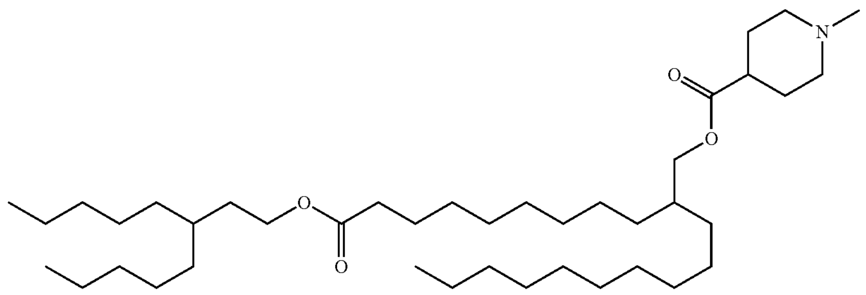 [SMILES: CCCCCCCCCCC(CCCCCCCCC(=O)OCCC(CCCCC)CCCCC)COC(=O)C1CCN(C)CC1]

A comparative compound lipid C1 is an ionizable lipid 2 (2-{9-oxo-9-[(3-pentyloctyl)oxy]nonyl}dodecyl 1-methylpiperidine-4-carboxylate) described in WO 2017/222016.

The title compound was synthesized according to a method described in [Example A-2] of the same document.

Comparative Example 2

1-(2-decyltetradecyl)5-octyl 3-((1-methylpiperidine-4-carbonyl)oxy)pentanedioate (Compound (C2))

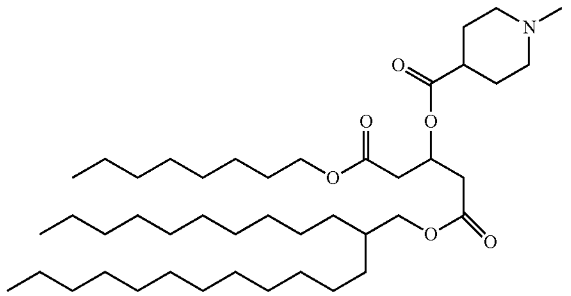 [SMILES: CCCCCCCCCCCCC(CCCCCCCCCC)COC(=O)CC(CC(=O)OCCCCCCCC)OC(=O)C1CCN(C)CC1]

A comparative compound lipid C2 is a compound of A42F40C23 (LNP-42) disclosed in PTL 8 (Chinese Patent No. 114874106).

The title compound was synthesized by a method described in the same document.

Comparative Example 3

((6Z,9Z,28Z,31Z)-Heptatriaconta-6,9,28,31-tetraen-19-yl 4-(dimethylamino)butanoate (Compound (C3))

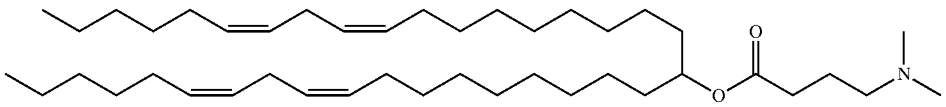 [SMILES: CCCCC/C=C\C/C=C\CCCCCCCCC(CCCCCCCC/C=C\C/C=C\CCCCC)OC(=O)CCCN(C)C]

A comparative compound lipid C3 is a compound that is used as a lipid component of a lipid nanoparticle formulation "Onpattro (registered trademark)" by Alnylam Pharmaceuticals, Inc. The compound was purchased from Amatek Chemical Co., Ltd.

B. Preparation and Analysis of Compositions (Nucleic Acid)

[SEQ ID No. 1 (Firefly Luciferase mRNA)]

[SEQ ID No. 2 (Human Erythropoietin mRNA)]

Compositions containing a lipid complex were prepared using ionizable lipids synthesized in the individual Examples and Comparative Examples and the nucleic acids.

Preparation Example 1: Preparation of Composition (1)

A Firefly Luciferase mRNA consisting of the base sequence of SEQ ID No. 1 was prepared by an in vitro transcription method according to a conventional method. This includes 5'UTR, ORF, 3'UTR, and polyA. The Firefly Luciferase mRNA was dissolved in 10 to 25 mM sodium acetate (pH 4.0 to 5.0) to produce an mRNA solution. In addition, ionizable lipids, DSPC (NIPPON SEIKA, DSPC-K2), Cholesterol (Nippon Fine Chemical Co., Ltd., Cholesterol HP or Dishman, CHOLESTEROL HP), MPEG 2000-DMG (NOF Corporation, SUNBRIGHT GM-020) were dissolved in ethanol in proportions of about 50/10/38.5/1.5 (molar ratio) to produce a lipid ethanol solution. The RNA/total lipid content of a final formulation was made to be about 0.06 weight ratios, and the mRNA solution and the lipid ethanol solution were mixed at a flow rate of 3:1 to obtain a nucleic acid lipid complex solution. The external fluid thereof was substituted into a phosphate buffer (PBS, pH 7.5) and, subsequently, a tris/sucrose buffer (20 mM Tris-HCl, 8% (w/v) Sucrose, pH 7.5) using a dialysis membrane (14 kDa or 100 kDa). After that, sterilization by filtration was performed to obtain a composition.

Preparation Example 2: Preparation of Composition (2)

A Human Erythropoietin mRNA consisting of the base sequence of SEQ ID No. 2 was prepared by the in vitro transcription method according to a conventional method. This includes 5'UTR, ORF, 3'UTR, and polyA. A composition was obtained in the same manner as in Preparation Example 1 except that the Human Erythropoietin mRNA consisting of the base sequence of SEQ ID No. 2 was used instead of the Firefly Luciferase mRNA consisting of the base sequence of SEQ ID No. 1.

[Analysis of Compositions]

1. Encapsulation Rate of mRNA in Lipid Complex

The encapsulation rates of the mRNA in the lipid complex were determined with respect to the compositions obtained in the Preparation Examples. Specifically, the compositions were diluted with a TE (Tris-EDTA) buffer (TaKaRa, catalog #T9111), and the mRNA concentration (A) measured using Quanti-iT Ribogreen RNA Reagent (Invitrogen, catalog #$R_{11491}$) was regarded as the concentration of mRNA present in the lipid complex external fluid. In addition, the mRNA concentration (B) measured by diluting the composition with 1% (v/v) Triton X-100 was regarded as the concentration of all mRNAs in the lipid complex. The encapsulation rate of mRNA in the lipid complex was then calculated using the following formula (F1):

$$\text{Encapsulation rate (\%)} = 100 - (A/B) \times 100 \, (F1)$$

2. Average Particle Size and Polydispersity Index into Lipid Complex

In addition, the average particle size (Z-Average) and polydispersity index (PDI) of the lipid complex were measured with a particle size analyzer (ZETASIZER Nano ZS, Malvern).

The results are shown in Table 1 and Table 3.

Table 1 shows the analysis results of the composition of the lipid complex encapsulating the Firefly Luciferase mRNA (SEQ ID No. 1) produced in Production Example 1. The composition was used in Test Example 1 to be described below.

Table 3 below shows the analysis results of the composition of the lipid complex encapsulating the Human Erythropoietin mRNA (SEQ ID No. 2) produced in Production Example 2. The composition was used in Test Example 2 to be described below.

TABLE 1

| Analysis of composition | | | |
|---|---|---|---|
| Lipid ID | Average particle size (nm) | Polydispersity index | Encapsulation rate |

As shown above, the lipid complexes prepared with the ionizable lipid of the present disclosure were all confirmed to have an encapsulation rate of nucleic acids of higher than 90% and a polydispersity index of lower than 0.1 and have excellent stability.

C. Test Examples

Test Example 1: Evaluation of Protein Production Effect in Mice of Composition

A method described in NPL 1 (Tanaka et al., ACS Nano 2023, 17, 2588 to 2601) was referenced. The composition obtained in Preparation Example 1 was diluted with saline so that the concentration of the Firefly Luciferase mRNA encapsulated in the lipid complex reached 20 μg/mL. Each composition was intravenously administered to ICR mice (females, n=4) at a dosage of about 10 mL/kg, and liver sections were collected after 24 hours. Glo Lysis Buffer, 1× (Promega, catalog #E2661), and zirconia beads (Bio Medical Science Inc., catalog #ZZ50-0003), which weighed about 10 times the weight of the liver sections, were added and homogenized using a multi-bead shocker (QIAGEN). After a tissue membrane component was removed by centrifugation, Luciferase protein in a supernatant was reacted with a Steady-Glo Luciferase assay System (Promega, catalog #E2510) to detect luminescence. In addition, the concentration of all proteins in the supernatant was quantified using a BCA reagent (Thermo Scientific, catalog #23231, 23232, and 23234), and the value was removed from the obtained luminescence intensity, thereby calculating the Luciferin luminescence intensity.

The Luciferin luminescence intensity of the group administered with the composition of C1 was regarded as 1.0 (100%), and the relative values of groups administered with the composition were calculated, respectively. The results are shown in Table 2.

TABLE 2

| Protein production effect in rodents | |
|---|---|
| Lipid ID | Relative Luciferin luminescence intensity after 24 hours from administration (n = 4, average) |

The results of Test Example 1 show that the compositions for which the ionizable lipids (E1 to E57) of the present disclosure are used are capable of releasing nucleic acids into cytoplasm.

The compositions for which the ionizable lipids (E1 to E57) of the present disclosure were used had luminescence intensities that were 200% or more, and furthermore, 1.5 times or more higher than the luminescence intensities of the compositions for which C1 or C2 was used as an ionizable lipid in mice, which suggested that the Luciferase protein production effect is high. This result indicates that the ionizable lipids of the present disclosure have an excellent mRNA delivery efficiency. Among these, the compositions for which the ionizable lipids (E1, E2, E4 to E6, E8 to E22, E24, E26 to E41, E43, E45 to E47, E49, E50, and E53 to E57) were used had luminescence intensities of 250% or more, and the compositions for which the ionizable lipids (E1, E2, E4, E6, E8 to E12, E14 to E22, E24, E26 to E39, E41, E43, E46, E47, E49, and E53 to E57) were used had luminescence intensities of 300% or more, all of which were particularly excellent in terms of the mRNA delivery efficiency. Furthermore, the ionizable lipid is preferably E1, E4, E6, E12, E13, E16, E17, or E29, more preferably E1, E4, E6, E12, or E17, and particularly preferably E4, E6, or E17 from the viewpoint of enabling the formation of lipid particles having low toxicity and/or excellent stability during refrigerated storage.

Test Example 2: Evaluation of Protein Production Effect in Monkeys of Composition The composition for which the ionizable lipid E1 produced in Preparation Example 2 was used was diluted with saline so that the concentration of the Human Erythropoietin mRNA encapsulated in the lipid complex reached 40 μg/mL. The composition was intravenously infused into crab-eating macaque (males, n=2) for 60 minutes at a dose of 5 mL/kg. Blood was collected in syringe barrels immediately before the administration, after two hours, after six hours, after 24 hours, after 48 hours, and after 72 hours. Serum was separated from centrifuged blood, and the concentration of the Human Erythropoietin protein in the serum was quantified using U-PLEX Human EPO Assay (Meso Scale Discovery, catalog #K151VXK). The results are shown in Table 4.

TABLE 3

| Analysis of composition | | | |
|---|---|---|---|
| Lipid ID | Average particle size (nm) | Polydispersity index | Encapsulation rate |

TABLE 4

| Protein production effect in primates | |
|---|---|
| Days | Concentration of Human Erythropoietin in serum (ng/ml, n = 2, average) |
| 0 (before administration) | Detection limit or less |
| 0.08 (After two hours from administration) | |
| 0.25 (After six hours from administration) | |

The compositions for which the ionizable lipid E1 of the present disclosure was used exhibited a Human Erythropoietin protein production effect in monkeys.

Test Example 3: Evaluation of Amount of Aldehyde Produced in Ethanol Solution by Ionizable Lipid A method described in NPL 2 (Hashiba et al., Commun. Biol., 2024, 7(1), 556) was generally followed. That is, a 0.25 mM 4-hydrazino-7-nitro-2,1,3-benzoxadiazole hydrazine (Tokyo Chemical Industry Co., Ltd., catalog #A5557. Hereinafter, NBD-H) solution (containing a powder dissolved in acetonitrile containing 0.025% (v/v) trifluoroacetic acid) was prepared. 10 μL of an ethanol solution containing 40 mM of an ionizable lipid was mixed with a 190 μL NBD-H solution and reacted at room temperature for 60 minutes. The fluorescence value of the lipid-mixed liquid was measured under conditions of excitation=470 nm and emission=550 nm. In addition, the fluorescence value was measured in the same manner using an ethanol solution containing no ionizable lipids as the background, and the value were reduced. In a case where the fluorescence value is the background or less, the fluorescent value is considered as not detected (N.D.). The results are shown in Table 5.

TABLE 5

| Evaluation of amount of aldehyde produced by ionizable lipid | |
|---|---|
| Lipid ID | Fluorescence intensity (n = 3, average) (a.u.) |

It became clear that the ionizable lipids E1 and E6 of the present disclosure had lower fluorescence values than the comparative compound lipid C3. This suggests that the amount of aldehyde, which is an impurity, produced in the ionizable lipid is small. The comparative compound lipid C3 is a compound that is used as a lipid component of a lipid nanoparticle formulation "Onpattro (registered trademark)" by Alnylam Pharmaceuticals, Inc. In NPL 2, it is suggested that the amount of aldehyde produced by the ionizable lipid and the activity (storage stability at lower than 4° C.) of an active pharmaceutical ingredient are negatively correlated with each other. The ionizable lipid of the present disclosure has a small amount of aldehyde produced compared with that of the comparative compound lipid C3, which suggests that the ionizable lipid of the present disclosure is excellent in terms of retention of active pharmaceutical ingredient activity (storage stability of an active pharmaceutical ingredient).

INDUSTRIAL APPLICABILITY

According to the present disclosure, it is possible to provide an ionizable lipid capable of releasing nucleic acids into cytoplasm.

The invention claimed is:
1. A compound or pharmaceutically acceptable salt thereof, wherein the compound is selected from the group consisting of:
(E1)
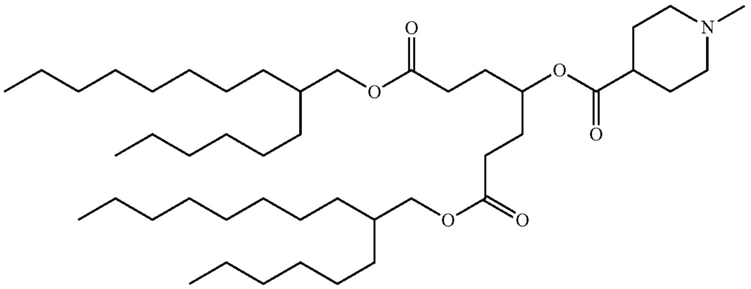
(E4)
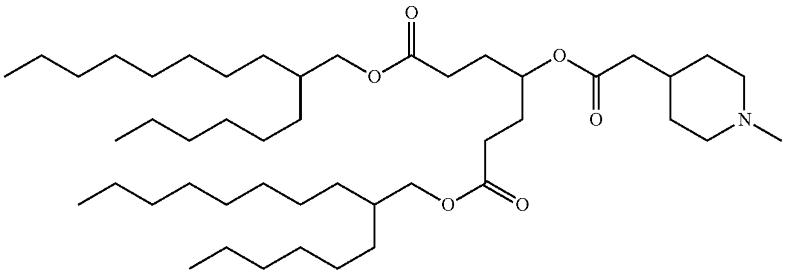
(E12)
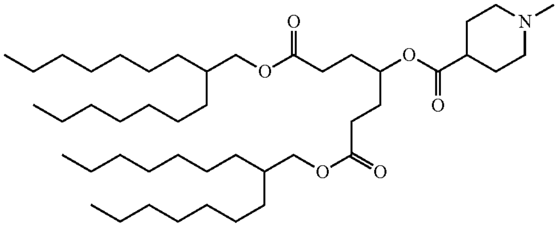
(E13)
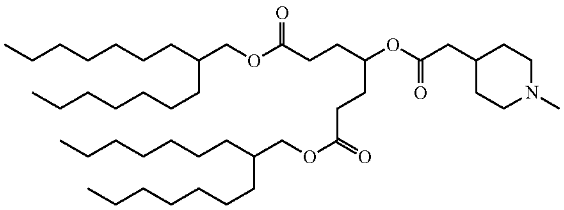
(E16)
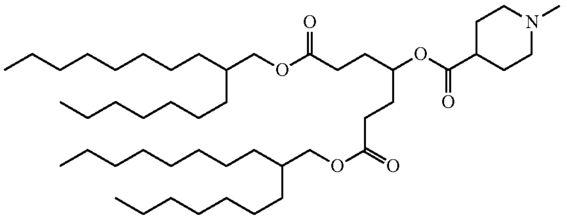

-continued

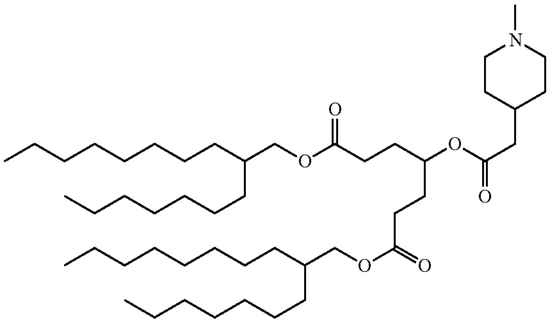

(E17)

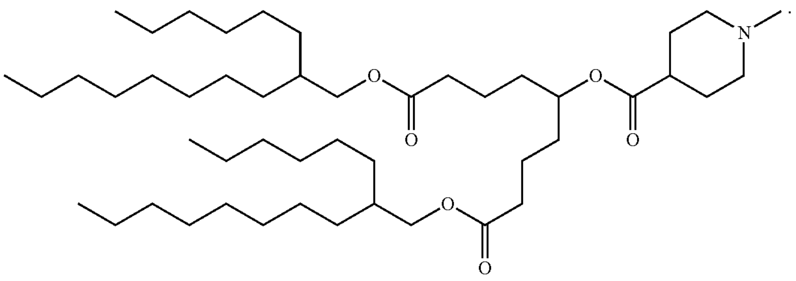

(E29)

2. A lipid complex comprising:

(I) the compound or pharmaceutically acceptable salt thereof according to claim 1; and (II) at least one lipid selected from the group consisting of a neutral lipid, a polyethylene glycol-modified lipid, and a sterol.

3. A composition comprising:

(I) the compound or pharmaceutically acceptable salt thereof according to claim 1;

(II) at least one lipid selected from the group consisting of a neutral lipid, a polyethylene glycol-modified lipid, and a sterol; and (III) a nucleic acid.

4. A method for producing a composition, the method comprising:

(I) mixing the compound or pharmaceutically acceptable salt thereof according to claim 1, a polar organic solvent-containing aqueous solution containing at least one lipid selected from the group consisting of a neutral lipid, a polyethylene glycol-modified lipid, and a sterol, and an aqueous solution containing a nucleic acid to obtain a liquid mixture; and (II) reducing a content of the polar organic solvent in the liquid mixture.

5. The compound or pharmaceutically acceptable salt thereof according to claim 1, wherein the compound is the following compound:

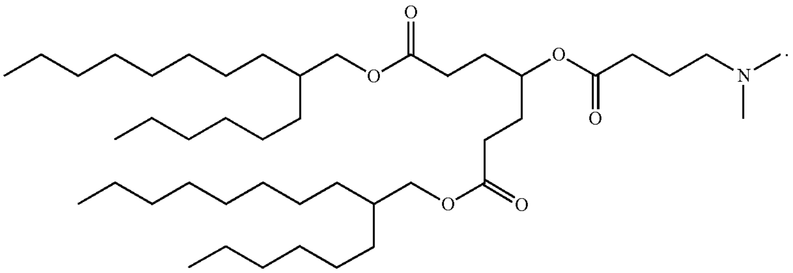

(E6)

6. A lipid complex comprising:

(I) the compound or pharmaceutically acceptable salt thereof according to claim 5; and (II) at least one lipid selected from the group consisting of a neutral lipid, a polyethylene glycol-modified lipid, and a sterol.

7. A composition comprising:

(I) the compound or pharmaceutically acceptable salt thereof according to claim 5;

(II) at least one lipid selected from the group consisting of a neutral lipid, a polyethylene glycol-modified lipid, and a sterol; and (III) a nucleic acid.

8. A method for producing a composition, the method comprising:

(I) mixing the compound or pharmaceutically acceptable salt thereof according to claim 5, a polar organic solvent-containing aqueous solution containing at least one lipid selected from the group consisting of a neutral lipid, a polyethylene glycol-modified lipid, and a sterol, and an aqueous solution containing a nucleic acid to obtain a liquid mixture; and (II) reducing a content of the polar organic solvent in the liquid mixture.

* * * * *